United States Patent
Ottosen et al.

(10) Patent No.: US 7,977,387 B2
(45) Date of Patent: Jul. 12, 2011

(54) AMINOBENZOPHENONE COMPOUNDS

(75) Inventors: Erik Rytter Ottosen, Ølstykke (DK);
Anne Marie Horneman, Humlebaek (DK); Xifu Liang, Glostrup (DK); Søren Christian Schou, København Nv (DK); Sophie Elisabeth Havez, Valby (DK); Thomas Peter Sabroe, Virum (DK)

(73) Assignee: Leo Pharma A/S, Ballerup (DK)

( * ) Notice: Subject to any disclaimer, the term of this patent is extended or adjusted under 35 U.S.C. 154(b) by 643 days.

(21) Appl. No.: 10/563,474

(22) PCT Filed: Jul. 9, 2004

(86) PCT No.: PCT/DK2004/000490
§ 371 (c)(1),
(2), (4) Date: Jan. 5, 2006

(87) PCT Pub. No.: WO2005/009940
PCT Pub. Date: Feb. 3, 2005

(65) Prior Publication Data
US 2006/0166990 A1 Jul. 27, 2006

Related U.S. Application Data

(60) Provisional application No. 60/489,488, filed on Jul. 24, 2003.

(51) Int. Cl.
*A61K 31/136* (2006.01)
*A61K 31/12* (2006.01)
*C07C 211/56* (2006.01)
*C07C 49/303* (2006.01)

(52) U.S. Cl. ......... 514/658; 514/676; 564/457; 568/367

(58) Field of Classification Search .................. 514/658, 514/676; 564/457; 568/367
See application file for complete search history.

(56) References Cited

U.S. PATENT DOCUMENTS 6,541,670 B2 * 4/2003 Ottosen .......................... 564/432
7,056,942 B2 * 6/2006 Hildesheim et al. .......... 514/411

FOREIGN PATENT DOCUMENTS

| WO | WO-98/32730 A | 7/1998 |
|----|----|----|
| WO | WO-01/05744 A | 1/2001 |
| WO | WO 01/05744 A1 * | 1/2001 |
| WO | WO-01/05745 A | 1/2001 |
| WO | WO-01/05746 A | 1/2001 |
| WO | WO-01/05749 A | 1/2001 |
| WO | WO-01/05751 A | 1/2001 |
| WO | WO-01/42189 A | 6/2001 |
| WO | WO-02/45752 A | 6/2002 |
| WO | WO-02/076447 A | 10/2002 |
| WO | WO 02/076447 A1 * | 10/2002 |

* cited by examiner

*Primary Examiner* — Joseph Kosack
(74) *Attorney, Agent, or Firm* — Birch, Stewart, Kolasch & Birch, LLP

(57) ABSTRACT

The invention provides novel compounds according to formula I relates to compounds with the general formula I said compounds being useful, e.g. in the treatment of inflammatory, ophthalmic diseases or cancer.

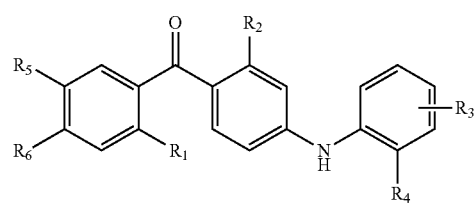

(I)

17 Claims, No Drawings

AMINOBENZOPHENONE COMPOUNDS

FIELD OF THE INVENTION

The present invention relates to a novel type of aminobenzophenones and to their use in therapy.

BACKGROUND OF THE INVENTION

Aminobenzophenones are well known from the scientific as well as the patent literature. Thus, WO 98/32730, WO 01/05746, WO 01/05749, WO 01/05751, WO 01/05744 and WO 01/05745 all disclose compounds with the common core structure

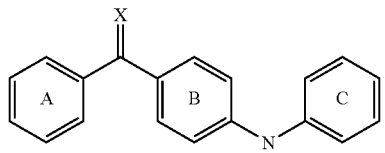

wherein the phenyl ring C is substituted by amine derivatives. Moreover, WO 01/42189 and WO 02/076447 disclose compounds with a similar structure, but with no nitrogen substituent in phenyl ring C. Finally, WO 01/90074 and WO 02/083622 disclose compounds where the phenyl rings A and C respectively are replaced by heterocycles. The compounds disclosed in these patent application are indicated to be inhibitors of interleukin 1β (IL-1β) and tumour necrosis factor α (TNF-α) secretion in vitro, which makes the compounds potentially useful in the treatment of inflammatory diseases where the production of cytokines is involved in the pathogenesis. Allegedly, aminobenzophenones exert their effect by inhibiting the p38 MAP kinase, which in turn inhibits the production of IL-1β and TNF-α.

The preparation of structurally related aminobenzophenones useful as dyes for textiles is disclosed in Man-Made Text. India (1987), 30(6), 275-6, Man-Made Text. India (1986), 29(5), 224-30, and Man-Made Text. India (1985), 28(11), 425, 427-9, 431.

SUMMARY OF THE INVENTION

It has surprisingly been found that novel aminobenzophenone derivatives are potent inhibitors of interleukin 1β (IL-1β) and tumour necrosis factor α (TNF-α) secretion in vitro and in vivo, suggesting their utility in the treatment and/or prevention of inflammatory diseases and other conditions where the secretion and modulation of proinflammatory cytokines is involved in the pathogenesis.

It has been found that aminobenzophenone derivatives of the present invention exert their anti-inflammatory effect by inhibiting or downregulating MAP kinases, more specifically the p38 MAP kinase, a stress-activated protein which is an important element of the signal transduction pathway leading to the production of proinflammatory cytokines.

The aminobenzophenone derivatives of the present invention may furthermore be useful in the treatment of cancer or ophthalmic diseases or conditions.

Accordingly, the present invention relates to a compound of general formula I

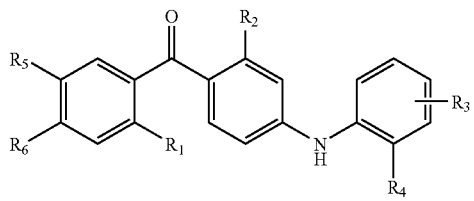

wherein
$R_1$ is halogen, hydroxy, mercapto, trifluoromethyl, amino, $C_{1-4}$alkyl, $C_{2-4}$alkenyl, $C_{2-4}$alkynyl, $C_{1-4}$alkoxy, $C_{1-4}$alkylthio, $C_{1-6}$alkylamino, $C_{1-4}$alkoxycarbonyl, cyano, —$CONH_2$ or nitro;

$R_2$ is hydrogen, halogen, hydroxy, mercapto, trifluoromethyl, amino, $C_{1-4}$alkyl, $C_{2-4}$alkenyl, $C_{2-4}$alkynyl, $C_{1-4}$alkoxy, $C_{1-4}$alkylthio, $C_{1-6}$alkylamino, $C_{1-4}$alkoxycarbonyl, cyano, —$CONH_2$, phenyl or nitro;

$R_3$ represents one or more, same or different substituents selected from the group consisting of hydrogen, halogen, hydroxy, mercapto, trifluoromethyl, cyano, carboxy, $CONH_2$, nitro, $C_{1-4}$alkyl, $C_{2-4}$alkenyl, $C_{2-4}$alkynyl, $C_{1-4}$alkoxy, $C_{1-4}$alkylthio, $C_{1-4}$ alkoxycarbonyl;

$R_4$ is hydrogen, halogen, nitro, $R_8$ or $Y_1R_8$;

$Y_1$ is —O—, —S—, —S(O)—, —S(O)$_2$—, —$NR_a$—, —$NR_aC(O)NR_b$—, —$NR_aC(O)$—, —$C(O)NR_a$—, —$C(O)NR_aO$—, —$C(O)$—, —$C(O)O$—, —$NR_aC(O)O$—, —$S(O)_2NR_a$—, —$NR_aS(O)_2$—;

$R_a$, $R_b$ and $R_c$ are the same or different, each representing hydrogen, $C_{1-4}$alkyl, $C_{2-4}$alkenyl, $C_{2-4}$ alkynyl, $C_{3-8}$carbocyclyl, $C_{1-12}$heterocyclyl or aryl, each of $C_{1-4}$alkyl, $C_{2-4}$alkenyl, $C_{2-4}$ alkynyl, $C_{3-8}$carbocyclyl, $C_{1-12}$heterocyclyl or aryl being optionally substituted by one or more, same or different substituents represented by $R_7$;

$R_8$ is hydrogen, $C_{1-10}$alkyl-$C_{1-12}$heterocyclyl, $C_{1-10}$alkyl-$C_{3-12}$carbocyclyl, $C_{1-10}$alkyl, $C_{2-10}$alkenyl, $C_{2-10}$ alkynyl, $C_{3-12}$carbocyclyl or $C_{1-12}$heterocyclyl, each of $C_{1-10}$alkyl-$C_{1-12}$heterocyclyl, $C_{1-10}$alkyl-$C_{3-12}$carbocyclyl, $C_{1-10}$alkyl, $C_{2-10}$alkenyl, $C_{2-10}$ alkynyl, $C_{3-12}$-carbocyclyl or $C_{1-12}$heterocyclyl being optionally substituted by one or more, same or different substituents represented by $R_7$;

$R_7$ is halogen, hydroxy, mercapto, trifluoromethyl, amino, $C_{1-4}$alkyl, $C_{1-6}$hydroxyalkyl, $C_{1-4}$alkoxy, $C_{1-4}$alkylthio, $C_{1-6}$ alkylamino, $C_{1-4}$alkoxycarbonyl, $C_{1-9}$ trialkylammonium in association with an anion, cyano, azido, nitro, —$S(O)_2NH_2$, —$S(O)_2NR_aR_b$, —$S(O)_2R$, —COOH, —$CONH_2$, —$NR_aC(O)R'$, —CONHR' or —CONRR', wherein R and R' are same or different, each representing hydrogen or $C_{1-3}$alkyl;

one of $R_5$ and $R_6$ is —COOH, —C(O)NHOH, —C(O)NHNH$_2$, $Y_2R_9$, $Y_2R_9Y_3R_{10}$, $C_{1-6}$alkyl-$Y_2R_9$, $C_{1-6}$alkyl-$Y_2R_9Y_3R_{10}$, $C_{2-6}$alkenyl-$Y_2R_9$, $C_{2-6}$alkenyl-$Y_2R_9Y_3R_{10}$, $Y_2R_9$—$C_{1-6}$-alkyl-$Y_3R_{10}$, $Y_2R_9$—$C_{2-6}$-alkenyl-$Y_3R_{10}$, $C_{3-12}$carbocyclyl-$Y_2R_9$, $C_{3-12}$carbocyclyl-$Y_2R_9Y_3R_{10}$, $C_{1-12}$heterocyclyl-$Y_2R_9$, $C_{1-12}$heterocyclyl-$Y_2R_9Y_3R_{10}$, $C_{3-12}$carbocyclyl-$C_{1-6}$-alkyl-$Y_2R_9$, $C_{3-12}$carbocyclyl-$C_{1-6}$-alkyl-$Y_2R_9Y_3R_{10}$, $C_{1-12}$heterocyclyl-$C_{1-6}$-alkyl-$Y_2R_9$, $C_{1-12}$heterocyclyl-$C_{1-6}$-alkyl-$Y_2R_9Y_3R_{10}$, $C_{3-12}$carbocyclyl-$C_{1-6}$-alkyl-$Y_3R_{10}$, $C_{1-12}$heterocyclyl-$C_{1-6}$-alkyl-$Y_3R_{10}$, $C_{1-12}$heterocyclyl-$C_{1-10}$alkyl, $C_{3-12}$carbocyclyl-$C_{1-10}$alkyl, $C_{1-10}$alkyl-$C_{1-12}$heterocyclyl-$C_{1-10}$alkyl-$C_{3-12}$carbocyclyl, $C_{1-10}$alkenyl, $C_{2-10}$ alkenyl, $C_{2-10}$ alkynyl, $C_{3-12}$carbocyclyl or $C_{1-12}$heterocyclyl, each of which being optionally substituted by one or more, same or different substituents represented by $R_7$, and the other is hydrogen, halogen, hydroxy, mercapto, trifluoromethyl, amino, $C_{1-4}$alkyl, $C_{2-4}$alkenyl, $C_{2-4}$alkynyl, $C_{1-4}$alkoxy, $C_{1-4}$ alkylthio, $C_{1-6}$alkylamino, $C_{1-4}$alkoxycarbonyl, cyano, —CONH$_2$ or nitro, with the proviso that when $R_5$ or $R_6$ is phenyl, $C_{1-5}$alkyl or $C_{2-3}$alkenyl, said $R_5$ or $R_6$ is substituted by one or more, same or different substituents represented by $R_7$ (except three fluorine when $R_5$ or $R_6$ is methyl) or by $Y_1R_8$, with the further proviso that when $R_5$ or $R_6$ is —COOH, $Y_1$ cannot be —NR$_a$—, —NR$_a$C(O)NR$_b$—, —NR$_a$C(O)— or —NR$_a$C(O)O—, and $R_3$ or $R_4$ cannot be nitro, with the further proviso that when $R_2$ is hydrogen, one of $R_5$ or $R_6$ is not hydrogen or optionally substituted ($C_3$-$C_{18}$ heterocyclyl, $C_{1-7}$alkyl, $C_{2-7}$alkenyl, $C_{2-7}$alkynyl or $C_{1-7}$alkoxy);

$Y_2$ is —O—, —S—, —S(O)—, —S(O)$_2$—, —NR$_a$—, —NR$_a$C(O)NR$_b$—, —NR$_a$C(O)—, —C(O)NR$_a$—, —C(O)NR$_a$O—, —C(O)—, —NR$_a$C(O)O—, —NR$_a$S(O)$_2$—, —OC(O)—, —C(O)O—, —C(O)NR$_a$NR$_b$C(S)NR$_c$—, —C(O)NR$_a$NR$_b$—, or —S(O)$_2$NR$_a$—;

$R_9$ is $C_{1-10}$alkyl-$C_{1-12}$heterocyclyl, $C_{1-10}$alkyl-$C_{3-12}$carbocyclyl, $C_{2-10}$alkenyl, $C_{2-10}$ alkynyl, $C_{3-12}$carbocyclyl, $C_{1-12}$heterocyclyl, $C_{3-12}$carbocyclyl-$C_{1-10}$alkyl, or $C_{1-12}$heterocyclyl-$C_{1-10}$alkyl, $C_{3-6}$carbocyclyl-$C_{1-6}$alkenyl, $C_{3-6}$carbocyclyl-$C_{2-6}$alkynyl, each being optionally substituted by one or more, same or different substituents represented by $R_7$, with the proviso that when $Y_2$ is —O—, —NR$_a$—, —S— or —C(O)O—, and $R_9$ is $C_{1-6}$alkyl, said $C_{1-6}$alkyl is substituted by one or more, same or different substituents represented by $R_7$ or by $Y_3R_{10}$;

$Y_3$ is —O—, —S—, —S(O)—, —S(O)$_2$—, —NR$_a$—, —NR$_a$C(O)NR$_b$—, —NR$_a$C(O)—, —C(O)NR$_a$—, —C(O)NR$_a$O—, —C(O)—, —NR$_a$C(O)O—, —NR$_a$S(O)$_2$—, —OC(O)— or —C(O)O—;

$R_{10}$ is $C_{1-10}$alkyl-$C_{1-12}$heterocyclyl, $C_{1-10}$alkyl-$C_{3-12}$carbocyclyl, $C_{1-10}$alkyl, $C_{2-10}$alkenyl, $C_{2-10}$ alkynyl, $C_{3-12}$carbocyclyl or $C_{1-12}$heterocyclyl, each being optionally substituted by one or more, same or different substituents represented by $R_7$;

or, when one of $R_5$ or $R_6$ is the group —C(O)NR$_a$R$_9$, $R_a$ and $R_9$ together with the nitrogen atom to which they are attached form a $C_{1-12}$heterocyclic ring optionally comprising one or more additional heteroatoms selected from the group consisting of O, S and N, optionally substituted with one or more substituents represented by $R_7$;

or a pharmaceutically acceptable salt, solvate, or ester thereof.

In another aspect, the invention relates to a pharmaceutical composition comprising a compound of formula I or a pharmaceutically acceptable salt, solvate, or ester thereof together with a pharmaceutically acceptable excipient or vehicle.

In a further aspect, the invention relates to a method of preventing, treating or ameliorating inflammatory diseases or conditions, or ophthalmic diseases or conditions, the method comprising administering to a patient in need thereof an effective amount of a compound of formula I.

In a further aspect, the invention relates to a method of treating or ameliorating cancer, the method comprising administering to a patient in need thereof an effective amount of a compound of formula I.

In a still further aspect, the invention relates to the use of a compound of formula I for the manufacture of a medicament for the prophylaxis, treatment or amelioration of inflammatory diseases or conditions, or ophthalmic diseases or conditions.

In a still further aspect, the invention relates to the use of a compound of formula I for the manufacture of a medicament for the treatment or amelioration of cancer.

In a still further aspect, the invention relates to a method for producing a compound of general structure I,

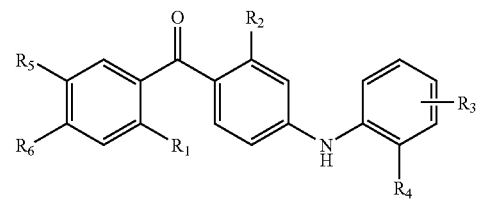

I wherein $R_1$, $R_2$, $R_3$, $R_4$, $R_5$, and $R_6$ are as defined above, comprising the steps of a) transforming a compound general structure VI,

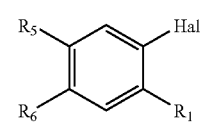

VI wherein Hal is a halogen, and $R_1$, $R_5$ and $R_6$ are as defined above, each of which are independently protected or unprotected, into an organometallic intermediate;

b) transmetalating said organometallic intermediate to an organozinc intermediate;

c) coupling said organozinc intermediate with an acid halide of general structure V,

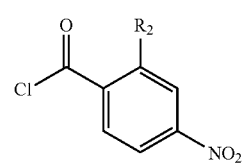

V wherein $R_2$ is as defined above 1, protected or unprotected, in the presence of a catalyst to give a compound of general structure IV,

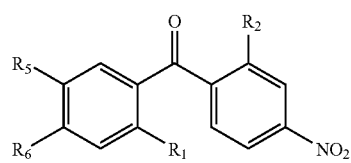

IV wherein $R_1$, $R_2$, $R_5$, and $R_6$ are defined as above, each of which are independently protected or unprotected;

d) optionally transforming, protecting or deprotecting one or more substituents or functional groups of $R_1$, $R_2$, $R_5$, and $R_6$ of the compound of general structure IV to give another compound of general structure IV;

e) reducing the compound of general structure IV from step c) or d) to an amine of general structure III,

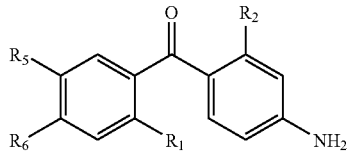

wherein $R_1$, $R_2$, $R_5$, and $R_6$ are defined as above, each of which are independently protected or unprotected;
f) optionally transforming, protecting or deprotecting one or more substituents or functional groups of $R_1$, $R_2$, $R_5$, and $R_6$ of the compound of general structure III to give another compound of general structure III;
g) coupling of the amine of general structure III from step e) or f) with a compound of general structure II,

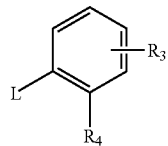

wherein L is triflate or halogen, $R_3$ and $R_4$ are as defined above, each of which are independently protected or unprotected, to give a compound of general structure I, wherein $R_1$, $R_2$, $R_3$, $R_4$, $R_5$, and $R_6$ are defined as above, each of which are independently protected or unprotected;
h) optionally transforming, protecting or deprotecting one or more substituents or functional groups of $R_1$, $R_2$, $R_3$, $R_4$, $R_5$, or $R_6$ of the compound of general structure I from step g) to give a another compound of general structure I.

In a still further aspect, the invention relates to a method for producing a compound of general structure I,

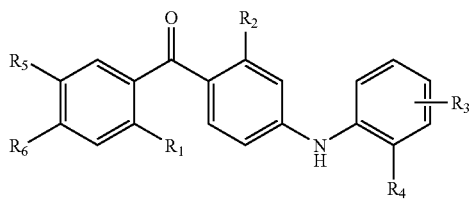

wherein $R_1$, $R_2$, $R_3$, $R_4$, $R_5$, and $R_6$ are as defined above, comprising the steps of
a) transforming a compound general structure VIIa,

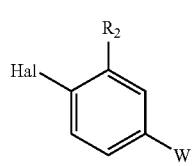

wherein Hal is halogen, W is halogen or triflate, and $R_2$ is as defined above, protected or unprotected, into an organometallic intermediate;
b) transmetalating said organometallic intermediate to an organozinc intermediate;
c) coupling said organozinc intermediate with an acid halide of general structure VIII,

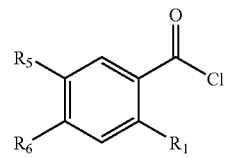

wherein $R_1$, $R_5$, and $R_6$ are as defined above, each of which are independently protected or unprotected, in the presence of a catalyst to give a compound of general structure IIa,

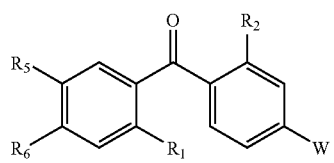

wherein W, $R_1$, $R_2$, $R_5$, $R_6$ are defined as above, each of which are independently protected or unprotected;
d) optionally transforming, protecting or deprotecting one or more substituents or functional groups of W, $R_1$, $R_2$, $R_5$, and $R_6$ of the compound of general structure IIIa to give another compound of general structure IIIa;
e) coupling of the compound of general structure IIIa from step c) or d) with an amine of general structure IIa,

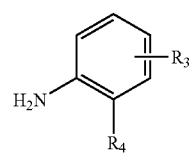

wherein $R_3$ and $R_4$ are as defined above, each of which are independently protected or unprotected, to give a compound of general structure I,
wherein $R_1$, $R_2$, $R_3$, $R_4$, $R_5$, and $R_6$ are as defined above, each of which are independently protected or unprotected;
f) optionally transforming, protecting or deprotecting one or more substituents or functional groups of $R_1$, $R_2$, $R_3$, $R_4$, $R_5$, or $R_6$ of the compound of general structure I from step e) to give another compound of general structure I.

DETAILED DESCRIPTION OF THE INVENTION

Definitions

In the present context, the term "alkyl" is intended to indicate a univalent radical derived from straight or branched alkane by removing a hydrogen atom from any carbon atom. The alkyl chain typically comprises 1-10 carbon atoms, in particular 1-6 carbon atoms. The term includes the subclasses normal alkyl (n-alkyl), secondary and tertiary alkyl, such as methyl, ethyl, n-propyl, isopropyl, n-butyl, isobutyl, sec.-butyl, tert.-butyl, pentyl, isopentyl, hexyl and isohexyl.

The term "alkoxy" is intended to indicate a radical of formula OR', wherein R' is alkyl as defined above, e.g. methoxy, ethoxy, propoxy, butoxy, etc.

The term "hydroxyalkyl" is intended to indicate an alkyl radical as defined above, wherein one or more hydrogen atoms are replaced by hydroxy.

The term "alkenyl" is intended to indicate a mono-, di-, tri-, tetra- or pentaunsaturated hydrocarbon radical typically comprising 2-10 carbon atoms, in particular 2-6 carbon atoms, e.g. ethenyl, propenyl, butenyl, pentenyl or hexenyl.

The term "alkynyl" is intended to indicate an hydrocarbon radical comprising 1-5 triple C—C bonds, the alkyne chain typically comprising 2-10 carbon atoms, in particular 2-6 carbon atoms, such as ethynyl, propynyl, butynyl, pentynyl or hexynyl.

The term "alkoxycarbonyl" is intended to indicate a radical of formula —COOR' wherein R' is alkyl as defined above, e.g. methoxycarbonyl, ethoxycarbonyl, n-propoxycarbonyl, isopropoxycarbonyl, etc.

The term "aryl" is intended to include radicals of carbocyclic aromatic rings, in particular 5- or 6-membered rings, optionally fused bicyclic rings, e.g. phenyl or naphthyl.

The term "heteroaryl" is intended to include radicals of heterocyclic aromatic rings, in particular 5- or 6-membered rings with 1-4 heteroatoms selected from O, S and N, or optionally fused bicyclic rings with 1-4 heteroatoms, e.g. pyridyl, tetrazolyl, thiazolyl, imidazolyl, pyrazolyl, oxazolyl, isoxazolyl, thienyl, pyrazinyl, isothiazolyl, benzimidazolyl, and benzofuranyl.

The term "carbocyclyl" includes saturated and unsaturated, optionally fused bicyclic, hydrocarbon rings typically comprising 3-12 carbon atoms, in particular 3-8 carbon atoms, such as cyclopropyl, cyclopentyl, cyclohexyl and cyclooctyl; or a $C_{3-12}$ cycloalkene group, such as cycloprop-2-enyl, cyclobut-2-enyl, cyclopent-2-enyl, cyclohex-3-enyl, cycloocta-4-enyl, cyclohex-3,5-dienyl, indanyl, indeneyl, 1,4-dihydronaphtyl, phenyl and naphtyl. The term "carbocyclyl" also includes cyclic hydrocarbons wherein one or more ring —$CH_2$— fragments have been replaced by a —C(O)— fragment and/or an exo-cyclic carbon-carbon double bond, such as oxocyclohexyl, oxocyclopentyl, 4-oxo-1,2,3,4-tetrahydronaphtalen-1-yl, 1-oxo-1,2,3,4-tetrahydronaphtalen-1-yl, 2-oxocyclohex-3-en-1-yl and 2-oxocyclohex-1-en-1-yl, and

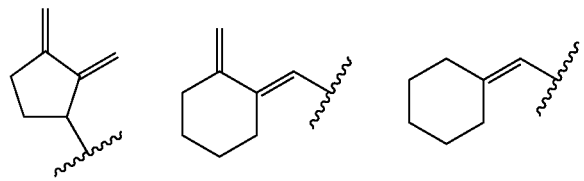

The term "heterocyclyl" is intended to indicate saturated or unsaturated, optionally fused carbocyclic rings comprising 1-12 carbon atoms, such as 1-12 carbon atoms, in particular 1-8 carbon atoms, and comprising one or more heteroatoms selected from the group consisting of O, N and S, such as tetrazolyl, triazolyl, pyrrolyl, furanyl, morpholyl, piperazyl, thiophenyl, imidazolyl, oxazolyl, thiazolyl, pyrazolyl, pyrrolidinyl, pyridinyl, pyrimidinyl, tetrahydrotiophenyl, tetrahydrofuranyl, tetrahydropyranyl, piperidinyl, putinyl, morpholinyl, furanyl, dioxolanyl, thiophenyl, quinolinyl, isoquinolinyl, 1,2-dihydroquinolinyl, etc. The term "heterocyclyl" thus includes "heteroaryl" as defined above and also includes heterocyclic groups wherein one or more ring —$CH_2$— fragments have been replaced by a —C(O)— fragment and/or an exo-cyclic carbon-carbon double bond, such as dioxopiperidinyl, dioxoimidazolidine, dioxohexahydropyrimidin, oxopyrrolidine, 1-oxo-3,4-dihydroisoquinolin-2(1H)-yl and

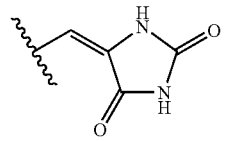

The term "alkylthio" is intended to indicate a radical of the formula —SR, where R is alkyl as defined above, for example $C_{1-10}$alkylthio, $C_{1-4}$alkylthio, methylthio, ethylthio, n-propylthio, 2-propylthio, etc.

The term "alkylamino" is intended to indicate a radical of the formula —NHR or —$NR_2$, wherein R is alkyl as defined above and includes, for example, methylamino, dimethylamino, di-(n-propyl)amino, n-butyl(ethyl)amino, etc.

The term "halogen" is intended to indicate fluoro, chloro, bromo or iodo.

The term "pharmaceutically acceptable salt" is intended to indicate salts prepared by reacting a compound of formula I with a suitable inorganic or organic acid, such as hydrochloric, hydrobromic, hydroiodic, sulfuric, nitric, phosphoric, formic, acetic, 2,2-dichloroacetic, adipic, ascorbic, L-aspartic, L-glutamic, galactaric, lactic, maleic, L-malic, phthalic, citric, propionic, benzoic, glutaric, gluconic, D-glucuronic, methanesulfonic, salicylic, succinic, malonic, tartaric, benzenesulfonic, ethane-1,2-disulfonic, 2-hydroxy ethanesulfonic acid, toluenesulfonic, sulfamic or fumaric acid. Pharmaceutically acceptable salts of compounds of formula I may also be prepared by reaction with a suitable base such as sodium hydroxide, potassium hydroxide, magnesium hydroxide, calcium hydroxide, ammonia, or suitable non-toxic amines, such as lower alkylamines, for example triethylamine, hydroxy-lower alkylamines, for example 2-hydroxyethylamine, bis-(2-hydroxyethyl)-amine, cycloalkylamines, for example dicyclohexylamine, or benzylamines, for example N,N'-dibenzylethylenediamine, and dibenzylamine, or L-arginine or L-lysine.

The term "solvate" is intended to indicate a species formed by interaction between a compound, e.g. a compound of formula I, and a solvent, e.g. alcohol, glycerol or water, wherein said species are in a solid form. When water is the solvent, said species is referred to as a hydrate.

The term "pharmaceutically acceptable ester" is intended to indicate easily hydrolysable esters such as alkanoyloxyalkyl, aralkanoyloxyalkyl, aroyloxyalkyl, e.g. acetoxymethyl, pivaloyloxymethyl, benzoyloxymethyl esters and the corresponding 1'-oxyethyl derivatives, or alkoxycarbonyloxyalkyl esters, e.g. methoxycarbonyloxymethyl esters and ethoxycarbonyloxymethyl esters and the corresponding 1'-oxyethyl derivatives, or iactonyl esters, e.g. phthalidyl esters, or dialkylaminoalkyl esters, e.g. dimethylaminoethyl esters. Easily hydrolysable esters include in vivo hydrolysable esters of the compounds of formula I. Such esters may be prepared by conventional methods known to persons skilled in the art, such as method disclosed in GB patent No. 1 490 852 incorporated herein by reference.

"p38 MAP kinase" is a stress-activated protein kinase existing in several isoforms (p38α, p38β, p38β2, p38γ and p38δ). The p38 MAP kinase is activated by different stimuli including heat, chemical, osmotic, pH and oxidative stress, growth factor withdrawal, high or low glucose and ultraviolet radiation. p38 is also stimulated by agents that mediate the initial physiological response to injury, infection and inflammation, such as LPS and pro-inflammatory cytokines IL-1β, TNF-α, FasL, CD40L and TGF-β. Like other MAP kinases, p38 is phosphorylated by kinases, including MKK3, MEK6 and MKK6, on a threonine and tyrosine in an activation loop (Thr-Xaa-Tyr) close to the ATP and substrate binding site. In turn, p38 phosphorylates and activates the serine-threonine protein kinases MAPKAP kinase-2, MAPKAP kinase-3, MAPKAP kinase-5, MNK-1 and MSK-1. It has been established that activation of p38 regulates cytokine biosynthesis in many cell types either directly by phosphorylating and activating transcription factors involved in the expression of cytokines or indirectly, e.g. by phosphorylating MSK-1 which, when activated, activates the transcription factor CREB. It has also been shown that certain pyridinyl imidazoles, e.g. SB203580, which inhibit p38, inhibit the production of IL-1β and TNF-α from LPS-treated human monocytes. It has therefore been concluded that p38 constitutes a potentially highly interesting target for the development of anti-inflammatory compounds (cf. J C Lee et al., *Immunopharmacology* 47, 2000, pp. 185-201 and references reviewed therein; P R Young, "Specific Inhibitors of p38 MAP kinase" in *Signaling Networks and Cell Cycle Control: The Molecular Basis of Cancer and Other Diseases*, J S Gutkind (Ed.), Humana Press, Inc., Totowa, N.J., and references reviewed therein).

There are several reports on p38 MAP kinase and inflammatory cytokines in relation to cell growth and apoptosis, such as tumor proliferation and metastasis. Though the exact mechanism of p38 MAP kinase mediated cell growth regulation is not known, it is believed that p38MAP kinase constitutes a potentially highly interesting target for the development of anti cancer drugs (S Nakada et al., Anticancer Research 21(1A), 2001, pp. 167-171 and references cited therein; C Denkert et al., Cancer Letters 195(1), 2003 p.p. 101-109 and references cited therein).

Compounds of formula I may comprise asymmetrically substituted (chiral) carbon atoms and carbon-carbon double bonds which may give rise to the existence of isomeric forms, e.g. enantiomers, diastereomers and geometric isomers. The present invention relates to all such isomers, either in pure form or as mixtures thereof. Pure stereoisomeric forms of the compounds and the intermediates of this invention may be obtained by the application of procedures known in the art. Diastereomers may be separated by physical separation methods such as selective crystallization and chromatographic techniques, e.g. liquid chromatography using chiral stationary phases. Enantiomers may be separated from each other by the selective crystallization of their diastereomeric salts with optically active acids. Alternatively, enantiomers may be separated by chromatographic techniques using chiral stationary phases. Said pure stereoisomeric forms may also be derived from the corresponding pure stereoisomeric forms of the appropriate starting materials, provided that the reaction occurs stereoselectively or stereospecifically. Preferably, if a specific stereoisomer is desired, said compound will be synthesized by stereoselective or stereospecific methods of preparation. These methods will advantageously employ chiral pure starting materials. Likewise, pure geometric isomers may be obtained from the corresponding pure geometric isomers of the appropriate starting materials. A mixture of geometric isomers will typically exhibit different physical properties, and they may thus be separated by standard chromatographic techniques well-known in the art.

Preferred Embodiments of the Compound of Formula I

In a currently preferred embodiment of the compounds of formula I, $R_1$ may be halogen, trifluoromethyl, $C_{1-4}$alkyl, $C_{1-4}$alkoxy or nitro. In particular, $R_1$ may be methyl, ethyl, methoxy, ethoxy, bromo, fluoro or chloro.

In a further preferred embodiment of the compounds of formula I, $R_2$ may be hydrogen, halogen, amino, $C_{1-4}$alkyl or $C_{1-4}$alkoxy. In particular, $R_2$ may be hydrogen, methyl, ethyl, methoxy, ethoxy, bromo, fluoro or chloro.

In a further preferred embodiment of the compounds of formula I, $R_3$ may be hydrogen, halogen, $C_{1-4}$alkyl or $C_{1-4}$alkoxy. In particular, $R_3$ may be methyl, ethyl, methoxy, ethoxy, bromo, fluoro or chloro.

In a further preferred embodiment of the compounds of formula I, $R_3$ represents one substituent. In particular, $R_3$ may be in the meta position with respect to $R_4$ and para with respect to —NH, or $R_3$ may be in the meta position with respect to $R_4$ and ortho with respect to —NH, or $R_3$ may be in the ortho position with respect to $R_4$ and meta with respect to —NH.

In a further preferred embodiment of the compounds of formula I, one of $R_3$ and $R_4$ may be fluorine.

In a further preferred embodiment of the compounds of formula I, $Y_1$ may be —O—, —$NR_a$—, —$NR_aC(O)N_b$—, —$NR_aC(O)$—, —$C(O)NR_a$—, —$NR_aC(O)O$— or $NR_aS(O)_2$.

In a further preferred embodiment of the compounds of formula I, $R_8$ may be $C_{1-4}$alkyl, $C_{2-4}$alkenyl, $C_{2-4}$alkynyl, $C_{3-6}$carbocyclyl or $C_{1-6}$heterocyclyl.

In a further preferred embodiment of the compounds of formula I, $R_4$ may be $C_{1-4}$alkyl, amino, halogen, nitro, —NHC(O)O—$C_{1-4}$alkyl, —NHC(O)$C_{1-4}$alkyl, —NHC(O)—$C_{1-4}$alkyl-COOH, —NHC(O)NH—$C_{1-4}$alkyl-OH, —CH=CH—$C_{1-4}$alkyl-$NH_2$, —NHC(O)NH—$C_{1-4}$alkyl, —NHC(O)NH—$C_{1-6}$cycloalkyl, NHC(O)$CF_3$ or —NHC(O)O—$C_{1-6}$cycloalkyl. In particular, $R_4$ may be methyl, ethyl, amino, bromo, fluoro, chloro, nitro, —NHC(O)O$CH_2CH_3$, —NHC(O)$CH_2CH_3$, —NHC(O)$CH_3$, —NHC(O)$CH_2CH_2COOH$, —NHC(O)NH$CH_2CH_2OH$, —CH=CH$CH_2NH_2$, —NHC(O)NH$CH_2CH_3$, —NHC(O)NH-cyclohexyl, NHC(O)$CF_3$ or —NHC(O)O-cyclopentyl.

In a further preferred embodiment of the compounds of formula I, $R_7$ may be halogen, hydroxy, amino, —S(O)$_2CH_3$, trifluoromethyl, cyano, $C_{1-4}$hydroxyalkyl, $C_{1-4}$alkoxy, $C_{1-4}$alkyl, $C_{1-4}$alkylthio, $C_{1-4}$alkylamino, $C_{1-4}$alkoxycarbonyl, —COOH, —$CONH_2$, —S(O)$_2NH_2$, azido, —CONR' or —CONRR', wherein R and R' are as defined above. In particular, $R_7$ may be methyl, ethyl, methoxy, ethoxy, hydroxy, methoxycarbonyl, ethoxycarbonyl, dimethylamino, ethylamino, amino, —COOH, fluoro, chloro, bromo, —$CONH_2$, —S(O)$_2NH_2$, azido, methylthio, —S(O)$_2CH_3$, trifluoromethyl, cyano or hydroxymethyl.

In a further preferred embodiment of the compounds of formula I, one of $R_5$ and $R_6$ may be $Y_2R_9$, $C_{1-4}$alkyl-$Y_2R_9$, $Y_2R_9Y_3R_{10}$, $C_{1-4}$alkyl-$Y_2R_9Y_3R_{10}$, $C_{2-4}$alkenyl-$Y_2R_9$, $C_{2-4}$alkenyl-$Y_2R_9Y_3R_{10}$, $Y_2R_9$—$C_{1-4}$-alkyl-$Y_3R_{10}$, $Y_2R_9$—$C_{2-4}$-alkenyl-$Y_3R_{10}$, $C_{1-6}$heterocyclyl-$C_{1-4}$-alkyl-$Y_2R_9$, $C_{1-4}$alkyl-$C_{1-6}$heterocyclyl, $C_{1-4}$alkyl-$C_{3-6}$carbocyclyl, $C_{3-6}$carbocyclyl-$C_{1-4}$alkyl, $C_{1-4}$alkyl substituted by $R_7$, $C_{2-4}$alkenyl, $C_{2-4}$ alkynyl, $C_{3-6}$carbocyclyl, $C_{1-6}$heterocyclyl, —COOH, —C(O)NHOH, or C(O)$NHNH_2$, and the other is hydrogen, halogen, $C_{1-4}$alkyl or $C_{1-4}$alkoxy. In particular, $R_5$ may be $Y_2R_9$, $C_{1-4}$alkyl-$Y_2R_9$, $Y_2R_9Y_3R_{10}$, $C_{1-4}$alkyl-$Y_2R_9Y_3R_{10}$, $C_{2-4}$alkenyl-$Y_2R_9$, $C_{2-4}$alkenyl-$Y_2R_9Y_3R_{10}$, $Y_2R_9$—$C_{1-4}$-alkyl-$Y_3R_{10}$, $Y_2R_9$—$C_{2-4}$-alkenyl-$Y_3R_{10}$, $C_{1-6}$heterocyclyl-$C_{1-4}$-alkyl-$Y_2R_9$, $C_{1-4}$alkyl-$C_{1-6}$heterocyclyl, $C_{1-4}$alkyl-$C_{3-6}$carbocyclyl, $C_{3-6}$carbocyclyl-$C_{1-4}$alkyl, $C_{1-4}$alkyl substituted by $R_7$, $C_{2-4}$alkenyl, $C_{2-4}$ alkynyl, $C_{3-6}$carbocyclyl, $C_{1-6}$heterocyclyl, —COOH, —C(O)NHOH, or C(O)$NHNH_2$, and $R_6$ is hydrogen, halogen, $C_{1-4}$alkyl or $C_{1-4}$alkoxy. In particular one of $R_5$ and $R_{6-12}$ $Y_2R_9$, $Y_2R_9Y_3R_{10}$, phenyl, methylphenyl, methyl, propenyl, phenyl-$Y_2R_9$, methyl-$Y_2R_9$, tetrazole, ethynyl, triazole, thiadiazole, dihydrooxazole, triazole-$Y_2R_9$, —COOH, —C(O)NHOH, or C(O)NHNH$_2$, and the other is hydrogen, fluoro, chloro, methyl or methoxy.

In a further preferred embodiment of the compounds of formula I, $R_5$ is hydrogen.

In a further preferred embodiment of the compounds of formula I, $R_6$ is hydrogen.

In another embodiment of the present invention, when $R_2$ is hydrogen and one of $R_5$ or $R_6$ is not hydrogen or optionally substituted ($C_3$-$C_{18}$ heterocyclyl, $C_{1-7}$alkyl, $C_{2-7}$alkenyl, $C_{2-7}$alkynyl or $C_{1-7}$alkoxy), said optionally substituted ($C_3$-$C_{18}$ heterocyclyl, $C_{1-7}$alkyl, $C_{2-7}$alkenyl, $C_{2-7}$alkynyl or $C_{1-7}$alkoxy) is $C_3$-$C_{18}$ heterocyclyl, $C_{1-7}$alkyl, $C_{2-7}$alkenyl, $C_{2-7}$alkynyl or $C_{1-7}$alkoxy independently substituted by one or more, halogen, hydroxy, cyano, $C_{1-7}$alkyl, $C_{1-7}$alkoxy, $C_3$-$C_{18}$ heterocyclyl or —NR$_x$R$_y$, where R$_x$ and R$_y$ are independently hydrogen or $C_{1-7}$alkyl, wherein the latter $C_{1-7}$alkyl, $C_{1-7}$alkoxy, $C_3$-$C_{18}$ heterocyclyl or —NR$_x$R$_y$ substituents may be further substituted by one or more substituents independently selected from halogen, hydroxy, cyano, $C_{1-7}$alkyl, $C_{1-7}$alkoxy, $C_3$-$C_{18}$ heterocyclyl or —NR$_x$R$_y$, where R$_x$ and R$_y$ are as defined above;

In a further preferred embodiment of the compounds of formula I, $Y_2$ may be —O—, —NR$_a$—, —NR$_a$C(O)NR$_b$—, —NR$_a$C(O)—, —C(O)NR$_a$, —C(O)NR$_a$O, —C(O)—, —NR$_a$C(O)O—, —NR$_a$S(O)$_2$—, —C(O)NR$_a$NR$_b$— or —S(O)$_2$NR$_a$—.

In a further preferred embodiment of the compounds of formula I, $Y_3$ may be —O—, —NR$_a$C(O)—, —C(O)NR$_a$—, —C(O)—, —C(O)O— or —NR$_a$C(O)O—.

In a further preferred embodiment of the compounds of formula I, $R_9$ may be $C_{1-4}$alkyl-$C_{1-6}$ heterocyclyl, $C_{1-4}$alkyl-$C_{3-6}$carbocyclyl, $C_{1-6}$alkyl, $C_{2-4}$alkenyl, $C_{2-4}$ alkynyl, $C_{3-10}$carbocyclyl, $C_{1-6}$heterocyclyl, $C_{3-6}$carbocyclyl-$C_{1-6}$alkyl, $C_{1-6}$heterocyclyl-$C_{1-6}$alkyl, $C_{3-6}$carbocyclyl-$C_{2-4}$alkenyl or $C_{3-6}$carbocyclyl-$C_{2-4}$alkynyl. In particular, $R_9$ may be $C_{1-4}$heterocyclyl, $C_{1-6}$alkyl, $C_{1-3}$alkyl-$C_{1-5}$heterocyclyl, $C_{6-10}$carbocyclyl, $C_{1-3}$alkyl-$C_6$carbocyclyl, $C_3$alkenyl, $C_6$carbocyclyl-$C_1$alkyl, $C_6$carbocyclyl-$C_3$alkenyl or $C_6$carbocyclyl-$C_2$alkynyl. More specifically, $R_9$ may be morpholinyl, propylmorpholinyl, piperazinyl, methyl, ethyl, n-propyl, n-butyl, tert-butyl, isobutyl, hexyl, isopropyl, dimethylpropyl, methyltetrahydrofuranyl, methylpyridinyl, ethylpiperazinyl, cyclohexyl, propyloxopyrrolidinyl, benzyl, methylcyclohexyl, propylphenyl, ethylphenyl, ethylmorpholinyl, allyl, ethylfuranyl, phenyl, methyldioxoimidazolidinyl, dioxohexahydropyrimidinyl, thiazolyl, methylphenyl, ethyl phenyl, methyldioxolanyl, methylthiazolyl, propenylphenyl, methylfuranyl, thiophenyl, tetrahydropyranyl or ethynylphenyl.

In a further preferred embodiment of the compounds of formula I, $R_{10}$ may be $C_{1-4}$alkyl, $C_{2-4}$alkenyl, $C_{3-6}$carbocyclyl or $C_{1-6}$heterocyclyl. In particular, $R_{10}$ may be methyl, ethyl, methacryl, tert-butyl, tetrahydropyranyl or ethenyl.

In a further preferred embodiment of the compounds of formula I, said heterocycle or heterocyclyl as above may contain one or two oxygen atoms or one sulphur atom, and/or up to two nitrogen atoms, or three or four nitrogen atoms, wherein optionally one or two CH$_2$ ring fragments is/are replaced by one or two —C(O)— fragments respectively.

In a further preferred embodiment of the compounds of formula I, Ra, Rb, or Rc independently represent hydrogen, methyl, ethyl, 2-hydroxyethyl or 2-methoxyethyl.

Specific examples of compounds of formula I may be selected from the group consisting of

[2-Chloro-4-(4-fluoro-2-methylphenylamino)phenyl]-[2-methyl-5-(morpholine-4-carbonyl)phenyl]-methanone (Compound 101),

[2-Chloro-4-(4-fluoro-2-methylphenylamino)phenyl]-[2-methyl-5-(4-methyl-piperazine-1-carbonyl)phenyl]-methanone (Compound 102), 3-[2-Chloro-4-(4-fluoro-2-methylphenylamino)benzoyl]-N-methoxy-4,N-dimethylbenzamide (Compound 103), 3-[2-Chloro-4-(4-fluoro-2-methylphenylamino)benzoyl]-4-methyl-N-(tetrahydrofuran-2-ylmethyl)benzamide (Compound 104), 3-[2-Chloro-4-(4-fluoro-2-methylphenylamino)benzoyl]-4, N-dimethyl-N-(tetrahydrofuran-2-ylmethyl)benzamide (Compound 105), 3-[2-Chloro-4-(4-fluoro-2-methyl-phenylamino)benzoyl]-N-(2-methoxyethyl)-4-methylbenzamide (Compound 106), 3-[2-Chloro-4-(4-fluoro-2-methylphenylamino)benzoyl]-4-methyl-N-(3-morpholin-4-yl-propyl)benzamide (Compound 107),

[2-Chloro-4-(4-fluoro-2-methylphenylamino)phenyl]-{5-[4-(2-methoxyethyppiperazine-1-carbonyl]-2-methylphenyl}-methanone (Compound 108), 3-[2-Chloro-4-(4-fluoro-2-methylphenylamino)benzoyl]-4-methyl-N-pyridin-4-ylmethylbenzamide (Compound 109), 3-[2-Chloro-4-(4-fluoro-2-methylphenylamino)benzoyl]-4-methyl-N-pyridin-2-ylmethylbenzamide (Compound 110), 3-[2-Chloro-4-(4-fluoro-2-methyl-phenylamino)-benzoyl]-4-methyl-N-pyridin-3-ylmethyl-benzamide (Compound 111), 3-[4-(2-Aminophenylamino)-2-chlorobenzoyl]-N-(2-hydroxyethyl)-4-methylbenzamide (Compound 112), 3-[4-(2-Amino-4-bromophenylamino)-2-chlorobenzoyl]-N-(2-hydroxyethyl)-4-methylbenzamide (Compound 113), 3-[4-(4-Bromo-2-methylphenylamino)-2-chlorobenzoyl]-N-(2-hydroxyethyl)-4-methylbenzamide (Compound 114), 3-[2-Chloro-4-(2,4-difluorophenylamino)benzoyl]-N-(2-hydroxyethyl)-4-methylbenzamide (Compound 115), 3-[4-(2-Aminophenylamino)-2-chlorobenzoyl]-N-(2-methoxyethyl)-4-methylbenzamide (Compound 116), 3-[4-(2-Aminophenylamino)-2-chlorobenzoyl]-N-ethyl-4-methylbenzamide (Compound 117), 3-[4-(2-Aminophenylamino)-2-chlorobenzoyl]-N-(3-hydroxypropyl)-4-methylbenzamide (Compound 118), 3-[2-Chloro-4-(4-fluoro-2-methylphenylamino)benzoyl]-N-(2-hydroxyethyl)-4-methylbenzamide (Compound 119), 3-[2-Chloro-4-(4-chloro-2-fluoro-phenylamino)-benzoyl]-N-(2-hydroxy-ethyl)-4-methyl-benzamide (Compound 120), 3-[2-Chloro-4-(4-chloro-2-fluoro-phenylamino)-benzoyl]-4,N-dimethyl-benzamide (Compound 121), (2-{3-[2-Chloro-4-(4-chloro-2-fluoro-phenylamino)-benzoyl]-4-methyl-benzoylamino}-acetylamino)-acetic acid ethyl ester (Compound 122), {3-[2-Chloro-4-(4-chloro-2-fluoro-phenylamino)-benzoyl]-4-methyl-benzoylamino}-acetic acid ethyl ester (Compound 123), 3-[2-Chloro-4-(4-chloro-2-fluoro-phenylamino)-benzoyl]-N-(2-methoxy-ethyl)-4-methyl-benzamide (Compound 124), 3-[2-Chloro-4-(4-chloro-2-fluoro-phenylamino)-benzoyl]-N-cyclohexyl-4-methyl-benzamide (Compound 125), 3-[2-Chloro-4-(4-chloro-2-fluoro-phenylamino)-benzoyl]-N-ethyl-4-methyl-benzamide (Compound 126),
3-[2-Chloro-4-(4-chloro-2-fluoro-phenylamino)-benzoyl]-N-(6-hydroxy-hexyl)-4-methyl-benzamide (Compound 127),
3-[2-Chloro-4-(4-chloro-2-fluoro-phenylamino)-benzoyl]-N-isopropyl-4-methyl-benzamide (Compound 128),
3-[2-Chloro-4-(4-chloro-2-fluoro-phenylamino)-benzoyl]-N-isobutyl-4-methyl-benzamide (Compound 129),
3-[2-Chloro-4-(4-chloro-2-fluoro-phenylamino)-benzoyl]-N-(2,2-dimethyl-propyl)-4-methyl-benzamide (Compound 130),
3-[2-Chloro-4-(4-chloro-2-fluoro-phenylamino)-benzoyl]-N-(3-methoxy-propyl)-4-methyl-benzamide (Compound 131),
3-[2-Chloro-4-(4-chloro-2-fluoro-phenylamino)-benzoyl]-4-methyl-N-[3-(2-oxo-pyrrolidin-1-yl)-propyl]-benzamide (Compound 132),
3-[2-Chloro-4-(4-chloro-2-fluoro-phenylamino)-benzoyl]-N-(2-dimethylamino-ethyl)-4-methyl-benzamide (Compound 133),
2-Methyl-acrylic acid 2-{3-[2-chloro-4-(4-chloro-2-fluoro-phenylamino)-benzoyl]-4-methyl-benzoylamino}-ethyl ester (Compound 134),
3-[2-Chloro-4-(4-chloro-2-fluoro-phenylamino)-benzoyl]-N-cis-(4-hydroxy-cyclohexyl)-4-methyl-benzamide (Compound 135),
3-[2-Chloro-4-(4-chloro-2-fluoro-phenylamino)-benzoyl]-N-trans-(4-hydroxy-cyclohexyl)-4-methyl-benzamide (Compound 136),
(2-{3-[2-Chloro-4-(4-chloro-2-fluoro-phenylamino)-benzoyl]-4-methyl-benzoylamino}-ethyl)-carbamic acid tert-butyl ester (Compound 137),
N-(2-Amino-ethyl)-3-[2-chloro-4-(4-chloro-2-fluoro-phenylamino)-benzoyl]-4-methyl-benzamide (Compound 138),
(2-{3-[2-Chloro-4-(4-chloro-2-fluoro-phenylamino)-benzoyl]-4-methyl-benzoylamino}-acetylamino)-acetic acid (Compound 139),
3-[2-Chloro-4-(2,4-difluoro-phenylamino)-benzoyl]-N-(2-hydroxy-ethyl)-4-methoxy-benzamide (compound 140),
3-[2-Chloro-4-(2,4-difluoro-phenylamino)-benzoyl]-N-(2,2-difluoro-ethyl)-4-methoxy-benzamide (compound 141),
3-[2-Chloro-4-(2,4-difluoro-phenylamino)-benzoyl]-N-(2-fluoro-ethyl)-4-methoxy-benzamide (compound 142),
3-[2-Chloro-4-(2,4-difluoro-phenylamino)-benzoyl]-N-(2,3-dihydroxy-propyl)-4-methoxy-benzamide (compound 143),
N-Carbamoylmethyl-3-[2-chloro-4-(2,4-difluoro-phenylamino)-benzoyl]-4-methoxy-benzamide (compound 144),
N-Carbamoylmethyl-3-[2-chloro-4-(2,4-difluoro-phenylamino)-benzoyl]-4-methyl-benzamide (Compound 145),
N-Benzyl-3-[2-chloro-4-(2,4-difluoro-phenylamino)-benzoyl]-4-methyl-benzamide (compound 146),
3-[2-Chloro-4-(2,4-difluoro-phenylamino)-benzoyl]-N-(2-fluoro-ethyl)-4-methyl-benzamide (compound 147),
3-[2-Chloro-4-(2,4-difluoro-phenylamino)-benzoyl]-4-methyl-N-(2,2,2-trifluoro-ethyl)-benzamide (compound 148),
3-[2-Chloro-4-(2,4-difluoro-phenylamino)-benzoyl]-N-ethyl-4-methyl-benzamide (compound 149),
3-[2-Chloro-4-(2,4-difluoro-phenylamino)-benzoyl]-N-cyclohexylmethyl-4-methyl-benzamide (compound 150),
3-[2-Chloro-4-(2,4-difluoro-phenylamino)-benzoyl]-N-(2-hydroxy-propyl)-4-methyl-benzamide (compound 151),
3-[2-Chloro-4-(2,4-difluoro-phenylamino)-benzoyl]-N-(2,3-dihydroxy-propyl)-4-methyl-benzamide (compound 152),
3-[2-Chloro-4-(2,4-difluoro-phenylamino)-benzoyl]-N-(1-hydroxymethyl-propyl)-4-methyl-benzamide (compound 153),
3-[2-Chloro-4-(2,4-difluoro-phenylamino)-benzoyl]-4-methyl-N-(2,2,3,3,3-pentafluoro-propyl)-benzamide (compound 154),
3-[2-Chloro-4-(2,4-difluoro-phenylamino)-benzoyl]-N-(3-hydroxy-propyl)-4-methyl-benzamide (compound 155),
3-[2-Chloro-4-(2,4-difluoro-phenylamino)-benzoyl]-N-(2-hydroxy-1,1-dimethyl-ethyl)-4-methyl-benzamide (compound 156),
3-[2-Chloro-4-(2,4-difluoro-phenylamino)-benzoyl]-N-(2-hydroxy-1-hydroxymethyl-1-methyl-ethyl)-4-methyl-benzamide (compound 157),
{3-[2-Chloro-4-(2,4-difluoro-phenylamino)-benzoyl]-4-methyl-benzoylamino}-acetic acid ethyl ester (compound 158),
3-[2-Chloro-4-(2,4-difluoro-phenylamino)-benzoyl]-N-(4-hydroxy-butyl)-4-methyl-benzamide (compound 159),
3-[2-Chloro-4-(2,4-difluoro-phenylamino)-benzoyl]-N-(3-hydroxy-1,1-dimethyl-butyl)-4-methyl-benzamide (compound 160),
3-[2-Chloro-4-(2,4-difluoro-phenylamino)-benzoyl]-4-methyl-N-(3-phenyl-propyl)-benzamide (compound 161),
(R)-3-[2-Chloro-4-(2,4-difluoro-phenylamino)-benzoyl]-N-(1-hydroxymethyl-3-methyl-butyl)-4-methyl-benzamide (compound 162),
3-[4-(2,4-Difluoro-phenylamino)-benzoyl]-N-(2-fluoro-ethyl)-4-methyl-benzamide (compound 163),
3-[2-Chloro-4-(2,4-difluoro-phenylamino)-benzoyl]-N-isopropyl-4-methyl-benzamide (compound 164),
3-[2-Chloro-4-(2,4-difluoro-phenylamino)-benzoyl]-N-cyclohexyl-4-methyl-benzamide (compound 165),
3-[2-Chloro-4-(2,4-difluoro-phenylamino)-benzoyl]-N-(2,2-difluoro-ethyl)-4-methyl-benzamide (compound 166),
5-{3-[2-Chloro-4-(2,4-difluoro-phenylamino)-benzoyl]-4-methyl-benzoylamino}-4-oxo-pentanoic acid methyl ester (compound 167),
N-[(2-Carbamoyl-ethylcarbamoyl)-methyl]-3-[2-chloro-4-(2,4-difluoro-phenylamino)-benzoyl]-4-methyl-benzamide (compound 168),
(2-{3-[2-Chloro-4-(2,4-difluoro-phenylamino)-benzoyl]-4-methyl-benzoylamino}-acetylamino)-acetic acid ethyl ester (compound 169),
N-Allyl-3-[2-chloro-4-(2,4-difluoro-phenylamino)-benzoyl]-4-methyl-benzamide (compound 170),
3-[2-Chloro-4-(2,4-difluoro-phenylamino)-benzoyl]-4-methyl-N-(2-sulfamoyl-ethyl)-benzamide (compound 171),
N-(2-Acetylamino-ethyl)-3-[2-chloro-4-(2,4-difluoro-phenylamino)-benzoyl]-4-methyl-benzamide (compound 172),
3-[2-Chloro-4-(2,6-difluoro-phenylamino)-benzoyl]-N-(2-hydroxy-ethyl)-4-methoxy-benzamide (compound 173),
3-[2-Chloro-4-(2,6-difluoro-phenylamino)-benzoyl]-N-(2-fluoro-ethyl)-4-methoxy-benzamide (compound 174),
3-[2-Chloro-4-(2,6-difluoro-phenylamino)-benzoyl]-N-(2,3-dihydroxy-propyl)-4-methoxy-benzamide (compound 175),
3-[2-Chloro-4-(2,6-difluoro-phenylamino)-benzoyl]-N-(3-hydroxy-propyl)-4-methoxy-benzamide (compound 176),
3-[2-Chloro-4-(2,6-difluoro-phenylamino)-benzoyl]-4-methoxy-N-phenethyl-benzamide (compound 177), 3-[2-Chloro-4-(2,6-difluoro-phenylamino)-benzoyl]-N-(2-hydroxy-1,1-dimethyl-ethyl)-4-methoxy-benzamide (compound 178),
3-[2-Chloro-4-(2,6-difluoro-phenylamino)-benzoyl]-4-methoxy-N-(2-morpholin-4-yl-ethyl)-benzamide (compound 179),
3-[2-Chloro-4-(2,6-difluoro-phenylamino)-benzoyl]-N-(2-hydroxy-1-hydroxymethyl-1-methyl-ethyl)-4-methoxy-benzamide (compound 180),
3-[2-Chloro-4-(2,6-difluoro-phenylamino)-benzoyl]-N-(2-hydroxy-ethyl)-4-methoxy-N-methyl-benzamide (compound 181),
{3-[(2-Chloro-4-(2,6-difluoro-phenylamino)-benzoyl]-4-methoxy-benzoylamino}-acetic acid ethyl ester (compound 182),
(2-{3-[2-Chloro-4-(2,6-difluoro-phenylamino)-benzoyl]-4-methoxy-benzoylamino}-acetylamino)-acetic acid ethyl ester (compound 183),
3-[2-Chloro-4-(2,6-difluoro-phenylamino)-benzoyl]-N,N-bis-(2-hydroxy-ethyl)-4-methoxy-benzamide (compound 184),
3-[2-Chloro-4-(2,6-difluoro-phenylamino)-benzoyl]-4-methoxy-N,N-bis-(2-methoxy-ethyl)-benzamide (compound 185),
3-[2-Chloro-4-(3-fluoro-2-methyl-phenylamino)-benzoyl]-N-(2-hydroxy-ethyl)-4-methyl-benzamide (compound 186),
3-[2-Chloro-4-(3-fluoro-2-methyl-phenylamino)-benzoyl]-4-methyl-N-(2,2,2-trifluoro-ethyl)-benzamide (compound 187),
3-[2-Chloro-4-(2-chloro-4-fluoro-phenylamino)-benzoyl]-N-(2-hydroxy-ethyl)-4-methyl-benzamide (compound 188),
3-[2-Chloro-4-(2-chloro-4-fluoro-phenylamino)-benzoyl]-4-methyl-N-(2,2,2-trifluoro-ethyl)-benzamide (compound 189),
3-[2-Chloro-4-(4-fluoro-phenylamino)-benzoyl]-N-(2-hydroxy-ethyl)-4-methyl-benzamide (compound 190),
3-(2-Chloro-4-phenylamino-benzoyl)-N-(2-hydroxy-ethyl)-4-methyl-benzamide (compound 191),
3-[2-Chloro-4-(3,5-difluoro-phenylamino)-benzoyl]-N-(2-hydroxy-ethyl)-4-methyl-benzamide (compound 192),
3-[2-Chloro-4-(3-fluoro-phenylamino)-benzoyl]-N-(2-hydroxy-ethyl)-4-methyl-benzamide (compound 193),
3-[2-Chloro-4-(4-fluoro-phenylamino)-benzoyl]-N-(2-hydroxy-ethyl)-4-methoxy-benzamide (compound 194),
3-(2-Chloro-4-phenylamino-benzoyl)-N-(2-hydroxy-ethyl)-4-methoxy-benzamide (compound 195),
3-[2-Chloro-4-(4-fluoro-phenylamino)-benzoyl]-N-(2,2-difluoro-ethyl)-4-methoxy-benzamide (compound 196),
3-[2-Chloro-4-(4-fluoro-phenylamino)-benzoyl]-N-(2-fluoro-ethyl)-4-methoxy-benzamide (compound 197),
3-[2-Chloro-4-(4-fluoro-phenylamino)-benzoyl]-N-(2,3-dihydroxy-propyl)-4-methoxy-benzamide (compound 198),
N-Carbamoylmethyl-3-[2-chloro-4-(4-fluoro-phenylamino)-benzoyl]-4-methoxy-benzamide (compound 199),
3-(2-Chloro-4-phenylamino-benzoyl)-N-(2,2-difluoro-ethyl)-4-methoxy-benzamide (compound 200),
3-(2-Chloro-4-phenylamino-benzoyl)-N-(2-fluoro-ethyl)-4-methoxy-benzamide (compound 201),
3-(2-Chloro-4-phenylamino-benzoyl)-N-(2,3-dihydroxy-propyl)-4-methoxy-benzamide (compound 202),
N-Carbamoylmethyl-3-(2-chloro-4-phenylamino-benzoyl)-4-methoxy-benzamide (compound 203),
4-Chloro-3-[2-chloro-4-(2,4-difluoro-phenylamino)-benzoyl]-N-(2-hydroxy-ethyl)-benzamide (compound 204),
(2-{3-Chloro-4-[5-(2-hydroxy-ethylcarbamoyl)-2-methyl-benzoyl]-phenylamino}-phenyl)-carbamic acid ethyl ester (compound 205),
3-[2-Chloro-4-(2-propionylamino-phenylamino)-benzoyl]-N-(2-hydroxy-ethyl)-4-methyl-benzamide (compound 206),
3-[4-(2-Acetylamino-phenylamino)-2-chloro-benzoyl]-N-(2-hydroxy-ethyl)-4-methyl-benzamide (compound 207),
N-(2-{3-Chloro-4-[5-(2-hydroxy-ethylcarbamoyl)-2-methyl-benzoyl]-phenylamino}-phenyl)-succinamic acid (compound 208),
3-(2-Chloro-4-{2-[3-(2-hydroxy-ethyl)-ureido]-phenylamino}-benzoyl)-N-(2-hydroxy-ethyl)-4-methyl-benzamide (compound 209),
[2-Chloro-4-(4-fluoro-2-methyl-phenylamino)-phenyl]-[2-methyl-4-(morpholine-4-carbonyl)-phenyl]-methanone (compound 210),
[4-(2-Amino-phenylamino)-2-chloro-phenyl]-{2-methyl-4-(2-(tetrahydro-pyran-2-yloxy)-ethoxy]-phenyl}-methanone (compound 211),
[4-(2-Amino-phenylamino)-2-chloro-phenyl]-[4-(2-hydroxy-ethoxy)-2-methyl-phenyl]-methanone (compound 212),
[4-(2-Amino-4-bromo-phenylamino)-2-chloro-phenyl]-{2-methyl-4-[2-(tetrahydro-pyran-2-yloxy)-ethoxy]-pheny (compound 213),
[4-(2-Amino-4-bromo-phenylamino)-2-chloro-phenyl]-[4-(2-hydroxy-ethoxy)-2-methyl-phenyl]-methanone (compound 214),
[4-(2-Amino-4-bromo-phenylamino)-2-chloro-phenyl]-{2-methyl-4-[3-(tetrahydro-pyran-2-yloxy)-propoxy]-phenyl}-methanone (compound 215),
[4-(2-Amino-4-bromo-phenylamino)-2-chloro-phenyl]-[4-(3-hydroxy-propoxy)-2-methyl-phenyl]-methanone (compound 216),
[4-(2-Amino-4-bromo-phenylamino)-2-chloro-phenyl]-[4-(2-fluoro-ethoxy)-2-methyl-phenyl]-methanone (compound 217),
[4-(4-Bromo-2-methyl-phenylamino)-2-chloro-phenyl]-[4-(2-fluoro-ethoxy)-2-methyl-phenyl]-methanone (compound 218),
[4-(2-Amino-4-bromo-phenylamino)-2-chloro-phenyl]-[4-(2-methoxy-ethoxy)-2-methyl-phenyl]-methanone (compound 219),
[4-(4-Bromo-2-methyl-phenylamino)-2-chloro-phenyl]-{2-methyl-4-[2-(tetrahydro-pyran-2-yloxy)-ethoxy]-phenyl}-methanone (compound 220),
[4-(4-Bromo-2-methyl-phenylamino)-2-chloro-phenyl]-[4-(2-hydroxy-ethoxy)-2-methyl-phenyl]-methanone (compound 221),
[4-(2-Azido-ethoxy)-2-methyl-phenyl]-[4-(4-bromo-2-methyl-phenylamino)-2-chloro-phenyl]-methanone (compound 222),
[4-(2-Amino-ethoxy)-2-methyl-phenyl]-[4-(4-bromo-2-methyl-phenylamino)-2-chloro-phenyl]-methanone (compound 223),
[4-(2-Bromo-phenylamino)-2-chloro-phenyl]-{2-methyl-4-[2-(tetrahydro-pyran-2-yloxy)-ethoxy]-phenyl}-methanone (compound 224),
{4-[2-(3-Amino-propenyl)-phenylamino]-2-chloro-phenyl}-{2-methyl-4-[(2-(tetrahydro-pyran-2-yloxy)-ethoxy]-phenyl}-methanone (compound 225),
{4-[2-(3-Amino-propenyl)-phenylamino]-2-chloro-phenyl}-[4-(2-hydroxy-ethoxy)-2-methyl-phenyl]-methanone (compound 226), 1-(2-{3-Chloro-4-[4-(2-hydroxy-ethoxy)-2-methyl-benzoyl]-phenylamino}-phenyl)-3-ethyl-urea (compound 227),
1-[(5-Bromo-2-(3-chloro-4-{2-methyl-4-[2-(tetrahydro-pyran-2-yloxy)-ethoxy]-benzoyl}-phenylamino)-phenyl]-3-ethyl-urea (compound 228),
1-(5-Bromo-2-{3-chloro-4-[4-(2-hydroxy-ethoxy)-2-methyl-benzoyl]-phenylamino}-phenyl)-3-ethyl-urea (compound 229),
1-[5-Bromo-2-(3-chloro-4-{2-methyl-4-[2-(tetrahydro-pyran-2-yloxy)-ethoxy]-benzoyl}-phenylamino)-phenyl]-3-cyclohexyl-urea (compound 230),
1-[5-Bromo-2-(3-chloro-4-{2-methyl-4-[2-(tetrahydro-pyran-2-yloxy)-ethoxy]-benzoyl}-phenylamino)-phenyl]-3-(2-hydroxy-ethyl)-urea (compound 231),
1-(5-Bromo-2-{3-chloro-4-[4-(2-hydroxy-ethoxy)-2-methyl-benzoyl]-phenylamino}-phenyl)-3-(2-hydroxy-ethyl)-urea (compound 232),
N-[5-Bromo-2-(3-chloro-4-{2-methyl-4-[2-(tetrahydro-pyran-2-yloxy)-ethoxy]-benzoyl}-phenylamino)-phenyl]-succinamic acid (compound 233),
(4-Allyloxy-2-methyl-phenyl)-[4-(2-amino-4-bromo-phenylamino)-2-chloro-phenyl]-methanone (compound 234),
N-{2-[4-(4-Allyloxy-2-methyl-benzoyl)-3-chloro-phenylamino]-5-bromo-phenyl}-acetamide (compound 235),
1-{2-[4-(4-Allyloxy-2-methyl-benzoyl)-3-chloro-phenylamino]-5-bromo-phenyl}-3-ethyl-urea (compound 236),
{2-[4-(4-Allyloxy-2-methyl-benzoyl)-3-chloro-phenylamino]-5-bromo-phenyl}-carbamic acid ethyl ester (compound 237),
N-{2-[4-(4-Allyloxy-2-methyl-benzoyl)-3-chloro-phenylamino]-5-bromo-phenyl}-2,2,2-trifluoro-acetamide (compound 238),
N-{2-[4-(4-Allyloxy-2-methyl-benzoyl)-3-chloro-phenylamino]-5-bromo-phenyl}-succinamic acid (compound 239),
{2-[4-(4-Allyloxy-2-methyl-benzoyl)-3-chloro-phenylamino]-5-bromo-phenyl}-carbamic acid cyclopentyl ester (compound 240),
N-{3-[2-Chloro-4-(2,4-difluoro-phenylamino)-benzoyl]-4-methyl-phenyl}-3-methoxy-propionamide (compound 241),
N-{3-[2-Chloro-4-(2,4-difluoro-phenylamino)-benzoyl]-4-methyl-phenyl}-propionamide (compound 242),
N-{3-[2-Chloro-4-(2,4-difluoro-phenylamino)-benzoyl]-4-methyl-phenyl}-2-(2-methoxy-ethoxy)-acetamide (compound 243),
N-{3-[2-Chloro-4-(2,4-difluoro-phenylamino)-benzoyl]-4-methyl-phenyl}-3-morpholin-4-yl-propionamide (compound 244),
N-{3-[2-Chloro-4-(2,4-difluoro-phenylamino)-benzoyl]-4-methyl-phenyl}-3-hydroxy-propionamide (compound 245),
N-{3-[2-Chloro-4-(2,4-difluoro-phenylamino)-benzoyl]-4-methyl-phenyl}-3-furan-2-yl-propionamide (compound 246),
N-{3-[2-Chloro-4-(2,4-difluoro-phenylamino)-benzoyl]-4-methyl-phenyl}-2-hydroxy-benzamide (compound 247),
N-{3-[2-Chloro-4-(2,4-difluoro-phenylamino)-benzoyl]-4-methyl-phenyl}-2-(2,5-dioxo-imidazolidin-4-yl)-acetamide (compound 248),
2,6-Dioxo-hexahydro-pyrimidine-4-carboxylic acid {3-[2-chloro-4-(2,4-difluoro-phenylamino)-benzoyl]-4-methyl-phenyl}-amide (compound 249),
Acrylic acid 2-{3-[2-chloro-4-(2,4-difluoro-phenylamino)-benzoyl]-4-methyl-phenylcarbamoyl}-ethyl ester (compound 250),
N-{3-[2-Chloro-4-(2,4-difluoro-phenylamino)-benzoyl]-4-methyl-phenyl}-3-methylsulfanyl-propionamide (compound 251),
N-{3-[2-Chloro-4-(2,4-difluoro-phenylamino)-benzoyl]-4-methyl-phenyl}-3-methanesulfonyl-propionamide (compound 252),
Ethanesulfonic acid {3-[2-chloro-4-(2,4-difluoro-phenylamino)-benzoyl]-4-methyl-phenyl}-amide (compound 253),
N-{3-[2-Chloro-4-(2,4-difluoro-phenylamino)-benzoyl]-4-methyl-phenyl}-4-methoxy-benzenesulfonamide (compound 254),
N-(5-{3-[2-Chloro-4-(2,4-difluoro-phenylamino)-benzoyl]-4-methyl-phenylsulfamoyl}-4-methyl-thiazol-2-yl)-acetamide (compound 255),
5-Acetyl-2-chloro-N-{3-[2-chloro-4-(2,4-difluoro-phenylamino)-benzoyl]-4-methyl-phenyl}-benzenesulfonamide (compound 256),
Naphthalene-2-sulfonic acid {3-[2-chloro-4-(2,4-difluoro-phenylamino)-benzoyl]-4-methyl-phenyl}-amide (compound 257),
N-{3-[2-Chloro-4-(2,4-difluoro-phenylamino)-benzoyl]-4-methyl-phenyl}-C-phenyl-methanesulfonamide (compound 258),
2-Methyl-acrylic acid 2-(3-{3-[2-chloro-4-(2,4-difluoro-phenylamino)-benzoyl]-4-methyl-phenyl}-ureido)-ethyl ester (compound 259),
1-{3-[2-Chloro-4-(2,4-difluoro-phenylamino)-benzoyl]-4-methyl-phenyl}-3-(2-hydroxy-ethyl)-urea (compound 260),
(3-{3-[2-Chloro-4-(2,4-difluoro-phenylamino)-benzoyl]-4-methyl-phenyl}-ureido)-acetic acid ethyl ester (compound 261),
1-{3-[2-Chloro-4-(2,4-difluoro-phenylamino)-benzoyl]-4-methyl-phenyl}-3-(3-methoxy-phenyl)-urea (compound 262),
1-{3-[2-Chloro-4-(2,4-difluoro-phenylamino)-benzoyl]-4-methyl-phenyl}-3-(3-trifluoromethyl-phenyl)-urea (compound 263),
1-{3-[2-Chloro-4-(2,4-difluoro-phenylamino)-benzoyl]-4-methyl-phenyl}-3-propyl-urea (compound 264),
3-(3-{3-[2-Chloro-4-(2,4-difluoro-phenylamino)-benzoyl]-4-methyl-phenyl}-ureido)-propionic acid ethyl ester (compound 265),
1-{3-[2-Chloro-4-(2,4-difluoro-phenylamino)-benzoyl]-4-methyl-phenyl}-3-cyclohexyl-urea (compound 266),
1-Allyl-3-{3-[2-chloro-4-(2,4-difluoro-phenylamino)-benzoyl]-4-methyl-phenyl}-urea (compound 267),
1-Benzyl-3-{3-[2-chloro-4-(2,4-difluoro-phenylamino)-benzoyl]-4-methyl-phenyl}-urea (compound 268),
1-{3-[2-Chloro-4-(2,4-difluoro-phenylamino)-benzoyl]-4-methyl-phenyl}-3-ethyl-urea (compound 269),
1-{3-[2-Chloro-4-(2,4-difluoro-phenylamino)-benzoyl]-4-methyl-phenyl}-3-phenyl-urea (compound 270),
1-Butyl-3-{3-[2-chloro-4-(2,4-difluoro-phenylamino)-benzoyl]-4-methyl-phenyl}-urea (compound 271),
1-{3-[2-Chloro-4-(2,4-difluoro-phenylamino)-benzoyl]-4-methyl-phenyl}-3-phenethyl-urea (compound 272),
2-(3-{3-[2-Chloro-4-(2,4-difluoro-phenylamino)-benzoyl]-4-methyl-phenyl}-ureido)-benzoic acid methyl ester (compound 273),
1-{3-[2-Chloro-4-(2,4-difluoro-phenylamino)-benzoyl]-4-methyl-phenyl}-3-(3-cyano-phenyl)-urea (compound 274),
1-{3-[2-Chloro-4-(2,4-difluoro-phenylamino)-benzoyl]-4-methyl-phenyl}-3-isopropyl-urea (compound 275), 1-{3-[2-Chloro-4-(2,4-difluoro-phenylamino)-benzoyl]-4-methyl-phenyl}-3-(4-methoxy-phenyl)-urea (compound 276),
{3-[2-Chloro-4-(2,4-difluoro-phenylamino)-benzoyl]-4-methyl-phenyl}-carbamic acid benzyl ester (compound 277),
{3-[2-Chloro-4-(2,4-difluoro-phenylamino)-benzoyl]-4-methyl-phenyl}-carbamic acid allyl ester (compound 278),
{3-[2-Chloro-4-(2,4-difluoro-phenylamino)-benzoyl]-4-methyl-phenyl}-carbamic acid ethyl ester (compound 279),
[2-Chloro-4-(2,4-difluoro-phenylamino)-phenyl]-[5-(3-hydroxy-butylamino)-2-methyl-phenyl]-methanone (compound 281),
[2-Chloro-4-(2,4-difluoro-phenylamino)-phenyl]-(3'-hydroxymethyl-4-methyl-biphenyl-3-yl)-methanone (compound 282),
[2-Chloro-4-(2,4-difluoro-phenylamino)-phenyl]-(3'-hydroxy-4-methyl-biphenyl-3-yl)-methanone (compound 283),
[2-Chloro-4-(2,4-difluoro-phenylamino)-phenyl]-(4'-methoxy-4-methyl-biphenyl-3-yl)-methanone (compound 284),
N-{3'-[2-Chloro-4-(2,4-difluoro-phenylamino)-benzoyl]-4'-methyl-biphenyl-3-yl}-acetamide (compound 285),
[2-Chloro-4-(2,4-difluoro-phenylamino)-phenyl]-(4-methyl-3'-trifluoromethoxy-biphenyl-3-yl)-methanone (compound 286),
[2-Chloro-4-(2,4-difluoro-phenylamino)-phenyl]-(3',4',5'-trifluoro-4-methyl-biphenyl-3-yl)-methanone (compound 288),
[2-Chloro-4-(2,4-difluoro-phenylamino)-phenyl]-(3',4'-dimethoxy-4-methyl-biphenyl-3-yl)-methanone (289),
3'-[2-Chloro-4-(2,4-difluoro-phenylamino)-benzoyl]-4'-methyl-biphenyl-3-carbonitrile (compound 290),
3-[2-Chloro-4-(2,4-difluoro-phenylamino)-benzoyl]-N-(2-hydroxy-ethyl)-4-methyl-benzenesulfonamide (compound 291),
3-[2-Chloro-4-(2,4-difluoro-phenylamino)-benzoyl]-4-methyl-N-(2-morpholin-4-yl-ethyl)-benzenesulfonamide (compound 292),
N-Allyl-3-[2-chloro-4-(2,4-difluoro-phenylamino)-benzoyl]-4-methyl-benzenesulfonamide (compound 293),
N-(2-{3-[2-Chloro-4-(2,4-difluoro-phenylamino)-benzoyl]-4-methyl-benzenesulfonylamino}-ethyl)-acetamide (compound 294),
3-[2-Chloro-4-(2,4-difluoro-phenylamino)-benzoyl]-4-methyl-N-propyl-benzenesulfonamide (compound 295),
3-[2-Chloro-4-(2,4-difluoro-phenylamino)-benzoyl]-N-(2,3-dihydroxy-propyl)-4-methyl-benzenesulfonamide (compound 296),
3-[2-Chloro-4-(2,4-difluoro-phenylamino)-benzoyl]-N-(2-methoxy-ethyl)-4-methyl-benzenesulfonamide (compound 297),
[4-(4-Fluoro-2-methyl-phenylamino)-2-nitro-phenyl]-[5-(4-methoxy-benzyloxy)-2-methyl-phenyl]-methanone (compound 298),
[4-(4-Fluoro-2-methyl-phenylamino)-2-nitro-phenyl]-[5-(3-hydroxy-propoxy)-2-methyl-phenyl]-methanone (compound 299),
[2-Amino-4-(4-fluoro-2-methyl-phenylamino)-phenyl]-[5-(3-hydroxy-propoxy)-2-methyl-phenyl]-methanone (compound 300),
[5-(2,2-Dimethyl-[1,3]dioxolan-4-ylmethoxy)-2-methyl-phenyl]-[4-(4-fluoro-2-methyl-phenylamino)-2-nitro-phenyl]-methanone (compound 301),
[5-(2,3-Dihydroxy-propoxy)-2-methyl-phenyl]-[4-(4-fluoro-2-methyl-phenylamino)-2-nitro-phenyl]-methanone (compound 302),
[2-Amino-4-(4-fluoro-2-methyl-phenylamino)-phenyl]-[5-(2,3-dihydroxy-propoxy)-2-methyl-phenyl]-methanone (303),
[4-(4-Fluoro-2-methyl-phenylamino)-2-nitro-phenyl]-[2-methyl-5-(2-morpholin-4-yl-ethoxy)-phenyl]-methanone (304),
[2-Amino-4-(4-fluoro-2-methyl-phenylamino)-phenyl]-[2-methyl-5-(2-morpholin-4-yl-ethoxy)-phenyl]-methanone (compound 305),
[4-(2,4-Difluoro-phenylamino)-2-nitro-phenyl]-[5-(4-methoxy-benzyloxy)-2-methyl-phenyl]-methanone (Compound 306),
[4-(2,4-Difluoro-phenylamino)-2-nitro-phenyl]-[5-(3-hydroxy-propoxy)-2-methyl-phenyl]-methanone (Compound 307),
[2-Amino-4-(2,4-difluoro-phenylamino)-phenyl]-[5-(3-hydroxy-propoxy)-2-methyl-phenyl]-methanone (compound 308),
[4-(2,4-Difluoro-phenylamino)-2-nitro-phenyl]-[2-methyl-5-(2-morpholin-4-yl-ethoxy)-phenyl]-methanone (compound 309),
[2-Amino-4-(2,4-difluoro-phenylamino)-phenyl]-[2-methyl-5-(2-morpholin-4-yl-ethoxy)-phenyl]-methanone (compound 310),
[4-(2,4-Difluoro-phenylamino)-2-nitro-phenyl]-[5-(2,2-dimethyl-[1,3]dioxolan-4-ylmethoxy)-2-methyl-phenyl]-methanone (compound 311),
[4-(2,4-Difluoro-phenylamino)-2-nitro-phenyl]-[5-(2,3-dihydroxy-propoxy)-2-methyl-phenyl]-methanone (compound 312),
[2-Amino-4-(2,4-difluoro-phenylamino)-phenyl]-[5-(2,3-dihydroxy-propoxy)-2-methyl-phenyl]-methanone (compound 313),
[2-Chloro-4-(2,4-difluoro-phenylamino)-phenyl]-[2-fluoro-5-(3-hydroxy-propoxy)-phenyl]-methanone (compound 314),
[2-Chloro-4-(2,4-difluoro-phenylamino)-phenyl]-[5-(2,2-dimethyl-[1,3]dioxolan-4-ylmethoxy)-2-fluoro-phenyl]-methanone (compound 315),
[2-Chloro-4-(2,4-difluoro-phenylamino)-phenyl]-[5-(2,3-dihydroxy-propoxy)-2-fluoro-phenyl]-methanone (Compound 316),
2-{3-[2-Chloro-4-(4-chloro-2-methyl-phenylamino)-benzoyl]-4-fluoro-phenoxy}-N-methyl-acetamide (compound 317),
[2-Chloro-4-(4-chloro-2-methyl-phenylamino)-phenyl]-[2-fluoro-5-(3-hydroxy-propoxy)-phenyl]-methanone (compound 318),
2-{3-[2-Chloro-4-(4-chloro-2-methyl-phenylamino)-benzoyl]-4-fluoro-phenoxy}-N,N-dimethyl-acetamide (compound 319),
[2-Chloro-4-(4-chloro-2-methyl-phenylamino)-phenyl]-[5-(2,2-dimethyl-[1,3]dioxolan-4-ylmethoxy)-2-fluoro-phenyl]-methanone (compound 320),
[2-Chloro-4-(4-chloro-2-methyl-phenylamino)-phenyl]-[5-(2,3-dihydroxy-propoxy)-2-fluoro-phenyl]-methanone (compound 321),
[2-Chloro-4-(4-fluoro-2-methyl-phenylamino)-phenyl]-[2-fluoro-5-(3-hydroxy-propoxy)-phenyl]-methanone (compound 322),
[2-Chloro-4-(4-fluoro-phenylamino)-phenyl]-[2-fluoro-5-(3-hydroxy-propoxy)-phenyl]-methanone (compound 323),
[2-Chloro-4-(4-fluoro-phenylamino)-phenyl]-[5-(2,2-dimethyl-[1,3]-dioxolan-4-ylmethoxy)-2-fluoro-phenyl]-methanone (compound 324),

[2-Chloro-4-(2-chloro-4-fluoro-phenylamino)-phenyl]-[2-fluoro-5-(3-hydroxy-propoxy)-phenyl]-methanone (compound 325),

[4-(2-Amino-phenylamino)-2-chloro-phenyl]-[5-(2,3-dihydroxy-propoxy)-2-fluoro-phenyl]-methanone (compound 326),

[4-(2-Amino-phenylamino)-2-chloro-phenyl]-[2-fluoro-5-(2-morpholin-4-yl-ethoxy)-phenyl]-methanone (compound 327),

[2-Chloro-4-(2,6-difluoro-phenylamino)-phenyl]-[2-chloro-5-(2-morpholin-4-yl-ethoxy)-phenyl]-methanone (compound 328), (±)-[2-Chloro-4-(2,6-difluoro-phenylamino)-phenyl]-[2-chloro-5-(2,3-dihydroxy-propoxy)-phenyl]-methanone (compound 329),

[5-(3-Bromo-propoxy)-2-chloro-phenyl]-[2-chloro-4-(2,6-difluoro-phenylamino)-phenyl]-methanone (compound 330),

[2-Chloro-4-(2,4-difluoro-phenylamino)-phenyl]-(5-hydroxymethyl-2-methyl-phenyl)-methanone (compound 331),

[2-Chloro-4-(2,4-difluoro-phenylamino)-phenyl]-(5-chloromethyl-2-methyl-phenyl)-methanone (compound 332), (5-Azidomethyl-2-methyl-phenyl)-[2-chloro-4-(2,4-difluoro-phenylamino)-phenyl]-methanone (compound 333), (5-Aminomethyl-2-methyl-phenyl)-[2-chloro-4-(2,4-difluoro-phenylamino)-phenyl]-methanone (compound 334),

[2-Chloro-4-(2,4-difluoro-phenylamino)-phenyl]-(5-hydroxymethyl-2-methoxy-phenyl)-methanone (compound 335), Acetic acid 3-[2-chloro-4-(2,4-difluoro-phenylamino)-benzoyl]-4-methoxy-benzyl ester (compound 336), N-tert-Butoxy-3-[2-chloro-4-(2,4-difluoro-phenylamino)-benzoyl]-4-methoxy-benzamide (compound 337), 3-[2-Chloro-4-(2,4-difluoro-phenylamino)-benzoyl]-N-methoxy-4-methyl-benzamide (compound 338), N-Butoxy-3-[2-chloro-4-(2,4-difluoro-phenylamino)-benzoyl]-4-methyl-benzamide (compound 339), 3-[2-Chloro-4-(2,4-difluoro-phenylamino)-benzoyl]-N-cyclohexylmethoxy-4-methyl-benzamide (compound 340), 3-[2-Chloro-4-(2,4-difluoro-phenylamino)-benzoyl]-4-methyl-N-(2-methyl-thiazol-4-ylmethoxy)-benzamide (compound 341), N-benzyloxy-3-[2-chloro-4-(2,4-difluoro-phenylamino)-benzoyl]-4-methyl-benzamide (compound 342), 3-[2-Chloro-4-(2,4-difluoro-phenylamino)-benzoyl]-N-(4-methoxy-benzyloxy)-4-methyl-benzamide (compound 343), 3-[2-Chloro-4-(2,4-difluoro-phenylamino)-benzoyl]-4-methyl-benzoic acid N'N'-dimethyl-hydrazide (compound 344), 3-[2-Chloro-4-(2,4-difluoro-phenylamino)-benzoyl]-4-methyl-N-morpholin-4-yl-benzamide (compound 345), 3-[2-Chloro-4-(2,4-difluoro-phenylamino)-benzoyl]-N-hydroxy-4-methyl-benzamide (compound 346), 4-[2-Chloro-4-(2,4-difluoro-phenylamino)-benzoyl]-N-(2-hydroxy-ethyl)-3-methyl-benzamide (compound 347),

[2-Chloro-4-(2,4-difluoro-phenylamino)-phenyl]-[5-(3-hydroxy-propenyl)-2-methyl-phenyl]-methanone (compound 348), 4-{3-[2-Chloro-4-(2,4-difluoro-phenylamino)-benzoyl]-4-methyl-benzoylamino}-thiophene-3-carboxylic acid methyl ester (compound 349), 3-[2-Chloro-4-(2,4-difluoro-phenylamino)-benzoyl]-N-furan-2-ylmethyl-4-methyl-benzamide (compound 350), 3-[2-Chloro-4-(2,4-difluoro-phenylamino)-benzoyl]-N-(3-methoxy-phenyl)-4-methyl-benzamide (compound 351), 2-{3-[2-Chloro-4-(2,4-difluoro-phenylamino)-benzoyl]-4-methyl-benzoylamino}-benzoic acid methyl ester (compound 352), 3-{3-[2-Chloro-4-(2,4-difluoro-phenylamino)-benzoyl]-4-methyl-benzoylamino}-thiophene-2-carboxylic acid methyl ester (compound 353), 4-{3-[2-Chloro-4-(2,4-difluoro-phenylamino)-benzoyl]-4-methyl-benzoylamino}-thiophene-3-carboxylic acid (compound 354), 2-{3-[2-Chloro-4-(2,4-difluoro-phenylamino)-benzoyl]-4-methyl-benzoylamino}-benzoic acid (compound 355), 3-[2-Chloro-4-(2,4-difluoro-phenylamino)-benzoyl]-N-[2-(2-hydroxy-ethylcarbamoyl)-phenyl]-4-methyl-benzamide (compound 356), 3-{3-[2-Chloro-4-(2,4-difluoro-phenylamino)-benzoyl]-4-methyl-benzoylamino}-thiophene-2-carboxylic acid (2-hydroxy-ethyl)-amide (compound 357),

[2-Chloro-4-(4-fluoro-2-methyl-phenylamino)-phenyl]-[2-methyl-5-(1H-tetrazol-5-yl)-phenyl]-methanone (compound 358),

[4-(2-Amino-phenylamino)-2-chloro-phenyl]-(5-ethynyl-2-methyl-phenyl)-methanone (compound 359),

[4-(2-Amino-phenylamino)-2-chloro-phenyl]-(2-methyl-5-{1-[2-(tetrahydro-pyran-2-yloxy)-ethyl]-1H-[1,2,3]triazol-4-yl}-phenyl)-methanone (compound 360),

[4-(2-Amino-phenylamino)-2-chloro-phenyl]-{5-[1-(2-hydroxy-ethyl)-1H-[1,2,3]triazol-4-yl]-2-methyl-phenyl}-methanone (compound 361),

[2-Chloro-4-(2,4-difluoro-phenylamino)-phenyl]-(5-ethynyl-2-methyl-phenyl)-methanone (compound 362), 3-[2-Chloro-4-(4-fluoro-phenylamino)-benzoyl]-4-methyl-benzoic acid hydrazide (compound 363), 3-[2-Chloro-4-(2,4-difluoro-phenylamino)-benzoyl]-4-methyl-benzoic acid hydrazide (compound 364), 1-{3-[2-Chloro-4-(2,4-difluoro-phenylamino)-benzoyl]-4-methyl-benzoyl}-4-ethyl-3-thio semicarbazide (compound 365),

[2-Chloro-4-(2,4-difluoro-phenylamino)-phenyl]-[5-(5-ethylamino-[1,3,4]thiadiazol-2-yl)-2-methyl-phenyl]-methanone (compound 366),

[2-Chloro-4-(2,4-difluoro-phenylamino)-phenyl]-[2-methyl-5-(1H-tetrazol-5-yl)-phenyl]-methanone (compound 367), 3-{3-[2-Chloro-4-(2,4-difluoro-phenylamino)-benzoyl]-4-methyl-phenyl}-3-oxo-propionic acid ethyl ester (compound 368),

[2-Chloro-4-(2,4-difluoro-phenylamino)-phenyl]-[5-(4,5-dihydro-oxazol-2-yl)-2-methyl-phenyl]-methanone (compound 369), 3-{2-Chloro-4-[2-(3-ethyl-ureido)-phenylamino]-benzoyl}-N-(2-hydroxy-ethyl)-4-methyl-benzamide (compound 370), 3-[2-Chloro-4-(2-nitrophenylamino)benzoyl]-N-(2-hydroxyethyl)-4-methylbenzamide (Compound 417), 3-[4-(4-Bromo-2-nitrophenylamino)-2-chlorobenzoyl]-N-(2-hydroxyethyl)-4-methylbenzamide (Compound 420),
3-[4-(4-Bromo-2-methylphenylamino)-2-chlorobenzoyl]-4-methylbenzoic acid (Compound 422),
3-[2-Chloro-4-(2,4-difluorophenylamino)benzoyl]-4-methylbenzoic acid (Compound 424),
2-Methylacrylic acid 2-{3-[2-chloro-4-(2,4-difluorophenylamino)benzoyl]-4-methylbenzoylamino}ethyl ester (Compound 425),
3-[2-Chloro-4-(2-nitrophenylamino)benzoyl]-N-(2-methoxyethyl)-4-methylbenzamide (Compound 426),
3-[2-Chloro-4-(4-chloro-2-fluoro-phenylamino)-benzoyl]-4-methyl-benzoic acid (Compound 432),
3-[2-Chloro-4-(2,4-difluoro-phenylamino)-benzoyl]-4-methoxy-benzoic acid (compound 437),
3-[2-Chloro-4-(2,6-difluoro-phenylamino)-benzoyl]-4-methoxy-benzoic acid (compound 443),
3-[2-Chloro-4-(3-fluoro-2-methyl-phenylamino)-benzoyl]-4-methyl-benzoic acid (Compound 446),
3-[2-Chloro-4-(2-chloro-4-fluoro-phenylamino)-benzoyl]-4-methyl-benzoic acid (Compound 449),
3-[2-Chloro-4-(4-fluoro-phenylamino)-benzoyl]-4-methoxy-benzoic acid (Compound 457),
3-(2-Chloro-4-phenylamino-benzoyl)-4-methoxy-benzoic acid (Compound 459),
[2-Chloro-4-(2-nitro-phenylamino)-phenyl]-{2-methyl-4-[2-(tetrahydro-pyran-2-yloxy)-ethoxy]-phenyl}-methanone (Compound 472),
[4-(4-Bromo-2-nitro-phenylamino)-2-chloro-phenyl]-{2-methyl-4-[2-(tetrahydro-pyran-2-yloxy)-ethoxy]-phenyl (Compound 473),
[4-(4-Bromo-2-nitro-phenylamino)-2-chloro-phenyl]-{2-methyl-4-[3-(tetrahydro-pyran-2-yloxy)-propoxy]-phenyl}-methanone (Compound 477),
[4-(4-Bromo-2-nitro-phenylamino)-2-chloro-phenyl]-[4-(2-fluoro-ethoxy)-2-methyl-phenyl]-methanone (Compound 481),
[4-(4-Bromo-2-nitro-phenylamino)-2-chloro-phenyl]-[4-(2-methoxy-ethoxy)-2-methyl-phenyl]-methanone (Compound 485),
[2-Chloro-4-(2-nitro-phenylamino)-phenyl]-[2-fluoro-5-(2-morpholin-4-yl-ethoxy)-phenyl]-methanone (compound 518),
[2-Chloro-4-(2-nitro-phenylamino)-phenyl]-[5-(2,2-dimethyl-[1,3]dioxolan-4-ylmethoxy)-2-fluoro-phenyl]-methanone (compound 519), and
[2-Chloro-4-(2-nitro-phenylamino)-phenyl]-[5-(2,3-dihydroxy-propoxy)-2-fluoro-phenyl]-methanone (compound 520).

In addition to the definition of $R_4$ indicated above, it is envisaged that $R_4$ may include substituents included in the definition of $R_6$ in WO 03/018535, the content of which is hereby incorporated by reference in its entirety.

It is further envisaged that the compounds of formula I may be N-substituted at the amino group between rings B and C of the core structure, using substituents substantially as disclosed in U.S. Provisional Application No. 60/434,798, the content of which is hereby incorporated by reference in its entirety.

Methods of Preparation

The compounds of the present invention may be prepared in a number of ways well known to those skilled in the art of organic synthesis. The compounds of the present invention can be synthesised using the methods outlined below, together with methods known in the art of synthetic organic chemistry, or variations thereof as appreciated by those skilled in the art. Preferred methods include, but are not limited to, those described below.

The compounds of formula I may be prepared using the reactions and techniques described in this section. The reactions are performed in solvents that are appropriate with respect to the reagents and materials employed and that are suitable for the transformations being effected. Also, in the synthetic methods described below, it is to be understood that all proposed reaction conditions, including choice of solvent, reaction atmosphere, reaction temperature, duration of experiment and work-up procedures, are chosen to be conditions of standard for that reaction, which should be readily recognised by one skilled in the art. It is understood by one skilled in the art of organic synthesis, that the functionality present on various positions of the molecules used as the starting compounds or intermediates in the syntheses, must be compatible with the reagents and reactions proposed. Not all compounds of formula I falling into a given class may be compatible with some of the reaction conditions required in some of the methods described. Such restrictions of substituents or functional groups which are compatible with the reaction conditions will be readily apparent to one skilled in the art and alternative methods can be used.

Compounds according to the present invention may be prepared by a process comprising coupling of an amine of formula III with a triflate or halide, such as a bromide, iodide, fluoride, chloride, of formula II, as shown in Scheme 1; or alternatively by a process comprising coupling of an amine of formula IIa with a triflate or halide, such as a bromide or iodide, of formula IIIa, as shown in Scheme 1; where $R_1$, $R_2$, $R_3$, $R_4$, $R_5$, and $R_6$ are as defined above; except that any substituents or functional groups which are potentially reactive in the coupling reaction may be protected before the coupling reaction is performed, and the protective groups removed subsequently.

Scheme 1

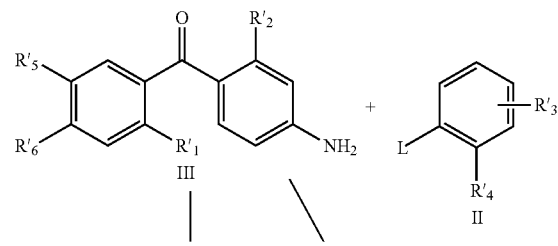

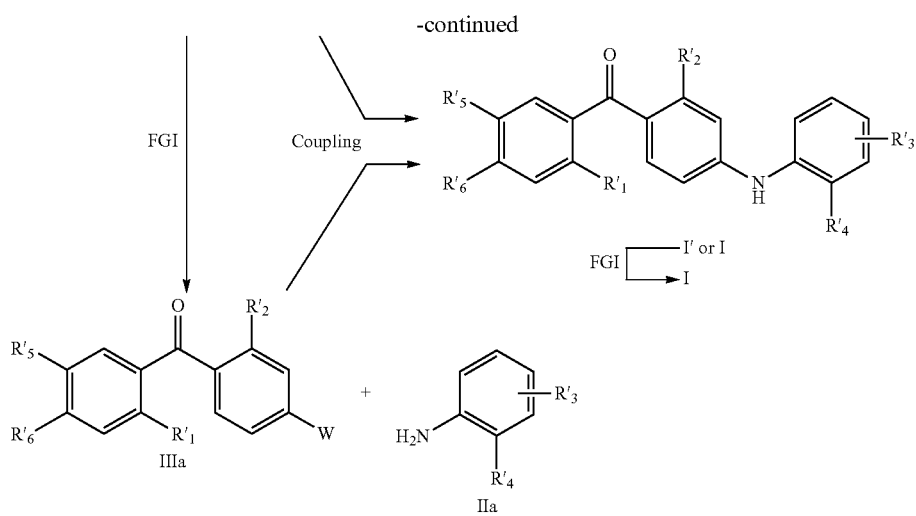

L: Br, I, OSO₂CF₃ or F and Cl (in special cases e.g. when R'₄ is EWG like NO₂)
W: Br, I, or OSO₂CF₃
FGI: Functional group interconversion
R'₁, R'₂, R'₃, R'₄, R'₅, and R'₆ stands for R₁, R₂, R₃, R₄, R₅, and R₆ respectively or any suitable FG (functional group) which may be transformed to R₁, R₂, R₃, R₄, R₅, and R₆

The coupling reaction is carried out by using a method for the formation of diphenylamines well known to one skilled in the art of organic synthesis. The preferred method is the palladium catalysed amination method which comprises coupling of an amine with an arylhalogenide (or aryltriflate) in the presence of a base, a suitable Pd source, and a suitable phosphine ligand in an inert solvent.

Different palladium compounds may be used in the process, non-limiting examples of which are palladium(II) acetate, palladium(II) chloride, palladium(II) bromide, dichlorobis(triphenylphosphine)palladium(II), tetrakis (triphenylphosphine)palladium(0), tris(dibenzylideneacetone)dipalladium(0). The preferred phosphine ligands include, but are not limited to, racemic or non-racemic 2,2'-bis(diphenylphosphino)-1,1'-binaphthyl (hereinafter referred to as BINAP), tri-o-tolylphosphine, tri-tert-butylphosphine, 1,1'-bis(diphenylphosphino)-ferrocene, bis[(2-diphenylphosphino)phenyl]ether (DPEphos), 2-dicyclohexylphosphanyl-2'-dimethylaminobiphenyl, 2-(di-tert-butylphosphino)biphenyl and 9,9-dimethyl-4,6-bis (diphenylphosphino)xanthene (Xantphos). The amount of palladium and ligand used in this catalytic process may be typically in the range 0.1 to 10% by mole relative to the amount of the aromatic halide (or triflate) used. Especially sodium-tert-butoxide (NaOt-Bu) and caesium carbonate (Cs₂CO₃) have proven to be the preferred bases in this process, but other bases may be used as well. The reaction is typically performed at elevated temperatures (80-120° C.) in inert solvents such as 1,4-dioxane, toluene, benzene, and tetrahydrofuran under an inert atmosphere, e.g. argon or nitrogen.

When R'₄ is an electron withdrawing group (EWG) such as nitro or cyano the above coupling may also be performed non-catalytically in the presence of strong bases like potassium- or sodium-tert-butoxide. The reaction is typically performed at room temperature or higher (20-200° C.) in aprotic solvents like dimethylsulfoxide (DMSO), N,N-dimethylformamide (DMF) or N-methylpyrrolidinone (NMP) under an inert atmosphere, e.g. argon or nitrogen.

Compounds according to the present invention of the general formula III may be prepared by several methods known to those skilled in the art of organic synthesis. One useful sequence is shown in Scheme 2. The key step comprises the coupling of a halide, preferably an iodide or bromide of general formula VI with an acid chloride of general formula V to afford a benzophenone of general formula IV. The benzophenone IV may then be reduced to the corresponding amine of general formula III by treatment with standard reducing agents. Examples of such reducing agents include, but are not limited to, stannous chloride dihydrate, hydrogen, ammonium formiate or hydrazine hydrate and a catalytic amount of palladium on carbon. The coupling reaction may be achieved by transforming the halide (VI) into a reactive organometallic intermediate, such as by treatment with isopropyl magnesium chloride to afford the corresponding magnesium derivative, or by treatment with n-butyllithium to afford the corresponding lithium derivative.

Scheme 2

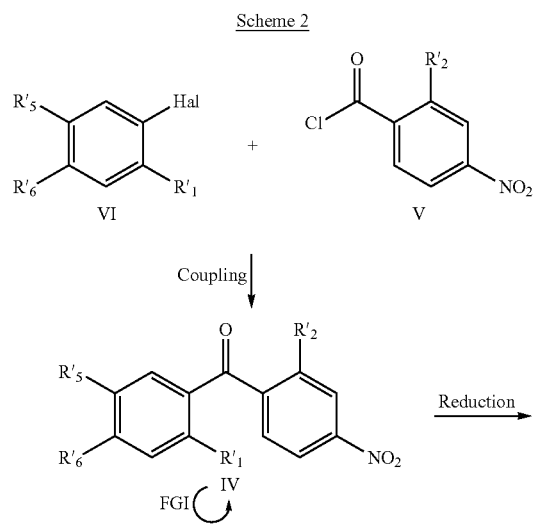

-continued

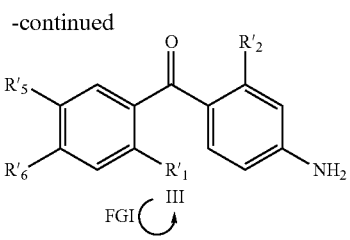

Hal: I or Br
FGI: Functional group interconversion
R'$_1$, R'$_2$, R'$_5$, and R'$_6$ stands for R$_1$, R$_2$, R$_5$, and R$_6$ respectively or any suitable FG (functional group) which may be transformed to R$_1$, R$_2$, R$_5$, and R$_6$ The reactivity of this organometallic intermediate is then modulated by transmetalation to e.g. zinc, by treatment with ZnCl$_2$, ZnBr$_2$, or ZnI$_2$. This organozinc compound is then coupled with the acid halide, such as an acid chloride of general formula V, in the presence or mediated by a catalytic amount of a palladium(0) complex. Examples of such palladium catalysts include but are not limited to tetrakis(triphenylphosphine)palladium(0), tetrakis(triphenylarsine)palladium(0), dichlorobis(triphenylphosphine)palladium(II), or benzylchlorobis(triphenylphosphine)palladium(II). Alternatively, the organozinc compound is coupled with the acid halide, such as the acid chloride, of general formula V, in the presence or mediated by an equimolar or substoichiometric or catalytic amount (with regard to V), such as 0.1-99 mol %, e.g. 0.5-10 mol %, e.g. 1-5 mol %, e.g. 2-3 mol % of copper (I) or (II) salts, such as copper(II) acetate or the soluble complex CuCN.2LiCl or CuCN.2LiBr. The coupling reaction is typically performed at room temperature in inert solvents such as 1,4-dioxane, toluene, benzene, and tetrahydrofuran under an inert atmosphere, e.g. argon or nitrogen.

Compounds accordingly to the present invention of general formula IIIa may be prepared by analogous zinc mediated cross-coupling procedures as shown in Scheme 3.

Scheme 3

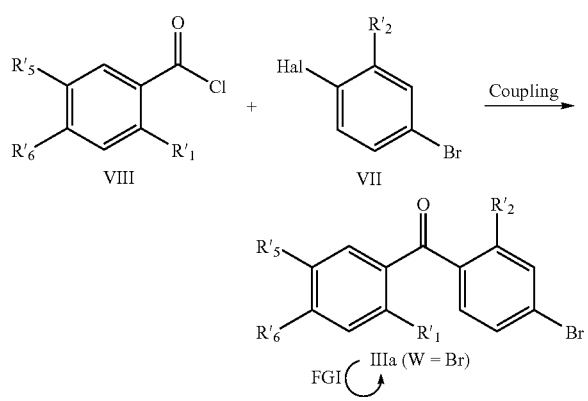

Hal: I or Br
FGI: Functional group interconversion
R'$_1$, R'$_2$, R'$_5$, and R'$_6$ stands for R$_1$, R$_2$, R$_5$, and R$_6$ respectively or any suitable FG (functional group) which may be transformed to R$_1$, R$_2$, R$_5$, and R$_6$ Compounds according to the present invention may in special cases be prepared by a simple functional group interconversion (FGI), meaning a standard process, known to those skilled in the art of organic synthesis, where a functional group in compounds with the general formula I or I' is transformed into a different functional group in one or more synthetic steps, leading to a new compound with the general formula I. Examples of such processes include, but are not limited to, hydrolysis of an ester to give an acid under basic conditions, deprotection of a methylether to give a phenol by treatment with e.g. borontribromide (BBr$_3$), and catalytic hydrogenation of an olefin to give a saturated hydrocarbon. Non limiting examples of such transformations are described in "Comprehensive Organic Transformations", by R. C. Larock, VCH 1989, which is hereby incorporated as reference and in general procedures. Especially, the use of general protective groups in one or more synthetic steps may be convenient in the synthesis of compounds with the general formula I. Examples of such general protective groups include, but are not limited to, methyl, ethyl, tert-butyl or benzyl esters as protective groups of an hydroxy group; tetrahydropyranyl- or silyl-ethers as protective groups of an hydroxy group.

As shown in Scheme 2 and 3 each intermediate compound may be transformed by an FGI process as described above to give new compounds with the same general formula (e.g. an hydroxy group may be protected as an tert-butyl-dimethylsilyl ether). This is only to illustrate the flexibility in the synthesis, and in general the described sequence of processes is only one of many possible strategies for the synthesis of compounds of the present invention. That is, it may be more advantageous in some cases to alter the sequence of the processes described above. The described sequence of processes is not considered as being limiting the preparation of compounds of the present invention of general formula I, and alteration of the reaction sequence may be an obvious alternative for those skilled in the art of organic synthesis. This aspect of the invention may especially be advantageous in the synthesis of compounds with different substituents in the R$_4$, R$_5$, and R$_6$ groups. Readily available intermediates may serve as starting point for the synthesis of various series of compounds covered by the general formula I.

Pharmaceutical Compositions

In another aspect, the invention relates to a pharmaceutical composition comprising, as an active component, a compound of formula I together with a pharmaceutically acceptable excipient, carrier or vehicle. Furthermore, the invention relates to the use of a compound of formula I for the preparation of a medicament for the prevention, treatment or amelioration of inflammatory diseases or conditions.

Pharmaceutical compositions of the invention may be in unit dosage form such as tablets, pills, capsules, powders, granules, elixirs, syrups, emulsions, ampoules, suppositories or parenteral solutions or suspensions; for oral, parenteral, ophthalmic, transdermal, intra-articular, topical, pulmonal, nasal, buccal or rectal administration or in any other manner appropriate for the formulation of anti-inflammatory compounds and in accordance with accepted practices such as those disclosed in *Remington: The Science and Practice of Pharmacy.* 19$^{th}$ Ed., Mack Publishing Company, 1995. In the composition of the invention, the active component may be present in an amount of from about 0.01 to about 99%, such as 0.1% to about 10% by weight of the composition.

For oral administration in the form of a tablet or capsule, a compound of formula I may suitably be combined with an oral, non-toxic, pharmaceutically acceptable carrier such as ethanol, glycerol, water or the like. Furthermore, suitable binders, lubricants, disintegrating agents, flavouring agents and colourants may be added to the mixture, as appropriate. Suitable binders include, e.g., lactose, glucose, starch, gelatin, acacia gum, tragacanth gum, sodium alginate, carboxymethylcellulose, polyethylene glycol, waxes or the like. Lubricants include, e.g., sodium oleate, sodium stearate, magnesium stearate, sodium benzoate, sodium acetate, sodium chloride or the like. Disintegrating agents include, e.g., starch, methyl cellulose, agar, bentonite, xanthan gum or the like. Additional excipients for capsules include macrogols or lipids.

For the preparation of solid compositions such as tablets, the active compound of formula I is mixed with one or more excipients, such as the ones described above, and other pharmaceutical diluents such as water to make a solid preformulation composition containing a homogenous mixture of a compound of formula I. The term "homogenous" is understood to mean that the compound of formula II is dispersed evenly throughout the composition so that the composition may readily be subdivided into equally effective unit dosage forms such as tablets or capsules. The preformulation composition may then be subdivided into unit dosage forms containing from about 0.05 to about 1000 mg, in particular from about 0.1 to about 500 mg, of the active compound of the invention.

Liquid formulations for either oral or parenteral administration of the compound of the invention include, e.g., aqueous solutions, syrups, aqueous or oil suspensions and emulsion with edible oils such as cottonseed oil, sesame oil, coconut oil or peanut oil. Suitable dispersing or suspending agents for aqueous suspensions include synthetic or natural gums such as tragacanth, alginate, acacia, dextran, sodium carboxymethylcellulose, gelatin, methylcellulose or polyvinylpyrolidone.

For parenteral administration, e.g. intramuscular, intraperitoneal, subcutaneous or intravenous injection or infusion, the pharmaceutical composition preferably comprises a compound of formula I dissolved or solubilised in an appropriate, pharmaceutically acceptable solvent. For parenteral administration, the composition of the invention may include a sterile aqueous or non-aqueous solvent, in particular water, isotonic saline, isotonic glucose solution, buffer solution or other solvent conventionally used for parenteral administration of therapeutically active substances. The composition may be sterilised by, for instance, filtration through a bacteria-retaining filter, addition of a sterilising agent to the composition, irradiation of the composition, or heating the composition. Alternatively, the compound of the invention may be provided as a sterile, solid preparation, e.g. a freeze-dried powder, which is dissolved in sterile solvent immediately prior to use.

The composition intended for parenteral administration may additionally comprise conventional additives such as stabilisers, buffers or preservatives, e.g. antioxidants such as methylhydroxybenzoate or the like.

Compositions for rectal administration may be in the form of a suppository incorporating the active ingredient and a carrier such as cocoa butter, or in the form of an enema.

Compositions suitable for intra-articular administration may be in the form of a sterile aqueous preparation of the active ingredient which may be in microcrystalline form, for example, in the form of an aqueous microcrystalline suspension. Liposomal formulations or biodegradable polymer systems may also be used to present the active ingredient for both intra-articular and ophthalmic administration.

Compositions suitable for topical administration, including ophthalmic treatment, include liquid or semi-liquid preparations such as liniments, lotions, gels, applicants, oil-in-water or water-In-oil emulsions such as creams, ointments or pastes; or solutions or suspensions such as drops. For topical administration, the compound of formula I may typically be present in an amount of from 0.01 to 20% by weight of the composition, such as 0.1% to about 10%, but may also be present in an amount of up to about 50% of the composition.

Compositions for ophthalmic treatment may preferably additionally contain a cyclodextrin.

Compositions suitable for administration to the nasal or buccal cavity or for inhalation include powder, self-propelling and spray formulations, such as aerosols and atomizers. Such compositions may comprise a compound of formula II in an amount of 0.01-20%, e.g. 2%, by weight of the composition.

The composition may additionally comprise one or more other active components conventionally used in the treatment of various inflammatory diseases and conditions. Examples of such additional active components may be selected from the group consisting of glucocorticoids, vitamin D and vitamin D analogues, antihistamines, platelet activating factor (PAF) antagonists, anticholinergic agents, methylxanthines, β-adrenergic agents, COX-2 inhibitors, salicylates, indomethacin, flufenamate, naproxen, timegadine, gold salts, penicillamine, serum cholesterol lowering agents, retinoids, zinc salts and salicylazosulfapyridine.

In a further aspect, the invention relates to a method of treating inflammatory diseases or conditions, or ophthalmic diseases or conditions, or cancer, the method comprising administering, to a patient in need thereof, an effective amount of a compound of formula I.

A suitable dosage of the compound of the invention will depend, inter alia, on the age and condition of the patient, the severity of the disease to be treated and other factors well known to the practicing physician. The compound may be administered either orally, parenterally or topically according to different dosing schedules, e.g. daily or with weekly intervals. In general a single dose will be in the range from 0.01 to 400 mg/kg body weight. The compound may be administered as a bolus (i.e. the entire daily dose is administered at once) or in divided doses two or more times a day.

Inflammatory diseases or conditions contemplated for treatment with the present compounds are inflammatory diseases where modulation of cytokine expression and secretion may be mediated by MAP kinases such as the p38 MAP kinase as discussed above. Examples of inflammatory diseases or conditions believed to be mediated by the p38 MAP kinase are selected from the group consisting of asthma, arthritis, including rheumatoid arthritis and spondylarthritis, gout, atherosclerosis, inflammatory bowel disease, Crohn's disease, neurological inflammations, inflammatory eye diseases, proliferative and inflammatory skin disorders, such as psoriasis, atopic dermatitis and acne vulgaris, uveitis, sepsis, septic shock and osteoporosis.

The treatment may additionally involve administration of one or more other anti-inflammatory active components such as glucocorticoids, vitamin D and vitamin D analogues, antihistamines, platelet activating factor (PAF) antagonists, anticholinergic agents, methylxanthines, β-adrenergic agents, COX-2 inhibitors, salicylates, indomethacin, flufenamate, naproxen, timegadine, gold salts, penicillamine, serum cholesterol lowering agents, retinoids, zinc salts and salicylazosulfapyridine. The administration of a compound of the present invention and another anti-inflammatory component may be either concomitantly or sequentially.

Ophthalmic diseases or conditions contemplated for treatment with the present compounds include the ophthalmic disease or condition is non-infectious (e.g. allergic) conjunctivitis, iritis, keratitis, uveitis, scleritis, episcleritis, sympathetic ophthalmitis, blepharitis or keratoconjunctivitis sicca.

Pharmacological Methods

To study the effect of compounds of the present invention in vitro, the inhibition of IL-1β and TNF-α secretion was determined using the following procedure:

Cytokine production was measured in the media from lipopolysaccharide (LPS) stimulated peripheral blood mononuclear cells. The mononuclear cells were isolated from human peripheral blood by Lymphoprep® (Nycomed, Norway) fractionation and suspended in RPMI 1640 (growth medium) with foetal calf serum (FCS, 2%), at a concentration of $5 \times 10^5$ cells/ml. The cells were incubated in 24-well tissue culture plates in 1 ml aliquots. Test compounds were dissolved in dimethylsulfoxide (DMSO, 10 mM) and were diluted with the medium. Compounds were added to the cells for 30 minutes, then LPS (1 mg/ml final concentration) was added. The plates were incubated for 18 hours, and the concentration of IL-β and TNF-α in the medium was determined by enzyme-linked immunosorbent assays. The median inhibitory concentrations ($IC_{50}$) of the compounds were calculated. The results are shown in Table 1.

TABLE 1

Inhibition of cytokines production in vitro by compounds of the present invention. The median inhibition concentration

| Compound No. | ($IC_{50}$, nM) of IL-1β | TNF-α |
|---|---|---|
| Compound 104 | 2.0 | 1.3 |
| Compound 106 | 2.0 | 1.0 |
| Compound 107 | 3.2 | 3.2 |
| Compound 109 | 4.0 | 3.2 |
| Compound 112 | 4.0 | 0.6 |
| Compound 113 | 4.0 | 1.8 |
| Compound 114 | 2.5 | 0.4 |
| Compound 115 | 1.3 | 0.3 |
| Compound 116 | 1.0 | 1.0 |
| Compound 117 | 4.0 | 1.0 |
| Compound 118 | 2.2 | 2.0 |
| Compound 119 | 1.3 | 0.4 |
| Compound 120 | 2.7 | 2.0 |
| Compound 121 | 2.8 | 0.6 |
| Compound 122 | 0.5 | 0.2 |
| Compound 123 | 0.5 | 0.3 |
| Compound 126 | 2.8 | 0.6 |
| Compound 129 | 2.5 | 1.3 |
| Compound 131 | 3.2 | 1.3 |
| Compound 135 | 4.0 | 2.0 |
| Compound 136 | 4.0 | 2.0 |
| Compound 140 | 1.4 | 1.0 |
| Compound 141 | 0.9 | 0.6 |
| Compound 143 | 2.5 | 1.6 |
| Compound 144 | 1.0 | 0.6 |
| Compound 145 | 1.3 | 0.3 |
| Compound 147 | 2.5 | 0.8 |
| Compound 148 | 0.6 | 0.2 |
| Compound 149 | 1.6 | 0.5 |
| Compound 151 | 1.8 | 0.4 |
| Compound 152 | 2.8 | 0.6 |
| Compound 153 | 8.9 | 1.6 |
| Compound 154 | 3.2 | 2.5 |
| Compound 155 | 0.6 | 0.2 |
| Compound 156 | 4.5 | 0.9 |
| Compound 157 | 2.2 | 0.9 |
| Compound 158 | 0.6 | 0.2 |
| Compound 159 | 7.9 | 1.3 |
| Compound 163 | 2.5 | 2.5 |
| Compound 164 | 1.3 | 2.0 |
| Compound 166 | 0.5 | 0.4 |
| Compound 167 | 1.7 | 2.0 |
| Compound 168 | 2.5 | 2.5 |
| Compound 169 | 0.4 | 0.4 |
| Compound 170 | 3.2 | 2.5 |
| Compound 173 | 2.5 | 2.0 |
| Compound 174 | 3.2 | 2.0 |
| Compound 176 | 3.2 | 2.0 |

TABLE 1-continued

Inhibition of cytokines production in vitro by compounds of the present invention. The median inhibition concentration

| Compound No. | ($IC_{50}$, nM) of IL-1β | TNF-α |
|---|---|---|
| Compound 178 | 6.3 | 1.6 |
| Compound 180 | 2.5 | 3.2 |
| Compound 182 | 8.9 | 2.2 |
| Compound 183 | 2.0 | 0.7 |
| Compound 186 | 0.8 | 0.5 |
| Compound 188 | 0.9 | 0.5 |
| Compound 190 | 0.6 | 0.3 |
| Compound 191 | 1.1 | 0.5 |
| Compound 193 | 4.0 | 2.5 |
| Compound 194 | 0.6 | 0.3 |
| Compound 195 | 2.2 | 1.0 |
| Compound 196 | 3.2 | 1.0 |
| Compound 197 | 3.2 | 1.8 |
| Compound 198 | 1.1 | 0.4 |
| Compound 201 | 7.9 | 3.2 |
| Compound 202 | 5.0 | 2.0 |
| Compound 203 | 6.3 | 3.2 |
| Compound 241 | 1.1 | 0.3 |
| Compound 242 | 1.4 | 0.5 |
| Compound 243 | 2.8 | 1.3 |
| Compound 244 | 1.3 | 0.5 |
| Compound 245 | 3.5 | 0.9 |
| Compound 246 |  | 3.2 |
| Compound 247 | 5.6 | 1.4 |
| Compound 248 | 1.0 | 0.7 |
| Compound 249 | 1.6 | 1.1 |
| Compound 251 | 1.1 | 0.4 |
| Compound 252 | 0.6 | 0.6 |
| Compound 260 | 1.8 | 0.5 |
| Compound 261 | 2.2 | 1.0 |
| Compound 262 | 2.0 | 0.6 |
| Compound 263 |  | 1.6 |
| Compound 264 | 1.0 | 0.3 |
| Compound 265 | 1.0 | 0.3 |
| Compound 266 | 0.9 | 0.4 |
| Compound 267 | 0.4 | 0.2 |
| Compound 269 | 0.8 | 0.6 |
| Compound 271 | 1.0 | 0.4 |
| Compound 272 | 3.2 | 1.4 |
| Compound 275 | 5.0 | 0.3 |
| Compound 277 | 2.5 | 0.8 |
| Compound 278 | 1.3 | 0.6 |
| Compound 279 | 0.6 | 0.5 |
| Compound 282 | 5.6 | 0.6 |
| Compound 285 | 1.4 | 0.6 |
| Compound 314 |  | 2.8 |
| Compound 335 | 2.7 | 2.5 |
| Compound 336 | 5.0 | 2.0 |
| Ref. comp. a | 13 | 7.1 |
| Ref. comp. b | 6.3 | 6.3 |
| Ref. comp. c | 32 | 6.3 |
| Ref. comp. d | 7.9 | 3.2 |
| Ref. comp. e | 6.3 | 3.2 |
| Ref. comp. f | 13 | 4.0 |

Ref. comp. a: (4-(2-aminophenylamino)-2-chloro-2'-methylbenzophenone, Compound 156 disclosed in WO 98/32730.
Ref. comp. b: 2'-[3-Chloro-4-(2-methylbenzoyl)phenylamino]octananilide, Compound 102 disclosed in WO 01/05746.
Ref. comp. c: 1-Acetoxymethyl N-[2-[3-chloro-4-(2-methylbenzoyl)phenylamino]phenyl] carbamate, Compound 109 disclosed in WO 01/05749.
Ref. comp. d: 1-Ethyl-3-[2-[3-chloro-4-(2-methylbenzoyl)phenylamino]-5-fluoro-phenyl] urea, Compound 114 disclosed in WO 01/05751.
Ref. comp. e: 2,2,2-Trifluoro-N-[2-[3-chloro-4-(2-methylbenzoyl)phenylamino]-5-fluoro-phenyl]acetamide, Compound 102 disclosed in WO 01/05745.
Ref. comp. f: 2-Chloro-4-(3-fluoro-2-methyl-phenylamino)-2'-methylbenzophenone, Compound 131 disclosed in WO 01/42189.

These results show that compounds of the present invention are highly potent inhibitors of the production of IL-β, TNF-α and show a surprisingly higher cytokine inhibitory activity than the reference compounds, thus making them potentially useful in the treatment of inflammatory diseases.

Furthermore, the novel aminobenzophenone derivatives have surprisingly favourable pharmacokinetic properties such as absorption and metabolic stability.

p38α MAP Kinase Assay
Cell Culture

COS-1 cells (derived from African green monkey kidney fibroblast-like cell containing wild-type T antigen under control of the SV40 promotor) were obtained from ATCC (ATCC no. CRL-1650) and grown in growth medium (DMEM without phenoired, 10% FCS, 2 mM L-glutamine, 100 U penicillin and 100 µg streptomycin/ml) at 37° C. with 5% $CO_2$. The cells were passaged twice a week by trypsination (0.25% trypsin, 1 mM EDTA in PBS) and were split 1:10. The medium was changed every second or third day. The cell line was regularly tested with the *Mycoplasma* PCR Primer Set (Stratagene) and found to be free of *Mycoplasma*. Tissue culture media, FCS, L-glutamine and penicillin and streptomycin are from Bribco BRL, Gaithersburg, Md., USA.

Transient Expression of COS-1 Cells

On day one COS-1 cells were seeded in 143 $cm^2$ petri dish with a density of $2 \times 10^4$ celler/$cm^2$ in growth medium. At day 2 the cells were co-transfected with 5 µg (total) of experimental plasmid DNA, expressing the FLAG-p38α and FLAG-MKK6(EE). The plasmids were introduced into the COS-1 cells in serum-free medium using DOTAP™ (Boehringer-Mannheim, Mannheim, Germany). Plasmid DNA was prepared and purified using the QIAGEN EndoToxin-free Maxiprep-500 kit (Hilden, Germany). Briefly, DNA and DOTAP™ were mixed for exactly 15 min. at 37° C. In the $CO_2$ incubator. The transfection-mixture was hereafter transferred to a 15-ml falcon-tube and transfection-medium (DMEM with L-Glutamine and Pen./Strep. but without serum) was added to the transfection-mixture, followed by addition to the cell-monolayer. After 4 hours of incubation with DOTAP™ and plasmids, the medium containing double amount of serum was added to the cells bringing the final concentration of serum up to 10%. The cells were then incubated for 24 hours before kinase reaction.

Immunoprecipitation

After 24 hrs of incubation the reaction was stopped by putting the petri dish on an ice-bath. The medium was aspirated, and the cell monolayer was washed once in ice-cold PBS (137 mM NaCl, 1.5 mM $KH_2PO_4$, 2.7 mM KCl, 8.1 mM $Na_2HPO_4.2H_2O$), and hereafter solubilised for 10 min. in 1.5 ml lysis buffer (50 mM HEPES, pH 7.5, 150 mM NaCl, 10 mM EDTA, 10 mM $Na_4P_2O_7$, 100 mM NaF, 2 mM $Na_3VO_4$, 1% Triton-X-100, Pefabloc 500 µM, Leupeptin 10 µg/µl, Aprotinin 10 µg/µl) was added. The cell-monolayer was scraped by a rubber-policeman, and transferred to an Eppendorf tube. The solubilised cells were clarified by centrifugation at 10.000×g for 10 min. at 4° C. The supernatant was transferred to 50 µprewashed Protein G Sepharose beads in HNT-buffer (30 mM HEPES, pH 7.5, 30 mM NaCl, 0.1% Triton X-100) and were incubated with 2 µg/sample of monoclonal anti-FLAG™ M2 antibody (raised against the FLAG-epitope, $NH_2$-Asp-Tyr-Lys-Asp-Asp-Asp-Asp-Lys-COOH) for 1 hour at room temperature. The anti-FLAG M2 monoclonal antibody was obtained from Sigma (cat. no. F-3165). Approx. 60 µg protein of clarified cell lysate were added to the preadsorbed anti-FLAG™ antibodies on Protein G Sepharose beads and incubated for 90 min. at 4° C. in a blood sample mixer. After the immunoprecipitation period the Sepharose beads were washed twice in lysis buffer and twice in a kinase reaction buffer (25 mM HEPES pH 7.5, 10 mM magnesium acetate, 50 µM ATP).

Incubation of the Compounds with Purified p38α Kinase

The pre-washed immunoprecipitated anti-FLAG-p38 adsorbed on Protein G Sepharose beads was washed twice in 1× kinase-buffer (25 mM HEPES pH 7.5, 10 mM magnesium acetate, 50 µM ATP), and the supernatant was aspirated. The compounds were diluted in 1× kinase buffer at the appropriate concentration. The compounds were added to the washed immunoprecipitated and activated FLAG-p38 adsorbed on the Protein G Sepharose beads for 30 min. at 30° C. in a volume of 100 µl. Every 10 min. the Eppendorf tubes were tapped to ensure that the beads and the compounds were in the solution. After 30 min. incubation, the beads were spun down and the supernatant was aspirated.

p38α MAP Kinase Reaction

The kinase reaction was started by adding 1 µg GST-ATF-2 substrate (Santa Cruz, LaJolla, Calif., USA, cat. no. sc-4114) together with 2 µCi γ-$^{32}$P-ATP in 1× kinase-buffer per sample. The reaction was allowed to proceed for 30 min. at 30° C., and it was stopped by adding 40 µl of 2×SDS-sample buffer to the kinase reaction. The samples were boiled, spinned down, and resolved on a 15% SDS-PAGE. The dried SDS-PAGE gel was exposed to a Phospho-Imager screen and the radioactive PHAS-1 bands were quantified by the STORM860 Phospho-Imager (Molecular Dynamics, Sunnyvale, Calif., USA) using the ImageQuaNT software.

In this assay, Compound 112 was found to be a potent p38 MAP kinase inhibitor with an $IC_{50}$ of 2 nM.

In Vivo Screening Model of LPS Induced TNF-α Response in Mice

To study the effect of compounds of the present invention in vivo, an in vivo screening model of LPS induced TNF-α response in mice was set up as follows: Groups of 6 mice (C3H/HeN, female, about 8 weeks (20 g), Bomholtgaard) were dosed with test compounds in suspension vehicle 1 hour prior to LPS administration (LPS from *E. coli* 055:B5, L-4005, Sigma). At time 0, the mice were dosed ip with 1.0 mg LPS/kg. After anesthetization with Hypnorm/Dormicum, the mice were bled from the periorbital venous plexus 80-90 minutes after LPS administration. The blood samples were sampled in EDTA stabilised tubes and centrifuged at 4000 rpm for 10 minutes at 4° C. The plasma level of TNF-α was analysed by ELISA. Compound 156 of WO 98/32730 was used as reference compound. The plasma level of TNF-α was determined using a sandwich ELISA. Microtiter plates were coated with a monoclonal antibody against mouse TNF-α, washed and blocked with a casein buffer. Samples of mouse TNF-α recombinant standards were added to the wells of the microtiter plates and incubated. All standards were tested in triplicate, all plasma samples in single. After sample and standard incubation, the plates were washed and incubated with biotinylated polyclonal secondary antibody against mouse TNF-α and washed. Enzyme conjugate was added to all wells and incubated. Substrate was added and the enzyme/substrate reaction stopped after 15 minutes at room temperature with 1M $H_2SO_4$. The colour development (OD) was measured at 450 nm on an ELISA reader and the background OD at 620 nm was subtracted. Experiments were approved if the group treated with the reference compound showed a significant inhibition ($p<0.05$) of the TNF-α response compared to the LPS treated control group. The results of the tested compounds are indicated as a percentage inhibition compared to an LPS treated control group. Compounds were tested at 10 mg/kg. The Mann-Whitney test was used to compare drug treated groups to the LPS treated control group ($p<0.05$).

The results are shown in Table 3.

TABLE 3

In vivo inhibition of LPS induced TNF-α production (in %)

| Compound No. | |
|---|---|
| Compound 104 | 95 |
| Compound 112 | 96 |
| Compound 113 | 83 |
| Compound 114 | 72 |
| Compound 115 | 96 |
| Compound 116 | 95 |
| Compound 117 | 71 |
| Compound 120 | 86 |
| Compound 123 | 47 |
| Compound 126 | 79 |
| Compound 129 | 73 |
| Compound 131 | 70 |
| Compound 140 | 76 |
| Compound 141 | 46 |
| Compound 145 | 94 |
| Compound 147 | 89 |
| Compound 148 | 71 |
| Compound 149 | 89 |
| Compound 151 | 99 |
| Compound 152 | 99 |
| Compound 153 | 86 |
| Compound 155 | 91 |
| Compound 156 | 73 |
| Compound 157 | 83 |
| Compound 163 | 66 |
| Compound 164 | 76 |
| Compound 166 | 83 |
| Compound 170 | 87 |
| Compound 173 | 90 |
| Compound 174 | 64 |
| Compound 176 | 52 |
| Compound 178 | 67 |
| Compound 186 | 92 |
| Compound 188 | 95 |
| Compound 196 | 66 |
| Compound 198 | 76 |
| Compound 202 | 67 |
| Compound 251 | 49 |
| Compound 260 | 95 |
| Compound 264 | 87 |
| Compound 266 | 54 |
| Compound 278 | 65 |
| Compound 424 | 44 |
| Ref. comp. a | 23 |

Ref. comp. a: (4-(2-aminophenylamino)-2-chloro-2'-methylbenzophenone, Compound 156 disclosed in WO 98/32730.

The results show that compounds of the present invention surprisingly show an improved biological activity in vivo with respect to inhibition of LPS induced TNF-α production in mice compared to the reference compound, thus making them potentially useful in the treatment of inflammatory diseases.

The invention is described in further detail in the following examples which are not in any way intended to limit the scope of the invention as claimed.

EXAMPLES

General Procedures

All melting points are uncorrected. For $^1$H nuclear magnetic resonance (NMR) spectra (300 MHz) and $^{13}$C NMR (75.6 MHz) chemical shift values (δ) (in ppm) are quoted, unless otherwise specified; for deuteriochloroform solutions relative to internal tetramethylsilane (δ=0.00) or chloroform (δ=7.26) or deuteriochloroform (δ=76.81 for $^{13}$C NMR) standard. The value of a multiplet, either defined (doublet (d), triplet (t), quartet (q)) or not (m) at the approximate mid point is given unless a range is quoted. All organic solvents used were anhydrous. Chromatography was performed on silica gel using the flash technique. Appropriate mixtures of ethyl acetate, dichloromethane, methanol, and petroleum ether (40-60) were used as eluents unless otherwise noted. The following abbreviations have been used:

| | |
|---|---|
| aq | aqueous |
| dba | Dibenzylideneacetone |
| DCM | Dichloromethane |
| DMAP | 4-Dimethylaminopyridine |
| DMF | N,N-Dimethylformamide |
| DIEA | Ethyl diisopropyl amine |
| EDCI | 1-(3-dimethylaminopropyl)-3-ethylcarbodiimide hydrochloride |
| EtOAc | Ethyl acetate |
| FDPP | Diphenyl-phosphinic acid pentafluorophenyl ester |
| h | Hour(s) |
| HATU | O-(7-Azabenzotriazol-1-yl)-N,N,N',N'-tetramethyluronium-hexafluorophosphate |
| min | Minutes |
| NMP | N-methylmorpholine |
| NMR | Nuclear magnetic resonance |
| rac-BINAP | Racemic 2,2'-bis(dlphenylphosphino)-1,1'-binaphtyl |
| RT | Room temperature |
| TBAF | Tetra-n-butylammonium fluoride |
| TFA | Trifluoroacetic acid |
| THF | Tetrahydrofuran |
| THP | Tetrahydropyran |
| TIPSCI | TriIsopropylsilyl chloride |
| v | Volume |

TABLE 4

Exemplified compounds of general formula I

| Compound | Example no. | Structure |
|---|---|---|
| 101 | 1 | 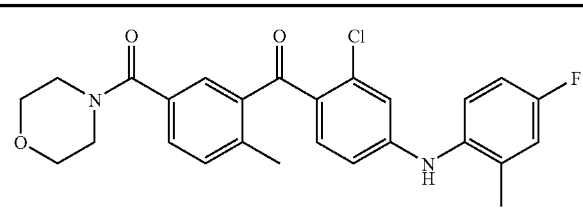 |

TABLE 4-continued

Exemplified compounds of general formula I

| Compound | Example no. | Structure |
|---|---|---|
| 102 | 2 | 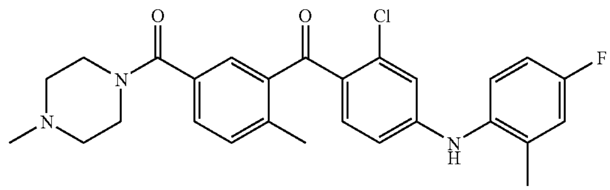 |
| 103 | 3 | 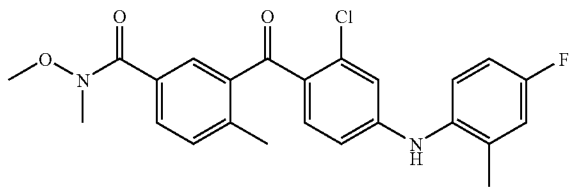 |
| 104 | 4 | 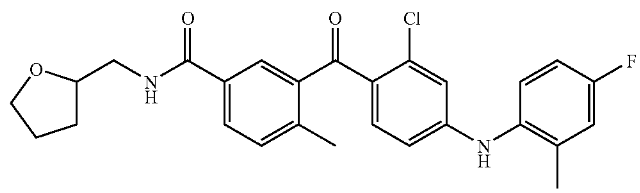 |
| 105 | 5 | 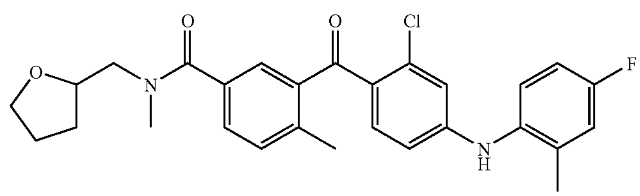 |
| 106 | 6 | 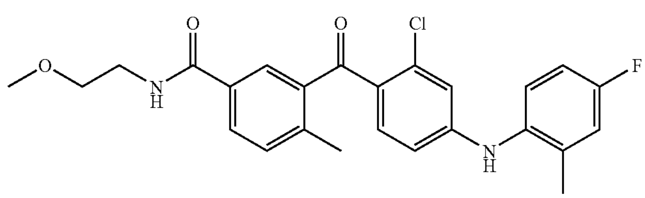 |
| 107 | 7 | 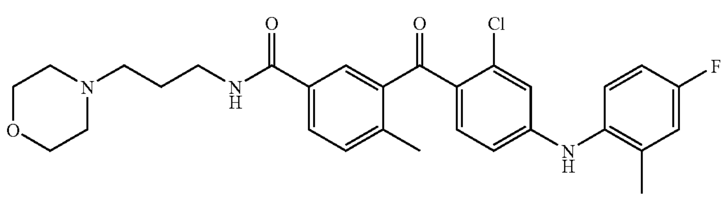 |
| 108 | 8 | 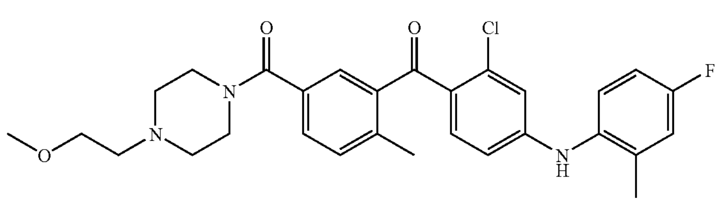 |

US 7,977,387 B2
39   40
TABLE 4-continued
Exemplified compounds of general formula I
| Compound | Example no. | Structure |
|---|---|---|
| 109 | 9 | 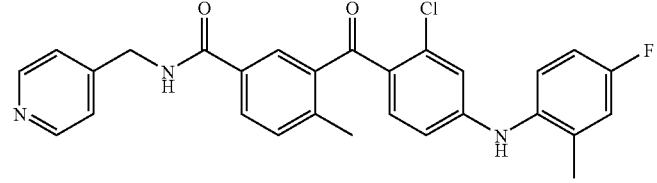 |
| 110 | 10 | 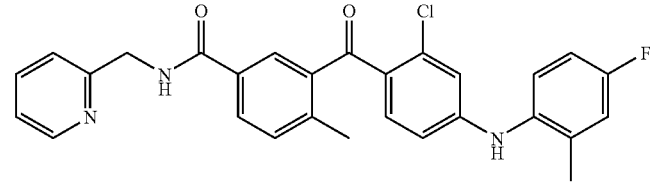 |
| 111 | 11 | 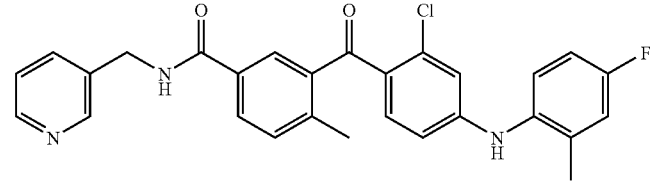 |
| 112 | 12 | 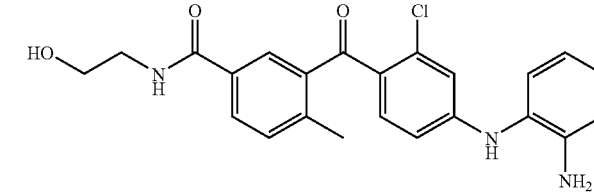 |
| 113 | 13 | 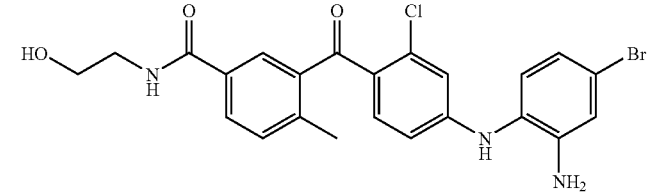 |
| 114 | 14 | 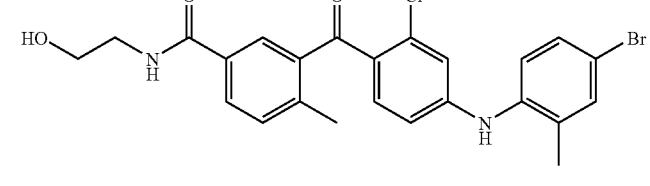 |
| 115 | 15 | 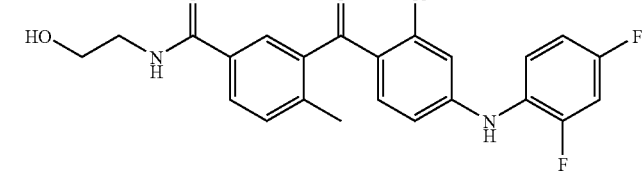 |

TABLE 4-continued

Exemplified compounds of general formula I

| Compound | Example no. | Structure |
|---|---|---|
| 116 | 16 | 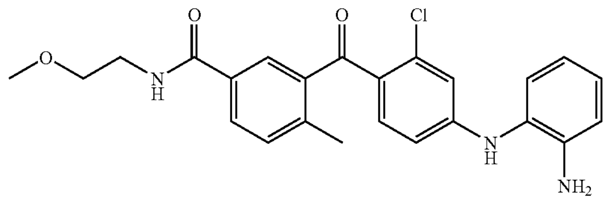 |
| 117 | 17 | 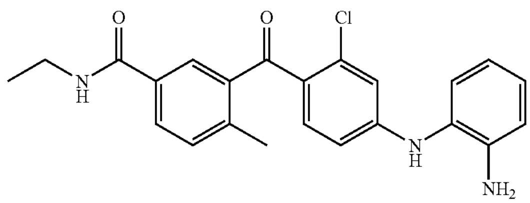 |
| 118 | 18 | 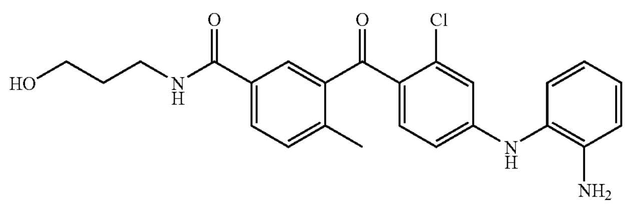 |
| 119 | 19 | 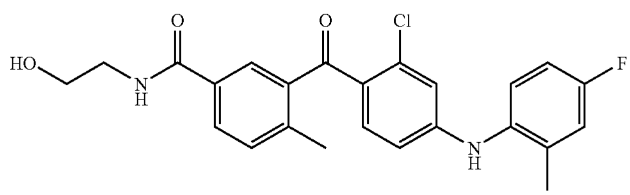 |
| 120 | 20 | 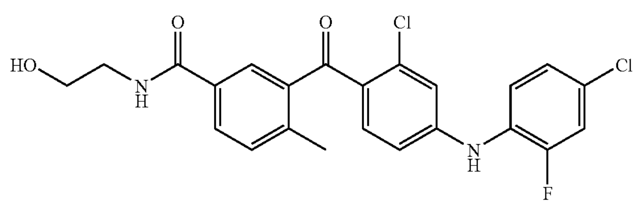 |
| 121 | 21 | 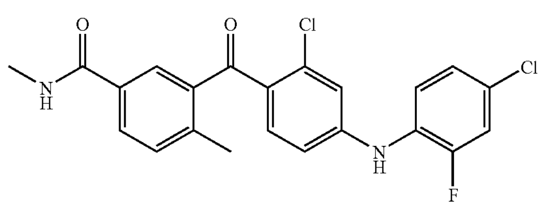 |
| 122 | 22 | 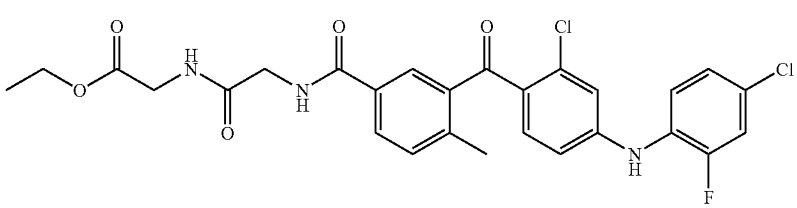 |

TABLE 4-continued

Exemplified compounds of general formula I

| Compound | Example no. | Structure |
|---|---|---|
| 123 | 23 | 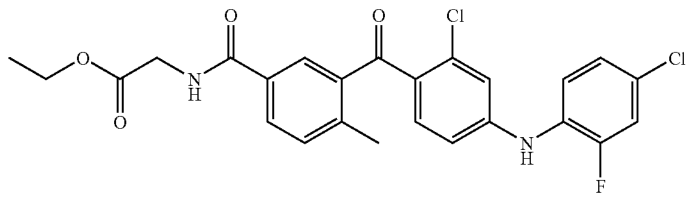 |
| 124 | 24 | 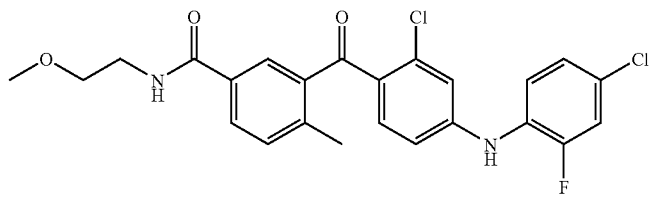 |
| 125 | 25 | 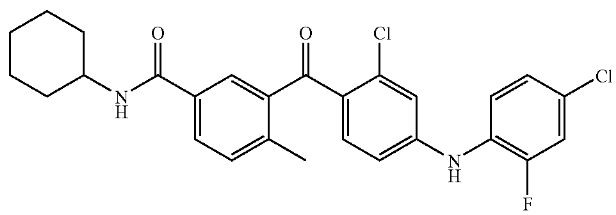 |
| 126 | 26 | 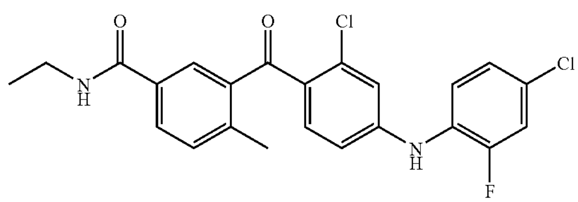 |
| 127 | 27 | 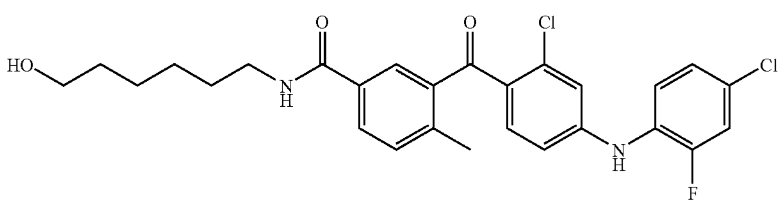 |
| 128 | 28 | 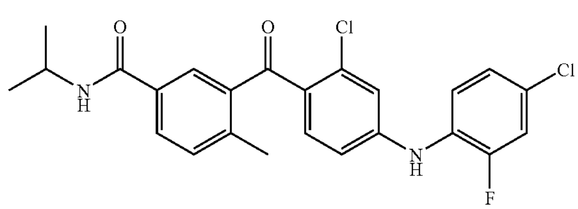 |
| 129 | 29 | 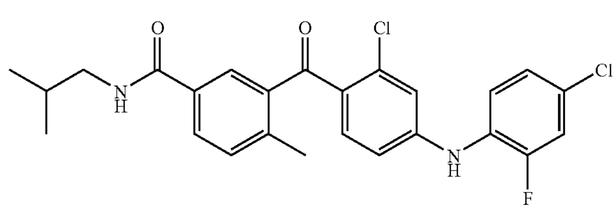 |

TABLE 4-continued

Exemplified compounds of general formula I

| Compound | Example no. | Structure |
|---|---|---|
| 130 | 30 | 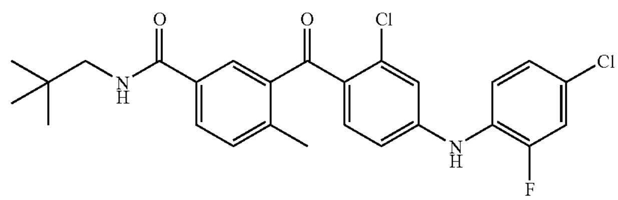 |
| 131 | 31 | 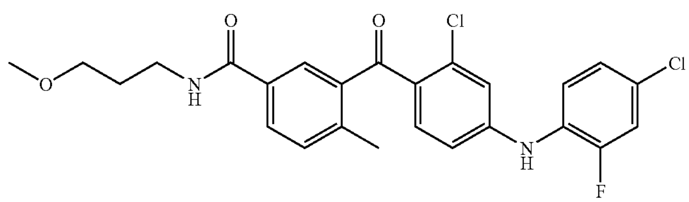 |
| 132 | 32 | 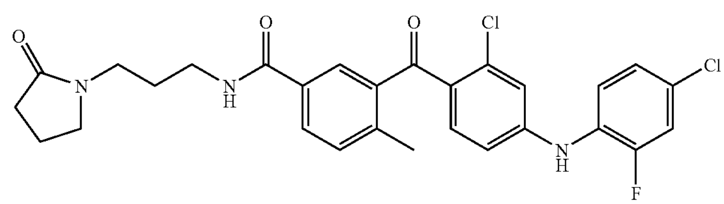 |
| 133 | 33 | 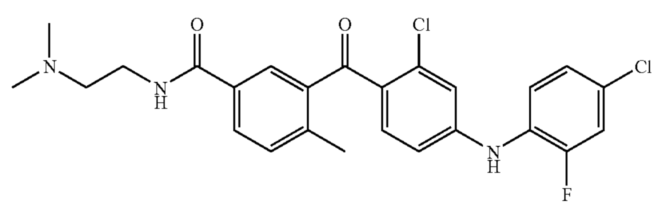 |
| 134 | 34 | 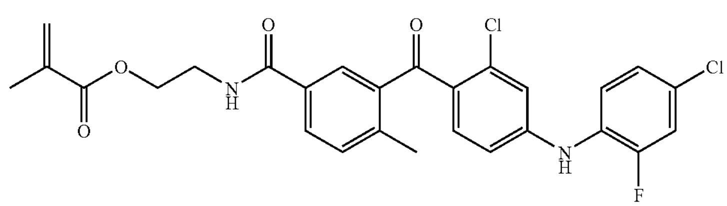 |
| 135 | 35 | 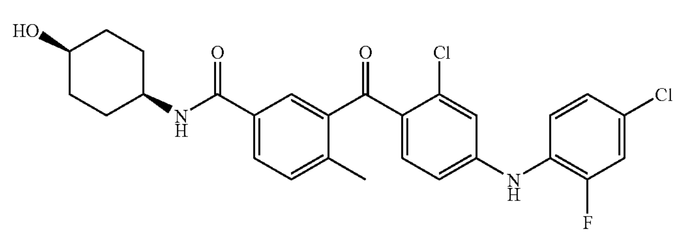 |
| 136 | 36 | 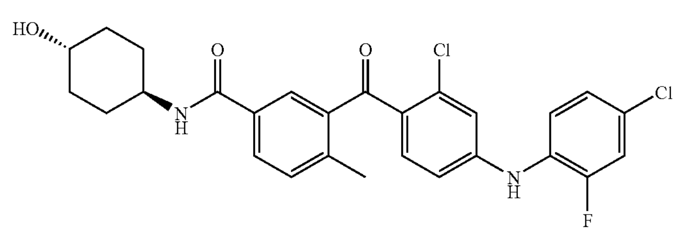 |

TABLE 4-continued

Exemplified compounds of general formula I

| Compound | Example no. | Structure |
|---|---|---|
| 137 | 37 | 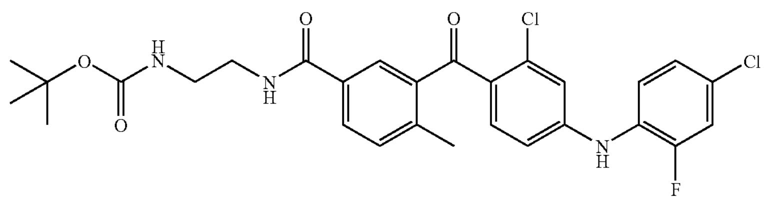 |
| 138 | 38 | 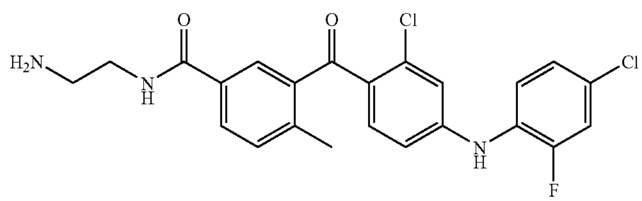 |
| 139 | 39 | 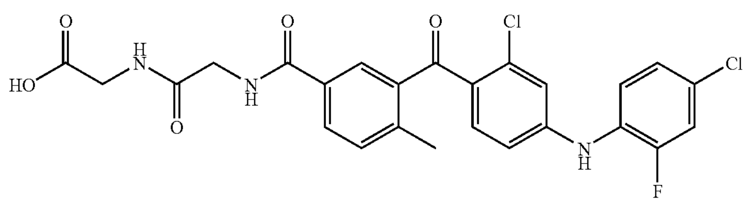 |
| 140 | 40 | 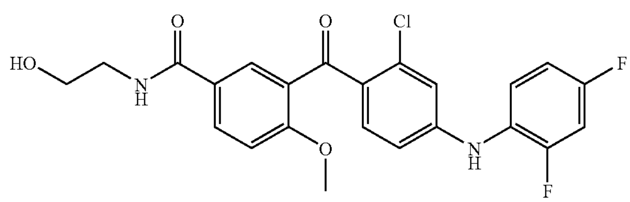 |
| 141 | 41 | 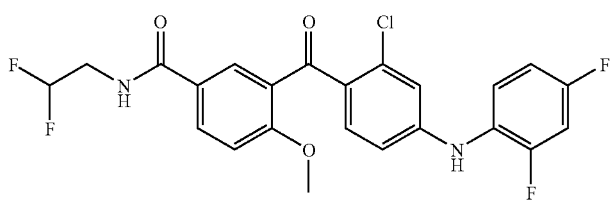 |
| 142 | 42 | 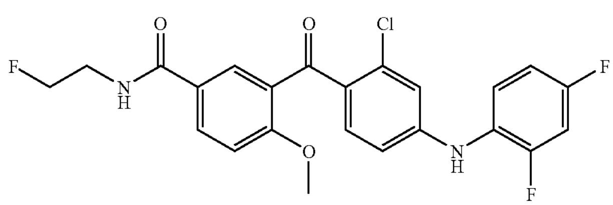 |
| 143 | 43 | 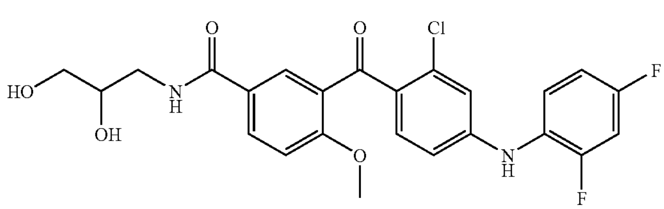 |

TABLE 4-continued

Exemplified compounds of general formula I

| Compound | Example no. | Structure |
|---|---|---|
| 144 | 44 | 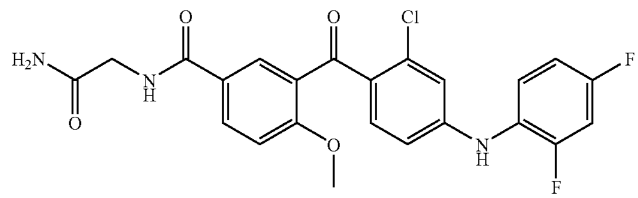 |
| 145 | 45 | 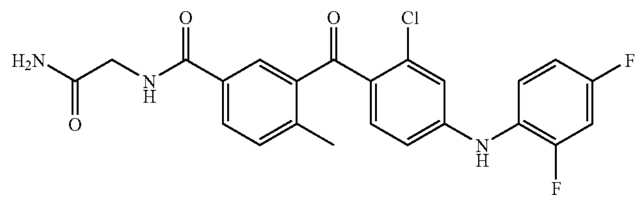 |
| 146 | 46 | 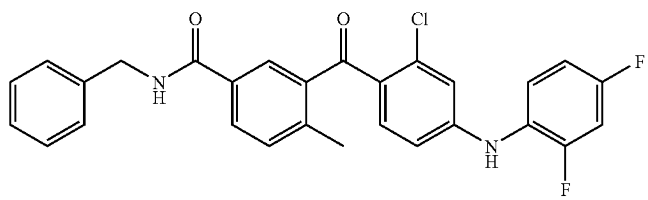 |
| 147 | 47 | 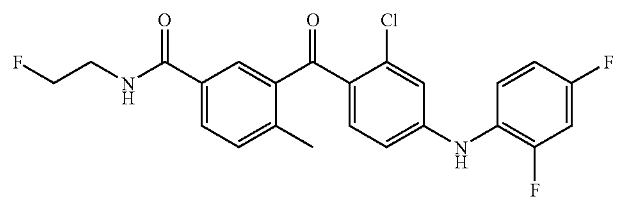 |
| 148 | 48 | 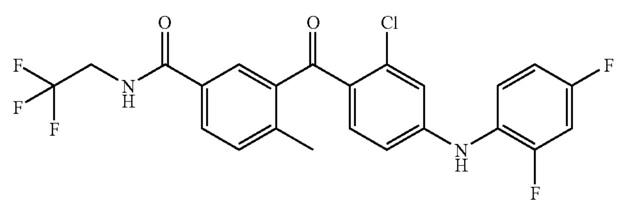 |
| 149 | 49 | 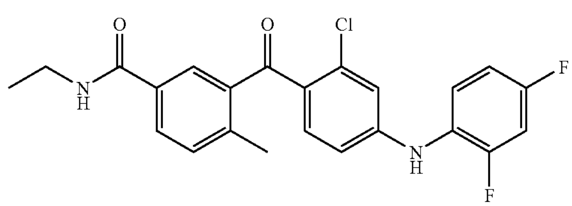 |
| 150 | 50 | 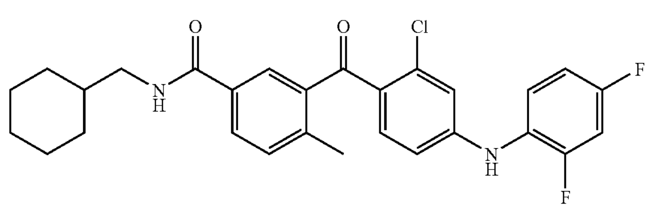 |

TABLE 4-continued

Exemplified compounds of general formula I

| Compound | Example no. | Structure |
|---|---|---|
| 151 | 51 | 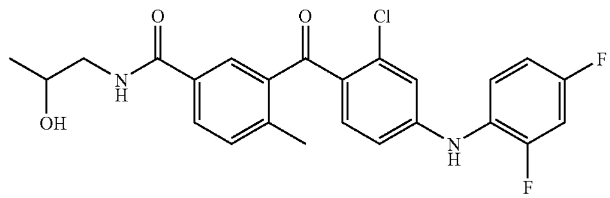 |
| 152 | 52 | 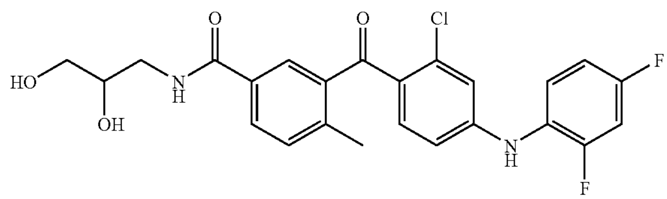 |
| 153 | 53 | 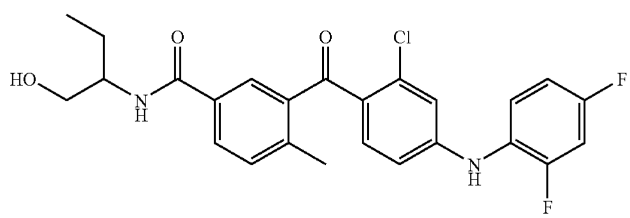 |
| 154 | 54 | 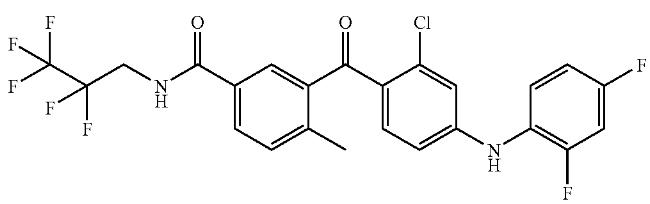 |
| 155 | 55 | 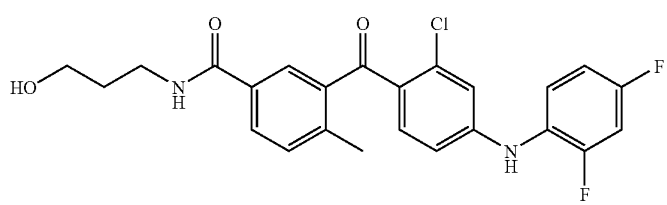 |
| 156 | 56 | 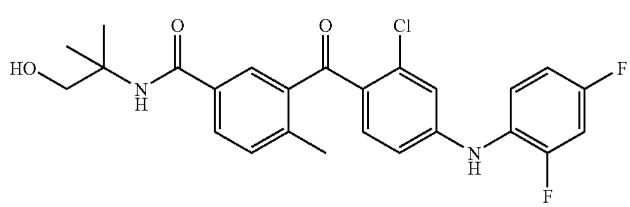 |
| 157 | 57 | 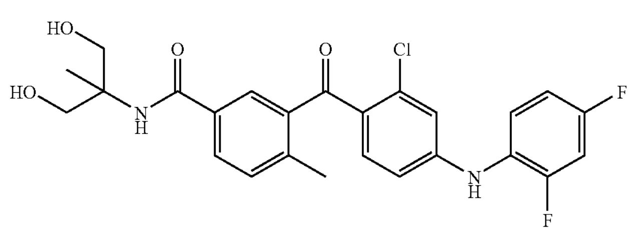 |

TABLE 4-continued
Exemplified compounds of general formula I
| Compound | Example no. | Structure |
|---|---|---|
| 158 | 58 | 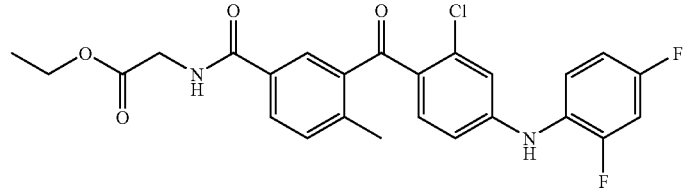 |
| 159 | 59 | 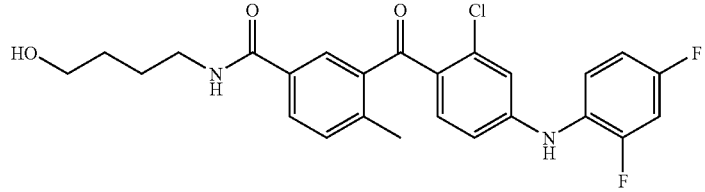 |
| 160 | 60 | 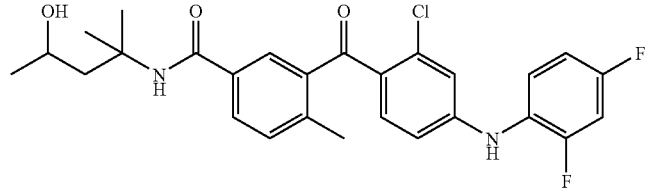 |
| 161 | 61 | 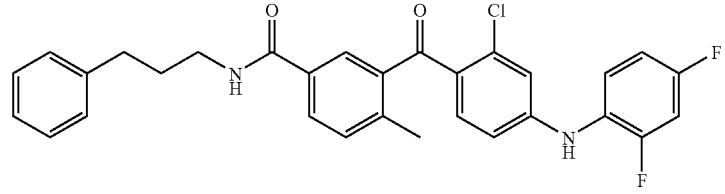 |
| 162 | 62 | 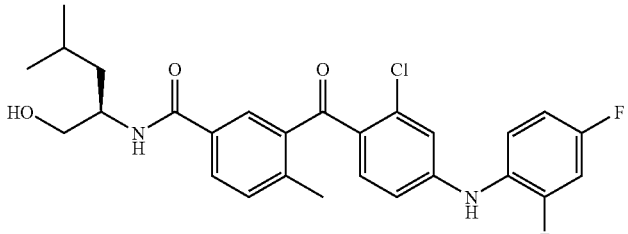 |
| 163 | 63 | 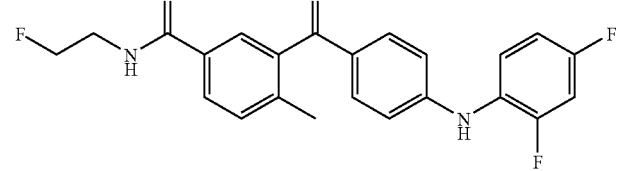 |
| 164 | 64 | 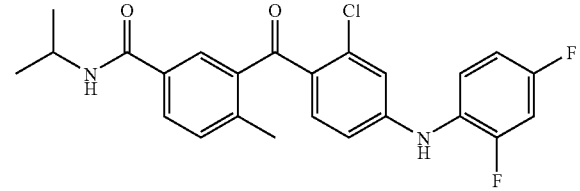 |

TABLE 4-continued

Exemplified compounds of general formula I

| Compound | Example no. | Structure |
|---|---|---|
| 165 | 65 | 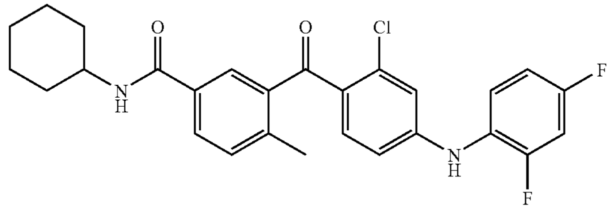 |
| 166 | 66 | 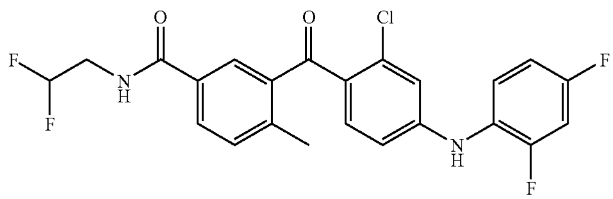 |
| 167 | 67 | 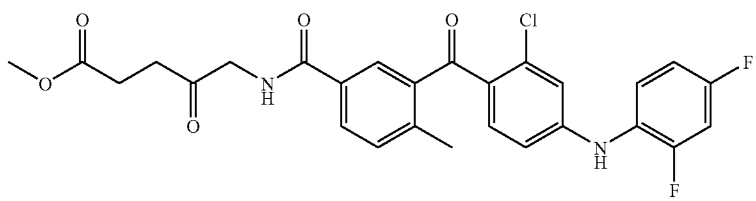 |
| 168 | 68 | 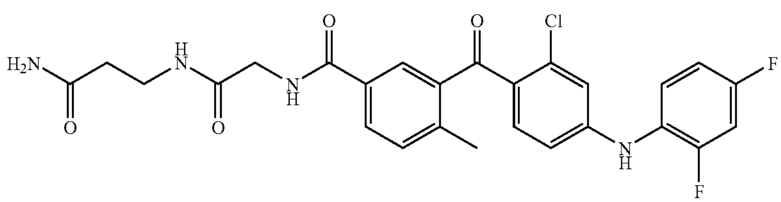 |
| 169 | 69 | 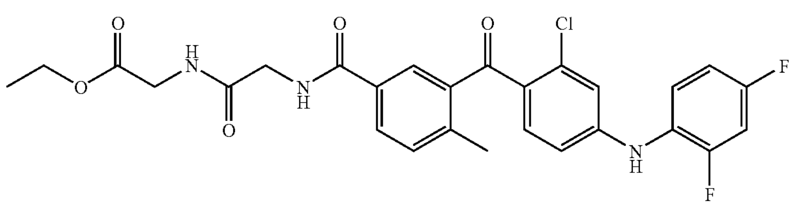 |
| 170 | 70 | 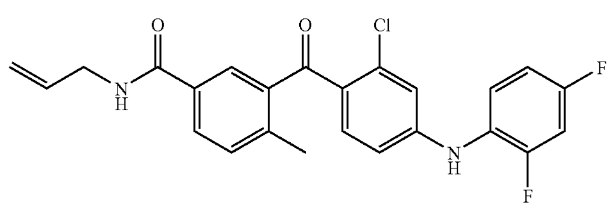 |
| 171 | 71 | 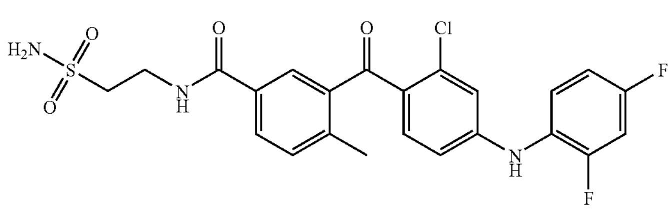 |

TABLE 4-continued

| Exemplified compounds of general formula I | | |
|---|---|---|
| Compound | Example no. | Structure |
| 172 | 72 | |
| 173 | 73 | |
| 174 | 74 | |
| 175 | 75 | |
| 176 | 76 | |
| 177 | 77 | |
| 178 | 78 | |

TABLE 4-continued

Exemplified compounds of general formula I

| Compound | Example no. | Structure |
|---|---|---|
| 179 | 79 | 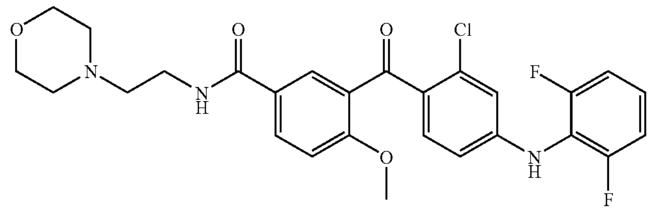 |
| 180 | 80 | 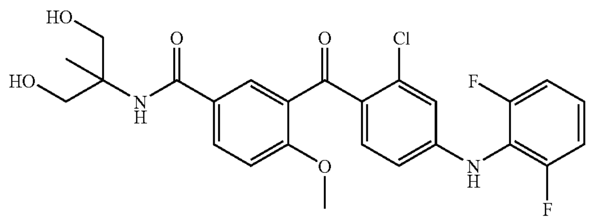 |
| 181 | 81 | 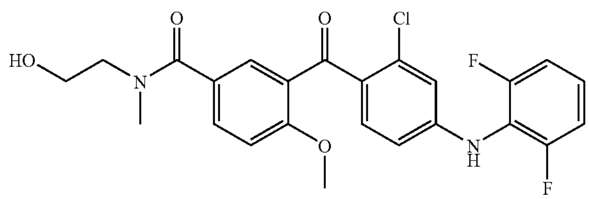 |
| 182 | 82 | 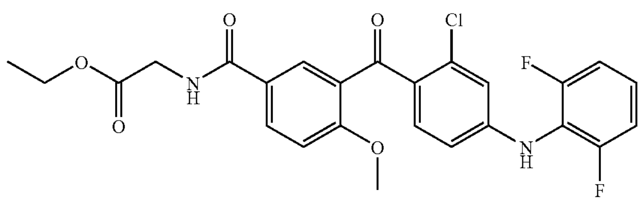 |
| 183 | 83 | 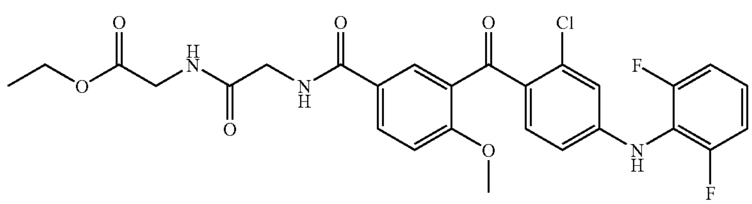 |
| 184 | 84 | 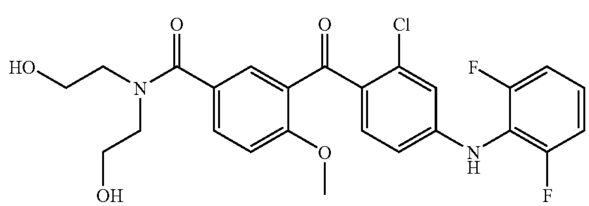 |
| 185 | 85 | 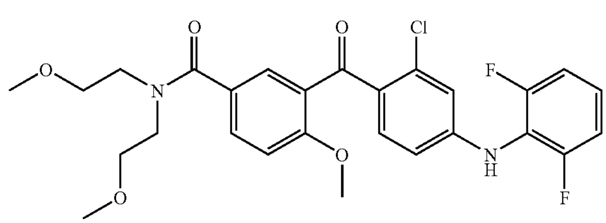 |

TABLE 4-continued

Exemplified compounds of general formula I

| Compound | Example no. | Structure |
|---|---|---|
| 186 | 86 | 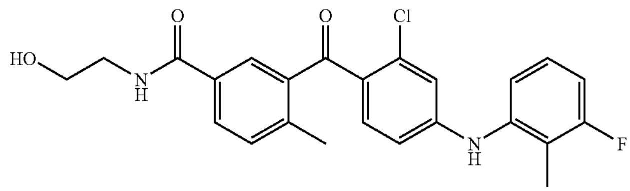 |
| 187 | 87 | 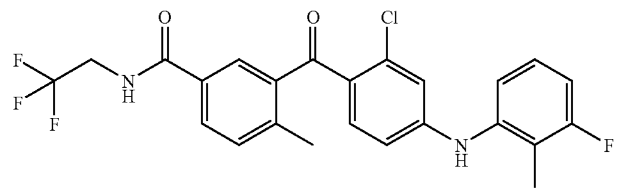 |
| 188 | 88 | 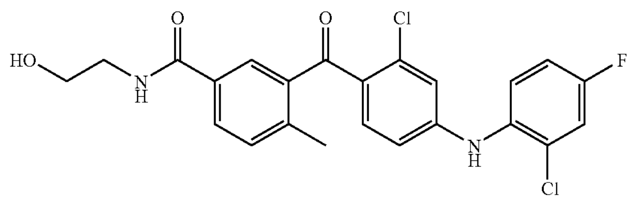 |
| 189 | 89 | 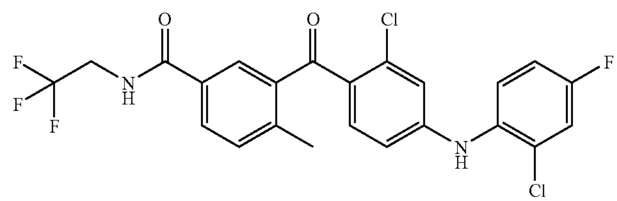 |
| 190 | 90 | 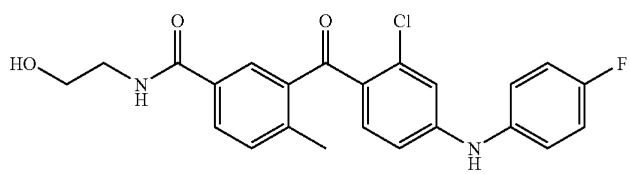 |
| 191 | 91 | 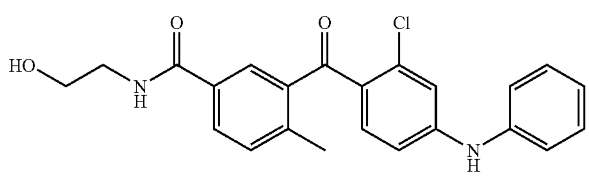 |
| 192 | 92 | 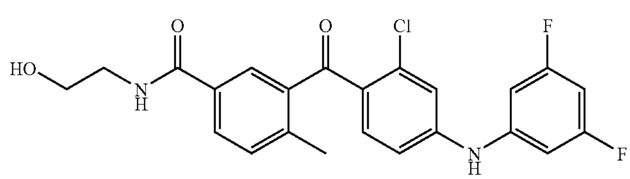 |
| 193 | 93 | 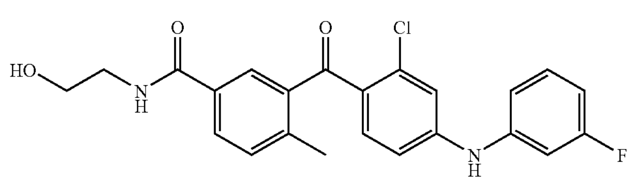 |

TABLE 4-continued

Exemplified compounds of general formula I

| Compound | Example no. | Structure |
|---|---|---|
| 194 | 94 | 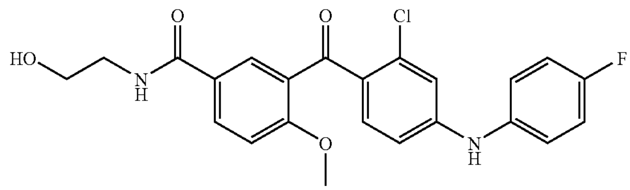 |
| 195 | 95 | 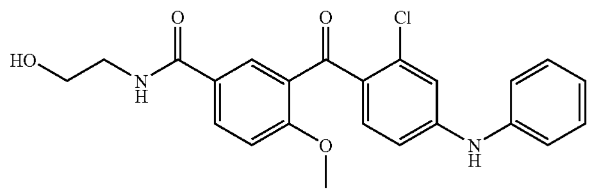 |
| 196 | 96 | 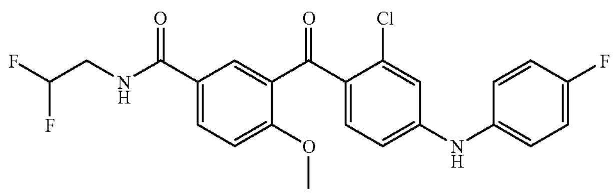 |
| 197 | 97 | 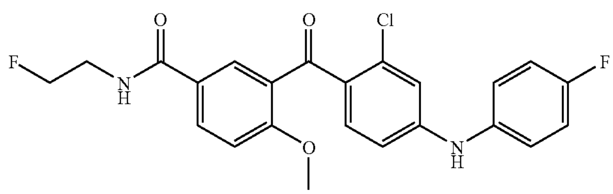 |
| 198 | 98 | 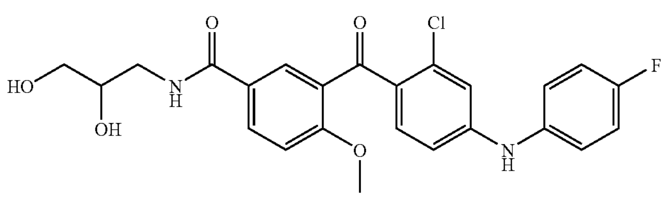 |
| 199 | 99 | 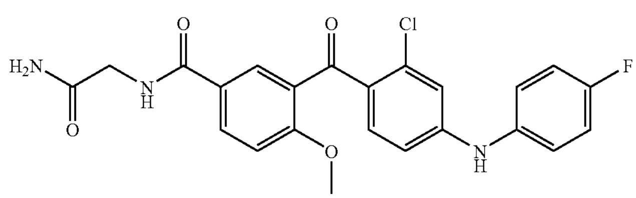 |
| 200 | 100 | 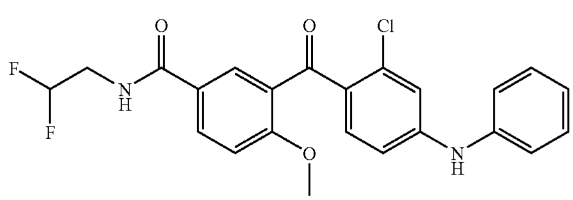 |

TABLE 4-continued

Exemplified compounds of general formula I

| Compound | Example no. | Structure |
|---|---|---|
| 201 | 101 | 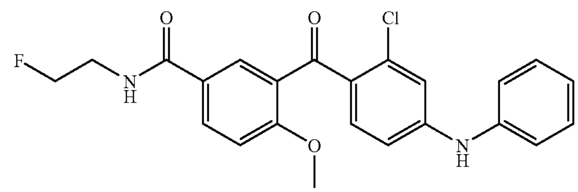 |
| 202 | 102 | 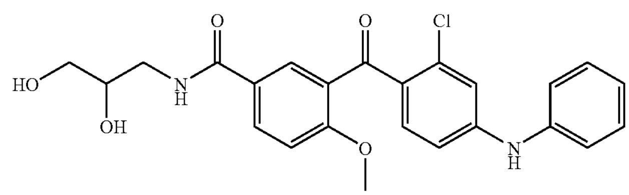 |
| 203 | 103 | 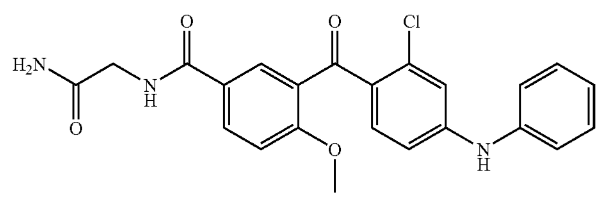 |
| 204 | 104 | 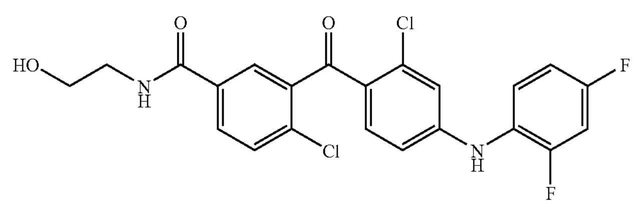 |
| 205 | 105 | 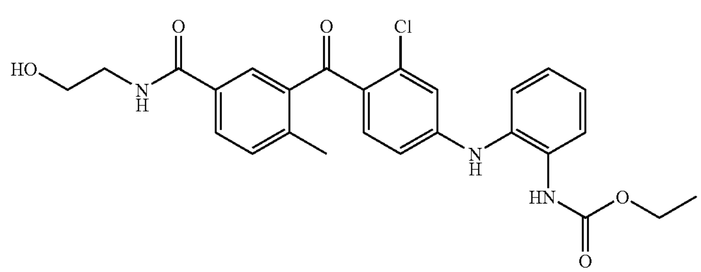 |
| 206 | 106 | 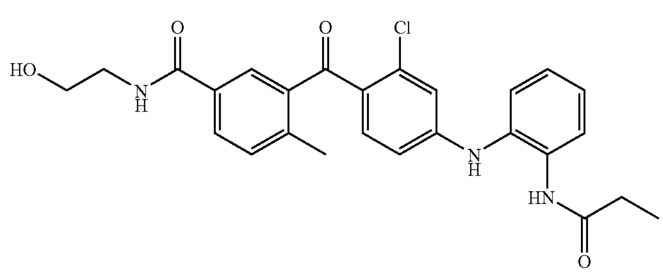 |

TABLE 4-continued

| Compound | Example no. | Structure |
|---|---|---|
| 207 | 107 | 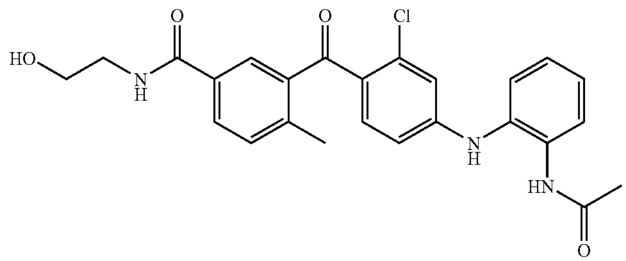 |
| 208 | 108 | 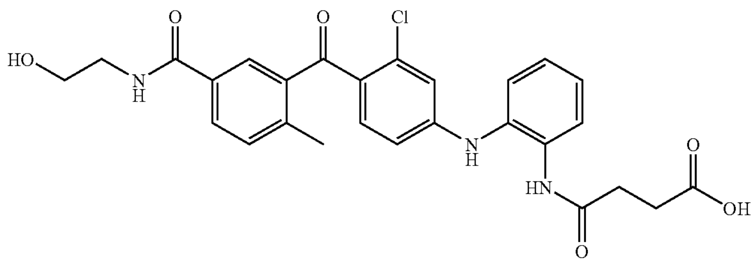 |
| 209 | 109 | 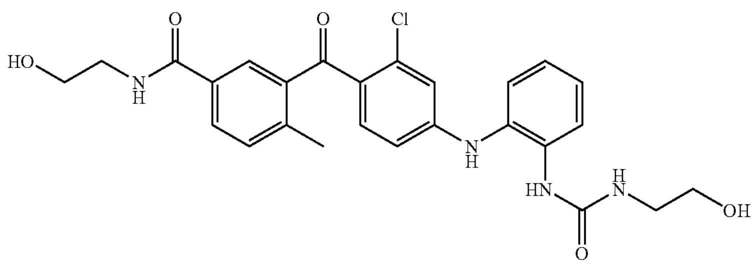 |
| 210 | 110 | 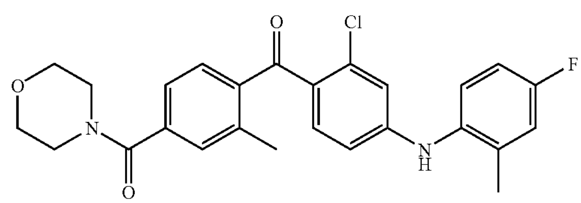 |
| 211 | 111 | 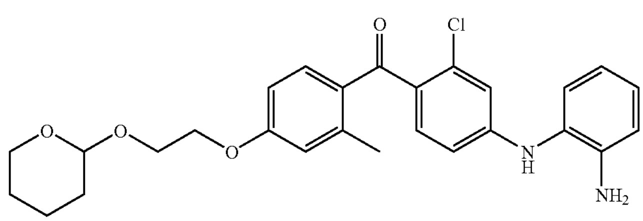 |
| 212 | 112 | 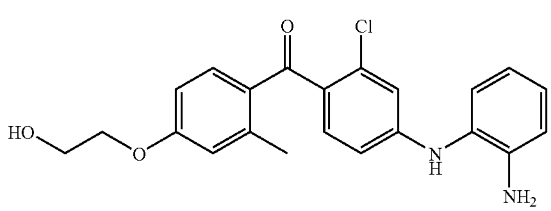 |

TABLE 4-continued

Exemplified compounds of general formula I

| Compound | Example no. | Structure |
|---|---|---|
| 213 | 113 | 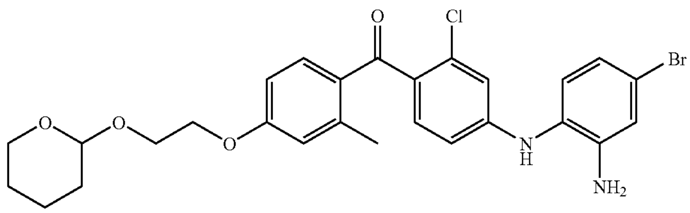 |
| 214 | 114 | 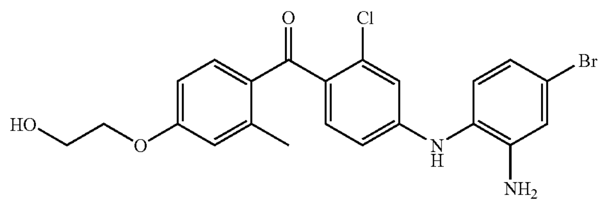 |
| 215 | 115 | 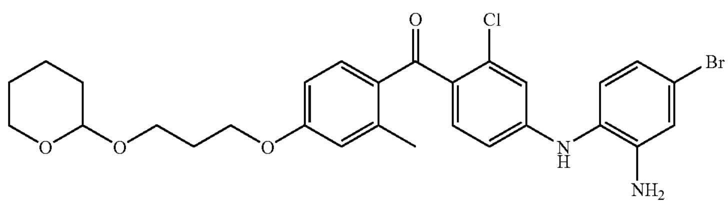 |
| 216 | 116 | 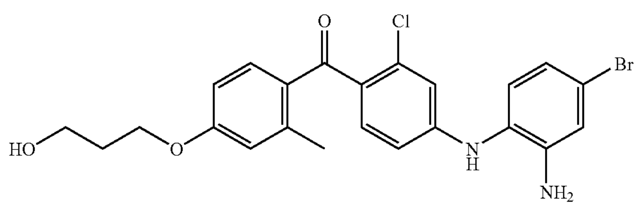 |
| 217 | 117 | 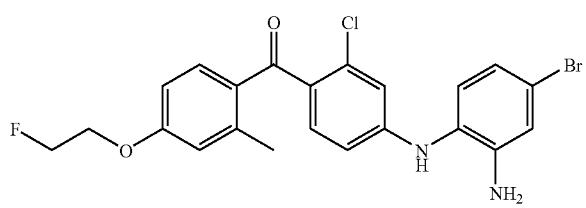 |
| 218 | 118 | 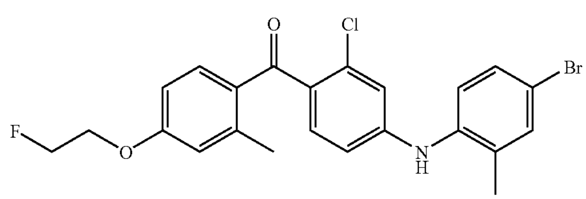 |
| 219 | 119 | 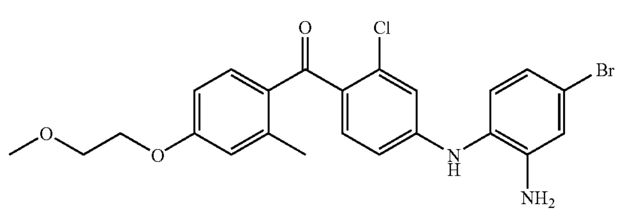 |

TABLE 4-continued

Exemplified compounds of general formula I

| Compound | Example no. | Structure |
|---|---|---|
| 220 | 120 | 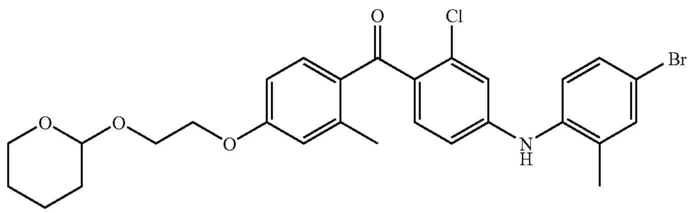 |
| 221 | 121 | 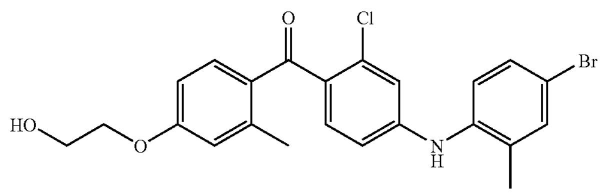 |
| 222 | 122 | 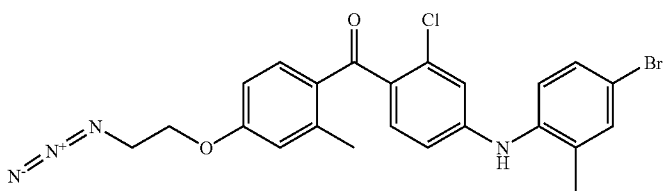 |
| 223 | 123 | 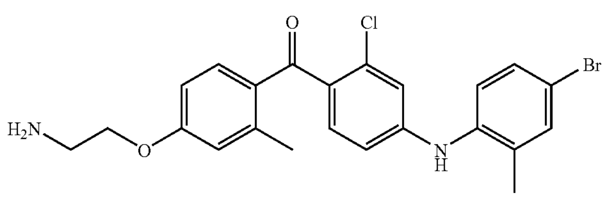 |
| 224 | 124 | 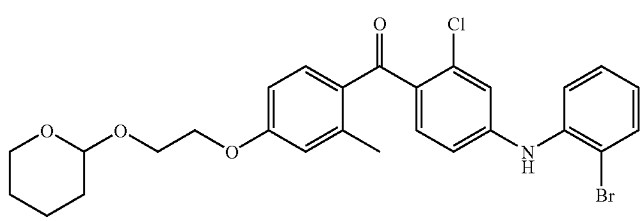 |
| 225 | 125 | 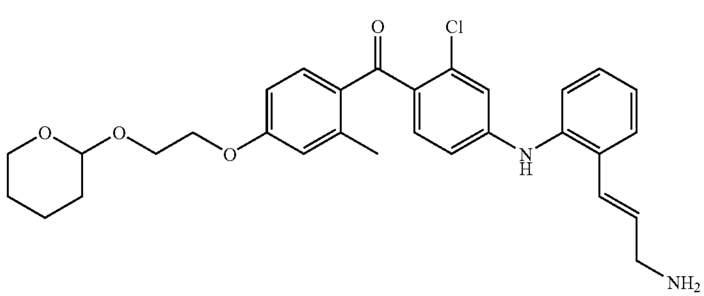 |

TABLE 4-continued

Exemplified compounds of general formula I

| Compound | Example no. | Structure |
|---|---|---|
| 226 | 126 | 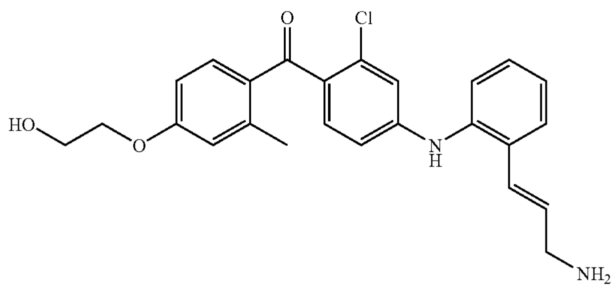 |
| 227 | 127 | 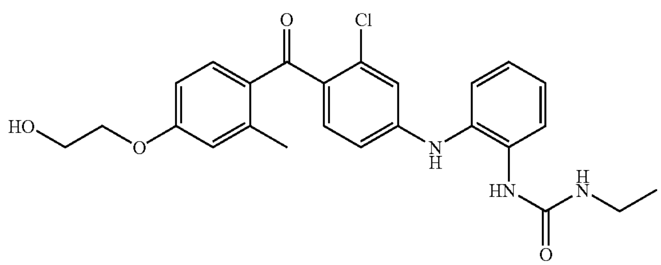 |
| 228 | 128 | 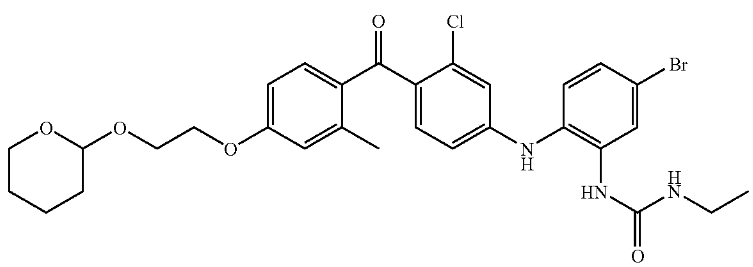 |
| 229 | 129 | 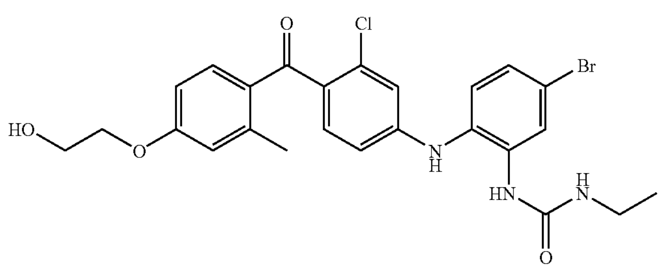 |
| 230 | 130 | 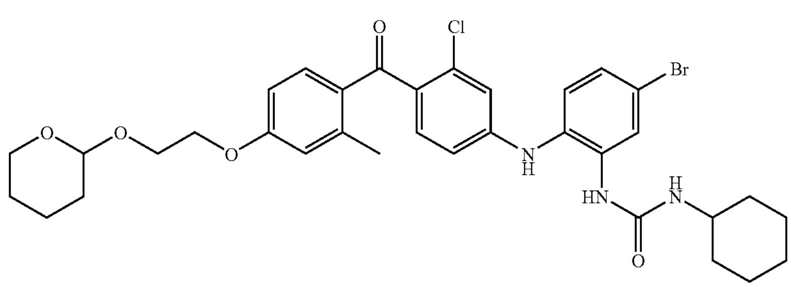 |

TABLE 4-continued
Exemplified compounds of general formula I
| Compound | Example no. | Structure |
|---|---|---|
| 231 | 131 | 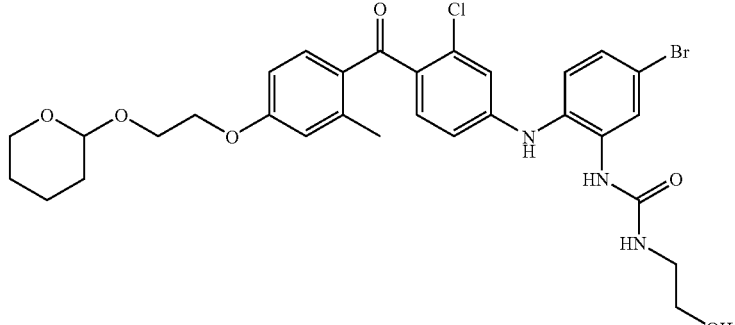 |
| 232 | 132 | 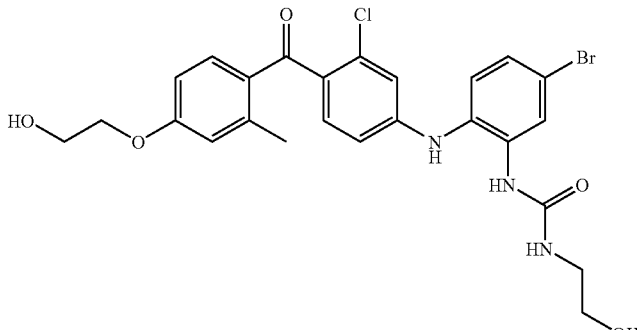 |
| 233 | 133 | 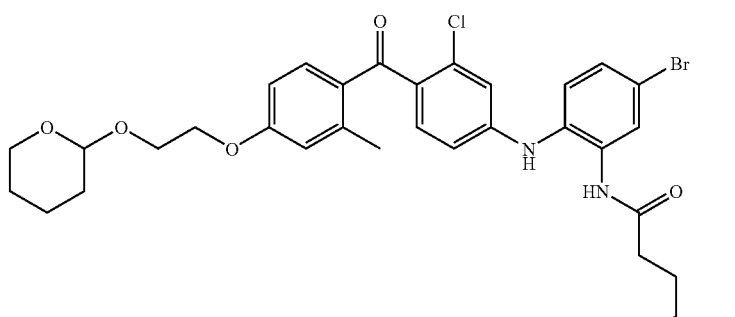 |
| 234 | 134 | 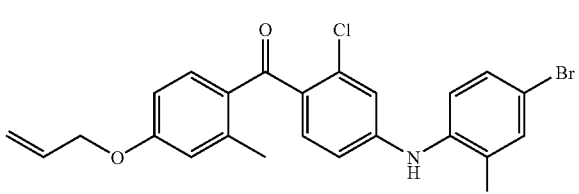 |
| 235 | 135 | 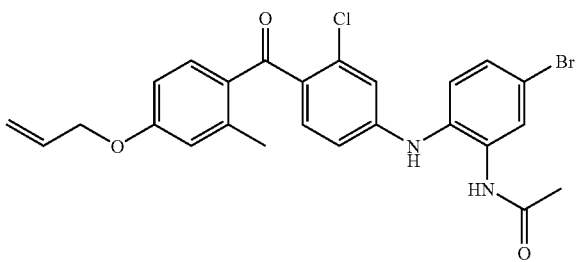 |

TABLE 4-continued
Exemplified compounds of general formula I
| Compound | Example no. | Structure |
|---|---|---|
| 236 | 136 | 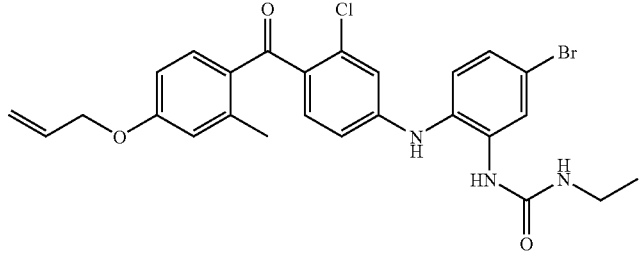 |
| 237 | 137 | 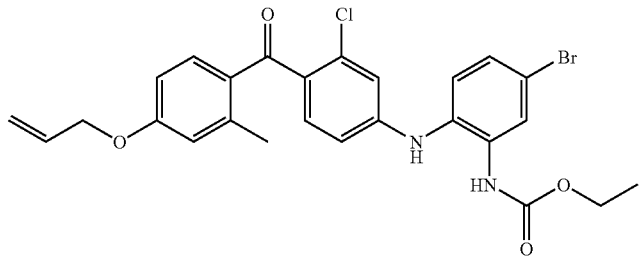 |
| 238 | 138 | 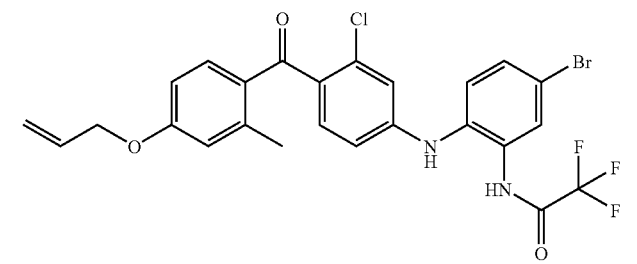 |
| 239 | 139 | 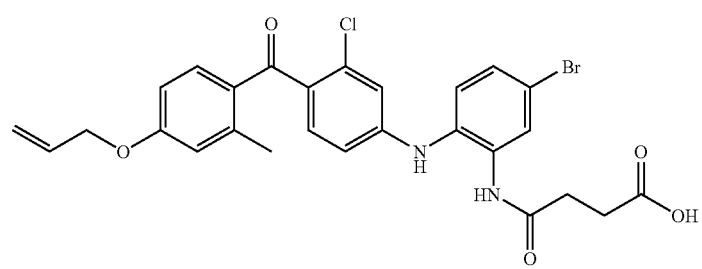 |
| 240 | 140 | 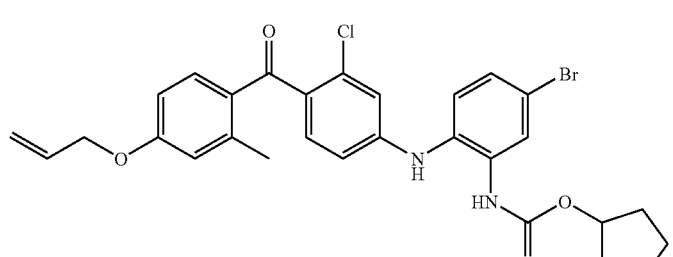 |
| 241 | 141 | 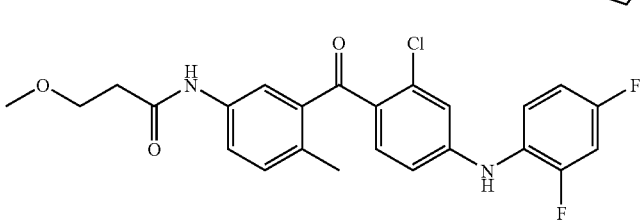 |

TABLE 4-continued

Exemplified compounds of general formula I

| Compound | Example no. | Structure |
|---|---|---|
| 242 | 142 | 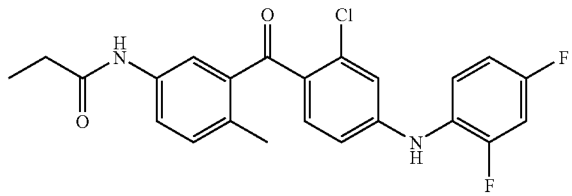 |
| 243 | 143 | 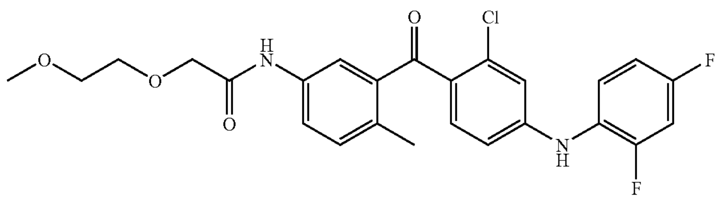 |
| 244 | 144 | 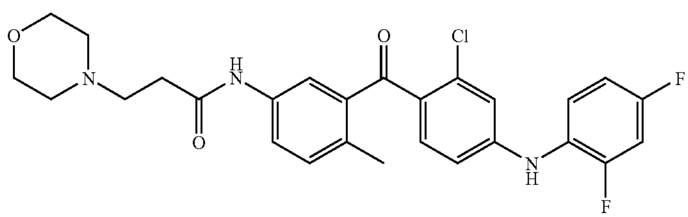 |
| 245 | 145 | 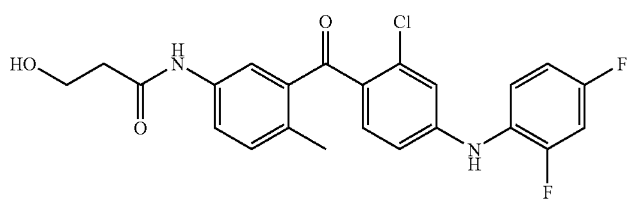 |
| 246 | 146 | 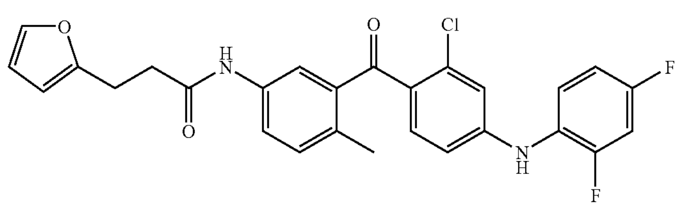 |
| 247 | 147 | 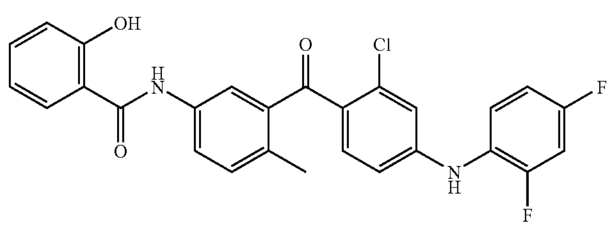 |
| 248 | 148 | 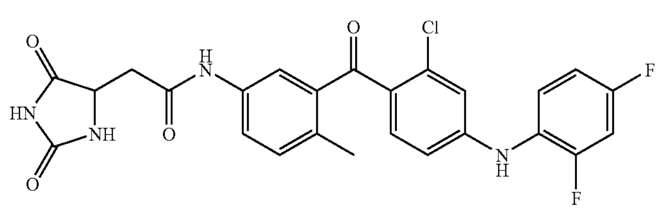 |

TABLE 4-continued

Exemplified compounds of general formula I

| Compound | Example no. | Structure |
|---|---|---|
| 249 | 149 | 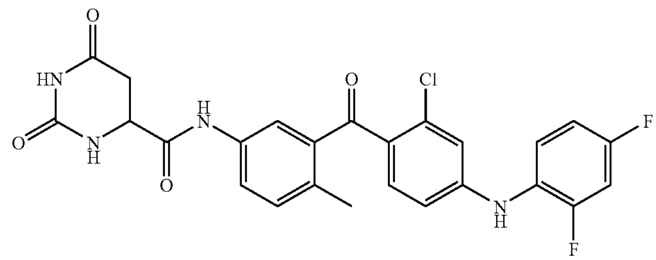 |
| 250 | 150 | 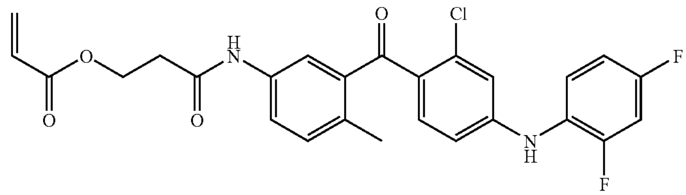 |
| 251 | 151 | 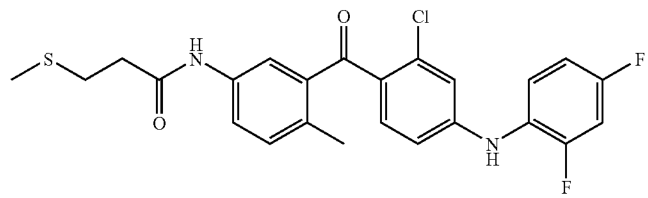 |
| 252 | 152 | 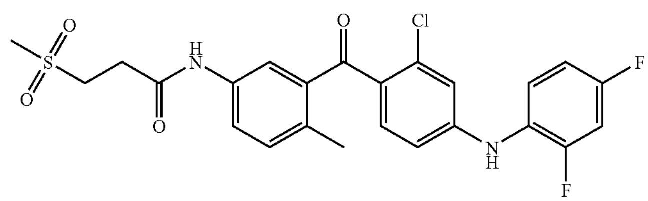 |
| 253 | 153 | 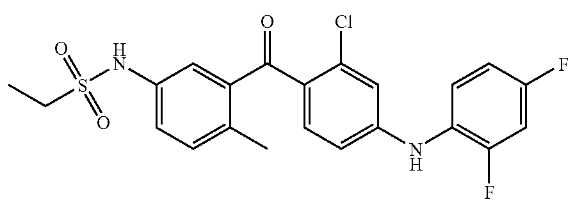 |
| 254 | 154 | 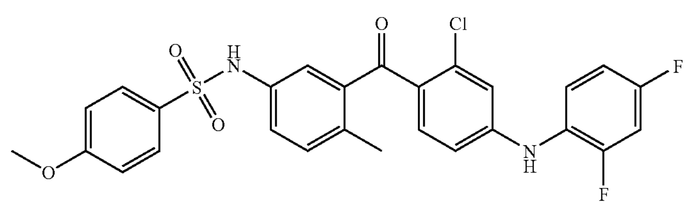 |
| 255 | 155 | 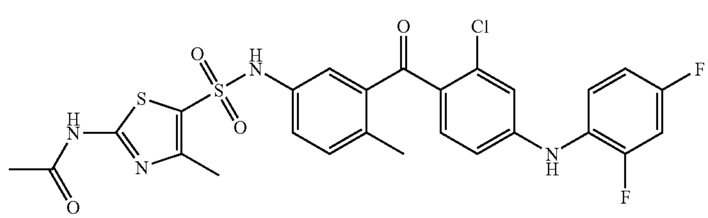 |

TABLE 4-continued

Exemplified compounds of general formula I

| Compound | Example no. | Structure |
|---|---|---|
| 256 | 156 | 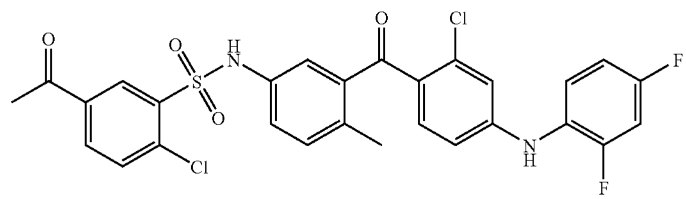 |
| 257 | 157 | 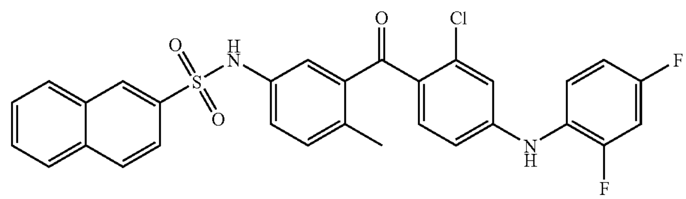 |
| 258 | 158 | 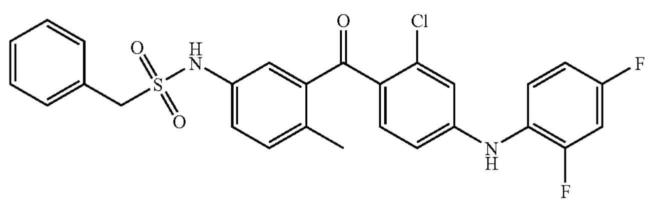 |
| 259 | 159 | 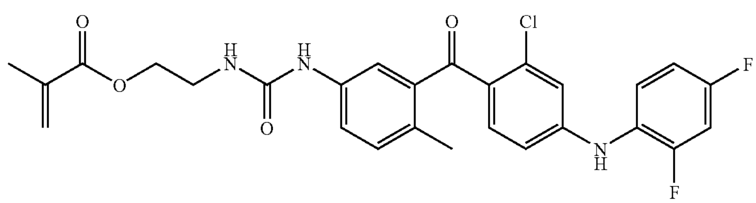 |
| 260 | 160 | 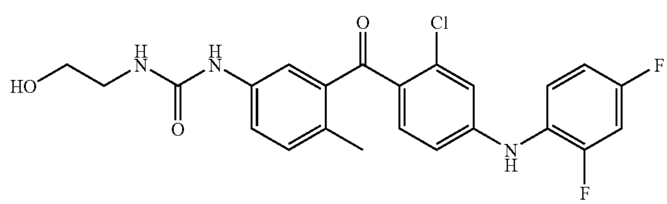 |
| 261 | 161 | 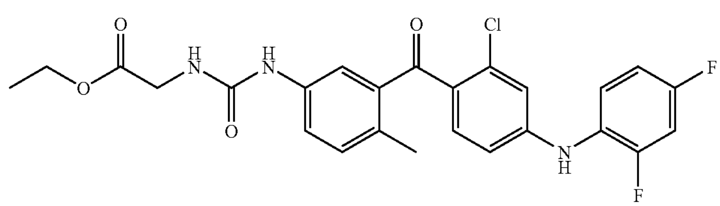 |
| 262 | 162 | 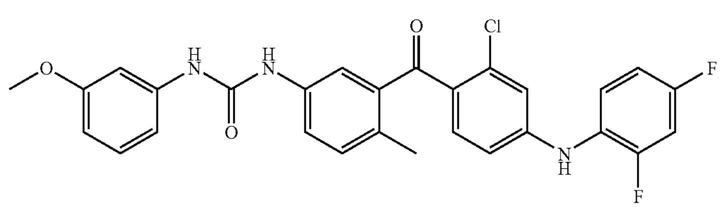 |

TABLE 4-continued

Exemplified compounds of general formula I

| Compound | Example no. | Structure |
|---|---|---|
| 263 | 163 | 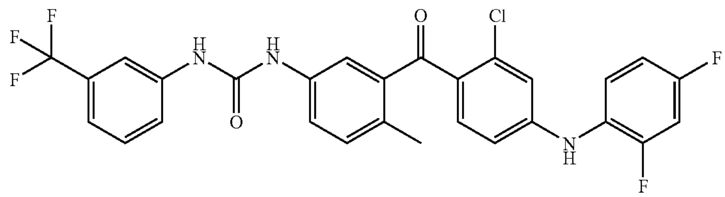 |
| 264 | 164 | 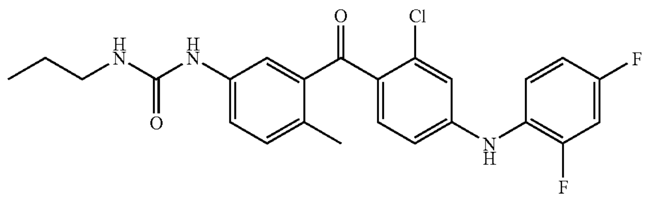 |
| 265 | 165 | 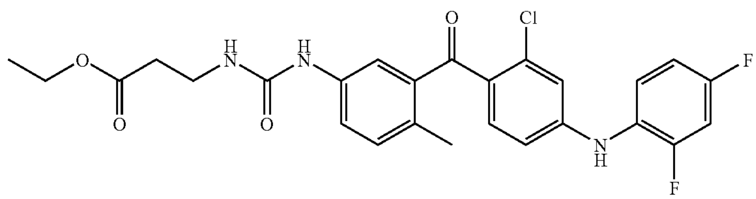 |
| 266 | 166 | 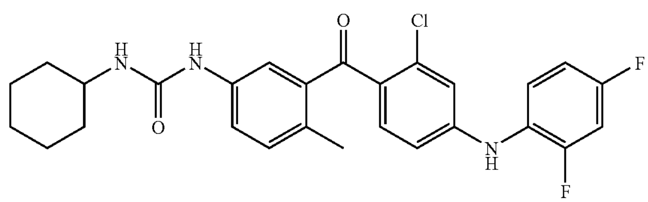 |
| 267 | 167 | 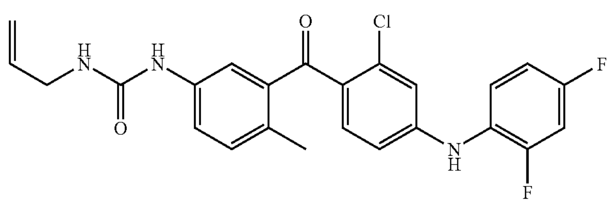 |
| 268 | 168 | 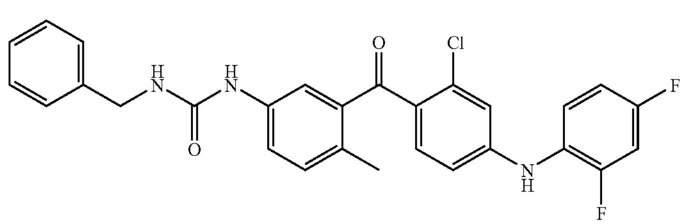 |
| 269 | 169 | 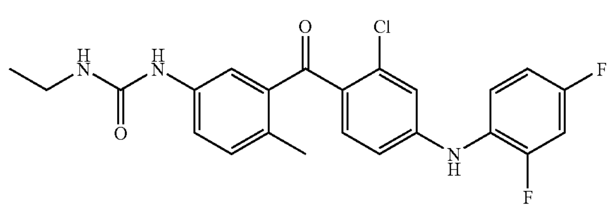 |

TABLE 4-continued

Exemplified compounds of general formula I

| Compound | Example no. | Structure |
|---|---|---|
| 270 | 170 | 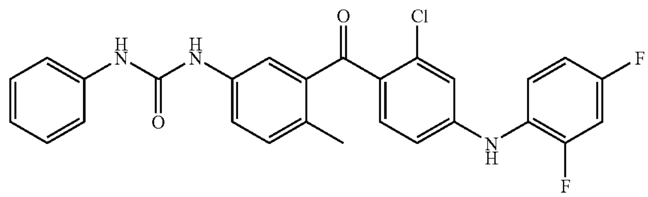 |
| 271 | 171 | 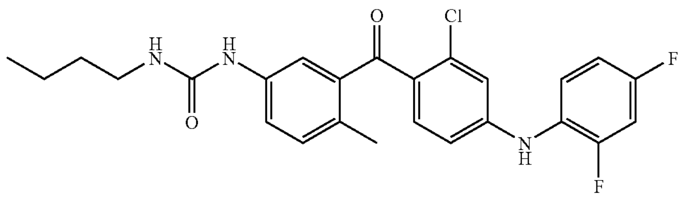 |
| 272 | 172 | 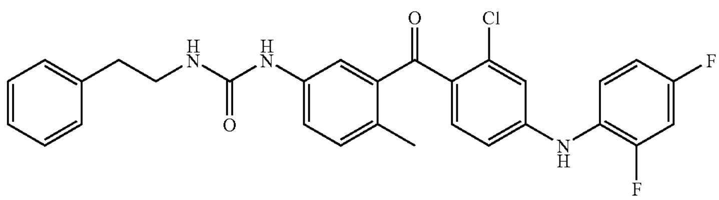 |
| 273 | 173 | 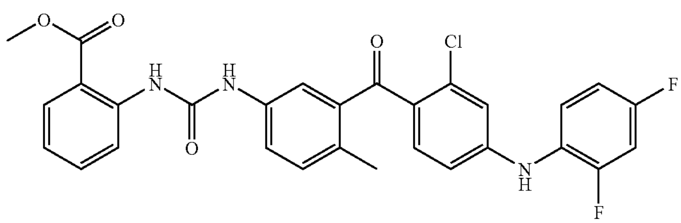 |
| 274 | 174 | 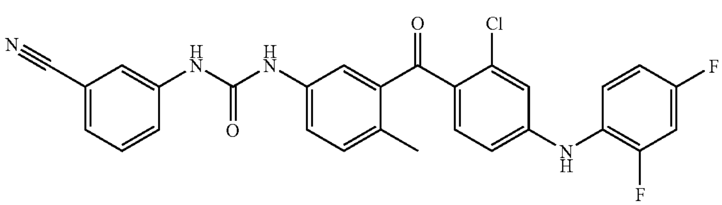 |
| 275 | 175 | 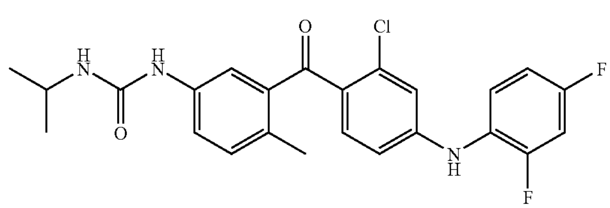 |
| 276 | 176 | 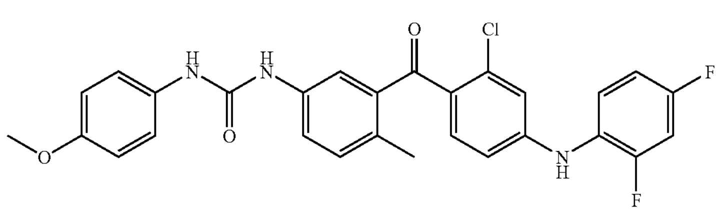 |

TABLE 4-continued

Exemplified compounds of general formula I

| Compound | Example no. | Structure |
|---|---|---|
| 277 | 177 | 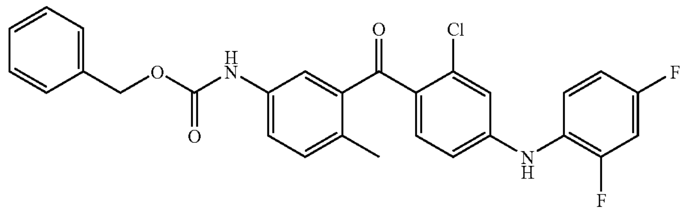 |
| 278 | 178 | 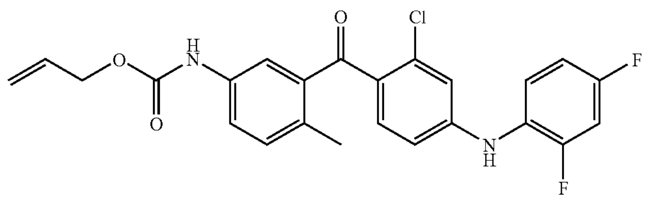 |
| 279 | 179 | 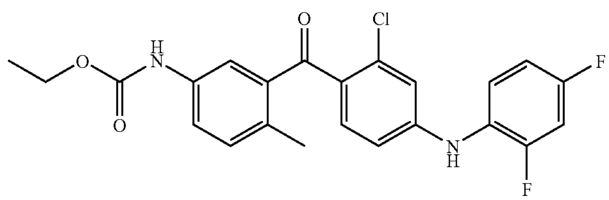 |
| 281 | 181 | 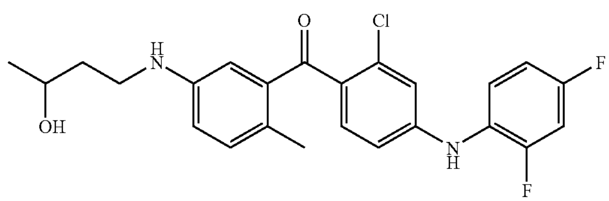 |
| 282 | 182 | 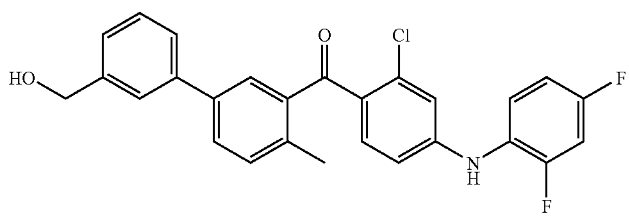 |
| 283 | 183 | 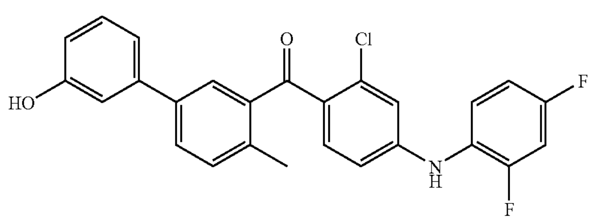 |
| 284 | 184 | 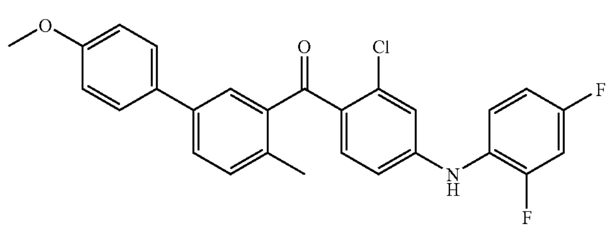 |

TABLE 4-continued

Exemplified compounds of general formula I

| Compound | Example no. | Structure |
|---|---|---|
| 285 | 185 | 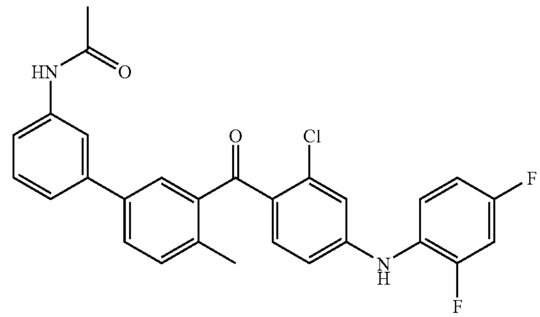 |
| 286 | 186 | 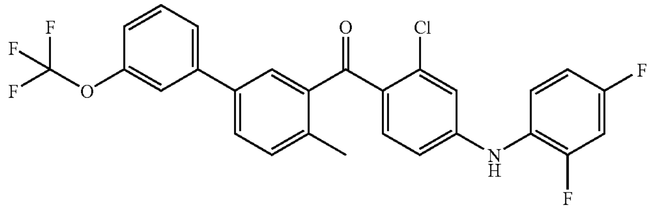 |
| 288 | 188 | 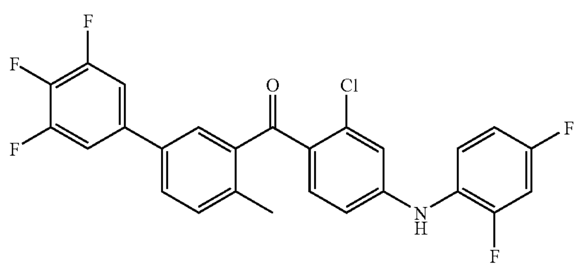 |
| 289 | 189 | 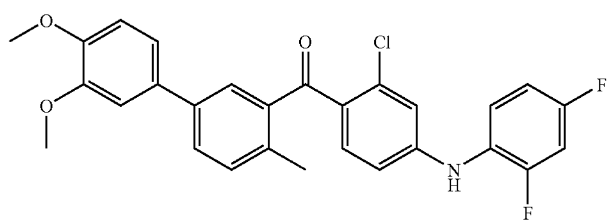 |
| 290 | 190 | 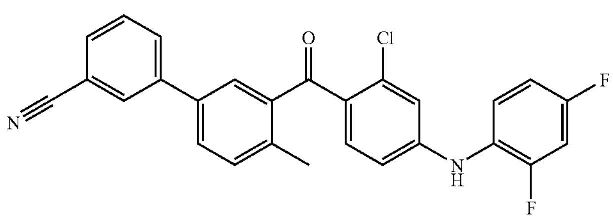 |
| 291 | 191 | 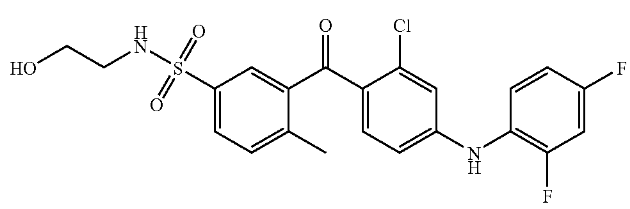 |

TABLE 4-continued

Exemplified compounds of general formula I

| Compound | Example no. | Structure |
|---|---|---|
| 292 | 192 | 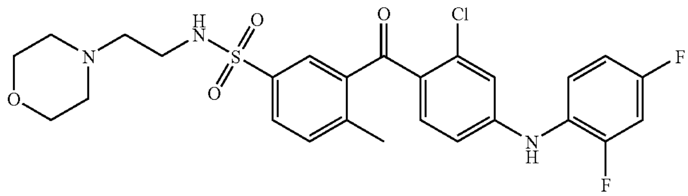 |
| 293 | 193 | 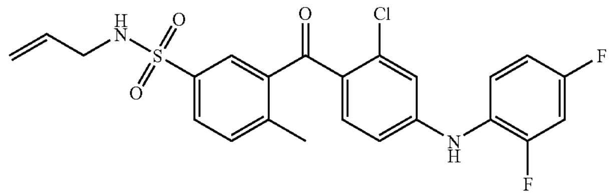 |
| 294 | 194 | 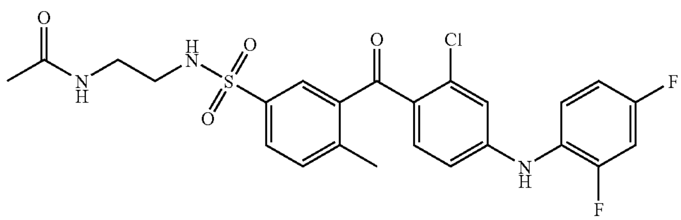 |
| 295 | 195 | 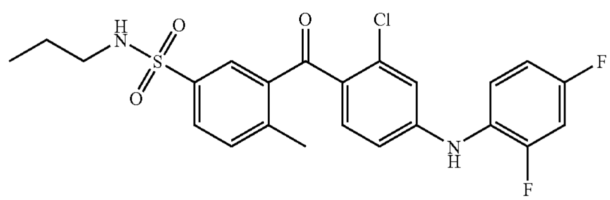 |
| 296 | 196 | 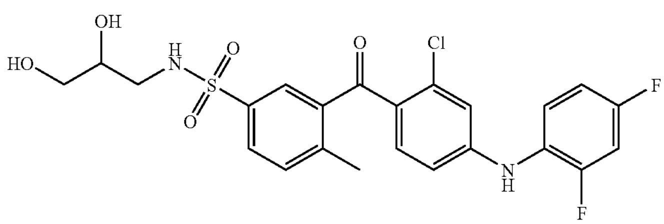 |
| 297 | 197 | 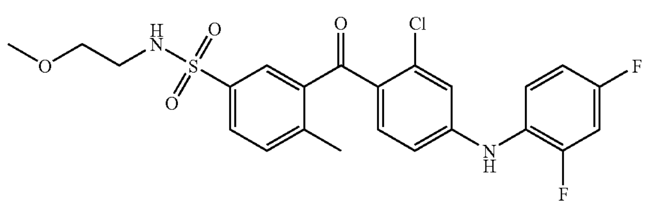 |
| 298 | 198 | 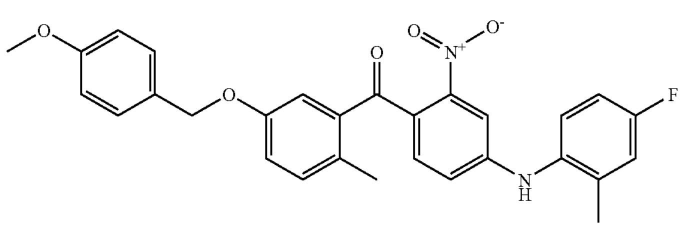 |

TABLE 4-continued

Exemplified compounds of general formula I

| Compound | Example no. | Structure |
|---|---|---|
| 299 | 199 | 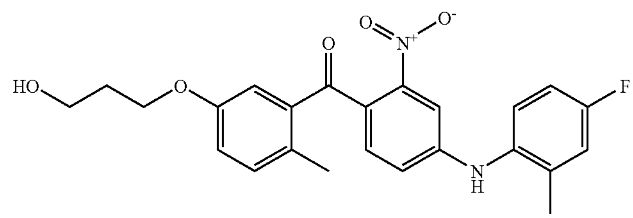 |
| 300 | 200 | 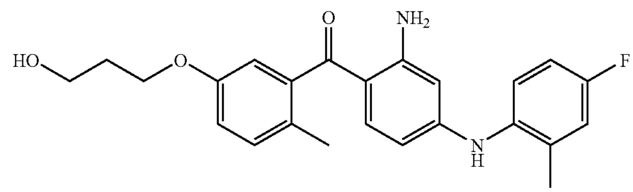 |
| 301 | 201 | 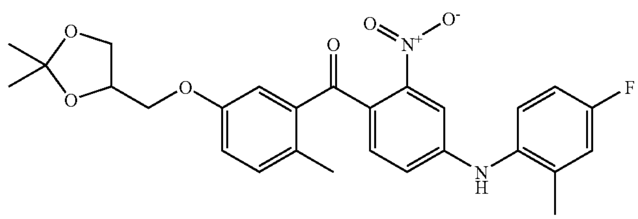 |
| 302 | 202 | 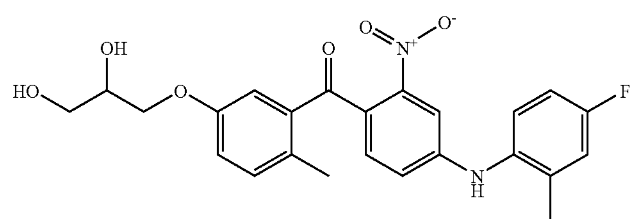 |
| 303 | 203 | 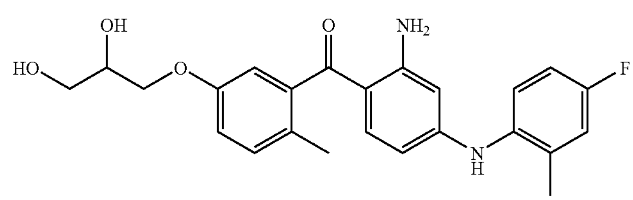 |
| 304 | 204 | 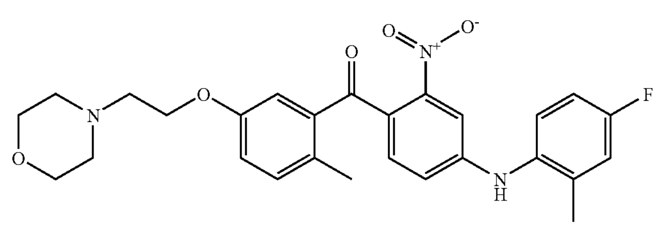 |
| 305 | 205 | 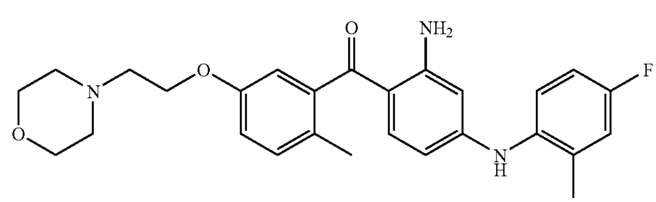 |

TABLE 4-continued

Exemplified compounds of general formula I

| Compound | Example no. | Structure |
|---|---|---|
| 306 | 206 | 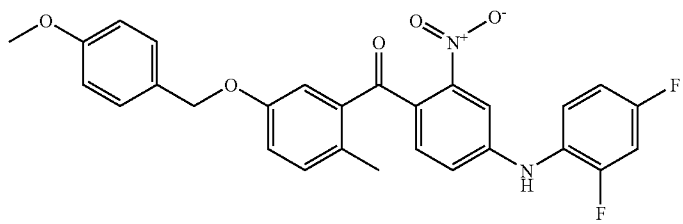 |
| 307 | 207 | 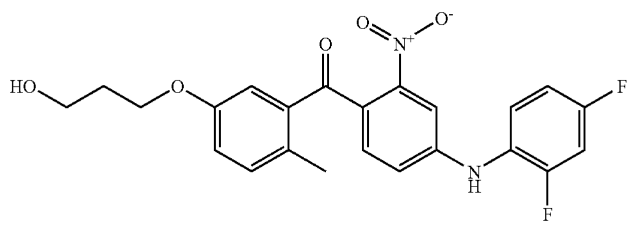 |
| 308 | 208 | 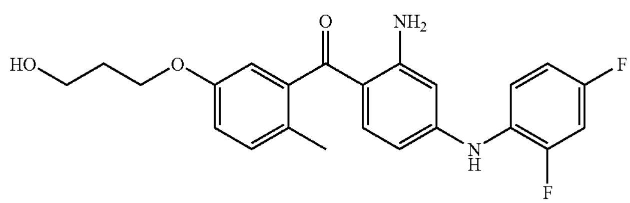 |
| 309 | 209 | 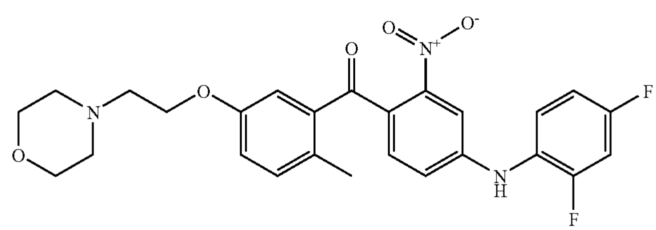 |
| 310 | 210 | 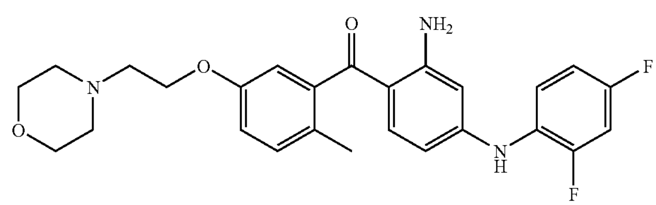 |
| 311 | 211 | 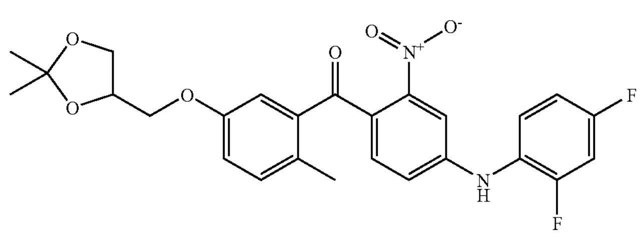 |

TABLE 4-continued
Exemplified compounds of general formula I
| Compound | Example no. | Structure |
|---|---|---|
| 312 | 212 | 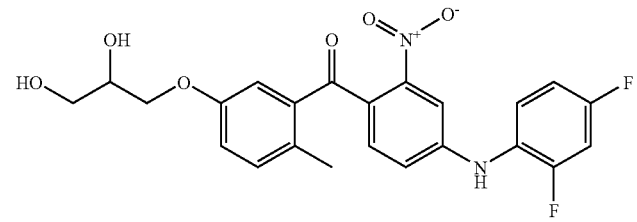 |
| 313 | 213 | 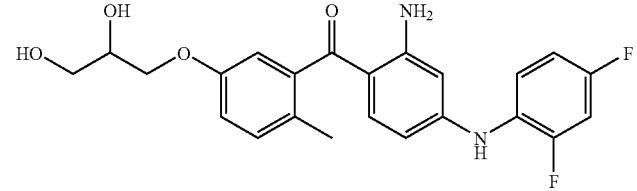 |
| 314 | 214 | 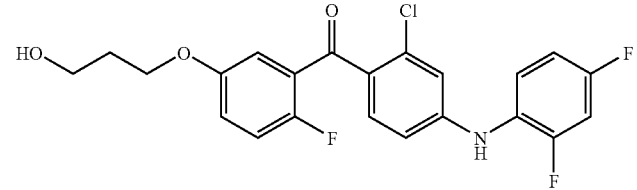 |
| 315 | 215 | 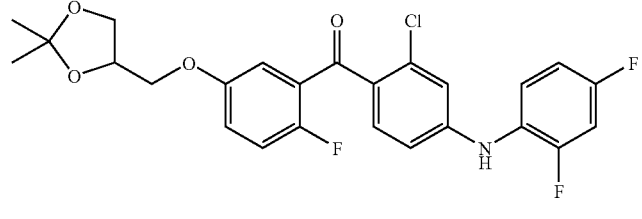 |
| 316 | 216 | 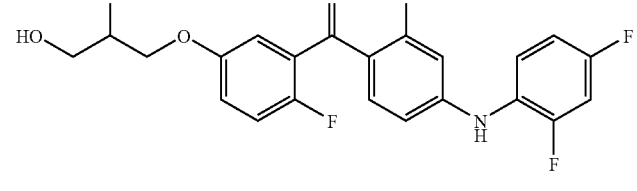 |
| 317 | 217 | 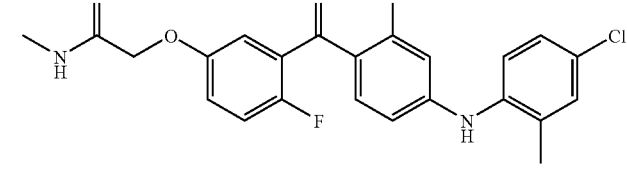 |
| 318 | 218 | 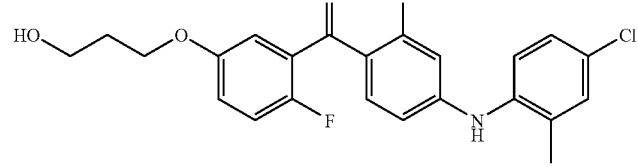 |

TABLE 4-continued

Exemplified compounds of general formula I

| Compound | Example no. | Structure |
|---|---|---|
| 319 | 219 | 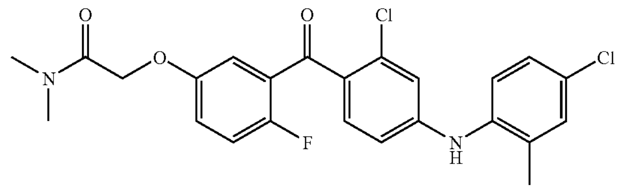 |
| 320 | 220 | 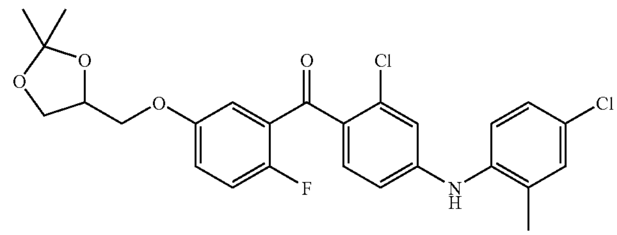 |
| 321 | 221 | 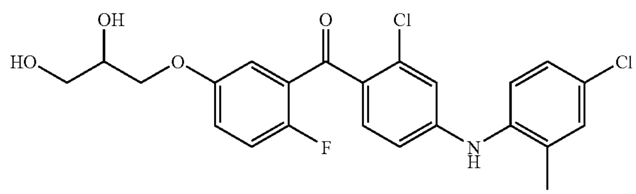 |
| 322 | 222 | 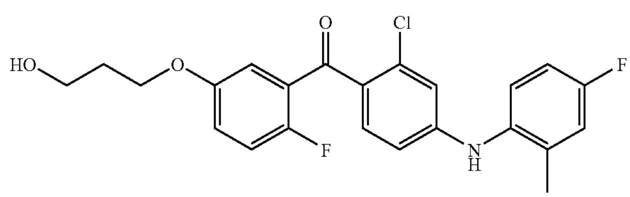 |
| 323 | 223 | 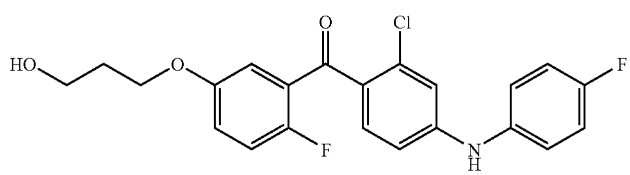 |
| 324 | 224 | 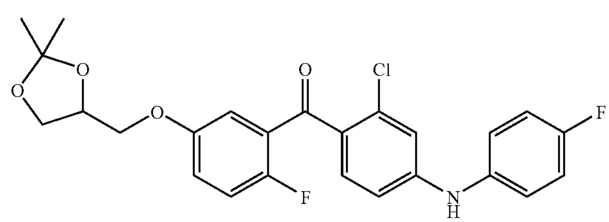 |
| 325 | 225 | 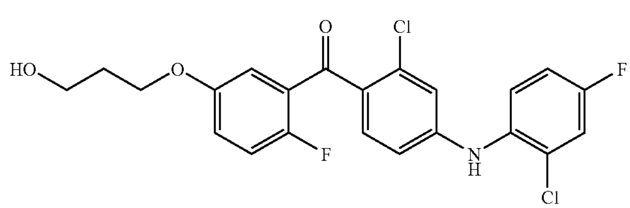 |

TABLE 4-continued
Exemplified compounds of general formula I
| Compound | Example no. | Structure |
|---|---|---|
| 326 | 226 | 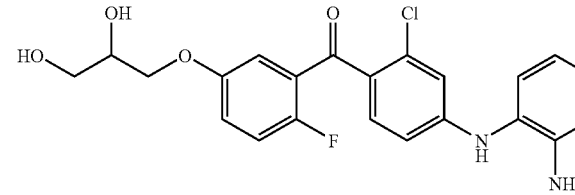 |
| 327 | 227 | 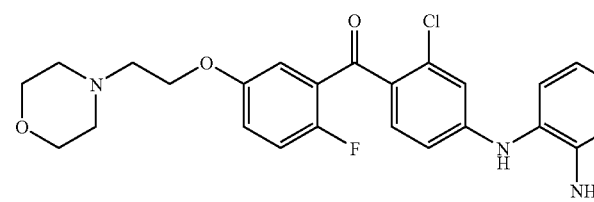 |
| 328 | 228 | 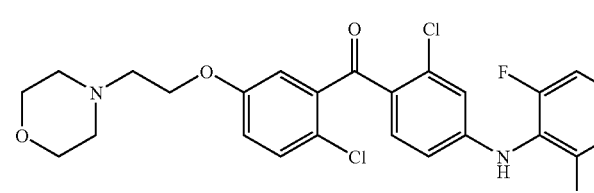 |
| 329 | 229 | 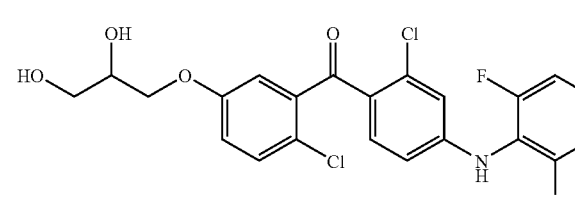 |
| 330 | 230 | 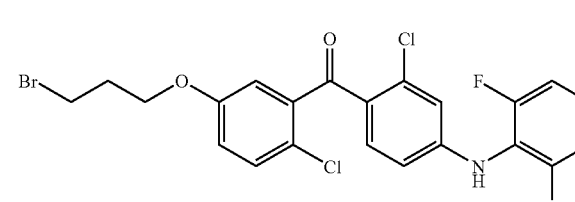 |
| 331 | 231 | 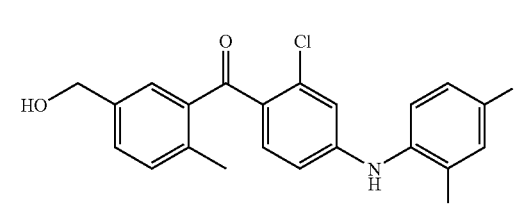 |
| 332 | 232 | 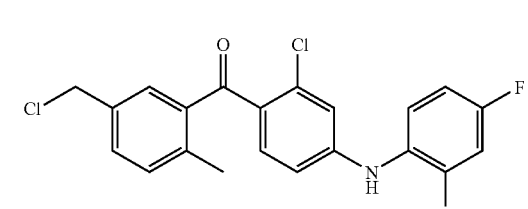 |

TABLE 4-continued

Exemplified compounds of general formula I

| Compound | Example no. | Structure |
|---|---|---|
| 333 | 233 | 5-(azidomethyl)-2'-chloro-4'-((2,4-difluorophenyl)amino)-2-methylbenzophenone |
| 334 | 234 | 5-(aminomethyl)-2'-chloro-4'-((2,4-difluorophenyl)amino)-2-methylbenzophenone |
| 335 | 235 | 2'-chloro-4'-((2,4-difluorophenyl)amino)-5-(hydroxymethyl)-2-methoxybenzophenone |
| 336 | 236 | (2'-chloro-4'-((2,4-difluorophenyl)amino)-4-methoxybenzophenone-3-yl)methyl acetate |
| 337 | 237 | N-tert-butoxy-3-(2-chloro-4-((2,4-difluorophenyl)amino)benzoyl)-4-methoxybenzamide |
| 338 | 238 | 3-(2-chloro-4-((2,4-difluorophenyl)amino)benzoyl)-N-methoxy-4-methylbenzamide |
| 339 | 239 | N-butoxy-3-(2-chloro-4-((2,4-difluorophenyl)amino)benzoyl)-4-methylbenzamide |

TABLE 4-continued

Exemplified compounds of general formula I

| Compound | Example no. | Structure |
|---|---|---|
| 340 | 240 | 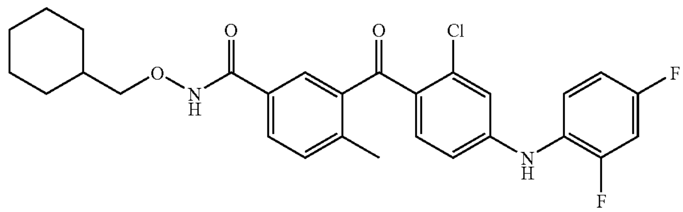 |
| 341 | 241 | 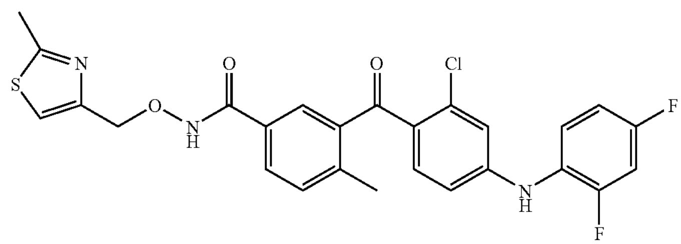 |
| 342 | 242 | 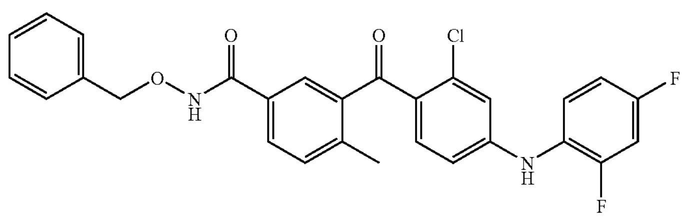 |
| 343 | 243 | 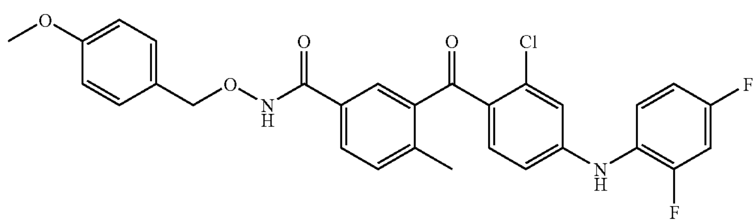 |
| 344 | 244 | 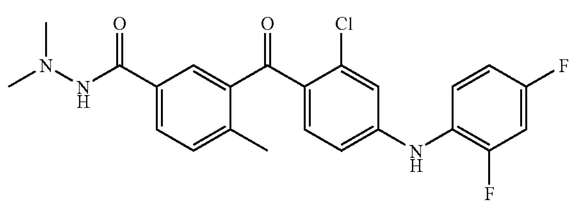 |
| 345 | 245 | 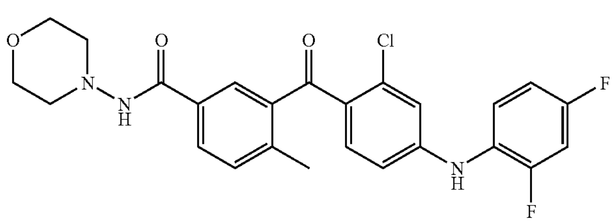 |
| 346 | 246 | 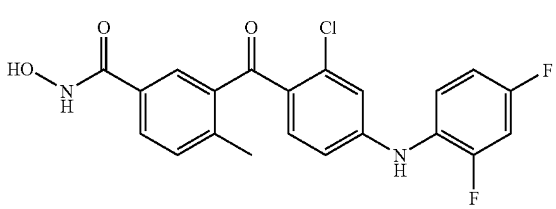 |

TABLE 4-continued

Exemplified compounds of general formula I

| Compound | Example no. | Structure |
|---|---|---|
| 347 | 247 | 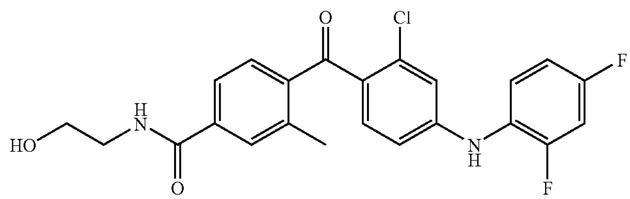 |
| 348 | 248 | 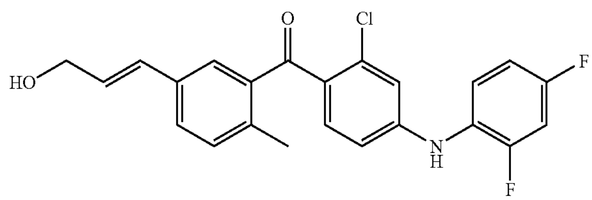 |
| 349 | 249 | 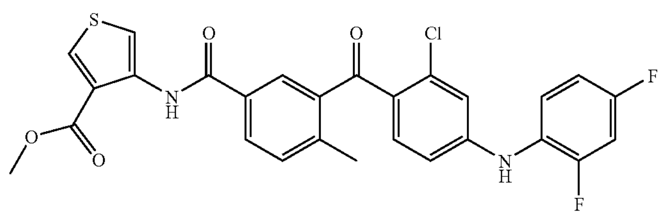 |
| 350 | 250 | 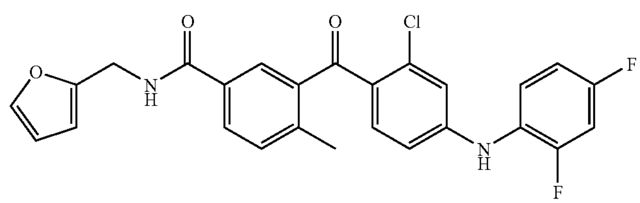 |
| 351 | 251 | 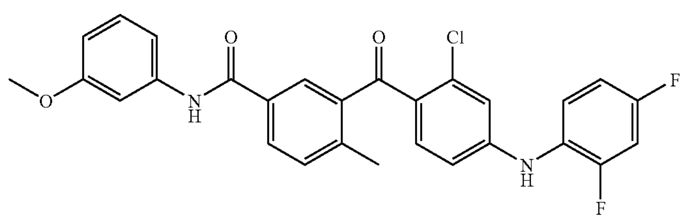 |
| 352 | 252 | 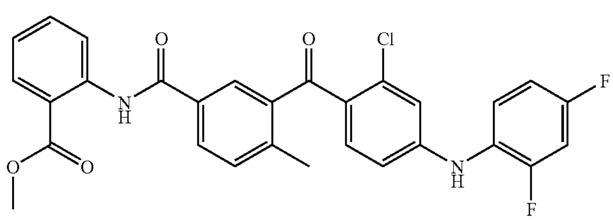 |
| 353 | 253 | 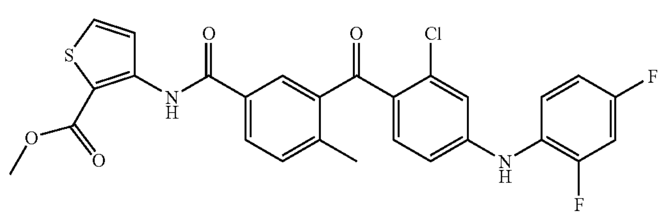 |

TABLE 4-continued

Exemplified compounds of general formula I

| Compound | Example no. | Structure |
|---|---|---|
| 354 | 254 | 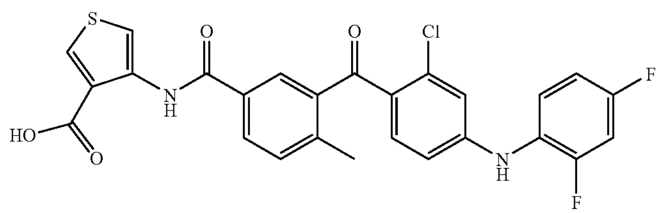 |
| 355 | 255 | 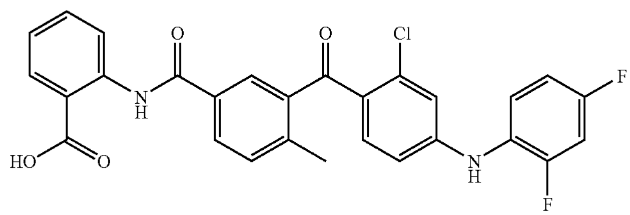 |
| 356 | 256 | 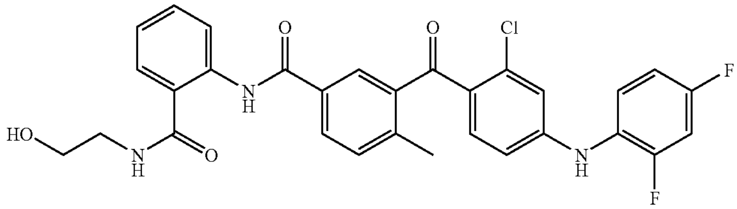 |
| 357 | 257 | 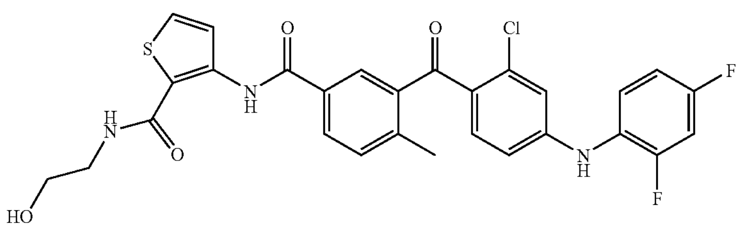 |
| 358 | 258 | 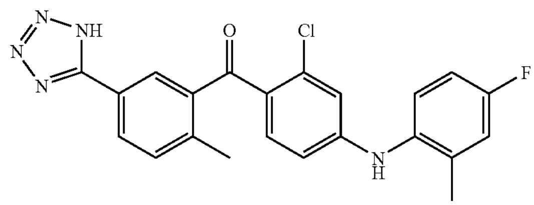 |
| 359 | 259 | 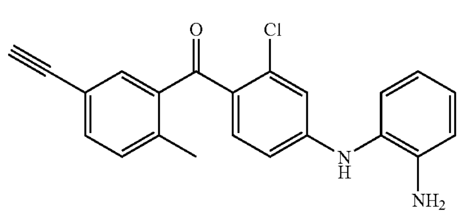 |

TABLE 4-continued

Exemplified compounds of general formula I

| Compound | Example no. | Structure |
|---|---|---|
| 360 | 260 | 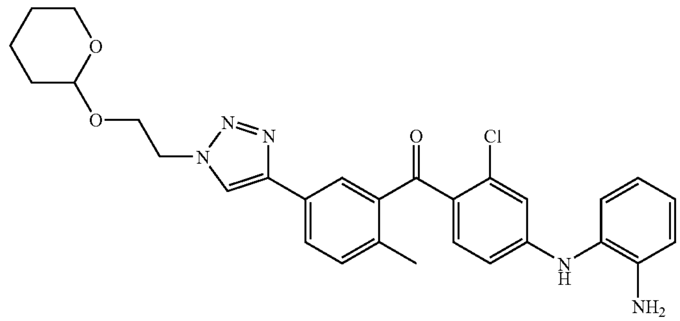 |
| 361 | 261 | 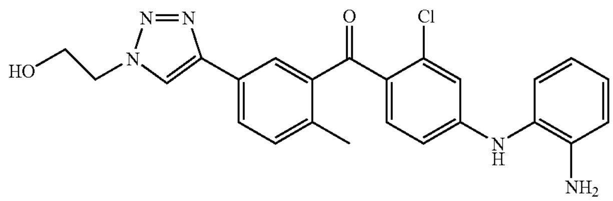 |
| 362 | 262 | 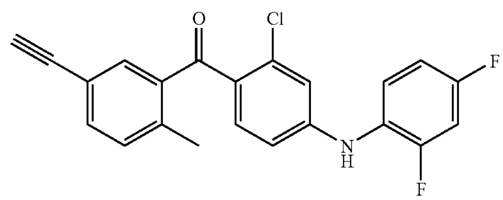 |
| 363 | 263 | 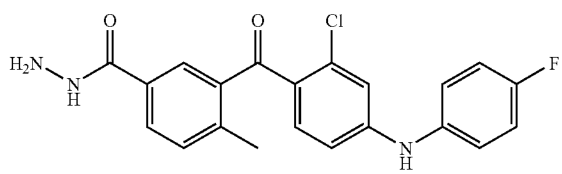 |
| 364 | 264 | 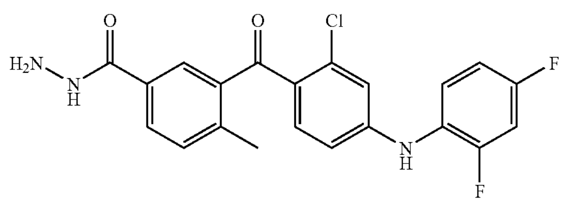 |
| 365 | 265 | 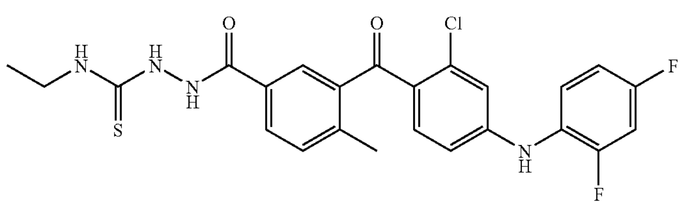 |
| 366 | 266 | 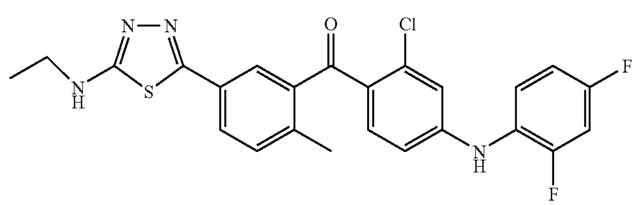 |

TABLE 4-continued

Exemplified compounds of general formula I

| Compound | Example no. | Structure |
|---|---|---|
| 367 | 267 | 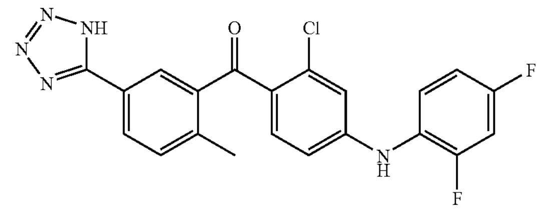 |
| 368 | 268 | 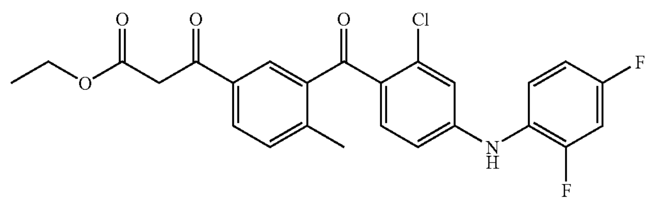 |
| 369 | 269 | 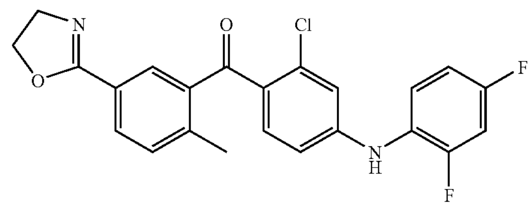 |
| 370 | 270 | 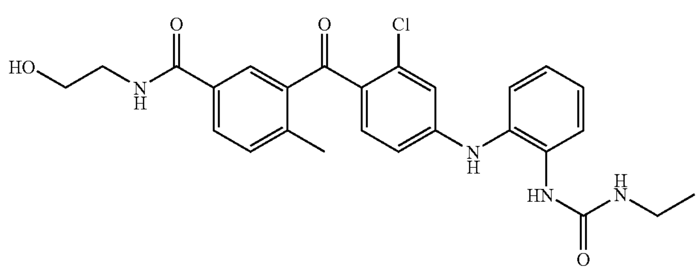 |
| 417 | 271 | 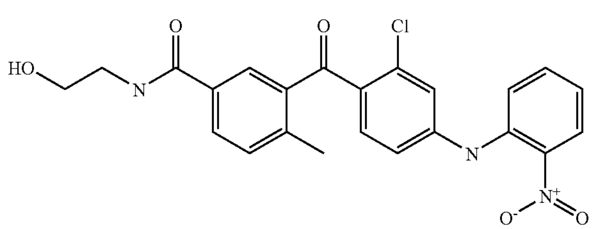 |
| 420 | 273 | 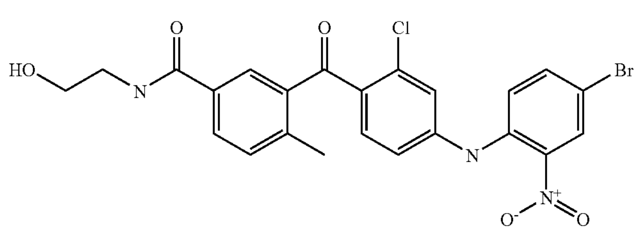 |
| 422 | 274 | 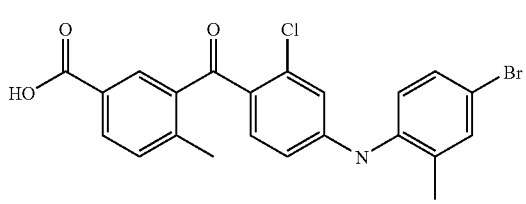 |

TABLE 4-continued

Exemplified compounds of general formula I

| Compound | Example no. | Structure |
|---|---|---|
| 424 | 275 | 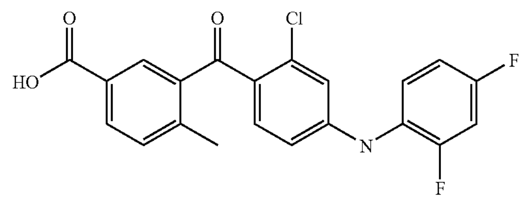 |
| 425 | 276 | 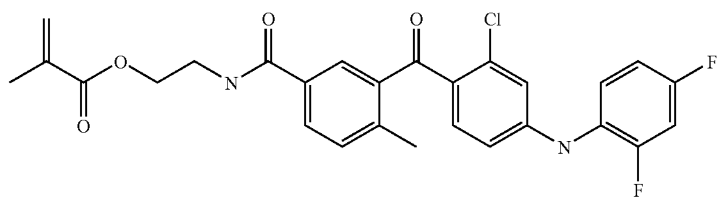 |
| 426 | 277 | 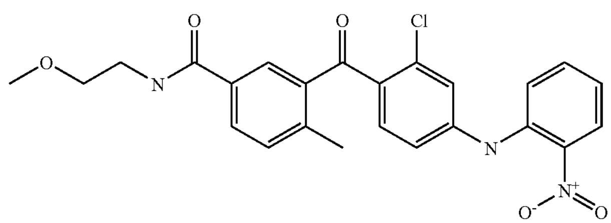 |
| 432 | 278 | 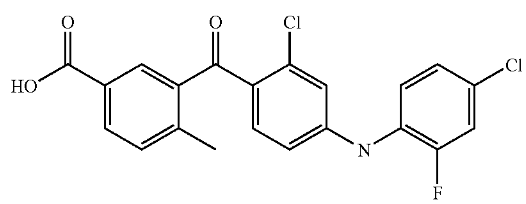 |
| 437 | 279 | 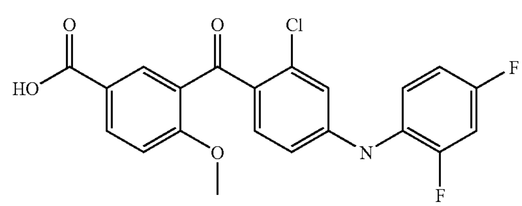 |
| 443 | 280 | 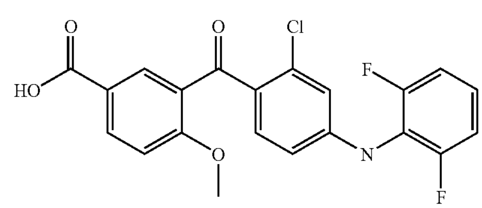 |
| 446 | 281 | 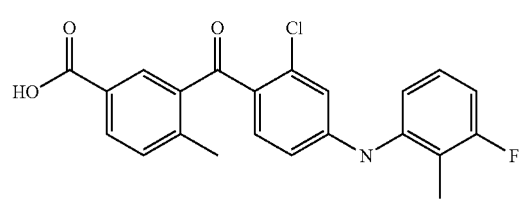 |

TABLE 4-continued

Exemplified compounds of general formula I

| Compound | Example no. | Structure |
|---|---|---|
| 449 | 282 | 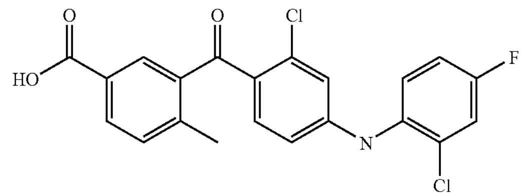 |
| 457 | 283 | 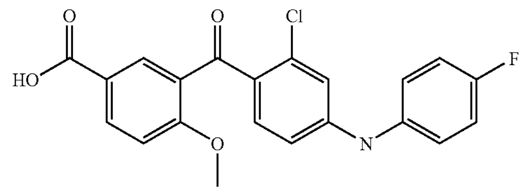 |
| 459 | 284 | 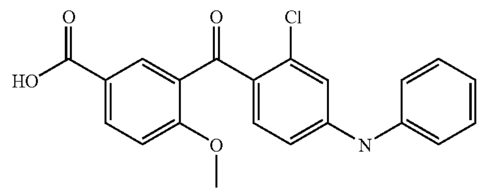 |
| 472 | 285 | 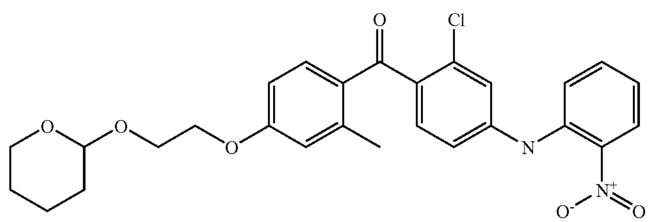 |
| 473 | 286 | 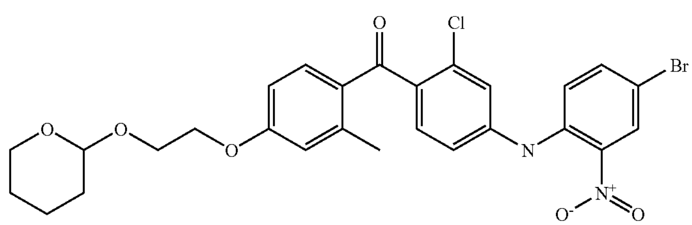 |
| 477 | 287 | 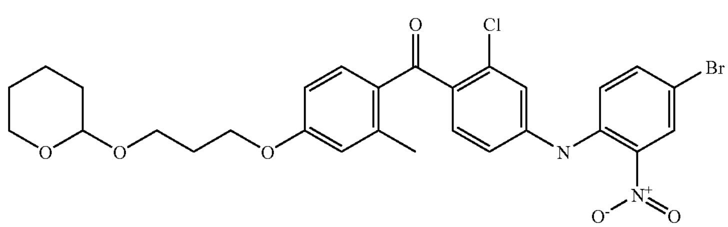 |
| 481 | 288 | 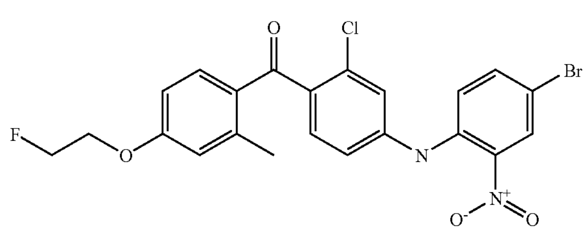 |

TABLE 4-continued

Exemplified compounds of general formula I

| Compound | Example no. | Structure |
|---|---|---|
| 485 | 289 | 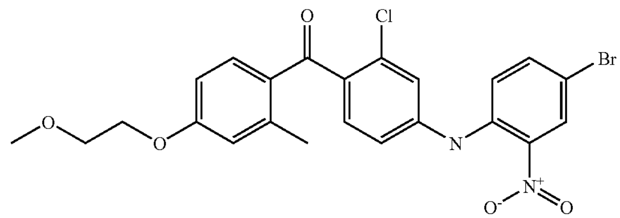 |
| 518 | 290 | 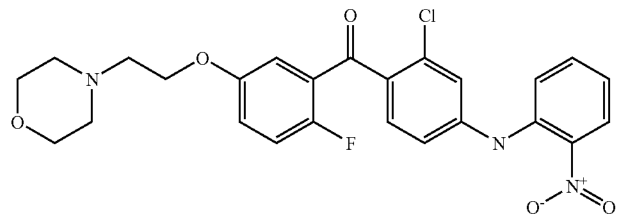 |
| 519 | 291 | 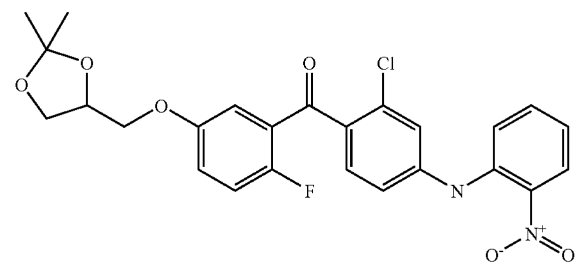 |
| 520 | 292 | 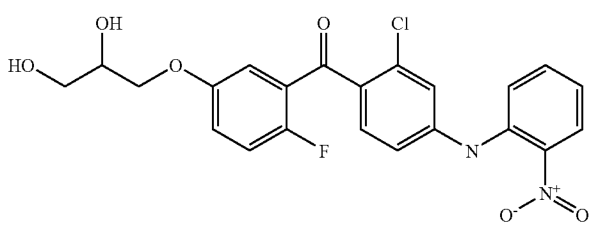 |

Preparation 1

3-(2-Chloro-4-nitrobenzoyl)-4-methylbenzoic acid methyl ester (Compound 401)

A dry flask was charged with 3-iodo-4-methylbenzoic acid methyl ester (21.6 g, 78.2 mmol) and the flask was evaporated and then filled with argon and this process repeated twice. Dry THF (140 mL) was added, and the solution cooled to −50° C.; then isopropylmagnesium chloride (41 mL, 2.0 M in diethyl ether, 82 mmol) was added slowly over 15 min keeping the temperature below −40° C. On completion of the addition the reaction mixture was stirred at −40° C. for 45 min. A THF solution of $ZnCl_2$ (10.78 g, 79.1 mmol, 0.8 M) was added dropwise over 20 min. The reaction mixture was stirred at 0° C. for 65 min; then 2-chloro-4-nitro-benzoyl chloride (17.2 g, 78.2 mmol) and tetrakis(triphenylphosphine)palladium(0) (4.03 g, 3.49 mmol) were added and the reaction mixture was allowed to warm to room temperature. After 4 h the reaction mixture was poured into a mixture of toluene/EtOAc/water, then shaken and separated. The aqueous phase was extracted with two more portions of EtOAc. The organic phases were combined, dried ($MgSO_4$), filtered, and concentrated in vacuo to afford the crude product. Crystallization from mixtures of EtOAc/petroleum ether (40-60) gave the title compound as yellow solid. The mother liquid was concentrated in vacuo and purified by chromatography using DCM as the eluent to give a second crop of the title compound.

Preparation 2

3-(4-Amino-2-chlorobenzoyl)-4-methylbenzoic acid methyl ester (Compound 402)

To a solution of compound 401 (7.83 g, 23.5 mmol) in methanol (100 mL) was added zinc dust (15.3 g, 235 mmol) and ammonium chloride (6.27 g, 117 mmol) in one portion under stirring. A $CaCl_2$ tube was mounted on the flask and the flask was placed in an oil bath with a temperature of 90° C. After 2 h the reaction mixture was cooled to RT, filtered, and then poured into a mixture of EtOAc/water. The aqueous phase was extracted with more EtOAc. The organic phases were combined, dried (MgSO4), filtered, and concentrated in vacuo to afford the crude product. Crystallization from a mixture of EtOAc/petroleum ether (40-60) (2:3) gave the title compound as light yellow solid.

Preparation 3

3-(4-Amino-2-chlorobenzoyl)-4-methylbenzoic acid (Compound 403)

To a solution of compound 402 (1.61 g, 5.3 mmol) in ethanol (50 mL) was added a solution of sodium hydroxide (2 M, 30 mL) and then stirred under reflux for 90 min. The reaction mixture was made weakly acidic (pH=5) by slowly addition of hydrochloric acid (4N), and then poured into a mixture of EtOAc/water. The aqueous phase was extracted with more EtOAc. The organic phases were combined, dried ($MgSO_4$), filtered, and concentrated in vacuo to afford the title compound as orange solid. It was used without any further purification.

Preparation 4

(4-Amino-2-chlorophenyl)-[2-methyl-5-(morpholine-4-carbonyl)phenyl]-methanone (Compound 404)

To a solution of compound 403 (150 mg, 0.47 mmol) in DMF (2.00 mL) in a reaction vial (8 mL) was added morpholine (41 µL, 0.47 mmol), FDPP (253 mg, 0.66 mmol) and DIEA (402 µL, 2.35 mmol). The vial was flushed with argon, closed, and then shaken at RT for 24 h.

The reaction mixture was concentrated in vacuo at 40° C. and then purified by chromatography using EtOAc/petroleum ether (40-60) 4:1 followed by EtOAc as the eluent to give the title compound as orange syrup.

Example 1

[2-Chloro-4-(4-fluoro-2-methylphenylamino)phenyl]-[2-methyl-5-(morpholine-4-carbonyl)phenyl]-methanone (Compound 101)

2-Bromo-5-fluorotoluene (47 µL, 0.37 mmol) was dissolved in 3 mL dry 1,4-dioxane in a vial under an argon atmosphere. Compound 404 (110 mg, 0.31 mmol) was added and dissolved in the solvent. Rac-BINAP (7.3 mg, 0.012 mmol), $Pd_2(dba)_3$ (7.0 mg, 0.008 mmol) and $Cs_2CO_3$ (141 mg, 0.43 mmol) were added, and the reaction mixture was stirred under an argon atmosphere at 100° C. for 72 h. The reaction mixture was filtered and then purified by continuous gradient flash chromatography using EtOAc/petroleum ether (40-60) (v:v=0:100 to 50:50) as the eluent to afford the title compound as brown oil. $^{13}C$ NMR ($CDCl_3$) δ 195.4, 169.7, 160.6, 150.3, 139.8, 139.7, 136.6, 135.4, 134.0, 133.7, 132.4, 131.5, 129.2, 127.9, 127.4, 127.0, 117.8, 115.0, 113.8, 111.7, 66.8, 48.3, 42.8, 20.2, 18.1.

Preparation 5

(4-Amino-2-chlorophenyl)-[2-methyl-5-(4-methylpiperazine-1-carbonyl)phenyl]-methanone (Compound 405)

The reaction was carried out as described in the preparation of compound 404, using N-methylpiperazine (52 µL, 0.47 mmol) as the amine. Purification was done by flash chromatography to afford the title compound as brown syrup.

Example 2

[2-Chloro-4-(4-fluoro-2-methylphenylamino)phenyl]-[2-methyl-5-(4-methylpiperazine-1-carbonyl)phenyl]-methanone (Compound 102)

The reaction was carried out as described in the preparation of compound 101, using compound 405 (143 mg, 0.45 mmol) as the amine. Purification was done by flash chromatography to afford the title compound as yellow foam. $^{13}C$ NMR ($CDCl_3$) δ195.5, 169.6, 160.6, 150.1, 139.6, 139.5, 136.5, 135.5, 134.0, 133.7, 133.0, 131.4, 129.2, 128.0, 127.4, 127.4, 117.9, 115.0, 113.9, 111.7, 54.8, 47.8, 46.0, 42.1, 20.2, 18.1.

Preparation 6

3-(4-Amino-2-chlorobenzoyl)-N-methoxy-4,N-dimethylbenzamide (Compound 406)

The reaction was carried out as described in the preparation of compound 404, using the salt N,O-dimethylhydroxylamine hydrochloride (46 mg, 0.47 mmol) as the amine. Purification was done by flash chromatography to afford the title compound as orange solid.

Example 3

3-[2-Chloro-4-(4-fluoro-2-methylphenylamino)benzoyl]-N-methoxy-4,N-dimethylbenzamide (Compound 103)

The reaction was carried out as described in the preparation of compound 101, using compound 406 (125 mg, 0.38 mmol) as the amine. Purification was done by flash chromatography to afford the title compound as yellow foam. $^{13}C$ NMR ($CDCl_3$) δ 195.6, 168.9, 160.6, 150.0, 140.7, 139.2, 136.5, 135.5, 133.9, 133.8, 131.1, 131.0, 130.5, 129.5, 127.7, 127.3, 117.9, 115.1, 113.9, 111.7, 65.9, 61.1, 20.4, 15.3.

Preparation 7

3-(4-Amino-2-chlorobenzoyl)-4-methyl-N-(tetrahydrofuran-2-ylmethyl)benzamide (Compound 407)

The reaction was carried out as described in the preparation of compound 404, using (tetrahydrofuran-2-yl)methylamine (31 mg, 0.31 mmol) as the amine. Purification was done by flash chromatography to afford the title compound as yellow oil.

Example 4

3-[2-Chloro-4-(4-fluoro-2-methylphenylamino)benzoyl]-4-methyl-N-(tetrahydrofuran-2-ylmethyl)benzamide (Compound 104)

The reaction was carried out as described in the preparation of compound 101, using compound 407 (85 mg, 0.23 mmol) as the amine. Purification was done by flash chromatography to afford the title compound as yellow foam. $^{13}C$ NMR ($CDCl_3$) δ 195.5, 166.8, 160.6, 150.3, 141.1, 140.1, 136.6, 135.7, 134.2, 133.8, 131.8, 131.4, 128.6, 127.6, 127.4, 127.0, 117.8, 115.2, 113.8, 111.6, 77.6, 68.2, 43.7, 28.7, 25.9, 20.2, 18.1.

Preparation 8

3-(4-Amino-2-chlorobenzoyl)-4,N-dimethyl-N-(tetrahydrofuran-2-ylmethyl)benzamide (Compound 408)

The reaction was carried out as described in the preparation of compound 404, using methyl(tetrahydrofuran-2-ylmethyl)amine (36 mg, 0.31 mmol) as the amine. Purification was done by flash chromatography to afford the title compound as yellow oil.

Example 5

3-[2-Chloro-4-(4-fluoro-2-methylphenylamino)benzoyl]-4,N-dimethyl-N-(tetrahydrofuran-2-ylmethyl)benzamide (Compound 105)

The reaction was carried out as described in the preparation of compound 101, using compound 408 (85 mg, 0.23 mmol) as the amine. Purification was done by flash chromatography to afford the title compound as brown syrup. $^1$H NMR (CDCl$_3$) δ 7.41-7.24 (m, 4H), 7.15 (dd, 1H), 6.97 (dd, 1H), 6.90 (dt, 1H), 6.61 (d, 1H), 6.48 (dd, 1H), 6.23 (bs, 1H), 4.17-3.0 (m, 8H), 2.41 (s, 3H), 2.21 (s, 3H), 2.0-1.45 (m, 4H).

Preparation 9

3-(4-Amino-2-chlorobenzoyl)-N-(2-methoxyethyl)-4-methylbenzamide (Compound 409)

The reaction was carried out as described in the preparation of compound 404, using 2-methoxyethylamine (23 mg, 0.31 mmol) as the amine. Purification was done by flash chromatography to afford the title compound as yellow oil.

Example 6

3-[2-Chloro-4-(4-fluoro-2-methyl-phenylamino)benzoyl]-N-(2-methoxyethyl)-4-methylbenzamide (Compound 106)

The reaction was carried out as described in the preparation of compound 101, using compound 409 (60 mg, 0.17 mmol) as the amine. Purification was done by flash chromatography to afford the title compound as syrup. $^{13}$C NMR (CDCl$_3$) δ 195.6, 166.9, 160.7, 150.2, 141.2, 140.1, 136.5, 135.7, 134.2, 133.6, 131.7, 131.4, 128.7, 127.6, 127.3, 127.3, 117.8, 115.2, 113.9, 111.7, 71.1, 58.9, 39.8, 20.3, 18.1.

Preparation 10

3-(4-Amino-2-chlorobenzoyl)-4-methyl-N-(3-morpholin-4-ylpropyl)benzamide (Compound 410)

The reaction was carried out as described in the preparation of compound 404, using 3-morpholin-4-yl-propylamine (45 mg, 0.31 mmol) as the amine. Purification was done by flash chromatography to afford the title compound as foam.

Example 7

3-[2-Chloro-4-(4-fluoro-2-methylphenylamino)benzoyl]-4-methyl-N-(3-morpholin-4-yl-propyl)benzamide (Compound 107)

The reaction was carried out as described in the preparation of compound 101, using compound 410 (37 mg, 0.09 mmol) as the amine. Purification was done by flash chromatography to afford the title compound as brown oil. $^{13}$C NMR (CDCl$_3$) δ 195.6, 166.6, 160.6, 150.3, 140.8, 140.3, 136.5, 135.7, 133.7, 133.7, 131.3, 128.6, 127.3, 127.3, 117.8, 115.2, 113.9, 111.7, 66.9, 58.7, 53.9, 40.6, 24.2, 20.2, 18.1.

Preparation 11

(4-Amino-2-chlorophenyl)-{5-[4-(2-methoxyethyl)piperazine-1-carbonyl]-2-methylphenyl}-methanone (Compound 411)

The reaction was carried out as described in the preparation of compound 404, using 1-(2-methoxyethyl)piperazine (45 mg, 0.31 mmol) as the amine. Purification was done by flash chromatography to afford the title compound as foam.

Example 8

[2-Chloro-4-(4-fluoro-2-methylphenylamino)phenyl]-{5-[4-(2-methoxyethyppiperazine-1-carbonyl]-2-methylphenyl}-methanone (Compound 108)

The reaction was carried out as described in the preparation of compound 101, using compound 411 (90 mg, 0.22 mmol) as the amine. Purification was done by flash chromatography to afford the title compound as yellow oil. $^{13}$C NMR (CDCl$_3$) δ 195.5, 169.5, 160.6, 150.3, 139.6, 139.4, 136.5, 135.4, 134.0, 133.8, 132.9, 131.4, 129.1, 127.9, 127.3, 127.0, 117.8, 115.0, 113.8, 111.6, 70.0, 58.9, 57.8, 53.8, 53.2, 47.7, 42.1, 20.2, 18.1.

Preparation 12

3-(4-Amino-2-chlorobenzoyl)-4-methyl-N-pyridin-4-ylmethylbenzamide (Compound 412)

The reaction was carried out as described in the preparation of compound 404, using C-pyridin-4-yl-methylamine (31 μL, 0.31 mmol) as the amine. Purification was done by flash chromatography to afford the title compound as yellow solid.

Example 9

3-[(2-Chloro-4-(4-fluoro-2-methylphenylamino)benzoyl]-4-methyl-N-pyridin-4-ylmethylbenzamide (Compound 109)

The reaction was carried out as described in the preparation of compound 101, using compound 412 (100 mg, 0.26 mmol) as the amine. Purification was done by flash chromatography to afford the title compound as yellow solid. $^{13}$C NMR (DMSO-d$_6$) δ 194.3, 165.5, 159.5, 151.0, 149.4, 148.4, 139.7, 136.2, 134.3, 134.1, 131.2, 131.1, 131.0, 128.9, 127.1, 127.0, 124.9, 122.1, 117.4, 114.1, 113.5, 111.0, 41.7, 19.5, 17.6.

Preparation 13

3-(4-Amino-2-chlorobenzoyl)-4-methyl-N-pyridin-2-ylmethylbenzamide (Compound 413)

The reaction was carried out as described in the preparation of compound 404, using C-pyridin-2-yl-methylamine (31 μL, 0.31 mmol) as the amine. Purification was done by flash chromatography to afford the title compound as yellow solid.

Example 10

3-[2-Chloro-4-(4-fluoro-2-methylphenylamino)benzoyl]-4-methyl-N-pyridin-2-ylmethylbenzamide (Compound 110)

The reaction was carried out as described in the preparation of compound 101, using compound 413 (79 mg, 0.21 mmol) as the amine. Purification was done by flash chromatography to afford the title compound as yellow solid. $^{13}$C NMR (DMSO-$d_6$) δ 194.3, 165.3, 159.5, 151.0, 148.8, 148.0, 139.7, 139.6, 136.2, 135.1, 134.9, 134.3, 134.1, 131.2, 131.0, 128.9, 127.1, 127.0, 124.9, 123.4, 117.4, 114.1, 113.4, 111.0, 40.3, 19.5, 17.6.

Preparation 14

3-(4-Amino-2-chlorobenzoyl)-4-methyl-N-pyridin-3-ylmethylbenzamide (Compound 414)

The reaction was carried out as described in the preparation of compound 404, using C-pyridin-3-yl-methylamine (31 μL, 0.31 mmol) as the amine. Purification was done by flash chromatography to afford the title compound as yellow foam.

Example 11

3-[2-Chloro-4-(4-fluoro-2-methyl-phenylamino)-benzoyl]-4-methyl-N-pyridin-3-ylmethyl-benzamide (Compound 111)

The reaction was carried out as described in the preparation of compound 101, using compound 414 (90 mg, 0.24 mmol) as the amine. Purification was done by flash chromatography to afford the title compound as solid. $^{13}$C NMR (DMSO-$d_6$) δ194.4, 165.3, 159.4, 157.8, 150.9, 148.7, 139.7, 136.6, 136.2, 134.3, 134.2, 134.1, 131.3, 131.0, 128.9, 127.1, 127.0, 125.0, 122.0, 120.9, 117.4, 114.1, 113.4, 111.0, 44.6, 19.5, 17.6.

Preparation 15

3-[2-Chloro-4-(2-nitrophenylamino)benzoyl]-4-methylbenzoic acid methyl ester (Compound 415)

A Schlenk tube was charged with compound 402 (4.00 g, 13.1 mmol) in 1,4-dioxane (40 mL), 1-iodo-2-nitro-benzene (3.91 g, 15.7 mmol), $Cs_2CO_3$ (5.98 g, 18.3 mmol), $Pd_2(dba)_3$ (302 mg, 0.33 mmol), and rac-BINAP (308 mg, 0.49 mmol). The tube was capped with a rubber septum, flushed with argon for 5 min, and then stirred at 100° C. for 2 h. The reaction mixture was allowed to cool to room temperature, and then poured into a mixture of water and EtOAc. The aqueous phase was extracted twice with more EtOAc. The combined organic phases were washed with brine, dried ($MgSO_4$), filtered and concentrated in vacuo. The crude product was purified by chromatography eluting with petroleum ether (40-60)/EtOAc 4:1 to afford the title compound as yellow solid.

Preparation 16

3-[2-Chloro-4-(2-nitrophenylamino)benzoyl]-4-methylbenzoic acid (Compound 416)

To a suspension of compound 415 (3.00 g, 7.06 mmol) in methanol (20 mL) was added water (4.0 mL) followed by lithium hydroxide (845 mg, 35 mmol). The mixture was then stirred at reflux for 30 min. The reaction mixture was made acidic (pH=5) by slowly addition of $H_2SO_4$ (1N), and then poured into a mixture of EtOAc/water. The aqueous phase was extracted with more EtOAc. The organic phases were combined, dried ($MgSO_4$), filtered, and concentrated in vacuo. The crude product was triturated in EtOAc/pentane 1:1 (20 mL) to afford the title compound as yellow solid.

Preparation 17/Example 271

3-[2-Chloro-4-(2-nitrophenylamino)benzoyl]-N-(2-hydroxyethyl)-4-methylbenzamide (Compound 417)

To a solution of compound 416 (2.42 g, 5.90 mmol) in DMF (20 mL) was added 2-amino-ethanol (541 mg, 8.85 mmol), FDPP (2.72 g, 7.08 mmol), and DIEA (5 mL, 30 mmol) at 0° C. The flask was flushed with argon and the temperature was allowed to come to RT. The reaction mixture was stirred at RT for 5 h, and then poured into a mixture of water (100 mL), $H_2SO_4$ (1N, 40 mL), and EtOAc (100 mL). The phases were separated and the aqueous phase was extracted with more EtOAc. The organic phases were combined, dried ($MgSO_4$), filtered, and concentrated in vacuo. The crude product was purified by chromatography eluting with DCM/methanol 100:2 to afford the title compound as orange solid.

Example 12

3-[4-(2-Aminophenylamino)-2-chlorobenzoyl]-N-(2-hydroxyethyl)-4-methylbenzamide (Compound 112)

To a solution of compound 417 (2.21 g, 4.87 mmol) in methanol (40 mL) was added zinc dust (3.18 g, 48.7 mmol) and ammonium chloride (1.30 g, 24.3 mmol) in one portion under stirring. A $CaCl_2$ tube was mounted on the flask and the flask was placed in an oil bath with a temperature of 90° C. After 1 h the reaction mixture was cooled to RT, filtered, and then poured into a mixture of EtOAc/water. The aqueous phase was extracted with more EtOAc. The organic phases were combined, dried ($MgSO_4$), filtered, and concentrated in vacuo to afford the crude product. The crude product was purified by chromatography eluting with DCM/methanol 100:5 (v:v) followed by 100:7 (v:v) to afford the title compound as yellow foam. $^{13}$C NMR ($CDCl_3$) δ 195.7, 167.8, 150.3, 142.8, 141.2, 140.1, 135.6, 134.2, 131.4, 128.9, 127.8, 127.4, 127.0, 126.8, 125.0, 119.2, 116.5, 115.4, 111.9, 62.1, 42.9, 20.2.

Preparation 18

3-[4-(4-Bromo-2-nitrophenylamino)-2-chlorobenzoyl]-4-methylbenzoic acid methyl ester (Compound 418)

To a solution of compound 402 (1.00 g, 3.29 mmol) and 4-bromo-1-fluoro-2-nitrobenzene (0.4 mL, 3.29 mmol) in DMSO (7.0 mL) was slowly added potassium tert-butoxide (816 mg, 7.27 mmol) under stirring. After 4 h at RT the reaction mixture was poured into a mixture of EtOAc/water. The aqueous phase was extracted with more EtOAc. The organic phases were combined, dried (MgSO$_4$), filtered, and concentrated in vacuo to afford the crude product. The crude product was purified by chromatography eluting with petroleum ether (40-60)/EtOAc 9:1 to afford the title compound as orange solid.

Preparation 19

3-[4-(4-Bromo-2-nitrophenylamino)-2-chlorobenzoyl]-4-methylbenzoic acid (Compound 419)

To a suspension of compound 418 (540 mg, 1.07 mmol) in methanol (5 mL) was added water (0.5 mL) and lithium hydroxide (128 mg, 5.35 mmol). The mixture was then stirred at reflux for 3 h. The reaction mixture was made acidic (pH=2) by slowly addition of HCl (aq.) (1N), and then poured into a mixture of EtOAc/water. The aqueous phase was extracted with more EtOAc. The organic phases were combined, dried (MgSO$_4$), filtered, and concentrated in vacuo to afford the title product as orange solid. It was used without any further purification.

Preparation 20/Example 273

3-[4-(4-Bromo-2-nitrophenylamino)-2-chlorobenzoyl]-N-(2-hydroxyethyl)-4-methylbenzamide (Compound 420)

The reaction was carried out as described in the preparation of compound 404, using 2-aminoethanol (56 µL, 0.94 mmol) as the amine and compound 419 (461 mg, 0.94 mmol) as the carboxylic acid. Purification was done by flash chromatography to afford the title compound as orange solid.

Example 13

3-[4-(2-Amino-4-bromophenylamino)-2-chlorobenzoyl]-N-(2-hydroxyethyl)-4-methylbenzamide (Compound 113)

The reaction was carried out as described in the preparation of compound 112, using compound 420 (280 mg, 0.53 mmol) as the nitro compound. Purification was done by flash chromatography to afford the title compound as a solid. $^{13}$C NMR (CD$_3$OD) δ 197.7, 169.5, 152.8, 147.0, 142.0, 141.8, 136.7, 135.4, 133.1, 132.4, 130.2, 129.4, 128.6, 127.2, 125.4, 121.3, 121.3, 119.4, 116.2, 112.7, 61.6, 43.6, 20.2.

Preparation 21

3-[4-(4-Bromo-2-methylphenylamino)-2-chlorobenzoyl]-4-methylbenzoic acid methyl ester (Compound 421)

A reaction vial was charged with compound 402 (100 mg, 0.33 mmol) in 1,4-dioxane (1.0 mL), 4-bromo-1-Iodo-2-methylbenzene (56 µL, 0.38 mmol), Cs$_2$CO$_3$ (15 mg, 0.46 mmol), Pd$_2$(dba)$_3$ (7.5 mg, 0.008 mmol), and rac-BINAP (7.7 mg, 0.012 mmol). The tube was flushed with argon for 5 min, closed and then stirred at 150° C. for 1 h in a microwave oven. The reaction mixture was allowed to cool to room temperature, and then poured into EtOAc. Filtration and concentration in vacuo gave the crude product. The crude product was purified by continuous gradient flash chromatography using EtOAc/petroleum ether (40-60) (v:v=10:90 to 30:70) as the eluent to afford the title compound as orange solid.

Preparation 22/Example 274

3-[4-(4-Bromo-2-methylphenylamino)-2-chlorobenzoyl]-4-methylbenzoic acid (Compound 422)

The reaction was carried out as described in the preparation of compound 419, using compound 421 (525 mg, 1.11 mmol) as the ester. Purification was done by flash chromatography to afford the title compound as orange solid. $^{13}$C NMR (DMSO-d$_6$) δ 194.2, 166.5, 149.8, 141.7, 139.5, 137.8, 135.1, 133.8, 133.8, 133.5, 131.5, 131.1, 129.5, 129.2, 128.2, 125.7, 125.6, 116.7, 114.8, 111.8, 19.8, 17.4

Example 14

3-[4-(4-Bromo-2-methylphenylamino)-2-chlorobenzoyl]-N-(2-hydroxyethyl)-4-methylbenzamide (Compound 114)

The reaction was carried out as described in the preparation of compound 404, using 2-aminoethanol (58 µL, 0.97 mmol) as the amine and compound 422 (431 mg, 0.97 mmol) as the carboxylic acid. Purification was done by flash chromatography to afford the title compound as yellow solid. $^{13}$C NMR (DMSO-d$_6$) δ 194.6, 165.2, 149.8, 139.4, 139.4, 137.8, 135.1, 134.1, 133.9, 133.5, 131.7, 130.9, 129.5, 128.9, 127.0, 125.7, 125.5, 116.6, 115.0, 111.8, 59.6, 42.1, 19.5, 17.4

Preparation 23

3-[2-Chloro-4-(2,4-difluorophenylamino)benzoyl]-4-methylbenzoic acid methyl ester (Compound 423)

A reaction vial was charged with compound 402 (750 mg, 2.47 mmol) in toluene (7.5 mL), 1-bromo-2,4-difluorobenzene (0.33 mL, 2.96 mmol), Cs$_2$CO$_3$ (1.13 g, 3.46 mmol), Pd$_2$(dba)$_3$ (114 mg, 0.12 mmol), and rac-BINAP (116 g, 0.18 mmol). The tube was flushed with argon for 5 min, closed and then warmed slowly to 200° C. The reaction vial was shaken at 200° C. for 4 h. The reaction mixture was allowed to cool to room temperature, and then poured into EtOAc. Filtration and concentration in vacuo gave the crude product. The crude product was purified by continuous gradient flash chromatography using EtOAc/petroleum ether (40-60) (v:v=2:98 to 20:80) as the eluent to afford the title compound as brown syrup.

Preparation 24/Example 275

3-[2-Chloro-4-(2,4-difluorophenylamino)benzoyl]-4-methylbenzoic acid (Compound 424)

The reaction was carried out as described in the preparation of compound 419, using compound 423 (360 mg, 0.87 mmol) as the ester. Purification was done by flash chromatography to afford the title compound as orange solid. $^{13}$C NMR (DMSO-d$_6$) δ 194.4, 166.5, 158.8 (dd), 155.8 (dd), 149.5, 141.8, 139.3, 133.6, 131.9, 131.5, 131.2, 129.4, 128.3, 126.5 (m), 126.3, 124.1 (dd), 114.7, 112.0 (dd), 111.8, 105.0 (dd), 19.8

Preparation 25/Example 276

2-Methylacrylic acid 2-{3-[2-chloro-4-(2,4-difluorophenylamino)benzoyl]-4-methylbenzoylamino}ethyl ester (Compound 425)

The reaction was carried out as described in the preparation of compound 404, using 2-methylacrylic acid 2-aminoethyl ester (54 mg, 0.33 mmol) as the amine and compound 424 (120 mg, 0.30 mmol) as the carboxylic acid. Purification was done by flash chromatography to afford the title compound as orange foam. $^{13}$C NMR (CDCl$_3$) δ 195.5, 167.8, 166.8, 159.2 (dd), 155.6 (dd), 148.1, 141.6, 139.7, 135.9, 135.3, 133.7, 131.7, 131.6, 128.9, 128.8, 127.8, 126.3, 124.5 (dd), 124.2 (dd), 116.2, 112.8, 111.6 (dd), 105.0 (dd), 63.4, 39.7, 20.4, 18.3

Example 15

3-[2-Chloro-4-(2,4-difluorophenylamino)benzoyl]-N-(2-hydroxyethyl)-4-methylbenzamide (Compound 115)

To a suspension of compound 425 (95 mg, 0.19 mmol) in methanol (1.0 mL) was added water (0.1 mL) and lithium hydroxide (23 mg, 0.95 mmol). The mixture was then stirred at reflux for 45 min. The reaction mixture was made acidic (pH=2) by slowly addition of HCl (aq.) (1N), and then poured into a mixture of EtOAc/water. The aqueous phase was extracted with more EtOAc. The organic phases were combined, dried (MgSO$_4$), filtered, and concentrated in vacuo. The crude product was purified by flash chromatography using EtOAc/petroleum ether (40-60) (v:v=4:1 and 6:1) as the eluent to afford the title compound as yellow oil. $^{13}$C NMR (CDCl$_3$) δ 195.6, 167.7, 159.4, 155.7, 148.3, 141.5, 139.8, 135.4, 133.8, 131.6, 131.5, 129.0, 128.6, 127.7, 124.6, 124.2, 116.2, 112.8, 111.7, 105.0, 62.3, 42.9, 20.3.

Preparation 26/Example 277

3-[2-Chloro-4-(2-nitrophenylamino)benzoyl]-N-(2-methoxyethyl)-4-methylbenzamide (Compound 426)

To a solution of compound 409 (85 mg, 0.25 mmol) and 1-fluoro-2-nitrobenzene (26 µL, 0.25 mmol) in DMSO (2.0 mL) was added potassium tert-butoxide (62 mg, 0.55 mmol) under stirring. After 2.5 h at RT the reaction mixture was poured into a mixture of EtOAc/water. The aqueous phase was extracted with more EtOAc. The organic phases were combined, dried (MgSO$_4$), filtered, and concentrated in vacuo to afford the crude product. The crude product was purified by chromatography eluting with DCM/EtOAc 4:1 to afford the title compound as orange oil.

Example 16

3-[4-(2-Aminophenylamino)-2-chlorobenzoyl]-N-(2-methoxyethyl)-4-methylbenzamide (Compound 116)

The reaction was carried out as described in the preparation of compound 112, using compound 426 (72 mg, 0.15 mmol) as the nitro compound. Purification was done by flash chromatography to afford the title compound as yellow foam. $^{13}$C NMR (DMSO-d$_6$) δ 194.4, 165.2, 151.2, 144.0, 139.9, 139.2, 134.1, 134.0, 131.5, 130.8, 128.7, 126.8, 126.6, 126.2, 124.4, 123.9, 116.3, 115.4, 114.2, 111.2, 70.3, 59.6, 57.8, 19.4.

Preparation 27

3-[4-(2-Aminophenylamino)-2-chlorobenzoyl]-4-methylbenzoic acid methyl ester (Compound 427)

The reaction was carried out as described in the preparation of compound 112, using compound 415 (1.8 g, 4.38 mmol) as the nitro compound. Purification was done by flash chromatography to afford the title compound as yellow syrup.

Preparation 28

3-[4-(2-Aminophenylamino)-2-chlorobenzoyl]-4-methylbenzoic acid (Compound 428)

To a solution of compound 427 (735 mg, 1.86 mmol) in ethanol (10 mL) was added a solution of sodium hydroxide (2 M, 10 mL). The mixture was then stirred under reflux for 2 h. The reaction mixture was made weakly acidic (pH=5) by slowly addition of glacial acetic acid (5.0 mL), and then poured into a mixture of EtOAc/water. The aqueous phase was extracted with more EtOAc. The organic phases were combined, dried (MgSO$_4$), filtered, and concentrated in vacuo. The crude product was purified by continuous gradient flash chromatography using DCM/methanol (v:v=90:10 to 85:15) as the eluent to afford the title compound as yellow syrup. $^{13}$C NMR (CD$_3$OD) δ 197.5, 169.1, 153.3, 145.1, 143.6, 141.7, 136.6, 135.3, 132.6, 132.5, 131.1, 129.6, 128.5, 128.1, 126.8, 126.6, 119.4, 117.6, 116.0, 112.6, 20.4

Example 17

3-[4-(2-Aminophenylamino)-2-chlorobenzoyl]-N-ethyl-4-methylbenzamide (Compound 117)

The reaction was carried out as described in the preparation of compound 404, using ethylamine hydrochloride (11 mg, 0.14 mmol) as the amine and compound 428 (54 mg, 0.14 mmol) as the carboxylic acid. Purification was done by flash chromatography to afford the title compound as yellow oil. $^{13}$C NMR (CDCl$_3$) δ 195.7, 166.8, 162.6, 150.4, 142.9, 140.8, 140.1, 135.6, 134.2, 132.0, 131.3, 128.7, 127.6, 127.3, 127.0, 126.7, 125.1, 118.9, 116.4, 115.4, 111.8, 35.0, 20.2, 14.8.

Example 18

3-[4-(2-Aminophenylamino)-2-chlorobenzoyl]-N-(3-hydroxypropyl)-4-methylbenzamide (Compound 118)

The reaction was carried out as described in the preparation of compound 404, using 3-aminopropane-1-ol (11 µL, 0.14 mmol) as the amine and compound 428 (54 mg, 0.14 mmol) as the carboxylic acid. Purification was done by flash chromatography to afford the title compound as yellow oil. $^{13}$C NMR (CDCl$_3$) δ 195.8, 167.7, 150.4, 142.9, 141.1, 140.1, 135.6, 134.2, 131.5, 131.4, 128.8, 127.7, 127.4, 127.0, 126.6, 125.1, 119.1, 116.5, 115.4, 111.8, 60.0, 37.4, 31.8, 20.2.

Preparation 29

3-(4-Amino-2-chlorobenzoyl)-N-(2-hydroxyethyl)-4-methylbenzamide (Compound 429)

The reaction was carried out as described in the preparation of compound 404, using 2-aminoethanol (190 µL, 3.13 mmol) as the amine and compound 403 (1.00 g, 3.13 mmol)

as the carboxylic acid. Purification was done by flash chromatography to afford the title compound as yellow solid.

Preparation 30

3-(4-Amino-2-chlorobenzoyl)-N-[2-(tert-butyldimethylsilanyloxy)ethyl]-4-methylbenzamide (Compound 430)

A solution of compound 429 (490 mg, 1.47 mmol), 1,5-diazabicyclo(5.4.0)undec-5-ene (0.9 mL, 5.88 mmol) and tert-butylchlorodimethylsilane (777 mg, 5.15 mmol) in acetonitrile (2.0 mL) was stirred for 2 h under an atmosphere of argon. The reaction mixture was poured into a mixture of EtOAc/water. The aqueous phase was extracted with more EtOAc. The organic phases were combined, dried ($MgSO_4$), filtered, and concentrated in vacuo to afford a syrup. The syrup was stirred in a mixture of ethanol (5.0 mL) and glacial acetic acid (0.5 mL) for 18 h and then poured into a mixture of EtOAc/water. The aqueous phase was extracted with more EtOAc. The organic phases were combined, dried ($MgSO_4$), filtered, and concentrated in vacuo to afford the crude product. The crude product was purified by chromatography eluting with DCM/EtOAc (v:v=4:1) to afford the title compound as yellow foam.

Example 19

3-[2-Chloro-4-(4-fluoro-2-methylphenylamino)benzoyl]-N-(2-hydroxyethyl)-4-methylbenzamide (Compound 119)

2-Bromo-5-fluorotoluene (8 µL, 0.11 mmol) was dissolved in 1 mL dry 1,4-dioxane in a vial under an argon atmosphere. Compound 430 (42 mg, 0.09 mmol) was added and dissolved in the solvent. Rac-BINAP (2.1 mg, 0.003 mmol), $Pd_2(dba)_3$ (2.0 mg, 0.002 mmol) and $Cs_2CO_3$ (41 mg, 0.13 mmol) were added, and the reaction mixture was stirred under an argon atmosphere at 100° C. for 72 h. The reaction mixture was filtered and then dissolved in THF (1.00 mL). Tetrabutylammonium fluoride trihydrate (37 mg, 0.12 mmol) was added to the solution and the mixture was stirred at 60° C. for 45 min. The reaction mixture was poured into a mixture of EtOAc/water. The organic phase was washed with $Na_2CO_3$ (aq.), water, dried ($MgSO_4$), filtered, and concentrated in vacuo to afford the crude product. The crude product was purified by chromatography eluting EtOAc to afford the title compound as yellow/brown oil. $^{13}C$ NMR ($CDCl_3$) δ 195.6, 167.8, 160.6, 150.4, 141.2, 140.2, 136.5, 135.7, 134.3, 133.6, 131.5, 131.4, 128.8, 127.4, 127.4, 126.9, 117.8, 115.2, 113.9, 111.7, 77.2, 62.2, 42.9, 20.2, 18.1.

Preparation 31

3-[2-Chloro-4-(4-chloro-2-fluoro-phenylamino)-benzoyl]-4-methyl-benzoic acid methyl ester (Compound 431)

1-Bromo-4-chloro-2-fluorobenzene (820 µL, 6.58 mmol) was dissolved in 20 mL dry 1,4-dioxane under an argon atmosphere. Compound 402 (2.00 g, 6.58 mmol) was added and dissolved in the solvent. Dicyclohexyl-(2',4',6'-triisopropyl-biphenyl-2-yl)-phosphane (125 mg, 0.26 mmol), $Pd(OAc)_2$ (30 mg, 0.13 mmol) and $Cs_2CO_3$ (2.68 g, 8.22 mmol) were added, and the reaction mixture was stirred under an argon atmosphere at 120° C. for 48 h. The reaction mixture was filtered and then purified by flash chromatography using EtOAc/petroleum ether (40-60) 1:9 as the eluent to afford the title compound as a solid.

Preparation 32/Example 278

3-[2-Chloro-4-(4-chloro-2-fluoro-phenylamino)-benzoyl]-4-methyl-benzoic acid (Compound 432)

The reaction was carried out as described in the preparation of compound 416, using compound 431 (1.71 g, 3.96 mmol) as the ester. The title compound was used without any further purification. $^{13}C$ NMR (DMSO-$d_6$) δ 194.6, 166.7, 154.8 (d), 148.3, 141.7, 139.0, 133.3, 131.5, 131.4, 129.5, 128.8, 127.7 (d), 127.2 (d), 127.2, 125.2 (d), 124.8 (d), 116.9 (d), 115.6, 112.7, 1.9.9

Preparation 33

3-[2-Chloro-4-(4-chloro-2-fluoro-phenylamino)-benzoyl]-4-methyl-benzoyl chloride (Compound 433)

To a suspension of compound 432 (100 mg, 0.24 mmol) in toluene (2 mL) was added thionyl chloride (35 µL, 0.48 mmol) and then refluxed for 2 h. The reaction mixture was concentrated in vacuo to afford the title compound without any further purification.

Example 20

3-[2-Chloro-4-(4-chloro-2-fluoro-phenylamino)-benzoyl]-N-(2-hydroxy-ethyl)-4-methyl-benzamide (Compound 120)

A solution of compound 433 (80 mg, 0.18 mmol), DIEA (31 µL, 0.18 mmol), and 2-amino-ethanol (22 µL; 0.37 mmol) in dry DCM (2 mL) was stirred until completion of the reaction as judged by TLC (1 h). The reaction mixture was poured into a mixture of EtOAc/water. The aqueous phase was extracted with more EtOAc. The organic phases were combined, dried ($MgSO_4$), filtered, and concentrated in vacuo to afford the crude product. Purification by continuous gradient flash chromatography using EtOAc/petroleum ether (40-60) (v:v=40:60 to 100:0) as the eluent afforded the title compound as brown oil. $^{13}C$ NMR ($CDCl_3$) δ 195.8, 167.7, 154.4 (d, J=248 Hz), 147.2, 141.5, 139.6, 135.2, 133.7, 131.6, 131.5, 129.1, 129.1, 128.7 (d, J=9.5 Hz), 127.8, 127.2 (d, J=11.7 Hz), 124.9 (d, J=3.6 Hz), 122.4 (d), 117.1, 117.0 (d, J=22.8 Hz), 113.6, 62.1, 42.9, 20.4.

Example 21

3-[2-Chloro-4-(4-chloro-2-fluoro-phenylamino)-benzoyl]-4,N-dimethyl-benzamide (Compound 121)

The reaction was carried out similarly as described in the preparation of compound 120, using methylamine (0.13 mmol) as the amine. $^{13}C$ NMR ($CDCl_3$) δ 195.7, 167.4, 154.4 (d), 147.1, 141.4, 139.4, 135.1, 133.5, 132.0, 131.6, 129.3, 129.0, 128.6 (d), 127.8, 127.3 (d), 124.9 (d), 122.4 (d), 117.1, 117.0 (d), 113.6, 26.8, 20.4.

Example 22

(2-{3-[2-Chloro-4-(4-chloro-2-fluoro-phenylamino)-benzoyl]-4-methyl-benzoylamino}-acetylamino)-acetic acid ethyl ester (Compound 122)

The reaction was carried out similarly as described in the preparation of compound 120, using (2-amino-acetylamino)-acetic acid ethyl ester (0.13 mmol) as the amine. $^{13}$C NMR (DMSO-d$_6$) δ 194.8, 169.6, 169.4, 165.4, 154.8 (d), 148.3, 139.9, 139.1, 133.6, 133.5, 131.3, 131.0, 129.4, 127.7 (d), 127.5, 127.2 (d), 127.1, 125.2 (d), 124.8 (d), 117.0 (d), 115.7, 112.6, 60.3, 42.3, 40.6, 19.6, 14.0.

Example 23

{3-[2-Chloro-4-(4-chloro-2-fluoro-phenylamino)-benzoyl]-4-methyl-benzoylamino}acetic acid ethyl ester (Compound 123)

The reaction was carried out similarly as described in the preparation of compound 120, using amino-acetic acid ethyl ester (0.13 mmol) as the amine. $^{13}$C NMR (CDCl$_3$) δ 195.6, 170.0, 166.7, 154.4 (d), 147.0, 141.9, 139.5, 135.2, 133.6, 131.7, 131.1, 129.3, 129.1, 128.5 (d), 128.1, 127.3 (d), 124.9 (d), 122.3 (d), 117.1, 117.0 (d), 113.7, 61.7, 41.9, 20.4, 14.1.

Example 24

3-[2-Chloro-4-(4-chloro-2-fluoro-phenylamino)-benzoyl]-N-(2-methoxy-ethyl)-4-methyl-benzamide (Compound 124)

The reaction was carried out similarly as described in the preparation of compound 120, using 2-methoxy-ethylamine (0.13 mmol) as the amine. $^{13}$C NMR (CDCl$_3$) δ 195.7, 166.7, 154.4 (d), 147.0, 141.5, 139.5, 135.2, 133.6, 131.9, 131.5, 129.4, 128.9, 128.5 (d), 128.0, 127.3 (d), 124.9 (d), 122.3 (d), 117.1, 117.0 (d), 113.7, 71.1, 58.8, 39.8, 20.4

Example 25

3-[2-Chloro-4-(4-chloro-2-fluoro-phenylamino)-benzoyl]-N-cyclohexyl-4-methyl-benzamide (Compound 125)

The reaction was carried out similarly as described in the preparation of compound 120, using cyclohexylamine (0.13 mmol) as the amine. $^{13}$C NMR (CDCl$_3$) δ 195.7, 165.8, 154.4 (d), 147.1, 141.1, 139.6, 135.2, 133.6, 132.5, 131.4, 129.3, 128.8, 128.6 (d), 127.8, 127.3 (d), 124.9 (d), 122.4 (d), 117.1, 117.0 (d), 113.6, 48.9, 33.2, 25.5, 24.9, 20.4

Example 26

3-[2-Chloro-4-(4-chloro-2-fluoro-phenylamino)-benzoyl]-N-ethyl-4-methyl-benzamide (Compound 126)

The reaction was carried out similarly as described in the preparation of compound 120, using ethylamine (0.13 mmol) as the amine. $^{13}$C NMR (CDCl$_3$) δ 195.7, 166.6, 154.4 (d), 147.1, 141.3, 139.5, 135.2, 133.6, 132.1, 131.5, 129.3, 128.9, 128.6 (d), 127.8, 127.3 (d), 124.8 (d), 122.4 (d), 117.1, 117.0 (d), 113.6, 35.0, 20.4, 14.8

Example 27

3-[2-Chloro-4-(4-chloro-2-fluoro-phenylamine)-benzoyl]-N-(6-hydroxy-hexyl)-4-methyl-benzamide (Compound 127)

The reaction was carried out similarly as described in the preparation of compound 120, using 6-aminohexanol (0.13 mmol) as the amine. $^{13}$C NMR (CDCl$_3$) δ 195.8, 166.9, 154.5 (d), 147.3, 141.2, 139.5, 135.1, 133.6, 132.1, 131.5, 129.0, 129.0, 128.6 (d), 127.8, 127.3 (d), 124.8 (d), 122.6 (d), 117.1, 117.0 (d), 113.5, 62.6, 40.0, 32.5, 29.5, 26.6, 25.3, 20.3

Example 28

3-[2-Chloro-4-(4-chloro-2-fluoro-phenylamino)-benzoyl]-N-isopropyl-4-methyl-benzamide (Compound 128)

The reaction was carried out similarly as described in the preparation of compound 120, using isopropylamine (0.13 mmol) as the amine. $^{13}$C NMR (CDCl$_3$) δ 195.7, 165.9, 154.5 (d), 147.2, 141.1, 139.6, 135.2, 133.6, 132.3, 131.4, 129.2, 128.8, 128.6 (d), 127.7, 127.3 (d), 124.8 (d), 122.5 (d), 117.1, 117.0 (d), 113.6, 42.1, 22.8, 20.3

Example 29

3-[2-Chloro-4-(4-chloro-2-fluoro-phenylamino)-benzoyl]-N-isobutyl-4-methyl-benzamide (Compound 129)

The reaction was carried out similarly as described in the preparation of compound 120, using isobutylamine (0.13 mmol) as the amine. $^{13}$C NMR (CDCl$_3$) δ 195.7, 166.8, 154.4 (d), 147.1, 141.3, 139.5, 135.1, 133.6, 132.3, 131.5, 129.3, 128.8, 128.6 (d), 127.9, 127.3 (d), 124.8 (d), 122.4 (d), 117.1, 117.0 (d), 113.6, 47.4, 28.6, 20.4, 20.2

Example 30

3-[2-Chloro-4-(4-chloro-2-fluoro-phenylamino)-benzoyl]-N-(2,2-dimethyl-propyl)-4-methyl-benzamide (Compound 130)

The reaction was carried out similarly as described in the preparation of compound 120, using 2,2-dimethyl-propylamine (0.13 mmol) as the amine. $^{13}$C NMR (CDCl$_3$) δ 195.7, 166.9, 154.5 (d), 147.2, 141.3, 139.6, 135.1, 133.6, 132.4, 131.5, 129.2, 128.7, 128.6 (d), 128.0, 127.3 (d), 124.8 (d), 122.5 (d), 117.1, 117.0 (d), 113.6, 51.0, 32.2, 27.3, 20.4

Example 31

3-[2-Chloro-4-(4-chloro-2-fluoro-phenylamino)-benzoyl]-N-(3-methoxy-propyl)-4-methyl-benzamide (Compound 131)

The reaction was carried out similarly as described in the preparation of compound 120, using 3-methoxy-propylamine (0.13 mmol) as the amine. $^{13}$C NMR (CDCl$_3$) δ 195.7, 166.4, 154.4 (d), 147.0, 141.4, 139.4, 135.1, 133.5, 132.1, 131.6, 129.4, 129.0, 128.5 (d), 127.9, 127.3 (d), 124.8 (d), 122.4 (d), 117.1, 117.0 (d), 113.6, 72.4, 58.8, 39.2, 28.7, 20.4

Example 32

3-[2-Chloro-4-(4-chloro-2-fluoro-phenylamino)-benzoyl]-4-methyl-N-[3-(2-oxo-pyrrolidin-1-yl)-propyl]-benzamide (Compound 132)

The reaction was carried out similarly as described in the preparation of compound 120, using 1-(3-amino-propyl)-pyrrolidin-2-one (0.13 mmol) as the amine. $^{13}$C NMR (CDCl$_3$) δ 195.9, 176.3, 166.3, 154.3 (d), 146.8, 141.5, 139.2, 135.0, 133.4, 131.8, 131.6, 129.7, 128.9, 128.7, 128.1 (d), 127.6 (d), 124.8 (d), 122.0 (d), 117.3, 116.9 (d), 113.8, 47.5, 39.6, 35.7, 30.9, 26.2, 20.5, 18.0

Example 33

3-[2-Chloro-4-(4-chloro-2-fluoro-phenylamino)-benzoyl]-N-(2-dimethylamino-ethyl)-4-methyl-benzamide (Compound 133)

The reaction was carried out similarly as described in the preparation of compound 120, using 2-dimethylamino-ethylamine (0.13 mmol) as the amine. $^{13}$C NMR (CDCl$_3$) δ 195.8, 166.7, 154.5 (d), 147.2, 141.4, 139.4, 135.1, 133.6, 131.8, 131.5, 129.3, 129.0, 128.5 (d), 128.3, 127.4 (d), 124.8 (d), 122.6 (d), 117.1, 117.0 (d), 113.6, 57.8, 44.9, 37.0, 20.4

Example 34

2-Methyl-acrylic acid 2-{3-[2-chloro-4-(4-chloro-2-fluoro-phenylamino)-benzoyl]-4-methyl-benzoylamino}-ethyl ester (Compound 134)

The reaction was carried out similarly as described in the preparation of compound 404, using 2-methylacrylic acid 2-aminoethyl ester (61 mg, 0.37 mmol) as the amine and compound 432 as the acid (140 mg, 0.33 mmol). Purification was done by flash chromatography to afford the title compound. $^{13}$C NMR (CDCl$_3$) δ 195.6, 167.8, 166.7, 154.5 (d), 146.9, 141.8, 139.5, 135.9, 135.2, 133.5, 131.7, 131.6, 129.6, 129.0, 128.6 (d), 128.0, 127.3 (d), 126.3, 124.9 (d), 122.1 (d), 117.2, 117.0 (d), 113.8, 63.4, 39.7, 20.4, 18.3

Example 35

3-[2-Chloro-4-(4-chloro-2-fluoro-phenylamino)-benzoyl]-N-cis-(4-hydroxy-cyclohexyl)-4-methyl-benzamide (Compound 135)

The reaction was carried out similarly as described in the preparation of compound 120, using 4-amino-cyclohexanol (0.13 mmol) as the amine. $^{13}$C NMR (CDCl$_3$) δ 195.6, 165.9, 154.3 (d), 146.9, 141.4, 139.5, 135.2, 133.6, 132.3, 131.6, 129.6, 128.9, 128.5 (d), 127.8, 127.3 (d), 124.9 (d), 122.1 (d), 117.3, 117.0 (d), 113.8, 66.1, 47.4, 31.4, 27.2, 20.4

Example 36

3-[2-Chloro-4-(4-chloro-2-fluoro-phenylamino)-benzoyl]-N-trans-(4-hydroxy-cyclohexyl)-4-methyl-benzamide (Compound 136)

The reaction was carried out similarly as described in the preparation of compound 120, using 4-Amino-cyclohexanol (0.13 mmol) as the amine. $^{13}$C NMR (CDCl$_3$) δ 195.6, 166.0, 154.4 (d), 146.9, 141.2, 139.6, 135.2, 133.6, 132.2, 131.5, 129.5, 128.9, 128.7 (d), 127.7, 127.2 (d), 124.9 (d), 122.2 (d), 117.2, 117.1 (d), 113.7, 69.8, 48.3, 34.0, 30.9, 20.4

Example 37

(2-{3-[2-Chloro-4-(4-chloro-2-fluoro-phenylamino)-benzoyl]-4-methyl-benzoylamino}-ethyl)-carbamic acid tert-butyl ester (Compound 137)

The reaction was carried out similarly as described in the preparation of compound 120, using (2-amino-ethyl)-carbamic acid tert-butyl ester (2.4 mmol) as the amine. $^{13}$C NMR (DMSO-d$_6$) δ 194.8; 165.3, 155.6, 154.8 (d), 148.4, 139.6, 139.2, 133.6, 133.6, 131.8, 131.0, 129.2, 127.8 (d), 127.2, 127.2 (d), 127.1, 125.2 (d), 124.8 (d), 117.0 (d), 115.8, 112.6, 77.6, 39.7, 39.5, 28.1, 19.6

Example 38

N-(2-Amino-ethyl)-3-[2-chloro-4-(4-chloro-2-fluoro-phenylamino)-benzoyl]-4-methyl-benzamide (Compound 138)

A solution of compound 137 (100 mg, 0.8 mmol) in a mixture of EtOAc (5 mL), methanol (5 mL), and 4M HCl (aq, 1.5 mL) was stirred at 70° C. for 2 h. The crude mixture was concentrated in vacuo and purified by flash chromatography using MeOH/DCM/triethyl amine 20:80:1 as the eluent to afford the title compound. $^{13}$C NMR (DMSO-d$_6$) δ 194.8, 165.4, 154.8 (d), 148.4, 139.6, 139.2, 133.6, 133.5, 131.7, 131.0, 129.2, 127.7 (d), 127.3, 127.1 (d), 127.0, 125.2 (d), 124.8 (d), 117.0 (d), 115.7, 112.6, 40.3, 40.0, 19.6

Example 39

(2-{3-[2-Chloro-4-(4-chloro-2-fluoro-phenylamino)-benzoyl]-4-methyl-benzoylamino}-acetylamino)-acetic acid (Compound 139)

To a suspension of compound 122 (100 mg, 0.18 mmol) in methanol (2 mL) was added water (0.2 mL) followed by lithium hydroxide (21 mg, 0.89 mmol). The mixture was then stirred at reflux for 90 min. The reaction mixture was made acidic (pH=5) by slowly addition of H$_2$SO$_4$ (1N), and then poured into a mixture of EtOAc/water. The aqueous phase was extracted with more EtOAc. The organic phases were combined, dried (MgSO$_4$), filtered, and concentrated in vacuo. The crude product was purified by flash chromatography using EtOAc with 0 to 2% acetic acid as the eluent to afford the title compound as yellow solid. $^{13}$C NMR (DMSO-d$_6$) δ 194.8, 171.0, 169.1, 165.4, 154.8 (d), 148.3, 139.9, 139.2, 133.5, 131.3, 131.0, 129.4, 127.7 (d), 127.5, 127.2 (d), 127.1, 125.2 (d), 124.8, 116.9 (d), 115.8, 112.6, 42.3, 40.7, 19.6

Preparation 34

3-(2-Chloro-4-nitro-benzoyl)-4-methoxy-benzoic acid methyl ester (Compound 434)

A dry flask was charged with 3-iodo-4-methoxy-benzoic acid methyl ester (8.9 g, 30.5 mmol) and the flask was evaporated and then filled with argon and this process repeated twice. Dry THF (50 mL) was added, and the solution cooled to −50° C.; then isopropylmagnesium chloride (15.2 mL, 2.0

M in diethyl ether, 30.5 mmol) was added slowly over 20 min keeping the temperature below −40° C. On completion of the addition the reaction mixture was stirred at −40° C. for 45 min. A THF solution of $ZnCl_2$ (5.19 g, 38.1 mmol, 1.0 M) was added dropwise over 20 min. The reaction mixture was stirred at 0° C. for 20 min; then 2-chloro-4-nitro-benzoyl chloride (7.04 g, 32.0 mmol) and $Cu(OAc)_2$ (122 mg, 0.61 mmol) were added and the reaction mixture was allowed to warm to room temperature. After 16 h the reaction mixture was poured into a mixture of EtOAc/water, then shaken and separated. The aqueous phase was extracted with more EtOAc. The organic phases were combined, dried ($MgSO_4$), filtered, and concentrated in vacuo to afford the crude product. The crude product was purified by flash chromatography using EtOAc/petroleum ether (40-60) 1:6 followed by 1:3 as the eluent to give the title compound as yellow solid.

Preparation 35

3-(4-Amino-2-chloro-benzoyl)-4-methoxy-benzoic acid methyl ester (Compound 435)

The reaction was carried out similarly as described in the preparation of compound 402, using compound 434 (22.9 mmol) as the nitro compound. Purification was done by flash chromatography to afford the title compound as yellow solid.

Preparation 36

3-[2-Chloro-4-(2,4-difluoro-phenylamino)-benzoyl]-4-methoxy-benzoic acid methyl ester (Compound 436)

The reaction was carried out similarly as described in the preparation of compound 431, using 1-bromo-2,4-difluorobenzene (3.94 mmol) and compound 435 (3.28 mmol). Purification was done by flash chromatography to afford the title compound as yellow foam.

Preparation 37/Example 279

3-[2-Chloro-4-(2,4-difluoro-phenylamino)-benzoyl]-4-methoxy-benzoic acid (Compound 437)

The reaction was carried out as described in the preparation of compound 416, using compound 436 (0.92 g, 2.13 mmol) as the ester. The title compound was used without any further purification. $^{13}$C NMR (DMSO-$d_6$) δ 191.4, 166.4, 160.6, 158.7 (dd), 155.7 (dd), 149.2, 133.8, 133.7, 133.5, 130.6, 129.2, 126.5, 126.4 (dd), 124.2 (dd), 122.8, 114.7, 112.0, 111.7, 105.0 (dd), 56.1

Preparation 38

3-[2-Chloro-4-(2,4-difluoro-phenylamino)-benzoyl]-4-methoxy-benzoyl chloride (Compound 438)

To a suspension of compound 437 (292 mg, 0.7 mmol) in toluene (3 mL) was added thionyl chloride (100 µL, 1 mmol) and then refluxed for 2 h. The reaction mixture was concentrated in vacuo to afford the title compound without any further purification.

Example 40

3-[2-Chloro-4-(2,4-difluoro-phenylamino)-benzoyl]-N-(2-hydroxy-ethyl)-4-methoxy-benzamide (Compound 140)

The reaction was carried out similarly as described in the preparation of compound 120, using 2-amino-ethanol (0.28 mmol) and compound 438 (0.14 mmol). Purification was done by flash chromatography to afford the title compound as yellow solid. $^{13}$C NMR (DMSO-$d_6$) δ 191.7, 165.0, 159.2, 158.8 (dd), 155.6 (dd), 149.2, 133.8, 133.6, 131.6, 129.0, 128.3, 126.6, 126.5, 126.4 (dd), 124.2 (dd), 114.8, 111.9 (dd), 111.7, 111.6, 105.0 (dd), 59.7, 56.0, 42.1

Example 41

3-[2-Chloro-4-(2,4-difluoro-phenylamino)-benzoyl]-N-(2,2-difluoro-ethyl)-4-methoxy-benzamide (Compound 141)

The reaction was carried out similarly as described in the preparation of compound 120, using 2,2-difluoro-ethylamine (0.28 mmol) and compound 438 (0.14 mmol). Purification was done by flash chromatography to afford the title compound as yellow solid. $^{13}$C NMR (DMSO-$d_6$) δ 191.6, 165.5, 159.5, 158.8 (dd), 155.6 (dd), 149.2, 133.8, 133.6, 131.8, 129.2, 128.4, 126.5, 126.4 (dd), 125.5, 124.2 (dd), 114.8, 114.5 (t), 11.2.0 (dd), 111.8, 111.7, 105.0 (dd), 56.1, 41.5

Example 42

3-[2-Chloro-4-(2,4-difluoro-phenylamino)-benzoyl]-N-(2-fluoro-ethyl)-4-methoxy-benzamide (Compound 142)

The reaction was carried out similarly as described in the preparation of compound 120, using 2-fluoro-ethylamine (0.28 mmol) and compound 438 (0.14 mmol). Purification was done by flash chromatography to afford the title compound as yellow foam. $^{13}$C NMR (CDCl$_3$) δ 192.7, 166.5, 160.6, 159.1 (dd), 155.5 (dd), 147.7, 134.9, 133.4, 132.4, 129.7, 129.5, 128.7, 126.4, 124.5 (dd), 124.1 (dd), 116.0, 112.9, 111.6 (dd), 111.5, 104.9 (dd), 82.8 (d), 56.1, 40.5 (d)

Example 43

3-[2-Chloro-4-(2,4-difluoro-phenylamino)-benzoyl]-N-(2,3-dihydroxy-propyl)-4-methoxy-benzamide (Compound 143)

The reaction was carried out similarly as described in the preparation of compound 120, using 3-amino-propane-1,2-diol (0.28 mmol) and compound 438 (0.14 mmol). Purification was done by flash chromatography to afford the title compound as yellow foam. $^{13}$C NMR (DMSO-$d_6$) δ 191.7, 165.3, 159.2, 158.8 (dd), 155.6 (dd), 149.2, 133.8, 133.6, 131.6, 129.0, 128.3, 126.6, 126.4, 126.4 (dd), 124.2 (dd), 114.8, 111.9 (dd), 111.7, 111.6, 105.0 (dd), 70.4, 63.9, 56.0, 42.9

Example 44

N-Carbamoylmethyl-3-[2-chloro-4-(2,4-difluoro-phenylamino)-benzoyl]-4-methoxy-benzamide (Compound 144)

The reaction was carried out similarly as described in the preparation of compound 120, using 2-amino-acetamide (0.28 mmol) and compound 438 (0.14 mmol). Purification was done by flash chromatography to afford the title compound as yellow solid. $^{13}$C NMR (DMSO-d$_6$) δ 191.8, 171.1, 165.2, 159.4, 158.8 (dd), 155.8 (dd), 149.3, 133.9, 133.7, 131.9, 129.1, 128.6, 126.7, 126.4 (dd), 126.2, 124.3 (dd), 114.9, 112.0 (dd), 111.8, 111.7, 105.1 (dd), 56.1, 42.4

Preparation 39

3-[2-Cloro-4-(2,4-difluoro-phenylamino)-benzoyl]-4-methyl-benzoyl chloride (Compound 439)

To a suspension of compound 424 (1.8 g, 4.5 mmol) in toluene (10 mL) was added thionyl chloride (650 µL, 9.0 mmol) and then refluxed for 2 h. The reaction mixture was concentrated in vacuo to afford the title compound without any further purification.

Example 45

N-Carbamoylmethyl-3-[2-chloro-4-(2,4-difluoro-phenylamino)-benzoyl]-4-methyl-benzamide (Compound 145)

The reaction was carried out similarly as described in the preparation of compound 120, using 2-amino-acetamide (4.48 mmol) and compound 439 (2.24 mmol). Purification was done by flash chromatography to afford the title compound as yellow foam. $^{13}$C NMR (DMSO-d$_6$) δ 194.7, 170.8, 165.3, 158.9 (dd), 155.6 (dd), 149.5, 139.7, 139.3, 133.8, 133.7, 131.4, 131.0, 129.2, 127.3, 126.5 (dd), 126.3, 124.1 (dd), 114.8, 111.9 (dd), 111.8, 105.0 (dd), 42.3, 19.6

Example 46

N-Benzyl-3-[2-chloro-4-(2,4-difluoro-phenylamino)-benzoyl]-4-methyl-benzamide (Compound 146)

The reaction was carried out similarly as described in the preparation of compound 120, using benzylamine (0.13 mmol) and compound 439 (0.11 mmol). Purification was done by flash chromatography to afford the title compound as yellow foam. $^{13}$C NMR (CDCl$_3$) δ 195.6, 166.6, 159.2 (dd), 155.7 (dd), 148.4, 141.4, 139.8, 138.1, 135.3, 133.8, 131.7, 131.5, 128.9, 128.7, 128.3, 127.9, 127.8, 127.6, 124.8 (dd), 124.2 (dd), 116.1, 112.6, 111.6 (dd), 104.9 (dd), 44.1, 20.3

Example 47

3-[2-Chloro-4-(2,4-difluoro-phenylamino)-benzoyl]-N-(2-fluoro-ethyl)-4-methyl-benzamide (Compound 147)

The reaction was carried out similarly as described in the preparation of compound 120, using 2-fluoro-ethylamine (0.13 mmol) and compound 439 (0.11 mmol). Purification was done by flash chromatography to afford the title compound as yellow foam. $^{13}$C NMR (CDCl$_3$) δ 195.6, 166.9, 159.3 (dd), 155.7 (dd), 148.4, 141.6, 139.9, 135.3, 133.8, 131.6, 131.4, 128.9, 128.4, 127.7, 124.7 (dd), 124.2 (dd), 116.2, 112.7, 111.6 (dd), 104.9 (dd), 82.7 (d), 40.5 (d), 20.3

Example 48

3-[2-Chloro-4-(2,4-difluoro-phenylamino)-benzoyl]-4-methyl-N-(2,2,2-trifluoro-ethyl) benzamide (Compound 148)

The reaction was carried out similarly as described in the preparation of compound 120, using 2,2,2-trifluoro-ethy-lamine (0.13 mmol) and compound 439 (0.11 mmol). Purification was done by flash chromatography to afford the title compound as yellow syrup. $^{13}$C NMR (CDCl$_3$) δ 195.5, 166.9, 159.4 (dd), 155.8 (dd), 148.5, 142.1, 140.0, 135.4, 133.9, 131.6, 130.6, 129.0, 128.2, 127.8, 124.8 (dd), 124.2 (q), 124.1 (dd), 116.2, 112.7, 111.7 (dd), 105.0 (dd), 41.1 (q), 20.3

Example 49

3-[2-Chloro-4-(2,4-difluoro-phenylamino)-benzoyl]-N-ethyl-4-methyl-benzamide (Compound 149)

The reaction was carried out similarly as described in the preparation of compound 120, using ethylamine (0.13 mmol) and compound 439 (0.11 mmol). Purification was done by flash chromatography to afford the title compound as yellow foam. $^{13}$C NMR (CDCl$_3$) δ 195.7, 166.7, 159.3 (dd), 155.7 (dd), 148.4, 141.1, 139.7, 135.3, 133.8, 132.1, 131.5, 128.9, 128.4, 127.6, 124.8 (dd), 124.2 (dd), 116.2, 112.6, 111.6 (dd), 104.9 (dd), 35.0, 20.3, 14.8

Example 50

3-[2-Chloro-4-[(2,4-difluoro-phenylamino]-benzoyl]-N-cyclohexylmethyl-4-methyl-benzamide (Compound 150)

LEO15592-000
The reaction was carried out similarly as described in the preparation of compound 120, using cyclohexyl-methy-lamine (0.13 mmol) and compound 439 (0.11 mmol). Purification was done by flash chromatography to afford the title compound as yellow foam. $^{13}$C NMR (CDCl$_3$) δ 195.6, 166.8, 159.3 (dd), 155.7 (dd), 148.2, 141.2, 139.7, 135.3, 133.8, 132.3, 131.5, 128.8, 128.7, 127.7, 124.5 (dd), 124.2 (dd), 116.2, 112.7, 111.6 (dd), 105.0 (dd), 46.3, 38.0, 30.9, 26.4, 25.8, 20.4

Example 51

3-[2-Chloro-4-(2,4-difluoro-phenylamino)-benzoyl]-N-(2-hydroxy-propyl)-4-methyl-benzamide (Compound 151)

The reaction was carried out similarly as described in the preparation of compound 120, using 1-amino-2-propanol (0.13 mmol) and compound 439 (0.11 mmol). Purification was done by flash chromatography to afford the title compound as yellow foam. $^{13}$C NMR (CDCl$_3$) δ 195.7, 167.6, 159.3 (dd), 155.7 (dd), 148.4, 141.4, 139.8, 135.4, 133.9, 131.6, 131.5, 129.1, 128.4, 127.7, 124.7 (dd), 124.2 (dd), 116.2, 112.7, 111.6 (dd), 105.0 (dd), 67.4, 47.6, 21.0, 20.3

Example 52

3-[2-Chloro-4-(2,4-difluoro-phenylamino)-benzoyl]-N-(2,3-dihydroxy-propyl)-4-methyl-benzamide (Compound 152)

The reaction was carried out similarly as described in the preparation of compound 120, using 3-amino-propane-1,2-diol (4.48 mmol) and compound 439 (2.24 mmol). Purification was done by flash chromatography to afford the title compound as yellow foam. $^{13}$C NMR (CDCl$_3$) δ 195.8, 168.3, 159.3 (dd), 155.8 (dd), 148.6, 141.5, 139.9, 135.4, 134.0, 131.5, 130.9, 129.2, 128.0, 127.6, 124.8 (d), 124.1 (dd), 116.1, 112.6, 111.6 (dd), 105.0 (dd), 71.1, 63.8, 42.8, 20.3

Example 53

3-[2-Chloro-4-(2,4-difluoro-phenylamino)-benzoyl]-N-(1-hydroxymethyl-propyl)-4-methyl-benzamide (Compound 153)

The reaction was carried out similarly as described in the preparation of compound 120, using 2-amino-butan-1-ol (0.13 mmol) and compound 439 (0.11 mmol). Purification was done by flash chromatography to afford the title compound as yellow syrup. $^{13}$C NMR (CDCl$_3$) δ 195.7, 167.4, 159.3 (dd), 155.7 (dd), 148.5, 141.2, 139.8, 135.4, 133.9, 131.8, 131.4, 128.9, 128.2, 127.7, 124.8 (dd), 124.2 (dd), 116.2, 112.6, 111.6 (dd), 105.0 (dd), 64.9, 53.8, 24.2, 20.3, 10.7

Example 54

3-[2-Chloro-4-(2,4-difluoro-phenylamino)-benzoyl]-4-methyl-N-(2,2,3,3,3-pentafluoro-propyl)-benzamide (Compound 154)

The reaction was carried out similarly as described in the preparation of compound 120, using 2,2,3,3,3-pentafluoropropylamine (0.13 mmol) and compound 439 (0.11 mmol). Purification was done by flash chromatography to afford the title compound as yellow syrup. $^{13}$C NMR (CDCl$_3$) δ 195.4, 166.9, 159.4 (dd), 155.7 (dd), 148.4, 142.2, 140.0, 135.4, 133.8, 131.7, 130.6, 129.0, 128.4, 127.9, 124.8 (dd), 124.1 (dd), 116.2, 112.7, 111.7 (dd), 105.0 (dd), 39.2 (t), 20.4

Example 55

3-[2-Chloro-4-(2,4-difluoro-phenylamino)-benzoyl]-N-(3-hydroxy-propyl)-4-methyl-benzamide (Compound 155)

The reaction was carried out similarly as described in the preparation of compound 120, using 3-amino-propanol (0.13 mmol) and compound 439 (0.11 mmol). Purification was done by flash chromatography to afford the title compound as yellow syrup. $^{13}$C NMR (CDCl$_3$) δ 195.7, 167.6, 159.3 (dd), 155.7 (dd), 148.4, 141.4, 139.8, 135.3, 133.8, 131.5, 128.9, 128.4, 127.7, 124.8 (dd), 124.2 (dd), 116.2, 112.7, 111.6 (dd), 105.0 (dd), 60.0, 37.4, 31.9, 20.3

Example 56

3-[2-Chloro-4-(2,4-difluoro-phenylamino)-benzoyl]-N-(2-hydroxy-1,1-dimethyl-ethyl)-4-methyl-benzamide (Compound 156)

The reaction was carried out similarly as described in the preparation of compound 120, using 2-amino-2-methyl-propane-1-ol (0.28 mmol) and compound 439 (0.14 mmol). Purification was done by flash chromatography to afford the title compound as yellow foam. $^{13}$C NMR (CDCl$_3$) δ 195.5, 167.6, 159.3 (dd), 155.7 (dd), 148.4, 141.3, 140.0, 135.4, 133.9, 132.2, 131.5, 128.7, 128.4, 127.6, 124.7 (dd), 124.1 (dd), 116.2, 112.7, 111.6 (dd), 105.0 (dd), 70.6, 56.6, 24.7, 20.3

Example 57

3-[2-Chloro-4-(2,4-difluoro-phenylamino)-benzoyl]-N-(2-hydroxy-1-hydroxymethyl-1-methyl-ethyl)-4-methyl-benzamide (Compound 157)

The reaction was carried out similarly as described in the preparation of compound 120, using 2-amino-2-methyl-propane-1,3-diol (0.28 mmol) and compound 439 (0.14 mmol). Purification was done by flash chromatography to afford the title compound as yellow foam. $^{13}$C NMR (CDCl$_3$) δ 195.6, 167.7, 159.3 (dd), 155.7 (dd), 148.4, 141.5, 140.0, 135.4, 133.9, 132.0, 131.5, 128.7, 128.4, 127.7, 124.7 (dd), 124.1 (dd), 116.2, 112.8, 111.7 (dd), 105.0 (dd), 67.7, 59.2, 20.3, 20.0

Example 58

{3-[2-Chloro-4-(2,4-difluoro-phenylamino)-benzoyl]-4-methyl-benzoylamino}-acetic acid ethyl ester (Compound 158)

The reaction was carried out similarly as described in the preparation of compound 120, using amino-acetic acid ethyl ester (0.28 mmol) and compound 439 (0.14 mmol). Purification was done by flash chromatography to afford the title compound as yellow foam. $^{13}$C NMR (CDCl$_3$) δ 195.5, 170.0, 166.6, 159.2 (dd), 155.6 (dd), 148.2, 141.9, 139.7, 135.3, 133.7, 131.6, 131.1, 129.0, 128.7, 128.0, 124.5 (dd), 124.3 (dd), 116.2, 112.8, 111.6 (dd), 105.0 (dd), 61.7, 41.9, 20.4, 14.1

Example 59

3-[2-Chloro-4-(2,4-difluoro-phenylamino)-benzoyl]-N-(4-hydroxy-butyl)-4-methyl-benzamide (Compound 159)

The reaction was carried out similarly as described in the preparation of compound 120, using 4-amino-butanol (0.28 mmol) and compound 439 (0.14 mmol). Purification was done by flash chromatography to afford the title compound as yellow foam. $^{13}$C NMR (CDCl$_3$) δ 195.7, 166.8, 159.3 (dd), 155.7 (dd), 148.2, 141.2, 139.6, 135.3, 133.7, 132.1, 131.5, 129.0, 128.7, 127.7, 124.6 (dd), 124.2 (dd), 116.2, 112.7, 111.6 (dd), 105.0 (dd), 62.4, 39.9, 29.8, 26.3, 20.4

Example 60

3-[2-Chloro-4-(2,4-difluoro-phenylamino)-benzoyl]-N-(3-hydroxy-1,1-dimethyl-butyl)-4-methyl-benzamide (Compound 160)

The reaction was carried out similarly as described in the preparation of compound 120, using 4-amino-4-methyl-pentan-2-ol (0.28 mmol) and compound 439 (0.14 mmol). Purification was done by flash chromatography to afford the title compound as yellow foam. $^{13}$C NMR (CDCl$_3$) δ 196.0, 165.8, 159.2 (dd), 155.6 (dd), 147.9, 141.0, 139.2, 135.1, 133.5, 133.3, 131.4, 129.1, 128.9, 128.2, 124.6 (dd), 124.3 (dd), 116.1, 112.7, 111.6 (dd), 105.0 (dd), 65.7, 53.8, 50.5, 28.4, 25.7, 24.6, 20.4

Example 61

3-[2-Chloro-4-(2,4-difluoro-phenylamino)-benzoyl]-4-methyl-N-(3-phenyl-propyl)-benzamide (Compound 161)

The reaction was carried out similarly as described in the preparation of compound 120, using 3-phenyl-propylamine (0.28 mmol) and compound 439 (0.14 mmol). Purification was done by flash chromatography to afford the title compound as yellow foam. $^{13}$C NMR (CDCl$_3$) δ 195.6, 166.6, 159.3 (dd), 155.6 (dd), 148.2, 141.4, 141.2, 139.6, 135.3, 133.8, 132.0, 131.5, 128.8, 128.7, 128.6, 128.4, 127.6, 126.1, 124.6 (dd), 124.2 (dd), 116.2, 112.7, 111.6 (dd), 105.0 (dd), 39.9, 33.5, 31.0, 20.3

Example 62

(R)-3-[2-Cloro-2,4-difluoro-phenylamino)-benzoyl]-N-(1-hydroxymethyl-3-methyl-butyl)-4-methyl-benzamide (Compound 162)

The reaction was carried out similarly as described in the preparation of compound 120, using (R)-leucinol (0.28 mmol) and compound 439 (0.14 mmol). Purification was done by flash chromatography to afford the title compound as yellow foam. $^{13}$C NMR (CDCl$_3$) δ 195.6, 167.4, 159.3 (dd), 155.7 (dd), 148.3, 141.4, 139.8, 135.4, 133.8, 131.8, 131.5, 128.8, 128.6, 127.8, 124.6 (dd), 124.2 (dd), 116.2, 112.8, 111.6 (dd), 105.0 (dd), 66.2, 50.6, 40.3, 25.1, 23.0, 22.3, 20.4

Example 63

3-[4-(2,4-Difluoro-phenylamino)-benzoyl]-N-(2-fluoro-ethyl)-4-methyl-benzamide (Compound 163)

The reaction was carried out similarly as described in the preparation of compound 120, using 2-fluoro-ethylamine (0.28 mmol) and compound 439 (0.14 mmol). Purification was done by flash chromatography to afford the title compound as yellow foam. $^{13}$C NMR (CDCl$_3$) δ 196.0, 167.1, 159.1 (dd), 155.6 (dd), 149.2, 140.0, 139.9, 132.6, 131.3, 131.1, 128.6, 128.2, 126.1, 124.6 (dd), 124.5 (dd), 114.1, 111.5 (dd), 104.8 (dd), 82.6 (d), 40.5 (d), 19.7

Example 64

3-[2-Chloro-4-(2,4-difluoro-phenylamino)-benzoyl]-N-isopropyl-4-methyl-benzamide (Compound 164)

The reaction was carried out similarly as described in the preparation of compound 120, using isopropylamine (0.28 mmol) and compound 439 (0.14 mmol). Purification was done by flash chromatography to afford the title compound as yellow foam. $^{13}$C NMR (CDCl$_3$) δ 195.7, 165.9, 159.2 (dd), 155.6 (dd), 148.2, 141.0, 139.8, 135.4, 133.8, 132.3, 131.4, 128.7, 128.7, 127.6, 124.6 (dd), 124.2 (dd), 116.2, 112.7, 111.6 (dd), 105.0 (dd), 42.0, 22.8, 20.3

Example 65

3-[2-Chloro-4-(2,4-difluoro-phenylamino)-benzoyl]-N-cyclohexyl-4-methyl-benzamide (Compound 165)

The reaction was carried out similarly as described in the preparation of compound 120, using cyclohexylamine (0.28 mmol) and compound 439 (0.14 mmol). Purification was done by flash chromatography to afford the title compound as yellow foam. $^{13}$C NMR (CDCl$_3$) δ 195.7, 165.8, 159.3 (dd), 155.7 (dd), 148.3, 141.0, 139.8, 135.4, 133.8, 132.5, 131.4, 128.8, 128.6, 127.6, 124.7 (dd), 124.3 (dd), 116.2, 112.7, 111.6 (dd), 105.0 (dd), 48.9, 33.2, 25.6, 24.9, 20.3

Example 66

3-[2-Chloro-4-(2,4-difluoro-phenylamino)-benzoyl]-N-2,2-difluoro-ethyl)-4-methyl-benzamide (Compound 166)

The reaction was carried out similarly as described in the preparation of compound 120, using 2,2-difluoro-ethylamine (0.28 mmol) and compound 439 (0.14 mmol). Purification was done by flash chromatography to afford the title compound as yellow foam. $^{13}$C NMR (CDCl$_3$) δ 195.4, 167.1, 159.3 (dd), 155.7 (dd), 148.3, 142.0, 140.0, 135.4, 133.8, 131.7, 130.8, 129.0, 128.6, 127.7, 124.6 (dd), 124.1 (dd), 116.2, 113.6 (t), 112.8, 111.7 (dd), 105.0 (dd), 42.3 (t), 20.4

Example 67

5-{3-[2-chloro-4-(2,4-difluoro-phenylamino)-benzoyl]-4-methyl-benzoylamino}-4-oxo-pentanoic acid methyl ester (Compound 167)

The reaction was carried out similarly as described in the preparation of compound 120, using 5-amino-4-oxo-pentanoic acid methyl ester (0.28 mmol) and compound 439 (0.14 mmol). Purification was done by flash chromatography to afford the title compound as yellow foam. $^{13}$C NMR (CDCl$_3$) δ 203.9, 195.5, 172.9, 166.5, 159.2 (dd), 155.5 (dd), 148.2, 141.9, 139.7, 135.3, 133.8, 131.6, 131.0, 129.0, 128.6, 127.9, 124.4 (dd), 124.3 (dd), 116.2, 112.8, 111.6 (dd), 105.0 (dd), 52.0, 49.6, 34.6, 27.6, 20.4

Example 68

N-[(2-Carbamoyl-ethylcarbamoyl)-methyl]-3-[2-chloro-4-(2,4-difluoro-phenylamino)-benzoyl]-4-methyl-benzamide (Compound 168)

The reaction was carried out similarly as described in the preparation of compound 120, using 3-(2-amino-acetylamino)-propionamide (0.28 mmol) and compound 439 (0.14 mmol). Purification was done by flash chromatography to afford the title compound as yellow solid. $^{13}$C NMR (CD$_3$OD) δ 197.6, 176.6, 171.8, 169.4, 161.2 (dd), 158.0 (dd), 151.6, 142.5, 141.5, 136.4, 135.2, 132.5, 130.5, 129.0, 128.3, 127.7 (dd), 125.8 (dd), 116.6, 113.0, 112.7 (dd), 105.8 (dd), 44.2, 37.0, 35.9, 20.3

Example 69

(2-{3-[2-Chloro-4-(2,4-difluoro-phenylamino)-benzoyl]-4-methyl-benzoylamino}-acetylamino)-acetic acid ethyl ester (Compound 169)

The reaction was carried out similarly as described in the preparation of compound 120, using (2-amino-acetylamino)-acetic acid ethyl ester (0.28 mmol) and compound 439 (0.14 mmol). Purification was done by flash chromatography to afford the title compound as yellow foam. $^{13}$C NMR (DMSO-d$_6$) δ 194.7, 169.7, 169.4, 165.4, 158.9 (dd), 155.7 (dd), 149.4, 139.9, 139.4, 133.8, 133.8, 131.2, 131.0, 129.3, 127.4, 126.5 (dd), 126.4, 124.1 (dd), 114.9, 112.0 (dd), 111.8, 105.0 (dd), 60.3, 42.2, 40.5, 19.6, 14.0

Example 70

N-Allyl-3-[2-chloro-4-(2,4-difluoro-phenylamino)-benzoyl]-4-methyl-benzamide (Compound 170)

The reaction was carried out similarly as described in the preparation of compound 120, using allylamine (0.50 mmol) and compound 439 (0.25 mmol). Purification was done by flash chromatography to afford the title compound. $^{13}$C NMR (CDCl$_3$) δ 195.6, 166.5, 159.3 (dd), 155.6 (dd), 148.1, 141.5, 139.7, 135.3, 134.0, 133.7, 131.8, 131.6, 128.9, 128.8, 127.7, 124.5 (dd), 124.2 (dd), 116.9, 116.2, 112.8, 111.6 (dd), 105.0 (dd), 42.5, 20.4

Example 71

3-[2-Chloro-4-(2,4-difluoro-phenylamino)-benzoyl]-4-methyl-N-(2-sulfamoyl-ethyl)-benzamide (Compound 171)

The reaction was carried out similarly as described in the preparation of compound 120, using 2-amino-ethanesulfonic acid amide (0.50 mmol) and compound 439 (0.25 mmol). Purification was done by flash chromatography to afford the title compound. $^{13}$C NMR (DMSO-d$_6$) δ 194.6, 165.3, 158.8 (dd), 155.8 (dd), 149.5, 139.8, 139.5, 133.8, 131.4, 131.1, 129.0, 127.1, 126.5 (dd), 126.2, 124.1 (dd), 114.9, 112.0 (dd), 111.8, 105.0 (dd), 53.5, 34.7, 19.6

Example 72

N-(2-Acetylamino-ethyl)-3-[2-chloro-4-(2,4-difluoro-phenylamino)-benzoyl]-4-methyl-benzamide (Compound 172)

The reaction was carried out similarly as described in the preparation of compound 120, using N-(2-amino-ethyl)-acetamide (0.50 mmol) and compound 439 (0.25 mmol). Purification was done by flash chromatography to afford the title compound. $^{13}$C NMR (CDCl$_3$) δ 195.9, 172.1, 167.6, 159.3 (dd), 155.8 (dd), 148.6, 141.3, 139.8, 135.3, 133.8, 131.5, 131.3, 129.0, 128.1, 127.9, 124.9 (dd), 124.2 (dd), 116.2, 112.5, 111.6 (dd), 104.9 (dd), 40.9, 39.8, 23.0, 20.3

Preparation 40

4-Bromo-2-chloro-thiobenzoic acid S-pyridin-2-yl ester (Compound 440)

A mixture of 4-bromo-3-chlorobenzoic acid (5.00 g, 21.24 mmol), 2,2'-dithiodipyridine (4.68 g, 21.24 mmol) and triphenylphosphine (5.57 g, 21.24 mmol) in acetonitrile (150 ml) was stirred at room temperature for 0.5 h. The crystals were filtered and washed with petroleum ether to give the title compound.

Preparation 41

3-(4-Bromo-2-chloro-benzoyl)-4-methoxy-benzoic acid methyl ester (Compound 441)

To a solution of 3-iodo-4-methoxy-benzoic acid methyl ester (6.31 g, 21.6 mmol) in THF (20 ml) was added 2 M solution of isopropylmagnesium chloride in THF (11.0 ml, 22.00 mmol) at −50° C. The reaction mixture was stirred at the same temperature for 30 min. Then compound 440 (5.91 g, 18 mmol) was added. The solution was warmed to room temperature and stirred for 2 h at the same temperature. Afterwards, the solution was quenched with saturated aqueous solution of NH$_4$Cl. The aqueous phase was extracted twice with diethyl ether. The combined organic phases were dried over MgSO$_4$ and concentrated in vacuo. The crude material was dissolved in ethyl acetate and silica gel added. The mixture was concentrated in vacuo. The residue was purified by chromatography (petroleum ether/ethyl acetate 5:1) to provide title compound as oil, which was solidified to a white solid.

Preparation 42

3-[2-Chloro-4-(2,6-difluoro-phenylamino)-benzoyl]-4-methoxy-benzoic acid methyl ester (Compound 442)

A mixture of compound 441 (4.65 g, 12.1 mmol), 2,6-difluoroamine (1.87 g, 14.5 mmol), dicyclohexyl-(2',4',6'-triisopropyl-biphenyl-2-yl)-phosphane (231 mg, 0.48 mmol), Pd(OAc)$_2$ (54 mg, 0.24 mmol), Cs$_2$CO$_3$ (8.3 g, 16.9 mmol) and celite (4.0 g) in 1,4-dioxane (30 ml) was stirred at 130° C. for 18 h. The mixture was concentrated together with silica gel. The residue was purified by chromatography (petroleum ether/ethyl acetate 3:1) to give the title compound as a yellow solid.

Preparation 43/Example 280

3-[2-Chloro-4-(2,6-difluoro-phenylamino)-benzoyl]-4-methoxy-benzoic acid (Compound 443)

The reaction was carried out as described in the preparation of compound 416, using compound 442 (1.00 g, 2.40 mmol) as the ester. The title compound was used without any further purification. $^{13}$C NMR (DMSO-d$_6$) δ 191.5, 166.4, 160.6, 157.5 (dd), 149.0, 133.9, 133.5, 133.3, 130.6, 129.1, 126.7, 126.5 (t), 122.9, 116.4 (t), 114.6, 112.5 (m), 112.0, 111.7, 56.1

Preparation 44

3-[2-Chloro-4-(2,6-difluoro-phenylamino)-benzoyl]-4-methoxy-benzoyl chloride (Compound 444)

To a suspension of compound 443 (590 mg, 1.4 mmol) in toluene (7 mL) was added thionyl chloride (206 μL, 2.8 mmol) and then refluxed for 2 h. The reaction mixture was concentrated in vacuo to afford the title compound without any further purification.

Example 73

3-[2-Chloro-4-(2,6-difluoro-phenylamino)-benzoyl]-N-(2-hydroxy-ethyl)-4-methoxy-benzamide (Compound 173)

The reaction was carried out similarly as described in the preparation of compound 120, using 2-amino-ethanol (0.28 mmol) and compound 444 (0.14 mmol). Purification was done by flash chromatography to afford the title compound. $^{13}$C NMR (CD$_3$CN) δ 193.6, 167.5, 161.1, 159.0 (dd), 149.9, 135.0, 134.4, 132.8, 130.5, 129.7, 129.4, 127.9, 127.6 (t), 117.8 (t), 116.3, 113.3 (m), 113.2, 112.8, 62.0, 56.9, 43.5

Example 74

3-[(2-Chloro-4-(2,6-difluoro-phenylamino)-benzoyl]-N-(2-fluoro-ethyl)-4-methoxy-benzamide (Compound 174)

The reaction was carried out similarly as described in the preparation of compound 120, using 2-fluoro-ethylamine (0.28 mmol) and compound 444 (0.14 mmol). Purification was done by flash chromatography to afford the title compound. $^{13}$C NMR (CDCl$_3$) δ 192.9, 166.6, 160.6, 157.5 (dd), 147.7, 134.6, 133.0, 132.4, 129.5, 129.4, 128.7, 126.4, 125.7 (t), 117.1 (t), 116.0, 112.8, 112.2 (m), 111.5, 82.7 (d), 56.0, 40.5 (d)

Example 75

3-[2-Chloro-4-(2,6-difluoro-phenylamino)-benzoyl]-N-(2,3-dihydroxy-propyl)-4-methoxy-benzamide (Compound 175)

The reaction was carried out similarly as described in the preparation of compound 120, using 3-amino-propane-1,2-diol (0.28 mmol) and compound 444 (0.14 mmol). Purification was done by flash chromatography to afford the title compound. $^{13}$C NMR (acetone-D$_6$) δ 192.8, 167.7, 161.1, 159.0 (dd), 149.8, 134.8, 134.1, 132.8, 130.6, 129.6, 129.5, 127.6, 127.4 (t), 118.1 (t), 116.1, 113.1 (m), 113.0, 112.4, 72.2, 64.6, 56.5, 43.9

Example 76

3-[2-Chloro-4-(2,6-difluoro-phenylamino)-benzoyl]-N-(3-hydroxy-propyl)-4-methoxy-benzamide (Compound 176)

The reaction was carried out similarly as described in the preparation of compound 120, using 3-amino-propan-1-ol (0.28 mmol) and compound 444 (0.14 mmol). Purification was done by flash chromatography to afford the title compound. $^{13}$C NMR (CDCl$_3$) δ 193.1, 167.4, 160.5, 157.5 (dd), 147.9, 134.6, 133.2, 132.4, 129.3, 129.1, 128.7, 126.4, 125.7 (t), 117.1 (t), 116.0, 112.7, 112.2 (m), 111.5, 59.7, 56.0, 37.1, 32.1

Example 77

3-[2-Chloro-4-(2,6-difluoro-phenylamino)-benzoyl]-4-methoxy-N-phenethyl-benzamide (Compound 177)

The reaction was carried out similarly as described in the preparation of compound 120, using phenylethylamine (0.28 mmol) and compound 444 (0.14 mmol). Purification was done by flash chromatography to afford the title compound. $^{13}$C NMR (CDCl$_3$) δ 192.8, 166.3, 160.5, 157.4 (dd), 147.5, 138.9, 134.5, 132.9, 132.5, 129.8, 129.2, 128.8, 128.7, 128.4, 126.9, 126.6, 125.6 (t), 117.1 (t), 116.0, 112.8, 112.2 (m), 111.6, 56.0, 41.3, 35.8

Example 78

3-[2-Chloro-4-(2,6-difluoro-phenylamino)-benzoyl]-N-(2-hydroxy-1,1-dimethyl-ethyl)-4-methoxy-benzamide (Compound 178)

The reaction was carried out similarly as described in the preparation of compound 120, using 2-amino-2-methyl-propan-1-ol (0.28 mmol) and compound 444 (0.14 mmol). Purification was done by flash chromatography to afford the title compound. $^{13}$C NMR (CDCl$_3$) δ 192.9, 167.3, 160.5, 157.5 (dd), 147.8, 134.6, 133.1, 132.5, 129.3, 129.3, 128.5, 127.0, 125.7 (t), 117.1 (t), 116.0, 112.7, 112.2 (m), 111.5, 70.7, 56.6, 56.0, 24.7

Example 79

3-[2-Chloro-4-(2,6-difluoro-phenylamino)-benzoyl]-4-methoxy-N-(2-morpholin-4-yl-ethyl)-benzamide (Compound 179)

The reaction was carried out similarly as described in the preparation of compound 120, using 2-morpholin-4-yl-ethylamine (0.28 mmol) and compound 444 (0.14 mmol). Purification was done by flash chromatography to afford the title compound. $^{13}$C NMR (CDCl$_3$) δ 192.9, 166.3, 160.5, 157.5 (dd), 147.7, 134.5, 133.0, 132.5, 129.5, 129.3, 128.6, 126.9, 125.7 (t), 117.1 (t), 116.0, 112.7, 112.2 (m), 111.6, 66.9, 57.0, 56.0, 53.3, 36.2

Example 80

3-[2-Chloro-4-(2,6-difluoro-phenylamino)-benzoyl]-N-(2-hydroxy-1-hydroxymethyl-1-methyl-ethyl)-4-methoxy-benzamide (Compound 180)

The reaction was carried out similarly as described in the preparation of compound 120, using 2-amino-2-methyl-propane-1,3-diol (0.28 mmol) and compound 444 (0.14 mmol). Purification was done by flash chromatography to afford the title compound. $^{13}$C NMR (CDCl$_3$) δ 193.0, 167.6, 160.6, 157.4 (dd), 147.7, 134.7, 133.2, 132.4, 129.3, 129.3, 128.8, 126.8, 125.7 (t), 117.1 (t), 116.0, 112.8, 112.2 (m), 111.4, 67.6, 59.3, 56.0, 20.0

Example 81

3-[2-Chloro-4-(2,6-difluoro-phenylamino)-benzoyl]-N-(2-hydroxy-ethyl)-4-methoxy-N-methyl-benzamide (Compound 181)

The reaction was carried out similarly as described in the preparation of compound 120, using 2-methylamino-ethanol (0.28 mmol) and compound 444 (0.14 mmol). Purification was done by flash chromatography to afford the title compound. $^{13}$C NMR (CDCl$_3$) δ 192.8, 159.4, 157.4 (dd), 147.5, 134.5, 133.0, 132.7, 129.7, 129.7, 129.1, 125.6 (t), 117.1 (t), 116.0, 112.8, 112.2 (m), 111.6, 61.2, 56.0

Example 82

{3-[(2-Chloro-4-(2,6-difluoro-phenylamino)-benzoyl]-4-methoxy-benzoylamino}-acetic acid ethyl ester (Compound 182)

The reaction was carried out similarly as described in the preparation of compound 120, using amino-acetic acid ethyl ester (0.84 mmol) and compound 444 (0.42 mmol). Purification was done by flash chromatography to afford the title compound. $^{13}$C NMR (CDCl$_3$) δ 192.8, 170.1, 166.4, 160.7, 157.5 (dd), 147.6, 134.6, 133.1, 132.4, 129.5, 129.4, 128.9, 126.0, 125.6 (t), 117.1 (t), 116.0, 112.8, 112.2 (m), 111.5, 61.6, 56.0, 41.9, 14.2

Example 83

(2-{3-[2-Chloro-4-(2,6-difluoro-phenylamino)-benzoyl]-4-methoxy-benzoylamino}-acetylamino)-acetic acid ethyl ester (Compound 183)

The reaction was carried out similarly as described in the preparation of compound 120, using (2-amino-acetylamino)-acetic acid ethyl ester (0.84 mmol) and compound 444 (0.42 mmol). Purification was done by flash chromatography to afford the title compound. $^{13}$C NMR (CDCl$_3$) δ 192.9, 169.9, 169.7, 166.9, 160.7, 157.5 (dd), 147.8, 134.6, 133.2, 132.4, 129.4, 129.3, 129.2, 125.7, 125.6 (t), 117.1 (t), 116.0, 112.8, 112.2 (m), 111.4, 61.5, 56.0, 43.7, 41.4, 14.1

Example 84

3-[2-Chloro-4-(2,6-difluoro-phenylamino)-benzoyl]-N,N-bis-(2-hydroxy-ethyl)-4-methoxy-benzamide (Compound 184)

The reaction was carried out similarly as described in the preparation of compound 120, using 2-(2-hydroxy-ethylamino)-ethanol (0.28 mmol) and compound 444 (0.14 mmol). Purification was done by flash chromatography to afford the title compound. $^{13}$C NMR (CDCl$_3$) δ 193.0, 172.8, 159.1, 157.4 (dd), 147.6, 134.5, 133.1, 132.5, 129.8, 129.5, 129.2, 128.3, 125.6 (t), 117.1 (t), 116.0, 112.8, 112.2 (m), 111.6, 60.7 (bs), 53.5 (bs), 49.9 (bs)

Example 85

3-[2-Chloro-4-(2,6-difluoro-phenylamino)-benzoyl]-4-methoxy-N,N-bis-(2-methoxy-ethyl)-benzamide (Compound 185)

The reaction was carried out similarly as described in the preparation of compound 120, using bis-(2-methoxy-ethyl)-amine (0.28 mmol) and compound 444 (0.14 mmol). Purification was done by flash chromatography to afford the title compound. $^{13}$C NMR (CDCl$_3$) δ 192.9, 171.4, 158.8, 157.5 (dd), 147.7, 134.5, 133.1, 132.2, 129.5, 129.5, 129.1, 128.8, 125.6 (t), 117.2 (t), 115.9, 112.6, 112.1 (m), 111.5, 70.6, 58.8, 56.0, 49.9 (bs), 45.5 (bs)

Preparation 45

3-[2-Chloro-4-(3-fluoro-2-methyl-phenylamino)-benzoyl]-4-methyl-benzoic acid methyl ester (Compound 445)

1-Bromo-3-fluoro-2-methyl-benzene (189 mg, 1.0 mmol) was dissolved in 4 mL dry 1,4-dioxane under an argon atmosphere. Compound 402 (304 mg, 1.00 mmol) was added and dissolved in the solvent. Dicyclohexyl-(2',4',6'-triisopropyl-biphenyl-2-yl)-phosphane (19 mg, 0.04 mmol), Pd(OAc)$_2$ (5 mg, 0.02 mmol) and Cs$_2$CO$_3$ (407 mg, 1.25 mmol) were added, and the reaction mixture was stirred under an argon atmosphere at 120° C. for 60 h. The reaction mixture was filtered and then purified by flash chromatography using EtOAc/petroleum ether (40-60) 1:4 as the eluent to afford the title compound as a solid. $^{13}$C NMR (CDCl$_3$) δ

Preparation 46/Example 281

3-[2-Chloro-4-(3-fluoro-2-methyl-phenylamino)-benzoyl]-4-methyl-benzoic acid (Compound 446)

The reaction was carried out as described in the preparation of compound 416, using compound 445 (185 mg, 0.45 mmol) as the ester. The title compound was used without any further purification. $^{13}$C NMR (DMSO-d$_6$) δ 194.3, 166.5, 161.3 (d), 149.9, 141.7, 140.3 (d), 139.4, 133.8, 133.7, 131.5, 131.2, 129.2, 128.2, 127.3 (d), 125.9, 119.4 (d), 119.2 (d), 115.0, 112.0, 111.2 (d), 19.8, 9.5 (d)

Preparation 47

3-[2-Chloro-4-(3-fluoro-2-methyl-phenylamino)-benzoyl]-4-methyl-benzoyl chloride (Compound 447)

To a suspension of compound 446 (158 mg, 0.4 mmol) in toluene (3 mL) was added thionyl chloride (58 μL, 0.8 mmol) and then refluxed for 2 h. The reaction mixture was concentrated in vacuo to afford the title compound without any further purification.

Example 86

3-[2-Chloro-4-(3-fluoro-2-methyl-phenylamino)-benzoyl]-N-(2-hydroxy-ethyl)-4-methyl-benzamide (Compound 186)

The reaction was carried out similarly as described in the preparation of compound 120, using 2-amino-ethanol (0.26 mmol) and compound 447 (0.13 mmol). Purification was done by flash chromatography to afford the title compound. $^{13}$C NMR (CDCl$_3$) δ 195.6, 167.8, 162.0 (d), 149.1, 141.4, 140.0, 139.8 (d), 135.5, 134.0, 131.5, 128.9, 127.9, 127.6, 127.2 (d), 119.7 (d), 119.0 (d), 116.3, 112.8, 112.0 (d), 62.3, 42.9, 20.3, 9.6 (d)

Example 87

3-[2-Chloro-4-(3-fluoro-2-methyl-phenylamino)-benzoyl]-4-methyl-N-(2,2,2-trifluoro-ethyl)-benzamide (Compound 187)

The reaction was carried out similarly as described in the preparation of compound 120, using 2,2,2-trifluoro-ethylamine (0.26 mmol) and compound 447 (0.13 mmol). Purification was done by flash chromatography to afford the title compound. $^{13}$C NMR (CDCl$_3$) δ 195.4, 166.8, 162.0 (d), 149.2, 142.0, 140.2, 139.7 (d), 135.5, 134.0, 131.6, 130.5, 128.9, 127.7, 127.2 (d), 124.1 (q), 119.9 (d), 119.2 (d), 116.3, 112.7, 112.1 (d), 41.1 (q), 20.3, 9.6 (d)

Preparation 48

3-[2-Chloro-4-(2-chloro-4-fluoro-phenylamino)-benzoyl]-4-methyl-benzoic acid methyl ester (Compound 448)

The reaction was carried out as described in the preparation of compound 445, using 1-bromo-2-chloro-4- fluoro-benzene (209 mg, 1.0 mmol) as the bromide. Purification was done by flash chromatography to afford the title compound.

Preparation 49/Example 282

3-[2-Chloro-4-(2-chloro-4-fluoro-phenylamino)-benzoyl]-4-methyl-benzoic acid (Compound 449)

The reaction was carried out as described in the preparation of compound 416, using compound 448 (142 mg, 0.33 mmol) as the ester. The title compound was used without any further purification. $^{13}$C NMR (DMSO-d$_6$) δ 194.4, 166.5, 158.9 (d), 149.7, 141.8, 139.3, 133.6, 131.5, 131.2, 129.6 (d), 129.3, 128.2, 127.6 (d), 126.3, 117.4 (d), 115.3 (d), 114.9, 111.9, 19.8

Preparation 50

3-[2-Chloro-4-(2-chloro-4-fluoro-phenylamino)-benzoyl]-4-methyl-benzoyl chloride (Compound 450)

To a suspension of compound 449 (102 mg, 0.24 mmol) in toluene (3 mL) was added thionyl chloride (35 μL, 0.5 mmol) and then refluxed for 2 h. The reaction mixture was concentrated in vacuo to afford the title compound without any further purification.

Example 88

3-[2-Chloro-4-(2-chloro-4-fluoro-phenylamino)-benzoyl]-N-(2-hydroxy-ethyl)-4-methyl-benzamide (Compound 188)

The reaction was carried out similarly as described in the preparation of compound 120, using 2-amino-ethanol (0.26 mmol) and compound 450 (0.13 mmol). Purification was done by flash chromatography to afford the title compound. $^{13}$C NMR (CDCl$_3$) δ 195.6, 167.7, 158.6 (d), 147.7, 141.5, 139.6, 135.3, 133.7, 133.4 (d), 131.6, 131.5, 129.1, 127.8, 127.3 (d), 123.2 (d), 117.5 (d), 117.0, 114.9 (d), 113.5, 62.2, 42.9, 20.4

Example 89

3-[2-Chloro-4-(2-chloro-4-fluoro-phenylamino)-benzoyl]-4-methyl-N-(2,2,2-trifluoro-ethyl)-benzamide (Compound 189)

The reaction was carried out similarly as described in the preparation of compound 120, using 2,2,2-trifluoro-ethylamine (0.26 mmol) and compound 450 (0.13 mmol). Purification was done by flash chromatography to afford the title compound. $^{13}$C NMR (CDCl$_3$) δ 195.4, 166.7, 158.7 (d), 147.7, 142.3, 139.9, 135.4, 133.7, 133.3 (d), 131.7, 130.6, 129.0, 127.9, 127.3 (d), 124.1 (q), 123.2 (d), 117.6 (d), 116.9, 114.9 (d), 113.5, 41.1 (q), 20.4

Preparation 51

3-[2-Chloro-4-(4-fluoro-phenylamino)-benzoyl]-4-methyl-benzoic acid methyl ester (Compound 451)

The reaction was carried out similarly as described in the preparation of compound 445, using 1-bromo-4-fluoro-benzene (110 μL, 1.0 mmol) as the bromide. Purification was done by flash chromatography to afford the title compound.

Example 90

3-[2-Chloro-4-(4-fluoro-phenylamino)-benzoyl]-N-(2-hydroxy-ethyl)-4-methyl-benzamide (Compound 190)

To a solution of compound 451 (96 mg, 0.24 mmol) in acetonitrile (0.7 mL) and 2-amino-ethanol (0.50 mL) was added K$_2$CO$_3$ (50 mg, 0.36 mmol) and stirred for 18 h at RT. The reaction mixture was poured into a mixture of EtOAc/water. The aqueous phase was extracted with more EtOAc. The organic phases were combined and concentrated on silica gel in vacuo. Purification was done by flash chromatography eluting with mixtures of MeOH/DCM to afford the title compound as yellow syrup. $^{13}$C NMR (CDCl$_3$) δ 195.9, 167.9, 159.5 (d), 149.5, 141.0, 140.0, 135.8 (d), 135.5, 134.2, 131.4, 128.9, 127.4, 126.8, 123.9 (d), 116.3 (d), 115.7, 112.1, 61.7, 42.9, 20.2

Preparation 52

3-(2-Chloro-4-phenylamino-benzoyl)-4-methyl-benzoic acid methyl ester (Compound 452)

The reaction was carried out similarly as described in the preparation of compound 445, using bromo-benzene (110 μL, 1.0 mmol) as the bromide. Purification was done by flash chromatography to afford the title compound.

Example 91

3-(2-Chloro-4-phenylamino-benzoyl)-N-(2-hydroxy-ethyl)-4-methyl-benzamide (Compound 191)

The reaction was carried out similarly as described in the preparation of compound 190, using 2-amino-ethanol (0.50 mL) and compound 452 (0.26 mmol). Purification was done by flash chromatography to afford the title compound. $^{13}$C NMR (DMSO-d$_6$) δ 194.6, 165.2, 148.7, 140.3, 139.4, 134.1, 133.9, 131.7, 130.9, 129.4, 129.0, 127.1, 126.1, 122.8, 120.2, 115.3, 112.2, 59.6, 42.1, 19.5

Preparation 53

3-[2-Chloro-4-(3,5-difluoro-phenylamino)-benzoyl]-4-methyl-benzoic acid methyl ester (Compound 453)

The reaction was carried out similarly as described in the preparation of compound 445, using 1-bromo-3,5-difluoro-benzene (115 μL, 1.0 mmol) as the bromide. Purification was done by flash chromatography to afford the title compound.

Example 92

3-[2-Chloro-4-(3,5-difluoro-phenylamino)-benzoyl]-N-(2-hydroxy-ethyl)-4-methyl-benzamide (Compound 192)

The reaction was carried out similarly as described in the preparation of compound 190, using 2-amino-ethanol (0.50 mL) and compound 453 (0.26 mmol). Purification was done by flash chromatography to afford the title compound. $^{13}$C NMR (DMSO-d$_6$) δ 194.9, 165.2, 163.1 (dd), 146.5, 143.9

(t), 139.8, 138.8, 133.5, 133.3, 131.8, 131.1, 129.3, 128.5, 127.5, 117.4, 114.1, 101.2 (m), 96.7 (t), 59.6, 42.1, 19.7

Preparation 54

3-[2-Chloro-4-(3-fluoro-phenylamino)-benzoyl]-4-methyl-benzoic acid methyl ester (Compound 454)

The reaction was carried out similarly as described in the preparation of compound 445, using 1-bromo-3-fluoro-benzene (110 µL, 1.0 mmol) as the bromide. Purification was done by flash chromatography to afford the title compound.

Example 93

3-[2-Chloro-4-(3-fluoro-phenylamino)-benzoyl]-N-(2-hydroxy-ethyl)-4-methyl-benzamide (Compound 193)

The reaction was carried out similarly as described in the preparation of compound 190, using 2-amino-ethanol (0.50 mL) and compound 454 (0.26 mmol). Purification was done by flash chromatography to afford the title compound. $^{13}$C NMR (DMSO-$d_6$) δ 194.8, 165.2, 162.8 (d), 147.6, 142.6 (d), 139.6, 139.1, 133.8, 133.6, 131.8, 131.0 (d), 131.0, 129.2, 127.3, 116.3, 115.2, 113.1, 108.7 (d), 105.9 (d), 59.6, 42.1, 19.6

Preparation 55

3-[2-Chloro-4-(4-fluoro-phenylamino)-benzoyl]-4-methoxy-benzoic acid methyl ester (Compound 455)

The reaction was carried out similarly as described in the preparation of compound 431, using 1-bromo-4-fluoro-benzene (1.88 mmol) and compound 435 (1.56 mmol). Purification was done by flash chromatography to afford the title compound as yellow foam.

Example 94

3-[2-Chloro-4-(4-fluoro-phenylamino)-benzoyl]-N-(2-hydroxy-ethyl)-4-methoxy-benzamide (Compound 194)

The reaction was carried out similarly as described in the preparation of compound 190, using 2-amino-ethanol (0.50 mL) and compound 455 (0.15 mmol). Purification was done by flash chromatography to afford the title compound. $^{13}$C NMR (DMSO-$d_6$) δ 191.6, 165.0, 159.1, 158.0 (d), 148.9, 136.6 (d), 134.1, 133.8, 131.5, 129.1, 128.2, 126.4, 126.2, 122.6 (d), 116.0 (d), 114.8, 111.7, 111.5, 59.7, 56.0, 42.1

Preparation 56

3-(2-Chloro-4-phenylamino-benzoyl)-4-methoxy-benzoic acid methyl ester (Compound 456)

The reaction was carried out similarly as described in the preparation of compound 431, using bromobenzene (1.88 mmol) and compound 435 (1.56 mmol). Purification was done by flash chromatography to afford the title compound as yellow foam.

Example 95

3-(2-Chloro-4-phenylamino-benzoyl)-N-(2-hydroxy-ethyl)-4-methoxy-benzamide (Compound 195)

The reaction was carried out similarly as described in the preparation of compound 190, using 2-amino-ethanol (0.50 mL) and compound 456 (0.15 mmol). Purification was done by flash chromatography to afford the title compound. $^{13}$C NMR (DMSO-$d_6$) δ 191.6, 165.0, 159.1, 148.4, 140.4, 134.0, 133.7, 131.5, 129.4, 129.1, 128.2, 126.4, 126.4, 122.7, 120.0, 115.2, 112.1, 111.5, 59.7, 56.0, 42.1

Preparation 57/Example 283

3-[2-Chloro-4-(4-fluoro-phenylamino)-benzoyl]-4-methoxy-benzoic acid (Compound 457)

The reaction was carried out as described in the preparation of compound 416, using compound 455 (230 mg, 0.56 mmol) as the ester. The title compound was used without any further purification.

Preparation 58

3-[2-Chloro-4-(4-fluoro-phenylamino)-benzoyl]-4-methoxy-benzoyl chloride (Compound 458)

A suspension of compound 457 (0.56 mmol) in toluene (2 mL) was added thionyl chloride (81 µL, 1.1 mmol) and then refluxed for 2 h. The reaction mixture was concentrated in vacuo to afford the title compound without any further purification.

Example 96

3-[2-Chloro-4-(4-fluoro-phenylamino)-benzoyl]-N-(2,2-difluoro-ethyl)-4-methoxy-benzamide (Compound 196)

The reaction was carried out similarly as described in the preparation of compound 120, using 2,2-difluoro-ethylamine (0.28 mmol) and compound 458 (0.14 mmol). Purification was done by flash chromatography to afford the title compound. $^{13}$C NMR (CDCl$_3$) δ 192.6, 166.8, 160.7, 159.6 (d), 148.8, 135.9 (d), 135.2, 133.7, 132.3, 129.8, 128.7, 128.5, 125.7, 124.1 (d), 116.4 (d), 115.5, 113.7 (t), 112.3, 111.5, 56.1, 42.3 (t)

Example 97

3-[2-Chloro-4-(4-fluoro-phenylamino)-benzoyl]-N-(2-fluoro-ethyl)-4-methoxy-benzamide (Compound 197)

The reaction was carried out similarly as described in the preparation of compound 120, using 2-fluoro-ethylamine (0.28 mmol) and compound 458 (0.14 mmol). Purification was done by flash chromatography to afford the title compound. $^{13}$C NMR (CDCl$_3$) δ 192.6, 166.6, 160.5, 159.6 (d), 148.7, 136.0 (d), 135.2, 133.7, 132.1, 129.7, 128.6, 128.6, 126.4, 124.0 (d), 116.4 (d), 115.5, 112.3, 111.5, 82.8 (d), 56.1, 40.5 (d)

Example 98

3-[2-Chloro-4-(4-fluoro-phenylamino)-benzoyl]-N-(2,3-dihydroxy-propyl)-4-methoxy-benzamide (Compound 198)

The reaction was carried out similarly as described in the preparation of compound 120, using 3-amino-propane-1,2-diol (0.28 mmol) and compound 458 (0.14 mmol). Purification was done by flash chromatography to afford the title compound. $^{13}$C NMR (mix) δ 193.2, 168.1, 160.5, 159.5 (d), 149.0, 136.1 (d), 135.3, 134.0, 132.4, 129.6, 128.9, 128.0, 126.0, 123.8 (d), 116.4 (d), 111.5, 71.1, 63.7, 56.1, 42.7

Example 99

N-Carbamoylmethyl-3-[2-chloro-4-(4-fluoro-phenylamino)-benzoyl]-4-methoxy-benzamide (Compound 199)

The reaction was carried out similarly as described in the preparation of compound 120, using 2-amino-acetamide (0.28 mmol) and compound 458 (0.14 mmol). Purification was done by flash chromatography to afford the title compound. $^{13}$C NMR (DMSO-d$_6$) δ 191.7, 171.1, 165.3, 159.4, 158.1 (d), 149.0, 136.8 (d), 134.1, 133.9, 131.8, 129.2, 128.5, 126.4, 126.2, 122.7 (d), 116.1 (d), 114.9, 111.8, 111.7, 56.1, 42.4

Preparation 59/Example 284

3-(2-Chloro-4-phenylamino-benzoyl)-4-methoxy-benzoic acid (Compound 459)

The reaction was carried out as described in the preparation of compound 416, using compound 456 (264 mg, 0.67 mmol) as the ester. The title compound was used without any further purification.

Preparation 60

3-(2-Chloro-4-phenylamino-benzoyl)-4-methoxy-benzoyl chloride (Compound 460)

To a suspension of compound 459 (0.67 mmol) in toluene (2 mL) was added thionyl chloride (98 µL, 1.3 mmol) and then refluxed for 2 h. The reaction mixture was concentrated in vacuo to afford the title compound without any further purification.

Example 100

3-(2-Chloro-4-phenylamino-benzoyl)-N-(2,2-difluoro-ethyl)-4-methoxy-benzamide (Compound 200)

The reaction was carried out similarly as described in the preparation of compound 120, using 2,2-difluoro-ethylamine (0.28 mmol) and compound 460 (0.14 mmol). Purification was done by flash chromatography to afford the title compound. $^{13}$C NMR (CDCl$_3$) δ 192.6, 166.8, 160.7, 148.1, 140.1, 135.1, 133.6, 132.4, 129.8, 129.6, 128.7, 125.7, 123.9, 121.1, 116.1, 113.7 (t), 112.9, 111.5, 56.1, 42.3 (t)

Example 101

3-(2-Chloro-4-phenylamino-benzoyl)-N-(2-fluoro-ethyl)-4-methoxy-benzamide (Compound 201)

The reaction was carried out similarly as described in the preparation of compound 120, using 2-fluoro-ethylamine (0.28 mmol) and compound 460 (0.14 mmol). Purification was done by flash chromatography to afford the title compound. $^{13}$C NMR (CDCl$_3$) δ 192.6, 166.6, 160.5, 148.0, 140.2, 135.1, 133.6, 132.2, 129.7, 129.6, 128.9, 128.6, 126.4, 123.8, 121.1, 116.1, 113.0, 111.5, 82.8, 56.1, 40.5

Example 102

3-(2-Chloro-4-phenylamino-benzoyl)-N-(2,3-dihydroxy-propyl)-4-methoxy-benzamide (Compound 202)

The reaction was carried out similarly as described in the preparation of compound 120, using 3-amino-propane-1,2-diol (0.28 mmol) and compound 460 (0.14 mmol). Purification was done by flash chromatography to afford the title compound. $^{13}$C NMR (mix) δ 193.2, 168.1, 160.5, 148.3, 140.1, 135.2, 133.9, 132.4, 129.6, 128.9, 128.2, 126.0, 123.7, 121.0, 116.0, 112.8, 111.5, 71.1, 63.7, 56.1, 42.7

Example 103

N-Carbamoylmethyl-3-(2-chloro-4-phenylamino-benzoyl)-4-methoxy-benzamide (Compound 203)

The reaction was carried out similarly as described in the preparation of compound 120, using 2-amino-acetamide (0.28 mmol) and compound 460 (0.14 mmol). Purification was done by flash chromatography to afford the title compound. $^{13}$C NMR (mix) δ 193.2, 172.2, 167.3, 160.7, 148.6, 140.3, 135.3, 133.9, 132.3, 129.8, 129.6, 129.2, 128.1, 125.7, 123.7, 121.0, 116.0, 112.8, 111.5, 56.1, 43.1

Preparation 61

4-Chloro-3-(2-chloro-4-nitro-benzoyl)-benzoic acid methyl ester (Compound 461)

A dry flask was charged with 4-chloro-3-iodo-benzoic acid methyl ester (5.0 g, 16.9 mmol) and the flask was evaporated and then filled with argon and this process repeated twice. Dry THF (35 mL) was added, and the solution cooled to −40° C.; then isopropylmagnesium chloride (8.85 mL, 2.0 M in diethyl ether, 17.7 mmol) was added slowly over 20 min keeping the temperature below −40° C. On completion of the addition the reaction mixture was stirred at −40° C. for 45 min. A THF solution of ZnCl$_2$ (2.32 g, 17.0 mmol, 0.9 M) was added dropwise over 20 min. The reaction mixture was stirred at 0° C. for 20 min; then 2-chloro-4-nitro-benzoyl chloride (3.7 g, 17 mmol) and Cu(OAc)$_2$ (68 mg, 0.34 mmol) were added and the reaction mixture was allowed to warm to room temperature. After 16 h the reaction mixture was poured into a mixture of EtOAc/water, then shaken and separated. The aqueous phase was extracted with more EtOAc. The organic phases were combined, dried (MgSO$_4$), filtered, and concentrated in vacuo to afford the crude product. The crude product was purified by flash chromatography using EtOAc/petroleum ether 1:6 as the eluent to give the title compound as yellow solid.

Preparation 62

3-(4-Amino-2-chloro-benzoyl)-4-chloro-benzoic acid methyl ester (Compound 462)

To a solution of compound 461 (3.31 g, 9.35 mmol) in methanol (125 mL) was added zinc dust (6.1 g, 94 mmol) and ammonium chloride (2.5 g, 47 mmol) in one portion under stirring. A CaCl₂ tube was mounted on the flask and the flask was placed in an oil bath with a temperature of 90° C. After 18 h the reaction mixture was cooled to RT, filtered, and then poured into a mixture of EtOAc/water. The aqueous phase was extracted with more EtOAc. The organic phases were combined, dried (MgSO₄), filtered, and concentrated in vacuo to afford the crude product. The crude product was purified by flash chromatography using EtOAc/pentane 1:1 as the eluent. The product was triturated in DCM and then filtered and dried to give the title compound as light yellow solid.

Preparation 63

4-Chloro-3-[2-chloro-4-(2,4-difluoro-phenylamino)-benzoyl]-benzoic acid methyl ester (Compound 463)

1-Bromo-2,4-difluorobenzene (87 µL, 0.77 mmol) was dissolved in 2.5 mL dry toluene under an argon atmosphere. Compound 462 (250 mg, 0.77 mmol) was added and dissolved in the solvent. 4,5-bis-diphenylphosphanyl-9,9-dimethyl-9H-xanthene (13 mg, 0.023 mmol), Pd(OAc)₂ (3.5 mg, 0.015 mmol) and Cs₂CO₃ (352 mg, 1.08 mmol) were added, and the reaction mixture was stirred under an argon atmosphere at 120° C. for 24 h. The reaction mixture was filtered and then purified by flash chromatography using EtOAc/petroleum ether 1:2 as the eluent to afford the title compound as a solid.

Example 104

4-Chloro-3-[2-chloro-4-(2,4-difluoro-phenylamino)-benzoyl]-4-(2-hydroxy-ethyl)-benzamide (Compound 204)

The reaction was carried out similarly as described in the preparation of compound 190, using 2-amino-ethanol (0.50 mL) and compound 463 (0.12 mmol). Purification was done by flash chromatography using MeOH/DCM 7:93 to afford the title compound. $^{13}$C NMR (DMSO-d₆) δ190.9, 164.6, 159.1 (dd), 156.0 (dd), 150.4, 139.4, 134.9, 134.8, 133.4, 132.9, 130.4, 130.0, 127.8, 127.0 (dd), 124.4, 123.9 (dd), 115.2, 112.1 (dd), 111.9, 105.2 (dd), 59.6, 42.4

Example 105

(2-{3-Chloro-4-[5-(2-hydroxy-ethylcarbamoyl)-2-methyl-benzoyl]-phenylamino}-phenyl)-carbamic acid ethyl ester (Compound 205)

To a solution of compound 112 (100 mg, 0.24 mmol) in DMF (1 mL) was added K₂CO₃ (66 mg, 0.48 mmol) and ethyl chloroformate (23 µL, 0.24 mmol) under stirring. After 1 h the reaction mixture was poured into a mixture of EtOAc/water. The aqueous phase was extracted with more EtOAc. The organic phases were combined, dried (MgSO₄), filtered, and concentrated in vacuo to afford the crude product. The crude product was purified by continuous gradient flash chromatography eluting with DCM/methanol (v:v=100:0 to 98:2) to afford the title compound as yellow foam. $^{13}$C NMR (DMSO-d₆) δ 194.6, 165.3, 154.0, 149.9, 139.6, 139.3, 133.8, 133.8, 132.4, 131.8, 131.6, 130.8, 128.9, 127.0, 125.6, 125.0, 124.6, 124.5, 124.0, 114.9, 111.8, 60.3, 59.6, 42.1, 19.5, 14.4

Example 106

3-[2-Chloro-4-(2-propionylamino-phenylamino)-benzoyl]-N-(2-hydroxy-ethyl)-4-methyl-benzamide (Compound 206)

To a solution of compound 112 (100 mg, 0.24 mmol) in glacial acetic acid (1 mL) was added propionic anhydride (33 µL, 0.26 mmol) under stirring. After 1 h the reaction mixture was concentrated in vacuo. Cyclohexane was added and the mixture was concentrated in vacuo. The crude product was purified by continuous gradient flash chromatography eluting with DCM/(EtOAc:MeOH:acetic acid 95:5:0.5) (v:v=95:5 to 90:10) to afford the title compound as yellow foam. $^{13}$C NMR (DMSO-d₆) δ 194.6, 172.3, 165.3, 149.7, 139.6, 139.3, 133.7, 132.3, 132.1, 131.8, 130.8, 128.9, 127.1, 125.7, 125.1, 124.7, 124.2, 115.0, 111.9, 59.6, 42.1, 29.0, 19.5, 9.5

Example 107

3-[4-(2-Acetylamino-phenylamino)-2-chloro-benzoyl]-N-(2-hydroxy-ethyl)-4-methyl-benzamide (Compound 207)

To a solution of compound 112 (100 mg, 0.24 mmol) in glacial acetic acid (1 mL) was added acetic anhydride (25 µL, 0.26 mmol) under stirring. After 1 h the reaction mixture was concentrated in vacuo. Cyclohexane was added and the mixture was concentrated in vacuo. The crude product was purified by flash chromatography eluting with EtOAc:MeOH:acetic acid 95:5:0.5 to afford the title compound as yellow foam. $^{13}$C NMR (DMSO-d₆) δ 194.6, 168.6, 165.3, 149.6, 139.5, 139.4, 133.7, 133.7, 132.1, 131.8, 130.9, 128.9, 127.2, 125.8, 125.1, 124.6, 123.9, 115.2, 111.9, 59.6, 42.1, 23.4, 19.5

Example 108

N-(2-{3-Chloro-4-[5-(2-hydroxy-ethylcarbamoyl)-2-methyl-benzoyl]-phenylamino}-phenyl)-succinamic acid (Compound 208)

To a solution of compound 112 (100 mg, 0.24 mmol) in glacial acetic acid (1 mL) was added succinic anhydride (26 mg, 0.26 mmol) under stirring. After 1 h the reaction mixture was concentrated in vacuo. Cyclohexane was added and the mixture was concentrated in vacuo. The crude product was purified by flash chromatography eluting with EtOAc:MeOH:acetic acid 90:10:1 to afford the title compound as yellow foam. $^{13}$C NMR (DMSO-d₆) δ 194.6, 173.8, 171.9, 165.3, 149.6, 139.5, 139.3, 133.8, 133.7, 132.1, 131.9, 131.7, 130.9, 128.9, 127.1, 125.8, 125.1, 124.9, 124.5, 123.7, 115.2, 112.0, 59.6, 42.1, 30.7, 28.9, 19.5

Preparation 64

2-Methyl-acrylic acid 2-[3-(2-{3-chloro-4-[5-(2-hydroxy-ethylcarbamoyl)-2-methyl-benzoyl]-phenylamino}-phenyl)-ureido]-ethyl ester (Compound 464)

To a solution of compound 112 (149 mg, 0.35 mmol) in dry pyridine (1 mL) was added 2-methyl-acrylic acid 2-isocyanato-ethyl ester (55 µL, 0.39 mmol) under stirring. After 1 h the reaction mixture was poured into a mixture of EtOAc/water. The aqueous phase was extracted with more EtOAc. The organic phases were combined, dried (MgSO₄), filtered, and concentrated in vacuo to afford the crude product. The crude product was purified by continuous gradient flash chromatography eluting with EtOAc/methanol (v:v=100:0 to 95:5) to afford the title compound as yellow foam.

Example 109

3-(2-Chloro-4-{2-[(3-(2-hydroxy-ethyl)-ureido]-phenylamino}-benzoyl)-N-(2-hydroxy-ethyl)-4-methyl-benzamide (Compound 209)

To a solution of compound 464 (115 mg, 0.20 mmol) in ethanol (1 mL) was added NaOH (2M, 150 µL, 0.30 mmol) and then refluxed for 2 h. The reaction mixture was cooled to RT and then poured into a mixture of EtOAc/water. The aqueous phase was extracted with more EtOAc. The organic phases were combined, dried ($MgSO_4$), filtered, and concentrated in vacuo to afford the crude product. The crude product was purified by flash chromatography eluting with MeOH/DCM 5:95 and 10:90 to afford the title compound as solid. $^{13}C$ NMR (DMSO-$d_6$) δ 194.7, 165.4, 155.4, 151.4, 139.8, 139.4, 136.6, 134.1, 134.0, 131.8, 130.9, 128.9, 128.1, 127.2, 126.4, 126.3, 125.3, 121.8, 120.2, 114.8, 111.4, 60.4, 59.7, 42.2, 41.9, 19.6

Preparation 65

4-(2-Chloro-4-nitro-benzoyl)-3-methyl-benzoic acid methyl ester (Compound 465)

The reaction was carried out similarly as described in the preparation of compound 401, using 4-iodo-3-methylbenzoic acid methyl ester (3.5 g, 12.5 mmol) as the iodide. Purification was done by flash chromatography using EtOAc/pentane 1:9 to afford the title compound as light brown solid.

Preparation 66

4-(4-Amino-2-chloro-benzoyl)-3-methyl-benzoic acid methyl ester (Compound 466)

The reaction was carried out similarly as described in the preparation of compound 402, using compound 465 (3.0 g, 9.1 mmol) as the nitro compound. Purification was done by flash chromatography using EtOAc/DCM 1:15 to afford the title compound as yellow foam.

Preparation 67

4-(4-Carboxy-2-methyl-benzoyl)-3-chloro-phenyl-ammonium acetate (Compound 467)

To a solution of compound 466 (250 mg, 0.82 mmol) in ethanol (10 mL) was added a solution of sodium hydroxide (2 M, 10 mL) and then stirred under reflux for 90 min. The reaction mixture was made weakly acidic (pH=4) by slowly addition of acetic acid (100), and then poured into a mixture of EtOAc/water. The aqueous phase was extracted with more EtOAc. The organic phases were combined, dried ($MgSO_4$), filtered, and concentrated in vacuo to afford the title compound as yellow syrup. It was used without any further purification.

Preparation 68

(4-Amino-2-chloro-phenyl)-[2-methyl-4-(morpholine-4-carbonyl)-phenyl]-methanone (Compound 468)

The reaction was carried out similarly as described in the preparation of compound 404, using compound 467 (106 mg, 0.37 mmol) as the acid. Purification was done by flash chromatography using MeOH/DCM 0:100, 1:100 and 2:100 to afford the title compound as foam.

Example 110

[2-Chloro-4-(4-fluoro-2-methyl-phenylamino)-phenyl]-[2-methyl-4-(morpholine-4-carbonyl)-phenyl]-methanone (Compound 210)

2-Bromo-5-fluorotoluene (56 µL, 0.44 mmol) was dissolved in 3 mL dry 1,4-dioxane in a vial under an argon atmosphere. Compound 468 (132 mg, 0.37 mmol) was added and dissolved in the solvent. Rac-BINAP (8.6 mg, 0.014 mmol), $Pd_2(dba)_3$ (8.5 mg, 0.009 mmol) and $Cs_2CO_3$ (169 mg, 0.52 mmol) were added, and the reaction mixture was stirred under an argon atmosphere at 100° C. for 48 h. The reaction mixture was filtered and then purified by flash chromatography using EtOAc/DCM 1:3 as the eluent to afford the title compound as yellow foam. $^{13}C$ NMR ($CDCl_3$) δ 195.5, 169.6, 160.7, 150.2, 141.1, 138.1, 137.2, 136.5, 135.7, 134.2, 133.6, 129.7, 129.2, 127.3, 127.3, 123.9, 117.9, 115.2, 113.9, 111.5, 66.9, 48.2, 42.5, 20.2, 18.1

Preparation 69

2-[2-(4-Bromo-3-methyl-phenoxy)-ethoxy]-tetrahydro-pyran (Compound 469)

A solution of 4-bromo-3-methyl-phenol (10.6 g, 56.9 mmol) and 2-(2-bromo-ethoxy)-tetrahydro-pyran (11.9, 56.9 mmol) were dissolved in dry DMF (25 mL). $K_2CO_3$ (19.7 g, 142 mmol) was added and the resulting reaction mixture was stirred at 80° C. for 48 h. The reaction mixture was cooled to RT and poured into a mixture of EtOAc and aqueous NaOH (2 N). The organic phase was separated, dried ($MgSO_4$), filtered, and concentrated in vacuo to give the crude product. The crude product was purified by flash chromatography using EtOAc/pentane 1:20 as the eluent to afford the title compound as colourless oil.

Preparation 70

(2-Chloro-4-nitro-phenyl)-{2-methyl-4-[2-(tetrahydro-pyran-2-yloxy)-ethoxy]-phenyl}-methanone (Compound 470)

n-Butyllithium (30.3 mL, 1.46 M in hexane, 44.3 mmol) was added dropwise (30 min) to a solution of compound 469 (13.95 g, 44.3 mmol) in THF (40 mL) at −78° C. and the resulting mixture was stirred for 30 min. A THF solution of dry $ZnCl_2$ (55 mmol, 1.0 M, 55 mL) was added with a syringe and the reaction mixture was allowed to warm to room temperature. After 2 h the reaction mixture was cooled to 0° C., and tetrakis(triphenylphosphine)palladium(0) (2.55 g, 2.21 mmol) was added followed by the addition of 2-chloro-4-nitrobenzoyl chloride (10.9 g, 46.0 mmol) in THF (10 mL). The stirring reaction mixture was allowed to warm to room temperature overnight. The mixture was partitioned between EtOAc (200 mL) and 1 N HCl (200 mL), and the aqueous phase was extracted with more EtOAc (200 mL). The combined organic extracts were washed with brine, dried over MgSO$_4$ and concentrated in vacuo. The residue was purified by flash chromatography using petroleum ether/EtOAc 9:1 to afford the title compound as a yellow syrup.

Preparation 71

(4-Amino-2-chloro-phenyl)-{2-methyl-4-[2-(tetrahydro-pyran-2-yloxy)-ethoxy]-phenyl}-methanone (Compound 471)

The reaction was carried out similarly as described in the preparation of compound 402, using compound 470 (3.0 g, 9.1 mmol) as the nitro compound. Purification was done by flash chromatography using EtOAc/petroleum ether 1:4 followed by 1:2 to afford the title compound as yellow foam.

Preparation 72/Example 285

[2-Chloro-4-(2-nitro-phenylamino)-phenyl]-{2-methyl-4-[2-(tetrahydro-pyran-2-yloxy)-ethoxy]-phenyl}-methanone (Compound 472)

1-Iodo-2-nitro-benzene (1.38 g, 5.54 mmol) was dissolved in 40 mL dry 1,4-dioxane under an argon atmosphere. Compound 471 (1.77 g, 4.54 mmol) was added and dissolved in the solvent. Rac-BINAP (106 mg, 0.17 mmol), Pd$_2$(dba)$_3$ (104 mg, 0.11 mmol) and Cs$_2$CO$_3$ (2.07 g, 6.30 mmol) were added, and the reaction mixture was stirred under an argon atmosphere at 100° C. for 24 h. The reaction mixture was poured into a mixture of EtOAc and water. The aqueous phase was washed with more EtOAc. The organic phases were combined and washed with brine, dried (MgSO$_4$), filtered and then purified by flash chromatography using EtOAc/petroleum ether 1:5 as the eluent to afford the title compound.

Example 111

[4-(2-Amino-phenylamino]-2-chloro-phenyl)-{2-methyl-4-[2-(tetrahydro-pyran-2-yloxy)-ethoxy]-phenyl}-methanone (Compound 211)

The reaction was carried out similarly as described in the preparation of compound 402, using compound 472 (2.14 g, 4.19 mmol) as the nitro compound. Purification was done by flash chromatography using EtOAc/petroleum ether 1:4 followed by 1:2 to afford the title compound as yellow foam. $^{13}$C NMR (CDCl$_3$) δ 195.6, 161.1, 148.9, 142.8, 141.7, 134.4, 133.4, 132.6, 131.3, 129.6, 127.5, 126.8, 125.7, 119.2, 117.7, 116.4, 115.1, 112.0, 111.0, 99.1, 67.4, 65.7, 62.2, 30.5, 25.4, 21.4, 19.4

Example 112

[4-(2-Amino-phenylamino)-2-chloro-phenyl]-[4-(2-hydroxy-ethoxy)-2-methyl-phenyl]-methanone (Compound 212)

A solution of compound 211 (1.10 g, 2.29 mmol) and toluene-4-sulfonic acid (653 mg, 3.43 mmol) in MeOH (20 mL) was stirred at RT for 3 h. The reaction mixture was poured into a mixture of aqueous NaOH (2N) and EtOAc. The aqueous phase was washed with more EtOAc. The organic phases were combined and washed with brine, dried (MgSO$_4$), filtered and then purified by flash chromatography using EtOAc/petroleum ether 1:1 followed by 2:1 as the eluent to afford the title compound as yellow foam. $^{13}$C NMR (CDCl$_3$) δ 195.6, 160.8, 149.0, 142.8, 141.7, 134.5, 133.3, 132.7, 131.7, 129.4, 127.5, 126.8, 125.6, 119.2, 117.5, 116.4, 115.2, 112.0, 110.9, 69.2, 61.3, 21.3

Preparation 73/Example 286

[4-(4-Bromo-2-nitro-phenylamino)-2-chloro-phenyl]-{2-methyl-4-[2-(tetrahydro-pyran-2-yloxy)-ethoxy]-pheny (Compound 473)

To a solution of compound 471 (2.74 g, 7.02 mmol) and 4-bromo-1-fluoro-2-nitro-benzene (1.49 g, 6.76 mmol) in DMSO (8.0 mL) was slowly added potassium tert-butoxide (1.68 g, 14.9 mmol) under stirring. After 4 h at RT the reaction mixture was poured into a mixture of EtOAc/water. The aqueous phase was extracted with more EtOAc. The organic phases were combined, dried (MgSO$_4$), filtered, and concentrated in vacuo to afford the crude product. The crude product was purified by chromatography eluting with EtOAc/petroleum ether 1:9 to afford the title compound as orange syrup.

Example 113

[4-(2-Amino-4-bromo-phenylamino)-2-chloro-phenyl]-{2-methyl-4-[2-(tetrahydro-pyran-2-yloxy)-ethoxy]-pheny (Compound 213)

The reaction was carried out similarly as described in the preparation of compound 402, using compound 473 (1.10 g, 1.86 mmol) as the nitro compound. Purification was done by flash chromatography using EtOAc/petroleum ether 1:3 to afford the title compound as foam. $^{13}$C NMR (CDCl$_3$) δ 195.5, 161.2, 148.3, 144.2, 141.8, 134.3, 133.5, 132.5, 131.1, 130.1, 128.2, 124.7, 121.9, 120.5, 118.9, 117.7, 115.3, 112.1, 111.0, 99.1, 67.4, 65.7, 62.3, 30.5, 25.4, 21.4, 19.4

Example 114

[4-(2-Amino-4-bromo-phenylamino)-2-chloro-phenyl]-[4-(2-hydroxy-ethoxy)-2-methyl-phenyl]-methanone (Compound 214)

The reaction was carried out similarly as described in the preparation of compound 212, using compound 213 (1.10 g, 1.86 mmol) as the THP ether protected compound. Purification was done by flash chromatography using EtOAc/petroleum ether 3:7 to afford the title compound as yellow foam. $^{13}$C NMR (CDCl$_3$) δ 195.6, 160.9, 148.4, 144.2, 141.9, 134.4, 133.4, 132.6, 131.5, 129.9, 128.2, 124.6, 121.9, 120.5, 118.9, 117.6, 115.2, 112.1, 110.9, 69.2, 61.3, 21.4

Preparation 74

2-[3-(4-Bromo-3-methyl-phenoxy)-propoxy]-tetrahydro-pyran (Compound 474)

The reaction was carried out similarly as described in the preparation of compound 469, using 2-(3-bromo-propoxy)-tetrahydro-pyran (5.58 g, 25 mmol) as the aliphatic bromide. Purification was done by flash chromatography using EtOAc/petroleum ether 1:4 to afford the title compound as colourless oil.

Preparation 75

(2-Chloro-4-nitro-phenyl)-{2-methyl-4-[3-(tetrahydro-Pyran-2-yloxy)-propoxy]-phenyl}-methanone (Compound 475)

The reaction was carried out similarly as described in the preparation of compound 470, using compound 474 (8.56 g, 26 mmol) as the bromide. Purification was done by flash chromatography using EtOAc/petroleum ether 1:9 to afford the title compound as yellow oil.

Preparation 76

(4-Amino-2-chloro-phenyl)-{2-methyl-4-[3-(tetrahydro-pyran-2-yloxy)-propoxy]-phenyl}-methanone (Compound 476)

The reaction was carried out similarly as described in the preparation of compound 402, using compound 475 (5.95 g, 13.71 mmol) as the nitro compound. The title compound was obtained without any further purification as yellow oil.

Preparation 77/Example 287

[4-(4-Bromo-2-nitro-phenylamino)-2-chloro-phenyl]-{2-methyl-4-[3-(tetrahydro-pyran-2-yloxy)-propoxy]-phenyl}-methanone (Compound 477)

The reaction was carried out similarly as described in the preparation of compound 473, using compound 476 (1.45 g, 3.59 mmol) as the amine. Purification was done by flash chromatography using EtOAc/petroleum ether 1:6 to afford the title compound as orange oil.

Example 115

[4-(2-Amino-4-bromo-phenylamino)-2-chloro-phenyl]-{2-methyl-4-[3-(tetrahydro-pyran-2-yloxy)-propoxy]-phenyl}-methanone (Compound 215)

The reaction was carried out similarly as described in the preparation of compound 402, using compound 477 (5.95 g, 13.71 mmol) as the nitro compound. The title compound was obtained without any further purification as yellow foam. $^{13}$C NMR (CDCl$_3$) 195.6, 161.4, 148.2, 142.9, 142.0, 134.2, 133.7, 132.4, 130.7, 130.2, 128.0, 125.4, 122.7, 120.2, 119.5, 117.6, 115.4, 112.3, 110.9, 99.0, 65.0, 63.9, 62.4, 30.7, 29.6, 25.4, 21.5, 19.6

Example 116

[4-(2-Amino-4-bromo-phenylamino)-2-chloro-phenyl]-[4-(3-hydroxy-propoxy)-2-methyl-phenyl]-methanone (Compound 216)

The reaction was carried out similarly as described in the preparation of compound 212, using compound 215 (1.30 g, 2.27 mmol) as the THP ether protected compound. Purification was done by flash chromatography using EtOAc/petroleum ether 1:1 to afford the title compound as yellow foam. Trituration in a mixture of diethyl ether and pentane afforded the title compound as white solid. $^{13}$C NMR (CDCl$_3$) δ 195.5, 161.1, 148.4, 144.3, 141.9, 134.3, 133.5, 132.5, 131.1, 130.0, 128.2, 124.7, 121.9, 120.5, 118.8, 117.6, 115.2, 112.1, 110.8, 65.5, 60.1, 31.9, 21.4

Preparation 78

1-Bromo-4-(2-fluoro-ethoxy)-2-methyl-benzene (Compound 478)

A solution of 4-bromo-3-methyl-phenol (3.74 g, 20 mmol), 2-fluoro-ethanol (2.29 mL, 22 mmol), and triphenylphosphine (5.77 g, 22 mmol) in dry THF (15 mL) was cooled to 0° C. under stirring. Diethyl azodicarboxylate (40% in toluene, 10 mL, 22 mmol) was added and the reaction mixture was allowed to come to RT overnight. After 18 h at RT the reaction mixture was poured into a mixture of EtOAc/water. The aqueous phase was extracted with more EtOAc. The organic phases were combined, dried (MgSO$_4$), filtered, and concentrated in vacuo to afford the crude product. The crude product was purified by chromatography eluting with DCM/petroleum ether 1:6 to afford the title compound as colourless oil.

Preparation 79

(2-Chloro-4-nitro-phenyl)-[4-(2-fluoro-ethoxy)-2-methyl-phenyl]-methanone (Compound 479)

The reaction was carried out similarly as described in the preparation of compound 470, using compound 478 (4.25 g, 18.2 mmol) as the bromide. Purification was done by flash chromatography using EtOAc/petroleum ether 1:9 followed by 1:6 to afford the title compound as yellow solid.

Preparation 80

(4-Amino-2-chloro-phenyl)-[4-(2-fluoro-ethoxy)-2-methyl-phenyl]-methanone (Compound 480)

A mixture of compound 479 (2.31 g, 6.84 mmol) and stannous chloride dihydrate (7.72 g, 34.2 mmol) in absolute ethanol was heated to reflux. After 1 h the solution was cooled to RT and then poured into a mixture of ice/aqueous NaOH (7N)/EtOAc. The aqueous phase was extracted with more EtOAc. The organic phases were combined, washed with brine, dried (MgSO$_4$), filtered and concentrated in vacuo. The crude product was triturated in a mixture of diethyl ether and petroleum ether 1:1 to afford the title compound as solid.

Preparation 81/Example 288

[4-(4-Bromo-2-nitro-phenylamino)-2-chloro-phenyl]-[4-(2-fluoro-ethoxy)-2-methyl-phenyl]-methanone (Compound 481)

The reaction was carried out similarly as described in the preparation of compound 473, using compound 480 (595 mg, 1.93 mmol) as the amine. Purification was done by flash chromatography using EtOAc/petroleum ether 1:9 followed by 1:6 to afford the title compound as foam. Trituration in ethanol gave a solid.

Example 117

[4-(2-Amino-4-bromo-phenylamino)-2-chloro-phenyl]-[4-(2-fluoro-ethoxy)-2-methyl-phenyl]-methanone (Compound 217)

The reaction was carried out similarly as described in the preparation of compound 480, using compound 481 (585 mg, 1.15 mmol) as the nitro compound. Purification was done by flash chromatography using EtOAc/petroleum ether 1:7 followed by 1:4 to afford the title compound as foam. Trituration in a mixture of diethyl ether and petroleum ether 2:3 afforded the title compound as solid. $^{13}$C NMR (CDCl$_3$) δ 195.5, 160.6, 148.4, 144.3, 141.8, 134.4, 133.3, 132.6, 131.7, 129.9, 128.2, 124.6, 121.9, 120.5, 118.8, 117.6, 115.3, 112.1, 110.9, 81.7 (d), 67.0 (d), 21.3

Example 118

[4-(4-Bromo-2-methyl-phenylamino)-2-chloro-phenyl]-[4-(2-fluoro-ethoxy)-2-methyl-phenyl]-methanone (Compound 218)

A Schlenk tube was charged with compound 480 (402 mg, 1.31 mmol) in 1,4-dioxane (3.0 mL), 5-bromo-1-iodo-toluene (358 mg, 1.19 mmol), sodium tert-butoxide (160 mg, 1.67 mmol), Pd$_2$(dba)$_3$ (27 mg, 0.03 mmol), and rac-BINAP (28 mg, 0.045 mmol). The tube was capped with a rubber septum, flushed with argon for 5 min, and then stirred at 100° C. for 72 h. The reaction mixture was allowed to cool to RT, and then poured into a mixture of water and EtOAc. The aqueous phase was extracted twice with more EtOAc. The combined organic phases were washed with brine, dried (MgSO$_4$), filtered and concentrated in vacuo. The crude product was purified by chromatography eluting with petroleum ether/EtOAc 4:1 to afford the title compound as yellow oil. $^{13}$C NMR (CDCl$_3$) δ 195.4, 160.6, 147.7, 141.9, 137.7, 134.3, 134.0, 133.9, 133.4, 132.6, 131.6, 130.3, 130.0, 124.5, 117.6, 117.6, 116.1, 112.9, 111.0, 81.7, 67.0, 21.3, 17.8

Preparation 82

1-Bromo-4-(2-methoxy-ethoxy)-2-methyl-benzene (Compound 482)

The reaction was carried out similarly as described in the preparation of compound 478, using 2-methoxy-ethanol (4.66 mL, 58.8 mmol) as the aliphatic alcohol. The crude product was purified by continuous gradient flash chromatography using EtOAc/petroleum ether (40-60) (v:v=0:100 to 20:80) as the eluent to afford the title compound as colourless oil.

Preparation 83

(2-Chloro-4-nitro-phenyl)-[4-(2-methoxy-ethoxy)-2-methyl-phenyl]-methanone (Compound 483)

The reaction was carried out similarly as described in the preparation of compound 470, using compound 482 (4.66 mL, 58.8 mmol) as the bromide. The crude product was purified by continuous gradient flash chromatography using EtOAc/petroleum ether (40-60) (v:v=15:85 to 50:50) as the eluent to afford the title compound as yellow syrup.

Preparation 84

(4-Amino-2-chloro-phenyl)-[4-(2-methoxy-ethoxy)-2-methyl-phenyl]-methanone (Compound 484)

The reaction was carried out similarly as described in the preparation of compound 480, using compound 483 (6.21 g, 17.8 mmol) as the nitro compound. The crude product was purified by continuous gradient flash chromatography using EtOAc/petroleum ether (40-60) (v:v=1:2 to 2:1) as the eluent to afford the title compound as yellow solid.

Preparation 85/Example 289

[4-(4-Bromo-2-nitro-phenylamino)-2-chloro-phenyl]-[4-(2-methoxy-ethoxy)-2-methyl-phenyl]-methanone (Compound 485)

The reaction was carried out similarly as described in the preparation of compound 473, using compound 484 (2.00 g, 6.25 mmol) as the amine. The crude product was purified by continuous gradient flash chromatography using DCM/petroleum ether (40-60) (v:v=20:80 to 50:50) as the eluent to afford the title compound as orange foam.

Example 119

[4-(2-Amino-4-bromo-phenylamino)-2-chloro-phenyl]-[4-(2-methoxy-ethoxy)-2-methyl-phenyl]-methanone (Compound 219)

The reaction was carried out similarly as described in the preparation of compound 402, using compound 485 (1.75 g, 3.37 mmol) as the nitro compound. The crude product was purified by continuous gradient flash chromatography using EtOAc/petroleum ether (40-60) (v:v=20:80 to 50:50 as the eluent. Crystallisation from DCM afforded the title compound as solid. $^{13}$C NMR (DMSO-d$_6$) δ 194.3, 160.4, 149.5, 145.6, 140.3, 132.6, 132.5, 132.3, 131.0, 127.4, 127.1, 123.9, 118.5, 118.3, 117.1, 114.0, 111.4, 111.1, 70.1, 66.9, 58.1, 20.6.

Example 120

[4-(4-Bromo-2-methyl-phenylamino)-2-chloro-phenyl]-{2-methyl-4-[2-(tetrahydro-pyran-2-yloxy)-ethoxy]-phenyl}-methanone (Compound 220)

A Schlenk tube was charged with compound 471 (4.25 g, 10.9 mmol) in 1,4-dioxane (40 mL), 5-bromo-1-Iodo-toluene (3.88 g, 13.1 mmol), Cs$_2$CO$_3$ (4.97 g, 15.26 mmol), Pd$_2$(dba)$_3$ (250 mg, 0.27 mmol), and rac-BINAP (255 mg, 0.41 mmol). The tube was capped with a rubber septum, flushed with argon for 5 min, and then stirred at 100° C. for 72 h. The reaction mixture was allowed to cool to RT, and then poured into a mixture of water and EtOAc. The aqueous phase was extracted twice with more EtOAc. The combined organic phases were washed with brine, dried (MgSO$_4$), filtered and concentrated in vacuo. The crude product was purified by chromatography eluting with petroleum ether/EtOAc 4:1 to afford the title compound as yellow foam. $^1$H NMR (CDCl$_3$) δ 7.39 (d, 1H), 7.35-7.25 (m, 3H), 7.14 (d, 1H), 6.81 (m, 2H), 6.69 (m, 2H), 5.63 (bs, 1H), 4.70 (bt, 1H), 4.23-4.00 (m, 3H), 3.95-3.77 (m, 2H), 3.53 (m, 1H), 2.51 (s, 3H), 2.23 (s, 3H), 1.92-1.45 (m, 6H)

Example 121

[4-(4-Bromo-2-methyl-phenylamino)-2-chloro-phenyl]-[4-(2-hydroxy-ethoxy)-2-methyl-phenyl]-methanone (Compound 221)

The reaction was carried out similarly as described in the preparation of compound 212, using compound 220 (3.82 g, 6.83 mmol) as the THP ether protected compound. Purification was done by flash chromatography using EtOAc/petroleum ether 1:2 followed by 2:3 to afford the title compound as yellow foam. $^{13}$C NMR (CDCl$_3$) δ 195.4, 160.9, 147.7, 141.9, 137.8, 134.3, 134.0, 133.9, 133.4, 132.5, 131.5, 130.3, 130.0, 124.5, 117.6, 117.5, 116.1, 112.9, 110.9, 69.2, 61.4, 21.4, 17.8

Example 122

[4-(2-Azido-ethoxy)-2-methyl-phenyl]-[4-(4-bromo-2-methyl-phenylamino)-2-chloro-phenyl]-methanone (Compound 222)

To a solution of compound 221 (101 mg, 0.21 mmol) in dry pyridine (2 mL) was added 4-methyl-benzenesulfonyl chloride (81 mg, 0.43 mmol) at 0° C. under stirring. After 5 h at RT the reaction mixture was poured into a mixture of water and EtOAc. The aqueous phase was extracted twice with more EtOAc. The combined organic phases were washed with brine, dried (MgSO$_4$), filtered and concentrated in vacuo. The crude tosylate was dissolved in dry DMF and sodium azide (17 mg, 0.26 mmol) was added to the solution. After 18 h at RT the
reaction mixture was poured into a mixture of water and EtOAc. The aqueous phase was extracted twice with more EtOAc. The combined organic phases were washed with brine, dried (MgSO$_4$), filtered and concentrated in vacuo. The crude product was purified by chromatography eluting with petroleum ether/EtOAc 2:1 to afford the title compound. $^{13}$C NMR (CDCl$_3$) δ 195.5, 160.4, 147.8, 141.8, 137.7, 134.4, 134.0, 134.0, 133.3, 132.6, 131.8, 130.1, 130.0, 124.6, 117.6, 116.1, 112.8, 110.9, 66.9, 50.1, 21.3, 17.8

Example 123

[4-(2-Amino-ethoxy)-2-methyl-phenyl]-[4-(4-bromo-2-methyl-phenylamino)-2-chloro-phenyl]-methanone (Compound 223)

A solution of compound 222 (22 mg, 0.051 mmol), triphenylphosphine (15 mg, 0.056 mmol), and water (1 μL, 0.056 mmol) in THF (1 mL) was stirred at RT for 48 h. The reaction mixture was concentrated in vacuo and purified by flash chromatography using DCM/MeOH/NH$_4$OH 90:10:1 as the eluent to afford the title compound. $^{13}$C NMR (DMSO-d$_6$) δ 194.3, 160.8, 148.5, 140.5, 138.3, 134.5, 133.4, 132.9, 132.6, 132.3, 130.5, 129.5, 128.2, 124.8, 117.3, 116.0, 114.8, 112.1, 111.1, 70.2, 40.7, 20.7, 17.4.

Example 124

[4-(2-Bromo-phenylamino)-2-chloro-phenyl]-{2-methyl-4-[2-(tetrahydro-pyran-2-yloxy)-ethoxy]-phenyl}-methanone (Compound 224)

The reaction was carried out similarly as described in the preparation of compound 220, using 1-bromo-2-iodo-benzene (1.19 mL, 9.23 mmol) as the iodide. Purification was done by flash chromatography using EtOAc/petroleum ether 1:4 followed by 1:2. Crystallisation from mixtures of diethyl ether and petroleum ether afforded the title compound as beige solid. $^{13}$C NMR (CDCl$_3$) δ 195.4, 161.4, 145.3, 142.2, 139.0, 133.9, 133.4, 132.3, 132.0, 130.6, 128.3, 123.6, 119.2, 118.1, 117.9, 115.1, 114.8, 111.0, 99.0, 67.4, 65.7, 62.2, 30.5, 25.4, 21.6, 19.3

Example 125

{4-[2-(3-Amino-propenyl)-phenylamino]-2-chloro-phenyl}-{2-methyl-4-[2-(tetrahydro-pyran-2-yloxy)-ethoxy]-phenyl}-methanone (Compound 225)

A solution of compound 224 (1.09 g, 2.00 mmol), Pd$_2$(dba)$_3$ (55 mg, 0.06 mmol), 3-tributylstannanyl-allylamine (727 mg, 2.1 mmol), CsF (668 mg, 4.4 mmol), and tri-tert-butyl-phosphane (0.2 mmol, 0.4 mL, 0.5 M in hexane) in dry 1,4-dioxane (5.0 mL) was stirred at 35° C. for 120 h under an atmosphere of argon. The reaction mixture was filtered. Acetonitrile (50 mL) was added and the resulting mixture was washed with petroleum ether (×3). The acetonitrile phase was concentrated in vacuo. The crude product was purified by chromatography eluting with petroleum ether/EtOAc 2:1 followed by DCM/MeOH/Et$_3$N 94:3:3 to afford the title compound as yellow foam. $^{13}$C NMR (CDCl$_3$) δ 195.7, 161.2, 148.1, 141.7, 138.0, 134.0, 133.5, 132.4, 131.2, 130.7, 129.8, 129.0, 128.7, 128.6, 127.5, 124.4, 122.4, 117.7, 116.3, 113.1, 111.0, 99.1, 67.4, 65.7, 62.2, 43.0, 30.5, 25.4, 21.4, 19.4

Example 126

{4-[2-(3-Amino-propenyl)-phenylamino]-2-chloro-phenyl}-[4-(2-hydroxy-ethoxy)-2-methyl-phenyl]-methanone (Compound 226)

The reaction was carried out similarly as described in the preparation of compound 212, using compound 225 (50 mg, 0.096 mmol) as the THP ether protected compound. Purification was done by flash chromatography using DCM/MeOH/Et$_3$N 92:5:3 to afford the title compound as yellow oil. $^{13}$C NMR (DMSO-d$_6$) δ 194.3, 160.8, 149.4, 140.3, 137.3, 132.7, 132.6, 132.6, 132.3, 131.9, 130.7, 128.0, 127.6, 126.4, 124.9, 124.5, 124.4, 117.2, 114.6, 111.8, 111.1, 69.6, 59.3, 43.5, 20.7

Example 127

1-(2-{3-Chloro-4-[4-(2-hydroxy-ethoxy)-2-methyl-benzoyl]-phenylamino}-phenyl)-3-ethyl-urea (Compound 227)

To a solution of compound 212 (150 mg, 0.38 mmol) in dry pyridine (1 mL) was added ethyl isocyanate (75 μL, 0.95 mmol) under stirring. After 5 h the reaction mixture was poured into a mixture of EtOAc/water. The aqueous phase was extracted with more EtOAc. The organic phases were combined, dried (MgSO$_4$), filtered, and concentrated in vacuo to afford the crude product. The crude product was purified by continuous gradient flash chromatography eluting with EtOAc/petroleum ether (v:v=10:90 to 67:33) to afford the title compound as yellow syrup. $^{13}$C NMR (DMSO-d$_6$): δ 194.4, 160.8, 155.0, 149.9, 140.4, 136.1, 132.6, 132.5, 132.3, 130.7, 128.7, 127.5, 125.8, 125.7, 121.8, 120.3, 117.2, 114.3, 111.5, 111.1, 69.6, 59.4, 33.8, 20.7, 15.2

Example 128

1-[5-Bromo-2-(3-chloro-4-{2-methyl-4-[2-(tetrahydro-pyran-2-yloxy)-ethoxy]-benzoyl}-phenylamino)-phenyl]-3-ethyl-urea (Compound 228)

To a solution of compound 213 (158 mg, 0.28 mmol) in dry pyridine (2 mL) was added ethyl isocyanate (33 μL, 0.42 mmol) under stirring. After 16 h the reaction mixture was poured into a mixture of EtOAc/water. The aqueous phase was extracted with more EtOAc. The organic phases were combined, dried (MgSO$_4$), filtered, and concentrated in vacuo to afford the crude product. The crude product was purified by flash chromatography eluting with EtOAc/petroleum ether 2:3 to afford the title compound. $^{13}$C NMR (CDCl$_3$) 196.3, 161.5, 155.7, 148.3, 141.9, 135.1, 134.0, 133.8, 132.3, 130.8, 130.2, 129.9, 126.9, 126.0, 125.0, 118.5, 117.9, 116.0, 112.7, 111.1, 99.2, 67.5, 65.8, 62.4, 35.3, 30.5, 25.4, 21.5, 19.5, 15.2

Example 129

1-(5-Bromo-2-{3-chloro-4-[4-(2-hydroxy-ethoxy)-2-methyl-benzoyl]-phenylamino}phenyl)-3-ethyl-urea (Compound 229)

The reaction was carried out similarly as described in the preparation of compound 212, using compound 228 (138 mg, 0.22 mmol) as the THP ether protected compound. Purification was done by flash chromatography using EtOAc/petroleum ether 3:1 as the eluent to afford the title compound as yellow solid. $^{13}$C NMR (DMSO-d$_6$) δ 194.4, 160.8, 154.7, 149.5, 140.5, 137.9, 132.8, 132.4, 132.2, 130.6, 128.0, 127.7, 127.5, 124.1, 121.8, 118.1, 117.3, 114.6, 111.7, 111.1, 69.6, 59.4, 33.8, 20.7, 15.1

Example 130

1-[5-Bromo-2-(3-chloro-4-{2-methyl-4-[2-(tetrahydro-pyran-2-yloxy)-ethoxy]-benzoyl}-phenylamino)-phenyl]-3-cyclohexyl-urea (Compound 230)

To a solution of compound 213 (151 mg, 0.34 mmol) in dry pyridine (2 mL) was added cyclohexyl isocyanate (65 μL, 0.51 mmol) under stirring. After 18 h the reaction mixture was poured into a mixture of EtOAc/water. The aqueous phase was extracted with more EtOAc. The organic phases were combined, dried (MgSO$_4$), filtered, and concentrated in vacuo to afford the crude product. The crude product was purified by flash chromatography eluting with EtOAc/petroleum ether 1:2 to afford the title compound as yellow solid. $^{13}$C NMR (DMSO-d$_6$) δ 194.4, 160.6, 154.0, 149.5, 140.5, 138.0, 132.7, 132.5, 132.2, 130.7, 128.0, 127.6, 127.5, 124.0, 121.7, 118.1, 117.3, 114.6, 111.7, 111.2, 98.0, 67.2, 65.0, 61.2, 47.7, 33.2, 32.7, 30.0, 24.9, 24.2, 20.7, 18.9

Preparation 86

2-Methyl-acrylic acid 2-{3-[5-bromo-2-(3-chloro-4-{2-methyl-4-[2-(tetrahydro-pyran-2-yloxy)-ethoxy]-benzoyl}-phenylamino)-phenyl]-ureido}-ethyl ester (Compound 486)

To a solution of compound 213 (158 mg, 0.28 mmol) in dry pyridine (2 mL) was added 2-methyl-acrylic acid 2-isocyanato-ethyl ester (60 μL, 0.42 mmol) under stirring. After 16 h the reaction mixture was poured into a mixture of EtOAc/ water. The aqueous phase was extracted with more EtOAc. The organic phases were combined, dried (MgSO$_4$), filtered, and concentrated in vacuo to afford the crude product. The crude product was purified by flash chromatography eluting with EtOAc/methanol 1:2 to afford the title compound as grey foam.

Example 131

1-[5-Bromo-2-(3-chloro-4-{2-methyl-4-[2-(tetrahydro-pyran-2-yloxy)-ethoxy]-benzoyl}-phenylamino)-phenyl]-3-(2-hydroxy-ethyl)-urea (Compound 231)

A solution of compound 486 (110 mg, 0.15 mmol) in ethanol (5 mL) was added a solution of sodium hydroxide (2 M, 0.5 mL) and then stirred under reflux for 90 min. The reaction mixture was poured into a mixture of EtOAc/water. The aqueous phase was extracted with more EtOAc. The organic phases were combined, dried (MgSO$_4$), filtered, and concentrated in vacuo. The crude product was purified by flash chromatography eluting with EtOAc/petroleum ether 6:1 to afford the title compound as a solid. $^{13}$C NMR (CDCl$_3$) δ 196.5, 161.6, 156.8, 148.5, 142.1, 135.1, 134.0, 130.6, 129.8, 126.9, 126.3, 124.8, 118.6, 117.9, 115.8, 112.6, 111.1, 99.2, 67.5, 65.7, 62.4, 42.7, 30.5, 25.4, 21.6, 19.4

Example 132

1-(5-Bromo-2-{3-chloro-4-[4-(2-hydroxy-2-methyl-benzoyl]-phenylamino}-phenyl)-3-(2-hydroxyethyl)-urea (Compound 232)

The reaction was carried out similarly as described in the preparation of compound 212, using compound 231 (70 mg, 0.11 mmol) as the THP ether protected compound. Purification was done by flash chromatography using EtOAc as the eluent to afford the title compound as yellow syrup. $^{13}$C NMR (CD$_3$CN) δ 196.1, 162.2, 156.7, 149.9, 142.2, 137.8, 134.1, 134.0, 133.0, 131.9, 130.3, 130.1, 128.0, 126.5, 124.5, 119.1, 118.4, 116.1, 113.3, 111.8, 70.5, 62.1, 61.1, 43.2, 21.2

Example 133

N-[5-Bromo-2-(3-chloro-4-{2-methyl-4-[2-(tetrahydro-pyran-2-yloxy)-ethoxy]-benzoyl}-phenylamino)-phenyl]-succinamic acid (Compound 233)

To a solution of compound 213 (200 mg, 0.36 mmol) in pyridine (3 mL) was added succinic anhydride (62 mg, 0.62 mmol) under stirring. After 24 h at 100° C. the reaction mixture was poured into a mixture of EtOAc/water. The aqueous phase was extracted with more EtOAc. The organic phases were combined, dried (MgSO$_4$), filtered, and concentrated in vacuo. The crude product was purified by flash chromatography eluting with EtOAc to afford the title compound as foam. $^{13}$C NMR (CDCl$_3$) δ 198.0, 171.0, 162.0, 146.8, 142.5, 134.7, 134.2, 133.3, 131.2, 130.3, 130.2, 129.9, 129.4, 128.2, 122.1, 118.1, 116.6, 115.2, 113.7, 111.2, 99.1, 67.5, 65.7, 62.3, 30.5, 29.2, 25.4, 21.8, 19.3

Preparation 87

4-Allyloxy-1-bromo-2-methyl-benzene (Compound 487)

The reaction was carried out similarly as described in the preparation of compound 469, using allyl bromide (5.44 g, 45 mmol) as the bromide. Purification was done by flash chromatography using EtOAc/petroleum ether 1:25 to afford the title compound as colourless oil.

Preparation 88

(4-Allyloxy-2-methyl-phenyl)-(2-chloro-4-nitro-phenyl)-methanone (Compound 488)

The reaction was carried out similarly as described in the preparation of compound 470, using compound 487 (6.85 g, 30.2 mmol) as the bromide. Purification was done by flash chromatography using EtOAc/petroleum ether 1:15 followed by 1:10 to afford the title compound.

Preparation 89

(4-Allyloxy-2-methyl-phenyl)-(4-amino-2-chloro-phenyl)-methanone (Compound 489)

The reaction was carried out similarly as described in the preparation of compound 480, using compound 488 (6.26 g, 18.9 mmol) as the nitro compound. The crude product was filtered through a pad of silica gel to give the pure title compound.

Preparation 90

(4-Allyloxy-2-methyl-phenyl)-[4-(4-bromo-2-nitro-phenylamino)-2-chloro-phenyl]-methanone (Compound 490)

The reaction was carried out similarly as described in the preparation of compound 473, using compound 489 (1.86 g, 6.16 mmol) as the amine. Purification was done by flash chromatography using DCM/petroleum ether 3:2 followed by 7:3 to afford the title compound.

Example 134

(4-Allyloxy-2-methyl-phenyl)-[4-(2-amino-4-bromo-phenylamino)-2-chloro-phenyl]-methanone (Compound 234)

The reaction was carried out similarly as described in the preparation of compound 480, using compound 490 (2.01 g, 4.01 mmol) as the nitro compound. The crude product was filtered through a pad of silica gel to give the pure title compound. $^{13}$C NMR (CDCl$_3$) δ 195.5, 160.9, 148.3, 144.2, 141.9, 134.3, 133.5, 132.7, 132.5, 131.1, 130.1, 128.2, 124.7, 121.9, 120.5, 118.9, 118.0, 117.8, 115.3, 112.1, 111.1, 68.8, 21.4

Example 135

N-{2-[(4-(4-Allyloxy-2-methyl-benzoyl)-3-chloro-phenylamino]-5-bromo-phenyl}-acetamide (Compound 235)

Compound 134 (50 mg, 0.1 mmol) was placed in a vial (4 mL). Acetic acid (0.5 mL) and acetic acid anhydride (1.0 mL) was added to the vial. After 2 h at 30° C. the reaction mixture was poured into a mixture of EtOAc/water. The organic phase was concentrated in vacuo and the residue was purified by continuous gradient flash chromatography using mixtures of 1,2-dichloro-ethane and petroleum ether to afford the title compound. $^{13}$C NMR (CDCl$_3$) δ 195.8, 169.4, 160.9, 147.5, 141.7, 133.8, 133.5, 132.9, 132.4, 132.0, 131.5, 130.5, 130.1, 128.6, 126.1, 125.4, 117.8, 117.6, 117.5, 116.0, 112.7, 110.9, 68.5, 23.9, 21.3

Example 136

1-{2-[4-(4-Allyloxy-2-methyl-benzoyl)-3-chloro-phenylamino]-5-bromo-phenyl}-3-ethyl-urea (Compound 236)

Compound 134 (50 mg, 0.1 mmol) was placed in a vial (4 mL). Pyridine (2.0 mL) and ethyl isocyanate (60 mg, 0.8 mmol) was added to the vial. After 2 h at 30° C. the reaction mixture was poured into a mixture of EtOAc/water. The organic phase was concentrated in vacuo and the residue was purified by crystallisation from a mixture of diethyl ether and hexane to afford the title compound as a solid. $^{13}$C NMR (DMSO-d$_6$) δ 194.5, 160.4, 154.8, 149.6, 140.6, 138.0, 133.3, 132.8, 132.6, 132.3, 130.9, 128.0, 127.8, 127.6, 124.2, 121.9, 118.2, 117.8, 117.6, 114.7, 111.8, 111.4, 68.3, 33.9, 20.8, 15.2

Example 137

{2-[4-(4-Allyloxy-2-methyl-benzoyl)-3-chloro-phenylamino]-5-bromo-phenyl}-carbamic acid ethyl ester (Compound 237)

To a solution of compound 134 (50 mg, 0.1 mmol) in DCM (2 mL) was added K$_2$CO$_3$ (45 mg) and ethyl chloroformate (40 μL, 0.4 mmol) under stirring. After 22 h at RT the reaction mixture was poured into a mixture of EtOAc/water. The organic phase was concentrated in vacuo and the residue was purified by crystallisation from ethanol to afford the title compound as a solid. $^{13}$C NMR (DMSO-d$_6$) δ 194.3, 160.3, 153.8, 148.0, 140.5, 133.4, 133.2, 132.8, 132.3, 132.0, 131.3, 130.7, 128.4, 127.0, 126.7, 125.3, 117.7, 117.5, 115.7, 115.0, 112.3, 111.3, 68.2, 60.6, 20.7, 14.3

Example 138

N-{2-[4-(4-Allyloxy-2-methyl-benzoyl)-3-chloro-phenylamino]-5-bromo-phenyl}-2,2,2-trifluoro-acetamide (Compound 238)

To a solution of compound 134 (50 mg, 0.1 mmol) in DCM (2 mL) was added trifluoroacetic acid anhydride (95 mg) and pyridine (50 μL) under stirring. After 1 h at RT the reaction mixture was poured into a mixture of EtOAc/water. The organic phase was concentrated in vacuo to afford the title compound as syrup. $^{13}$C NMR (CDCl$_3$) δ 195.7, 161.3, 155.1 (q), 147.3, 142.4, 134.0, 134.0, 132.6, 132.1, 132.0, 131.9, 131.1, 130.5, 130.3, 127.3, 125.6, 119.7, 118.1, 118.0, 116.5, 115.5 (q), 113.3, 111.2, 68.8, 21.6

Example 139

N-{2-[4-(4-Allyloxy-2-methyl-benzoyl)-3-chloro-phenylamino]-5-bromo-phenyl}-succinamic acid (Compound 239)

To a solution of compound 134 (50 mg, 0.1 mmol) in acetic acid (2 mL) was added succinic anhydride (63 mg) under stirring. After 1 h at RT the reaction mixture was poured into a mixture of DCM/water. The organic phase was concentrated in vacuo to afford the title compound as syrup. $^{13}$C NMR (CDCl$_3$) δ 198.3, 179.0, 170.9, 161.8, 146.7, 142.7, 134.9, 134.5, 133.2, 132.5, 131.0, 130.1, 129.9, 129.5, 128.4, 121.7, 118.2, 116.6, 114.9, 113.7, 111.3, 68.8, 30.4, 29.1, 21.9

Example 140

{2-[4-(4-Allyloxy-2-methyl-benzoyl)-3-chloro-phenylamino]-5-bromo-phenyl}-carbamic acid cyclopentyl ester (Compound 240)

To a solution of compound 134 (50 mg, 0.1 mmol) in DCM (2 mL) was added K$_2$CO$_3$ (45 mg) and cyclopentyl chloroformate (0.4 mmol) under stirring. After 22 h at RT the reaction mixture was poured into a mixture of EtOAc/water. The organic phase was concentrated in vacuo and the residue was purified by crystallisation from ethanol to afford the title compound as a solid. $^{13}$C NMR (CDCl$_3$) δ 195.6, 161.0, 153.6, 148.3, 142.0, 135.2, 134.1, 133.6, 132.7, 132.3, 130.9, 130.6, 129.2, 127.2, 127.2, 123.8, 119.6, 118.0, 117.8, 116.0, 112.7, 111.1, 78.8, 68.8, 32.7, 23.7, 21.5

Preparation 91

2-Methyl-5-nitro-thiobenzoic acid S-pyridin-2-yl ester (Compound 491)

2-Methyl-5-nitrobenzoic acid (22.5 g, 124 mmol), 2,2'-dithiopyridine (27.5 g, 124 mmol) and triphenylphosphine (32.6 g, 124 mmol) were dissolved in CH$_3$CN (650 mL). The solution was stirred at room temperature for 18 h. The reaction mixture was filtered and the solid was washed with small amounts of CH$_3$CN. This afforded the title compound as a colourless solid.

Preparation 92

(4-Bromo-2-chloro-phenyl)-(2-methyl-5-nitro-phenyl)-methanone (Compound 492)

The reaction was run under an argon atmosphere using dry glassware. 4-Bromo-2-chloroiodobenzene (25.5 g, 80.9 mmol) was dissolved in dry THF (400 mL) and cooled to –60° C. Isopropylmagnesium chloride (2 M in THF, 40.4 mL, 80.9 mmol) was added under stirring during 30 minutes. The reaction mixture was allowed to warm up to –40° C. and the mixture was stirred at –40° C. for 4 h. Compound 491 (22.2 g, 80.9 mmol) was added and the mixture was stirred at –40° C. for 3 h after which it was allowed to warm to room temperature and stirred for 17 h. A saturated aqueous solution of NH$_4$Cl (200 mL) was added and the mixture was stirred for 1 h. The phases were separated and the aqueous phase was extracted with Et$_2$O (4×100 mL). The combined organic phases were washed with brine, dried (MgSO$_4$), filtered and concentrated in vacuo. The crude product was purified by flash chromatography using CH$_2$Cl$_2$/petroleum ether (40-60) 2:3 as the eluent to afford the title compound as yellow crystalline compound.

Preparation 93

[2-Chloro-4-(2,4-difluoro-phenylamino)-phenyl]-(2-methyl-5-nitro-phenyl)-methanone (Compound 493)

Compound 492 (5.4 g, 15.2 mmol) was dissolved in dry 1,4-dioxan (150 mL) in a 200 mL screw cap vessel. 2,4-Difluoroaniline (1.7 mL, 16.7 mmol) was added and argon was blown over the mixture. Cs$_2$CO$_3$ (14.9 g, 45.7 mmol), BINAP (0.38 g, 0.6 mmol) and Pd(OAc)$_2$ (0.14 g, 0.6 mmol) were added and argon was blown through the mixture and the screw cap vessel was closed. The mixture was stirred at 100° C. for 7 h. The reaction mixture was poured into H$_2$O (100 mL) and EtOAc (200 mL). The water phase was extracted with EtOAc (×3) and the combined organic phases were washed with brine, dried (MgSO$_4$), filtered and concentrated in vacuo. The crude product was purified by flash chromatography using CH$_2$Cl$_2$/petroleum ether (40-60) 2:3→1:1→1:0 followed by EtOAc as the eluent to afford the title compound as a yellow crystalline compound.

Preparation 94

(5-Amino-2-methyl-phenyl)-[2-chloro-4-(2,4-difluoro-phenylamino)-phenyl]-methanone (Compound 494)

Compound 493 (6.0 g, 14.9 mmol) was dissolved in MeOH (350 mL). Zinc-dust (12.69 g, 194 mmol) and NH$_4$Cl (5.59 g, 104 mmol) were added. The reaction mixture was heated at reflux temperature for 1 h. The mixture was filtered and washed with MeOH. The filtrate was concentrated and the solid was dissolved in EtOAc (150 mL) and saturated aqueous Na$_2$CO$_3$ (100 mL). The water phase was extracted with EtOAc and the combined organic phases were dried (MgSO$_4$), filtered and concentrated in vacuo. The crude product was purified by flash chromatography using EtOAc/petroleum ether (40-60) 1:2 as the eluent to afford the title compound as a slightly coloured crystalline compound.

Preparation 95

[2-Chloro-4-(2,4-difluoro-phenylamino)-phenyl]-(5-iodo-2-methyl-phenyl)-methanone (Compound 495)

Compound 494 (0.62 g, 1.66 mmol) was dissolved in acetone (14 mL). Concentrated HCl (37%, 0.69 mL, 8.3 mmol) was added and the solution was cooled on an ice bath. NaNO$_2$ (0.14 g, 1.99 mmol) was dissolved in H$_2$O (1 mL) and added to the above solution during 15 minutes. The internal temperature was kept at 0° C.-2° C. during the addition. The suspension was stirred on an ice bath for 0.5 h, after which a solution of KI (0.41 g, 2.45 mmol) and I$_2$ (0.31 g, 1.22 mmol) in H$_2$O (4 mL) was added drop wise during 5 minutes. The mixture was stirred at 0° C. for 2 h. H$_2$O (20 mL) and EtOAc (20 mL) was added and stirred and the phases were separated. The organic phase was washed with aqueous NaHSO$_3$, then with aqueous Na$_2$CO$_3$, dried (MgSO$_4$), filtered and concentrated in vacuo. The crude product was purified by flash chromatography using EtOAc/petroleum ether (40-60) 1:5 to afford the title compound as a slightly coloured crystalline compound.

Example 141

N-{3-[2-Chloro-4-(2,4-difluoro-phenylamino)-benzoyl]-4-methyl-phenyl}-3-methoxy-propionamide (Compound 241)

3-Methoxypropionic acid (0.022 mL, 0.23 mmol) was dissolved in dry DMF (5 mL). O-(7-Azabenzotriazol-1-yl)-N,N,N',N'-tetramethyluronium-hexafluorophosphate (HATU) (0.09 g, 0.23 mmol) was added followed by addition of 2,4,6-trimethylpyridine (0.048 mL, 0.36 mmol). The mixture was stirred for 0.5 h after which compound 494 (0.067 g, 0.18 mmol) was added. The mixture was stirred at room temperature for 18 h. The reaction mixture was concentrated in vacuo and the crude product was purified by flash chromatography using a gradient of EtOAc/petroleum ether (40-60) 1:4→4:1 as the eluent. This afforded the title compound as a slightly coloured crystalline compound. $^{13}$C NMR (CDCl$_3$) δ 195.8, 169.8, 159.1 (dd), 155.5 (dd), 147.7, 139.6, 135.6, 135.2, 133.7, 133.4, 131.8, 129.2, 124.4 (dd), 124.2 (dd), 122.5, 120.8, 116.3, 112.8, 111.6 (dd), 104.9 (dd), 68.5, 58.9, 37.9, 19.8

Example 142

N-{3-[2-Chloro-4-(2,4-difluoro-phenylamino)-benzoyl]-4-methyl-phenyl}-propionamide (Compound 242)

Propionic acid (0.01 mL, 0.13 mmol) was dissolved in dry DMF (5 mL). HATU (0.05 g, 0.13 mmol) was added followed by addition of 2,4,6-trimethylpyridine (0.027 mL, 0.2 mmol). The mixture was stirred for 0.5 h after which compound 494 (0.038 g, 0.10 mmol) was added. The mixture was stirred at room temperature for 18 h. The reaction mixture was concentrated in vacuo and the crude product was purified by flash chromatography using a gradient of EtOAc/petroleum ether (40-60) 1:4→4:1 as the eluent. This afforded the title compound as yellow oil. $^{13}$C NMR (CDCl$_3$) δ 196.1, 172.4, 159.2 (dd), 155.6 (dd), 148.0, 139.5, 135.7, 135.1, 133.7, 133.2, 131.8, 128.8, 124.6 (dd), 124.3 (dd), 122.5, 120.7, 116.2, 112.6, 111.6 (dd), 104.9 (dd), 30.5, 19.7, 9.6

Example 143

N-{3-[2-Chloro-4-(2,4-difluoro-phenylamino)-benzoyl]-4-methyl-phenyl}-2-(2-methoxy-ethoxy)-acetamide (Compound 243)

2-(2-Methoxyethoxy)acetic acid (0.017 mL, 0.15 mmol) was dissolved in dry DMF (5 mL). HATU (0.055 g, 0.15 mmol) was added followed by addition of 2,4,6-trimethylpyridine (0.03 mL, 0.22 mmol). The mixture was stirred for 0.5 h after which compound 494 (0.042 g, 0.11 mmol) was added. The mixture was stirred at room temperature for 18 h. The reaction mixture was concentrated in vacuo and the crude product was purified by flash chromatography using a gradient of EtOAc/petroleum ether (40-60) 1:4→4:1 as the eluent. This afforded the title compound as yellow oil. $^{13}$C NMR (CDCl$_3$) δ 195.9, 168.4, 159.1 (dd), 155.6 (dd), 147.9, 139.4, 135.1, 135.1, 133.7, 133.5, 131.9, 129.2, 124.5 (dd), 124.4 (dd), 122.3, 120.7, 116.1, 112.7, 111.6 (dd), 104.9 (dd), 71.4, 71.3, 70.4, 58.9, 19.8

Example 144

N-{3-[2-Chloro-4-(2,4-difluoro-phenylamino)-benzoyl]-4-methyl-phenyl}-3-morpholin-4-yl-propionamide (Compound 244)

3-(4-Morpholino)propionic acid hydrochloride (0.027 g, 0.14 mmol) was dissolved in dry DMF (5 mL). HATU (0.052 g, 0.14 mmol) was added followed by addition of 2,4,6-trimethylpyridine (0.035 mL, 0.26 mmol). The mixture was stirred for 0.5 h after which compound 494 (0.039 g, 0.10 mmol) was added. The mixture was stirred at room temperature for 18 h. The reaction mixture was concentrated in vacuo and the crude product was purified by flash chromatography using a gradient of MeOH/dichloromethane 1:50→1:12 as the eluent. This afforded the title compound as yellow oil. $^{13}$C NMR (CDCl$_3$) δ 195.9, 170.2, 159.1 (dd), 155.5 (dd), 147.6, 138.9, 136.2, 134.8, 133.5, 133.2, 132.1, 129.6, 124.5 (dd), 124.2 (dd), 122.1, 121.0, 116.1, 112.8, 111.6 (dd), 104.9 (dd), 66.9, 54.0, 52.7, 32.1, 20.0

Example 145

N-{3-[2-Chloro-4-(2,4-difluoro-phenylamino)-benzoyl]-4-methyl-phenyl}-3-hydroxy-propionamide (Compound 245)

3-Hydroxypropionic acid (30% in H$_2$O, 0.33 mmol) was dissolved in dry DMF (5 mL). HATU (0.125 g, 0.33 mmol) was added followed by addition of 2,4,6-trimethylpyridine (0.061 mL, 0.5 mmol). The mixture was stirred for 0.5 h after which compound 494 (0.094 g, 0.25 mmol) was added. The mixture was stirred at room temperature for 18 h. The reaction mixture was concentrated in vacuo and the crude product was purified by flash chromatography using EtOAc/petroleum ether (40-60) 1:1 as the eluent. This afforded the title compound as a yellow oil. $^{13}$C NMR (DMSO-d$_6$) δ 195.1, 169.8, 158.8 (dd), 155.6 (dd), 149.1, 139.0, 136.9, 133.4, 133.3, 131.3, 130.9, 127.0, 126.4 (dd), 124.3 (dd), 121.1, 119.4, 114.7, 111.9 (dd), 111.8, 105.0 (dd), 57.3, 40.0, 19.1

Example 146

N-{3-[2-Chloro-4-(2,4-difluoro-phenylamino)-benzoyl]-4-methyl-phenyl}-3-furan-2-yl-propionamide (Compound 246)

3-(2-Furfuryl)propionic acid (0.02 g, 0.14 mmol) was dissolved in dry DMF (4 mL). HATU (0.053 g, 0.14 mmol) was added followed by addition of 2,4,6-trimethylpyridine (0.029 mL, 0.22 mmol). The mixture was stirred for 0.5 h after which compound 494 (0.040 g, 0.11 mmol) was added. The mixture was stirred at room temperature for 18 h. The reaction mixture was concentrated in vacuo and the crude product was purified by flash chromatography using a gradient of EtOAc/petroleum ether (40-60) 1:9→2:3 as the eluent. This afforded the title compound as yellow oil. $^{13}$C NMR (CDCl$_3$) δ 196.0, 170.1, 159.2 (dd), 155.6 (dd), 154.1, 147.9, 141.3, 139.5, 135.4, 135.1, 133.7, 133.5, 131.8, 128.9, 124.4 (dd), 124.3 (dd), 122.6, 120.8, 116.2, 112.7, 111.6 (dd), 110.3, 105.7, 104.9 (dd), 35.8, 23.8, 19.8

Example 147

N-{3-[2-Chloro-4-(2,4-difluoro-phenylamino)-benzoyl]-4-methyl-phenyl}-2-hydroxy-benzamide (Compound 247)

2-Hydroxybenzoic acid (0.019 g, 0.14 mmol) was dissolved in dry DMF (4 mL). HATU (0.053 g, 0.14 mmol) was added followed by addition of 2,4,6-trimethylpyridine (0.029 mL, 0.22 mmol). The mixture was stirred for 0.5 h after which compound 494 (0.040 g, 0.11 mmol) was added. The mixture was stirred at room temperature for 18 h. The reaction mixture was concentrated in vacuo and the crude product was purified by flash chromatography using a gradient of EtOAc/petroleum ether (40-60) 1:9→3:2 as the eluent. This afforded the title compound as yellow oil. $^{13}$C NMR (CDCl$_3$) δ 196.0, 168.5, 161.7, 159.2 (dd), 155.6 (dd), 148.1, 139.7, 135.3, 134.7, 134.5, 134.4, 133.8, 132.0, 128.7, 125.9, 124.5 (dd), 124.2 (dd), 124.0, 122.1, 119.0, 118.8, 116.2, 114.6, 112.7, 111.6 (dd), 105.0 (dd), 19.8

Example 148

N-{3-[2-Chloro-4-(2,4-difluoro-phenylamino)-benzoyl]-4-methyl-phenyl}-2-(2,5-dioxo-imidazolidin-4-yl)-acetamide (Compound 248)

Hydantoin-5-acetic acid (0.022 g, 0.14 mmol) was dissolved in dry DMF (4 mL). HATU (0.053 g, 0.14 mmol) was added followed by addition of 2,4,6-trimethylpyridine (0.029 mL, 0.22 mmol). The mixture was stirred for 0.5 h after which compound 494 (0.040 g, 0.11 mmol) was added. The mixture was stirred at room temperature for 18 h. The reaction mixture was concentrated in vacuo and the crude product was purified by flash chromatography using MeOH/CH$_2$Cl$_2$ 3:100 as the eluent. This afforded the title compound as a yellow oil. $^{13}$C NMR (CD$_3$OD) δ 198.1, 177.6, 169.6, 161.1 (dd), 160.0, 157.9 (dd), 151.3, 141.1, 137.5, 136.1, 134.9, 134.1, 132.7, 128.8, 127.5 (dd), 126.0 (dd), 123.4, 121.8, 116.5, 113.0, 112.7 (dd), 105.8 (dd), 56.7, 39.2, 19.8

Example 149

2,6-Dioxo-hexahydro-pyrimidine-4-carboxylic acid {3-[2-chloro-4-(2,4-difluoro-phenylamino)-benzoyl]-4-methyl-phenyl}-amide (Compound 249)

D,L-Dihydroorotic acid (0.022 g, 0.14 mmol) was dissolved in dry DMF (4 mL). HATU (0.053 g, 0.14 mmol) was added followed by addition of 2,4,6-trimethylpyridine (0.029 mL, 0.22 mmol). The mixture was stirred for 0.5 h after which compound 494 (0.040 g, 0.11 mmol) was added. The mixture was stirred at room temperature for 18 h. The reaction mixture was concentrated in vacuo and the crude product was purified by flash chromatography using EtOAc/acetone 10:1 as the eluent. This afforded the title compound as a colourless solid. $^{13}$C NMR (DMSO-d$_6$) δ 194.9, 169.2, 169.0, 158.7 (dd), 155.7 (dd), 153.6, 149.2, 139.2, 136.1, 133.4, 133.3, 131.7, 131.5, 126.8, 126.4 (dd), 124.2 (dd), 121.4, 119.6, 114.7, 112.0 (dd), 111.8, 105.0 (dd), 50.3, 38.9, 19.1

Example 150

Acrylic acid 2-{3-[2-chloro-4-(2,4-difluoro-phenylamino)-benzoyl]-4-methyl-phenylcarbamoyl}-ethyl ester (Compound 250)

2-Carboxyethyl acrylate (0.041 mL, 0.35 mmol) was dissolved in dry DMF (7 mL). HATU (0.13 g, 0.35 mmol) was added followed by addition of 2,4,6-trimethylpyridine (0.07 mL, 0.54 mmol). The mixture was stirred for 0.5 h after which compound 494 (0.10 g, 0.27 mmol) was added. The mixture was stirred at room temperature for 18 h. The reaction mixture was concentrated in vacuo and the crude product was purified by flash chromatography using a gradient of EtOAc/petroleum ether (40-60) 15:85→70:30 as the eluent. This afforded the title compound as oil. $^{13}$C NMR (DMSO-d$_6$) δ 196.1, 168.3, 166.1, 159.2 (dd), 155.6 (dd), 148.2, 139.6, 135.4, 135.1, 133.8, 133.5, 131.8, 131.4, 128.6, 128.0, 124.6 (dd), 124.3 (dd), 122.6, 120.7, 116.2, 112.6, 111.6 (dd), 104.9 (dd), 60.4, 36.6, 19.7

Example 151

N-{3-[2-Chloro-4-(2,4-difluoro-phenylamino)-benzoyl]-4-methyl-phenyl}-3-methylsulfanyl-propionamide (Compound 251)

3-Methylthiopropionic acid (0.067 g, 0.55 mmol) was dissolved in dry DMF (16 mL). HATU (0.21 g, 0.55 mmol) was added followed by addition of 2,4,6-trimethylpyridine (0.11 mL, 0.86 mmol). The mixture was stirred for 0.5 h after which compound 494 (0.16 g, 0.43 mmol) was added. The mixture was stirred at room temperature for 18 h. The reaction mixture was concentrated in vacuo and the crude product was purified by flash chromatography using a gradient of EtOAc/petroleum ether (40-60) 1:9→1:1 as the eluent. This afforded the title compound as yellow oil. $^{13}$C NMR (CDCl$_3$) δ 196.1, 169.8, 159.2 (dd), 155.6 (dd), 148.0, 139.6, 135.5, 135.2, 133.8, 133.5, 131.8, 128.7, 124.5 (dd), 124.3 (dd), 122.6, 120.7, 116.2, 112.6, 111.6 (dd), 104.9 (dd), 37.2, 29.7, 19.8, 15.7

Example 152

N-{3-[2-Chloro-4-(2,4-difluoro-phenylamino)-benzoyl]-4-methyl-phenyl}-3-methanesulfonyl-propionamide (Compound 252)

Compound 251 (0.22 g, 0.45 mmol) was dissolved in CH$_2$Cl$_2$ (5 mL). 3-Chloroperoxybenzoic acid (0.3 g, ca. 1.4 mmol) was added slowly and the mixture was stirred at room temperature for 1 h. Na$_2$S$_2$O$_5$ (0.34 g) was added and stirring was continued for 0.5 h. The mixture was filtered and the filtrate was stirred with K$_2$CO$_3$ for 0.5 h. MgSO$_4$ was added and the mixture was filtered. The filtrate was concentrated in vacuo and the crude product was purified by flash chromatography using a gradient of EtOAc/petroleum ether (40-60) 30:70→100:0 as the eluent. This afforded the title compound as yellow oil. $^{13}$C NMR (CDCl$_3$) δ 196.0, 167.4, 159.2 (dd), 155.6 (dd), 148.0, 139.7, 135.3, 135.2, 133.8, 133.6, 131.9, 128.8, 124.5 (dd), 124.2 (dd), 122.6, 120.6, 116.2, 112.7, 111.6 (dd), 105.0 (dd), 50.1, 41.6, 29.4, 19.8

Example 153

Ethanesulfonic acid {3-[2-chloro-4-(2,4-difluoro-phenylamino)-benzoyl]-4-methyl-phenyl}-amide (Compound 253)

Compound 494 (0.045 g, 0.12 mmol) was dissolved in pyridine (0.3 mL). Ethanesulphonyl chloride (0.017 mL, 0.18 mmol) was added and the solution was stirred at room temperature for 1 h. The reaction mixture was concentrated in vacuo and the oil was dissolved in EtOAc and washed with H$_2$O. The water phase was extracted with EtOAc and the combined organic phases were dried (MgSO$_4$), filtered and concentrated in vacuo. The crude product was purified by flash chromatography using a gradient of EtOAc/petroleum ether (40-60) 15:85→40:60 as the eluent. This afforded the title compound as yellow solid. $^{13}$C NMR (CDCl$_3$) δ 195.5, 159.3 (dd), 155.7 (dd), 148.3, 140.4, 135.3, 134.5, 134.5, 133.8, 132.5, 128.5, 124.6 (dd), 124.2 (dd), 123.2, 121.6, 116.1, 112.8, 111.6 (dd), 105.0 (dd), 45.9, 19.7, 8.1

Example 154

N-{3-[2-Chloro-4-(2,4-difluoro-phenylamino)-benzoyl]-4-methyl-phenyl}-4-methoxy-benzenesulfonamide (Compound 254)

The compound was prepared as described in the preparation of compound 253 using compound 494 (0.04 g, 0.11 mmol) and 4-methoxybenzenesulphonyl chloride (0.033 g, 0.16 mmol) in pyridine (0.3 mL). The crude product was purified by flash chromatography using a gradient of EtOAc/ petroleum ether (40-60) 10:90→50:50 as the eluent. This afforded the title compound as yellow oil. $^{13}$C NMR (CDCl$_3$) δ 195.6, 163.1, 159.2 (dd), 155.6 (dd), 148.0, 139.8, 135.1, 134.9, 134.1, 133.5, 132.2, 130.3, 129.4, 128.7, 124.6, 124.5 (dd), 124.3 (dd), 122.9, 116.1, 114.2, 112.7, 111.6 (dd), 104.9 (dd), 55.6, 19.7

Example 155

N-(5-{3-[2-Chloro-4-(2,4-difluoro-phenylamino)-benzoyl]-4-methyl-phenylsulfamoyl}-4-methyl-thiazol-2-yl)-acetamide (Compound 255)

The compound was prepared as described in the preparation of compound 253 using compound 494 (0.042 g, 0.11 mmol) and 2-acetamido-4-methyl-5-thiazolesulphonyl chloride (0.043 g, 0.17 mmol) in pyridine (0.3 mL). The crude product was purified by flash chromatography using a gradient of EtOAc/petroleum ether (40-60) 25:75→0:100 as the eluent. This afforded the title compound as yellow oil. $^{13}$C NMR (CDCl$_3$) δ 195.9, 169.1, 159.7, 159.2 (dd), 155.6 (dd), 153.3, 148.4, 140.2, 135.5, 135.1, 133.7, 133.6, 132.3, 128.0, 125.5, 124.6 (dd), 124.2 (dd), 123.6, 122.0, 116.2, 112.7, 111.6 (dd), 104.9 (dd), 22.9, 19.8, 16.3

Example 156

5-Acetyl-2-chloro-N-{3-[2-chloro-4-(2,4-difluoro-phenylamino)-benzoyl]-4-methyl-phenyl}-benzenesulfonamide (Compound 256)

The compound was prepared as described in the preparation of compound 253 using compound 494 (0.043 g, 0.12 mmol) and 2-chloro-5-acetylbenzenesulphonyl chloride (0.044 g, 0.17 mmol) in pyridine (0.3 mL). The crude product was purified by flash chromatography using a gradient of EtOAc/petroleum ether (40-60) 10:90→50:50 as the eluent. This afforded the title compound as yellow oil. $^{13}$C NMR (CDCl$_3$) δ 195.6, 195.3, 159.3 (dd), 155.7 (dd), 148.3, 140.2, 136.5, 136.2, 135.8, 135.6, 135.1, 133.5, 133.3, 132.8, 132.4, 132.1, 131.9, 128.4, 124.7 (dd), 124.6, 124.1 (dd), 122.7, 116.0, 112.7, 111.7 (dd), 105.0 (dd), 26.6, 19.7

Example 157

Naphthalene-2-sulfonic acid {3-[2-chloro-4-(2,4-difluoro-phenylamino)-benzoyl]-4-methyl-phenyl}-amide (Compound 257)

The compound was prepared as described in the preparation of compound 253 using compound 494 (0.041 g, 0.11 mmol) and naphthalene-2-sulphonyl chloride (0.037 g, 0.16 mmol) in pyridine (0.3 mL). The crude product was purified by flash chromatography using a gradient of EtOAc/petroleum ether (40-60) 10:90→50:50 as the eluent. This afforded the title compound as yellow oil. $^{13}$C NMR (CDCl$_3$) δ 195.4, 159.1 (dd), 155.5 (dd), 147.7, 139.8, 135.8, 135.4, 135.0, 135.0, 133.8, 133.3, 132.3, 132.0, 129.4, 129.4, 128.9, 128.8, 127.9, 127.5, 125.0, 124.4 (dd), 124.2 (dd), 123.4, 122.3, 116.1, 112.7, 111.6 (dd), 105.0 (dd), 19.7

Example 158

N-{3-[2-Chloro-4-(2,4-difluoro-phenylamino)-benzoyl]-4-methyl-phenyl}-C-phenyl-methanesulfonamide (Compound 258)

The compound was prepared as described in the preparation of compound 253 using compound 494 (0.041 g, 0.11 mmol) and α-toluenesulphonyl chloride (0.031 g, 0.16 mmol) in pyridine (0.3 mL). The crude product was purified by flash chromatography using a gradient of EtOAc/petroleum ether (40-60) 10:90→50:50 as the eluent. This afforded the title compound as yellow oil. $^{13}$C NMR (CDCl$_3$) δ 195.5, 159.3 (dd), 155.7 (dd), 148.2, 140.2, 135.1, 134.4, 134.4, 133.7, 132.5, 130.8, 128.9, 128.9, 128.7, 128.4, 124.7 (dd), 124.2 (dd), 122.8, 121.2, 116.0, 112.8, 111.6 (dd), 105.0 (dd), 57.4, 19.7

Example 159

2-Methyl-acrylic acid 2-(3-{3-[2-chloro-4-(2,4-difluoro-phenylamino)-benzoyl]-4-methyl-phenyl}-ureido)-ethyl ester (Compound 259)

Compound 494 (0.055 g, 0.15 mmol) was dissolved in dry pyridine (0.3 mL) and isocyanatoethyl methylacrylate (0.031 mL, 0.22 mmol) was added. The solution was stirred at room temperature for 1 h. H$_2$O was added and the water phase was extracted with EtOAc (×2). The combined organic phases were washed with brine, dried (MgSO$_4$), filtered and concentrated in vacuo. The crude product was purified by flash chromatography using EtOAc/petroleum ether (40-60) 2:1 as the eluent. This afforded the title compound as oil. $^{13}$C NMR (CDCl$_3$) δ 196.5, 167.5, 159.2 (dd), 155.8, 155.6 (dd), 148.2, 139.7, 136.3, 135.9, 135.1, 133.9, 132.4, 132.0, 128.6, 126.1, 124.5 (dd), 124.2 (dd), 123.3, 121.2, 116.3, 112.7, 111.6 (dd), 104.9 (dd), 63.9, 39.3, 19.6, 18.2

Example 160

1-{3-[2-Chloro-4-(2,4-difluoro-phenylamino)-benzoyl]-4-methyl-phenyl}-3-(2-hydroxy-ethyl)-urea (Compound 260)

Compound 259 (0.05 g, 0.095 mmol) was dissolved in EtOH (2.5 mL). 2 N NaOH (0.25 mL) was added and the solution was heated to reflux for 3 h. The reaction mixture was cooled to room temperature and saturated aqueous NaHCO$_3$ (2 mL) was added. H$_2$O and EtOAc were added and the phases were separated. The water phase was extracted with EtOAc. The combined organic phases were washed with brine, dried (MgSO$_4$), filtered and concentrated in vacuo. The crude product was purified by flash chromatography using EtOAc as the eluent. This afforded the title compound as a slightly coloured solid. $^{13}$C NMR (CD$_3$OD) δ 198.5, 161.1 (dd), 158.4, 157.9 (dd), 151.2, 141.0, 138.8, 136.1, 135.0, 132.7, 132.2, 128.9, 127.4 (dd), 126.0 (dd), 122.6, 120.9, 116.6, 112.9, 112.7 (dd), 105.8 (dd), 62.3, 43.3, 19.7

Example 161

(3-{3-[2-Chloro-4-(2,4-difluoro-phenylamino)-benzoyl]-4-methyl-phenyl}-ureido)-acetic acid ethyl ester (Compound 261)

Compound 494 (0.047 g, 0.13 mmol) was dissolved in pyridine (0.3 mL) and ethyl isocyanatoacetate (0.022 mL, 0.19 mmol) was added. The solution was stirred at room temperature for 2 h. Work up as described in the preparation of compound 259. The crude product was purified by flash chromatography using EtOAc/petroleum ether (40-60) 1:1 as the eluent. This afforded the title compound as a slightly coloured solid. $^{13}$C NMR (DMSO-d$_6$) δ 195.2, 170.7, 158.7 (dd), 155.7 (dd), 155.0, 149.0, 139.0, 137.8, 133.3, 131.4, 129.1, 127.0, 126.3 (dd), 124.3 (dd), 120.0, 118.1, 114.8, 111.9 (dd), 111.8, 105.0 (dd), 60.2, 41.3, 19.0, 14.0

Example 162

1-{3-[2-Chloro-4-(2,4-difluoro-phenylamino)-benzoyl]-4-methyl-phenyl}-3-(3-methoxy-phenyl)-urea (Compound 262)

Compound 494 (0.03 g, 0.08 mmol) was dissolved in pyridine (0.2 mL) and 3-methoxyphenyl isocyanate (0.016 mL, 0.12 mmol) was added. The solution was stirred at room temperature for 1.5 h. Work up as described in the preparation of compound 259. The crude product was purified by flash chromatography using EtOAc/petroleum ether (40-60) 2:3 as the eluent. This afforded the title compound as a slightly coloured solid. $^{13}$C NMR (CD$_3$OD) δ 198.3, 161.7, 161.0 (dd), 157.9 (dd), 155.3, 151.2, 141.6, 141.2, 138.3, 136.2, 135.0, 132.7, 132.6, 130.6, 128.7, 127.4 (dd), 126.0 (dd), 122.8, 121.1, 116.7, 113.0, 112.7, 112.6 (dd), 109.5, 106.3, 105.8 (dd), 55.7, 19.7

Example 163

1-{3-[2-Chloro-4-(2,4-difluoro-phenylamino)-benzoyl]-4-methyl-phenyl}-3-(3-trifluoromethyl-phenyl)-urea (Compound 263)

Compound 494 (0.03 g, 0.08 mmol) was dissolved in pyridine (0.2 mL) and 3-(trifluoromethyl)phenyl isocyanate (0.017 mL, 0.12 mmol) was added. The solution was stirred at room temperature for 1.5 h. Work up as described in the preparation of compound 259. The crude product was purified by flash chromatography using EtOAc/petroleum ether (40-60) 2:3 as the eluent. This afforded the title compound as a slightly coloured solid. $^{13}$C NMR (CD$_3$OD) δ 198.3, 161.1 (dd), 157.9 (dd), 155.0, 151.3, 141.5, 141.2, 138.1, 136.2, 135.0, 132.9, 132.8, 132.2 (q), 130.7, 128.8, 127.5 (dd), 126.0 (dd), 125.6 (q), 123.4, 123.0, 121.2, 120.0 (q), 116.6, 116.5 (q), 113.0, 112.6 (dd), 105.8 (dd), 19.7

Example 164

1-{3-[2-Chloro-4-(2,4-difluoro-phenylamino)-benzoyl]-4-methyl-phenyl}-3-propyl-urea (Compound 264)

Compound 494 (0.03 g, 0.08 mmol) was dissolved in pyridine (0.2 mL) and n-propyl isocyanate (0.011 mL, 0.12 mmol) was added. The solution was stirred at room temperature for 18 h. Work up as described in, the preparation of compound 259. The crude product was purified by flash chromatography using EtOAc/petroleum ether (40-60) 1:1 as the eluent. This afforded the title compound as a slightly coloured solid. $^{13}$C NMR (CD$_3$OD) δ 198.5, 161.0 (dd), 158.3, 157.9 (dd), 151.1, 141.0, 138.9, 136.1, 135.0, 132.7, 132.1, 128.9, 127.4 (dd), 126.0 (dd), 122.5, 120.9, 116.6, 112.9, 112.6 (dd), 105.8 (dd), 42.6, 24.4, 19.7, 11.6

Example 165

3-(3-{3-[2-Chloro-4-(2,4-difluoro-phenylamino)-benzoyl]-4-methyl-phenyl}-ureido)-propionic acid ethyl ester (Compound 265)

Compound 494 (0.03 g, 0.08 mmol) was dissolved in pyridine (0.2 mL) and ethyl 3-Isocyanatopropionate (0.016 mL, 0.12 mmol) was added. The solution was stirred at room temperature for 1.5 h. Work up as described in the preparation of compound 259. The crude product was purified by flash chromatography using EtOAc/petroleum ether (40-60) 1:1 as the eluent. This afforded the title compound as a slightly coloured solid. $^{13}$C NMR (CD$_3$OD) δ 198.4, 173.8, 161.0 (dd), 158.0, 157.8 (dd), 151.1, 141.0, 138.7, 136.1, 135.0, 132.7, 132.2, 128.8, 127.4 (dd), 126.0 (dd), 122.6, 120.9, 116.6, 112.9, 112.6 (dd), 105.8 (dd), 61.7, 36.7, 35.8, 19.7, 14.5

Example 166

1-{3-[2-Chloro-4-(2,4-difluoro-phenylamino)-benzoyl]-4-methyl-phenyl}-3-cyclohexyl-urea (Compound 266)

Compound 494 (0.07 g, 0.18 mmol) was dissolved in pyridine (0.5 mL) and cyclohexyl isocyanate (0.036 mL, 0.28 mmol) was added. The solution was stirred at room temperature for 18 h. Work up as described in the preparation of compound 259. The crude product was purified by flash chromatography using a gradient of EtOAc/petroleum ether (40-60) 15:85→60:40 as the eluent. This afforded the title compound as a slightly coloured solid. $^{13}$C NMR (CD$_3$OD) δ 198.5, 161.0 (dd), 157.9 (dd), 157.4, 151.1, 141.0, 138.9, 136.1, 135.0, 132.7, 132.0, 128.9, 127.4 (dd), 126.0 (dd), 122.5, 120.8, 116.6, 112.9, 112.6 (dd), 105.8 (dd), 49.8, 34.5, 26.7, 26.0, 19.7

Example 167

1-Allyl-3-{3-[2-chloro-4-(2,4-difluoro-phenylamino)-benzoyl]-4-methyl-phenyl}-urea (Compound 267)

Compound 494 (0.07 g, 0.18 mmol) was dissolved in pyridine (0.5 mL) and allyl isocyanate (0.025 mL, 0.28 mmol) was added. The solution was stirred at room temperature for 18 h. Work up as described in the preparation of compound 259. The crude product was purified by flash chromatography using a gradient of EtOAc/petroleum ether (40-60) 15:85→60:40 as the eluent. This afforded the title compound as a slightly coloured solid. $^{13}$C NMR (CD$_3$OD) δ 198.5, 161.1 (dd), 158.0, 157.9 (dd), 151.2, 141.0, 138.8, 136.6, 136.1, 135.0, 132.7, 132.2, 128.9, 127.5 (dd), 126.0 (dd), 122.6, 121.0, 116.6, 115.7, 112.9, 112.7 (dd), 105.8 (dd), 43.2, 19.7

Example 168

1-Benzyl-3-{3-[2-chloro-4-(2,4-difluoro-phenylamino)-benzoyl]-4-methyl-phenyl}-urea (Compound 268)

Compound 494 (0.07 g, 0.18 mmol) was dissolved in pyridine (0.5 mL) and benzyl isocyanate (0.035 mL, 0.28 mmol) was added. The solution was stirred at room temperature for 18 h. Work up as described in the preparation of compound 259. The crude product was purified by flash chromatography using a MeOH/CH$_2$Cl$_2$ 1:100 as the eluent. This afforded the title compound as slightly coloured solid. $^{13}$C NMR (DMSO-d$_6$) δ 195.3, 158.8 (dd), 155.8 (dd), 155.2, 149.1, 140.3, 139.1, 138.2, 133.4, 131.4, 129.0, 128.3, 127.1, 126.7, 126.4 (dd), 124.4 (dd), 120.1, 118.2, 114.9, 112.0 (dd), 111.9, 105.1 (dd), 42.7, 19.1

Example 169

1-{3-[2-Chloro-4-(2,4-difluoro-phenylamino)-benzoyl]-4-methyl-phenyl}-3-ethyl-urea (Compound 269)

Compound 494 (0.04 g, 0.11 mmol) was dissolved in 1,4-dioxan (0.5 mL) and ethyl isocyanate (0.013 mL, 0.16 mmol) was added. The solution was stirred at room temperature for 18 h. Work up as described in the preparation of compound 259. The crude product was purified by flash chromatography using a gradient of EtOAc/petroleum ether (40-60) 30:70→100:0 as the eluent. This afforded the title compound as an amorphous compound. $^{13}$C NMR (DMSO-$d_6$) δ 195.6, 159.0 (dd), 156.0 (dd), 155.3, 149.2, 139.3, 138.3, 133.7, 133.5, 131.5, 129.2, 127.5, 126.4 (dd), 124.5 (dd), 120.2, 118.4, 115.1, 112.1 (dd), 112.0, 105.1 (dd), 34.0, 19.1, 15.4

Example 170

1-{3-[2-Chloro-4-(2,4-difluoro-phenylamino)-benzoyl]-4-methyl-phenyl}-3-phenyl-urea (Compound 270)

Compound 494 (0.03 g, 0.08 mmol) was dissolved in 1,4-dioxan (0.5 mL) and phenyl isocyanate (0.013 mL, 0.12 mmol) was added. The solution was stirred at 50° C. for 18 h. Work up as described in the preparation of compound 259. The crude product was purified by flash chromatography using a gradient of EtOAc/petroleum ether (40-60) 15:85→60:40 as the eluent. This afforded the title compound as an amorphous compound. $^{13}$C NMR (DMSO-$d_6$) δ 195.1, 158.7 (dd), 155.7 (dd), 152.3, 148.9, 139.3, 139.1, 137.2, 133.4, 131.5, 129.6, 128.7, 127.0, 126.2 (dd), 124.2 (dd), 121.8, 120.3, 118.4, 118.2, 118.1, 114.8, 111.9 (dd), 111.8, 105.0 (dd), 19.0

Example 171

1-Butyl-3-{3-[2-chloro-4-(2,4-difluoro-phenylamino)-benzoyl]-4-methyl-phenyl}-urea (Compound 271)

Compound 494 (0.03 g, 0.08 mmol) was dissolved in 1,4-dioxan (0.5 mL) and n-butyl isocyanate (0.014 mL, 0.12 mmol) was added. The solution was stirred at 50° C. for 18 h. Work up as described in the preparation of compound 259. The crude product was purified by flash chromatography using a gradient of EtOAc/petroleum ether (40-60) 15:85→60:40 as the eluent. This afforded the title compound as a slightly coloured solid. $^{13}$C NMR (CD$_3$OD) δ 198.5, 161.0 (dd), 158.3, 157.9 (dd), 151.1, 141.0, 138.9, 136.1, 135.0, 132.7, 132.1, 128.9, 127.4 (dd), 126.0 (dd), 122.5, 120.9, 116.6, 112.9, 112.6 (dd), 105.8 (dd), 40.6, 33.3, 21.0, 19.7, 14.1

Example 172

1-{3-[2-Chloro-4-(2,4-difluoro-phenylamino)-benzoyl]-4-methyl-phenyl}-3-phenethyl-urea (Compound 272)

Compound 494 (0.03 g, 0.08 mmol) was dissolved in 1,4-dioxan (0.5 mL) and 2-phenylethyl isocyanate (0.016 mL, 0.12 mmol) was added. The solution was stirred at 50° C. for 18 h. Work up as described in the preparation of compound 259. The crude product was purified by flash chromatography using a gradient of EtOAc/petroleum ether (40-60) 15:85→60:40 as the eluent. This afforded the title compound as a slightly coloured solid. $^{13}$C NMR (CDCl$_3$) δ 196.5, 159.2 (dd), 156.0, 155.6 (dd), 148.1, 139.6, 138.9, 136.5, 135.1, 133.9, 132.2, 131.9, 128.7, 128.5, 126.4, 124.6 (dd), 124.2 (dd), 123.1, 121.1, 116.2, 112.7, 111.6 (dd), 104.9 (dd), 41.5, 36.3, 19.6

Example 173

2-(3-{3-[2-Chloro-4-(2,4-difluoro-phenylamino)-benzoyl]-4-methyl-phenyl}-ureido)-benzoic acid methyl ester (Compound 273)

Compound 494 (0.03 g, 0.08 mmol) was dissolved in 1,4-dioxan (0.5 mL) and methyl 2-isocyanatobenzoate (0.021 mL, 0.12 mmol) was added. The solution was stirred at 50° C. for 24 h. Methyl 2-isocyanatobenzoate (0.01 mL, 0.06 mmol) was added. The solution was stirred at 50° C. for 24 h. Work up as described in the preparation of compound 259. The crude product was purified by flash chromatography using a gradient of EtOAc/petroleum ether (40-60) 10:90→40:60 as the eluent. This afforded the title compound as yellow oil. $^{13}$C NMR (CDCl$_3$) δ 195.8, 169.0, 159.0 (dd), 155.4 (dd), 152.4, 147.6, 142.5, 139.5, 135.6, 135.1, 134.6, 133.6, 133.4, 132.1, 130.8, 129.4, 124.5 (dd), 124.1 (dd), 123.3, 121.7, 121.3, 119.8, 116.3, 114.3, 112.8, 111.5 (dd), 104.9 (dd), 52.2, 19.8

Example 174

1-{3-[2-Chloro-4-(2,4-difluoro-phenylamino)-benzoyl]-4-methyl-phenyl}-3-(3-cyano-phenyl)-urea (Compound 274)

Compound 494 (0.03 g, 0.08 mmol) was dissolved in 1,4-dioxan (0.5 mL) and 3-cyanophenyl isocyanate (0.017 g, 0.12 mmol) was added. The solution was stirred at 50° C. for 24 h. 3-Cyanophenyl isocyanate (0.09 g, 0.06 mmol) was added. The solution was stirred at 50° C. for 24 h. Work up as described in the preparation of compound 259. The crude product was purified by flash chromatography using MeOH/CH$_2$Cl$_2$ 1:100 as the eluent. This afforded the title compound as yellow oil. $^{13}$C NMR (DMSO-$d_6$) δ 195.1, 158.8 (dd), 155.8 (dd), 152.4, 149.2, 140.5, 139.3, 137.0, 133.5, 131.6, 130.2, 130.1, 126.9, 126.5 (dd), 125.4, 124.3 (dd), 123.0, 121.1, 120.8, 118.9, 118.8, 114.9, 112.0 (dd), 111.9, 111.6, 105.1 (dd), 19.1

Example 175

1-{3-[2-Chloro-4-(2,4-difluoro-phenylamino)-benzoyl]-4-methyl-phenyl}-3-isopropyl-urea (Compound 275)

Compound 494 (0.03 g, 0.08 mmol) was dissolved in 1,4-dioxan (0.5 mL) and isopropyl isocyanate (0.012 mL, 0.12 mmol) was added. The solution was stirred at 50° C. for 24 h. Isopropyl isocyanate (0.006 mL, 0.06 mmol) was added. The solution was stirred at 50° C. for 24 h. Work up as described in the preparation of compound 259. The crude product was purified by flash chromatography using a gradient of EtOAc/petroleum ether (40-60) 15:85→60:40 as the eluent. This afforded the title compound as a slightly coloured solid. $^{13}$C NMR (CD$_3$OD) δ 198.4, 160.9 (dd), 157.8 (dd), 157.4, 151.1, 140.9, 138.7, 136.1, 134.9, 132.6, 131.9, 128.7, 127.3 (dd), 125.9 (dd), 122.4, 120.7, 116.6, 112.9, 112.6 (dd), 105.7 (dd), 42.8, 23.4, 19.6

Example 176

1-{3-[2-Chloro-4-(2,4-difluoro-phenylamino)-benzoyl]-4-methyl-phenyl}-3-(4-methoxy-phenyl)-urea (Compound 276)

Compound 494 (0.03 g, 0.08 mmol) was dissolved in 1,4-dioxan (0.5 mL) and 4-methoxyphenyl isocyanate (0.016 mL, 0.12 mmol) was added. The solution was stirred at 50° C. for 18 h. Work up as described in the preparation of compound 259. The crude product was purified by flash chromatography using MeOH/CH$_2$Cl$_2$ 1:100 the eluent. This afforded the title compound as oil. $^{13}$C NMR (DMSO-d$_6$) δ 195.2, 158.8 (dd), 155.8 (dd), 154.6, 152.7, 149.1, 139.2, 137.6, 133.5, 132.5, 131.5, 129.5, 127.0, 126.4 (dd), 124.4 (dd), 120.4, 120.2, 119.9, 118.5, 114.9, 114.0, 112.0 (dd), 111.9, 105.1 (dd), 55.2, 19.1

Example 177

{3-[2-Chloro-4-(2,4-difluoro-phenylamino)-benzoyl]-4-methyl-phenyl}-carbamic acid benzyl ester (Compound 277)

Compound 494 (0.06 g, 0.16 mmol) was suspended in dry CH$_2$Cl$_2$ (1.5 mL) under an argon atmosphere in a screw cap vessel. K$_2$CO$_3$ (0.044 g, 0.32 mmol) was added followed by benzyl chloroformate (0.046 mL, 0.032 mmol). The suspension was stirred for 18 h at room temperature. H$_2$O and CH$_2$Cl$_2$ were added and the phases were separated. The water phase was washed with CH$_2$Cl$_2$ (×2) and the combined organic phases were washed with brine, dried (MgSO$_4$), filtered and concentrated in vacuo. The crude product was purified by flash chromatography using EtOAc/petroleum ether (40-60) 1:4 as the eluent. This afforded the title compound as yellow oil. $^{13}$C NMR (CD$_3$OD) δ 198.3, 161.0 (dd), 157.8 (dd), 155.8, 151.1, 141.1, 138.0, 136.2, 135.0, 132.8, 132.7, 129.5, 129.1, 129.0, 128.7, 127.3 (dd), 126.0 (dd), 122.3, 120.6, 116.7, 112.9, 112.6 (dd), 105.7 (dd), 67.6, 19.7

Example 178

{3-[2-Chloro-4-(2,4-difluoro-phenylamino)-benzoyl]-4-methyl-phenyl}-carbamic acid allyl ester (Compound 278)

Compound 494 (0.06 g, 0.16 mmol) was suspended in dry CH$_2$Cl$_2$ (1.5 mL) under an argon atmosphere in a screw cap vessel. K$_2$CO$_3$ (0.044 g, 0.32 mmol) was added followed by allyl chloroformate (0.034 mL, 0.032 mmol). The suspension was stirred for 48 h at room temperature. Work up as described in the preparation of compound 277. The crude product was purified by flash chromatography using a gradient of EtOAc/petroleum ether (40-60) 5:95→30:70 as the eluent. This afforded the title compound as yellow oil. $^{13}$C NMR (CDCl$_3$) δ 195.8, 159.1 (dd), 155.5 (dd), 153.2, 147.7, 139.6, 135.4, 135.2, 133.6, 132.9, 132.3, 132.0, 129.3, 124.4 (dd), 124.2 (dd), 121.3, 119.7, 118.3, 116.3, 112.8, 111.6 (dd), 105.0 (dd), 65.9, 19.7

Example 179

{3-[2-Chloro-4-(2,4-difluoro-phenylamino)-benzoyl]-4-methyl-phenyl}-carbamic acid ethyl ester (Compound 279)

Compound 494 (0.039 g, 0.1 mmol) was suspended in dry CH$_2$Cl$_2$ (1 mL) under an argon atmosphere. K$_2$CO$_3$ (0.029 g, 0.21 mmol) was added followed by ethyl chloroformate (0.02 mL, 0.021 mmol). The suspension was stirred for 48 h at room temperature. Work up as described in the preparation of compound 277. The crude product was purified by flash chromatography using EtOAc/petroleum ether (40-60) 1:2 as the eluent. This afforded the title compound as oil. $^{13}$C NMR (CDCl$_3$) δ 196.0, 159.1 (dd), 155.6 (dd), 153.7, 147.9, 139.5, 135.6, 135.1, 133.6, 132.6, 131.9, 129.1, 124.4 (dd), 124.3 (dd), 121.3, 119.8, 116.2, 112.7, 111.6 (dd), 104.9 (dd), 61.3, 19.7, 14.5

Example 181

[2-Chloro-4-(2,4-difluoro-phenylamino)-phenyl]-[5-(3-hydroxy-butylamino)-2-methyl-phenyl]-methanone (Compound 281)

Compound 494 (0.033 g, 0.09 mmol) was suspended in MeOH (1 mL). 3-Hydroxy-butyraldehyde (0.023 g, 0.27 mmol) and NaCN(BH$_3$) (0.055 g, 0.88 mmol) were added. The suspension was stirred at room temperature for 18 h. 3-Hydroxy-butyraldehyde (0.023 g, 0.27 mmol) and NaCN(BH$_3$) (0.055 g, 0.88 mmol) were added again and the suspension was stirred at room temperature for 24 h. The reaction mixture was concentrated in vacuo. The residue was dissolved in EtOAc and the organic phase was washed with brine. The water phase was extracted with EtOAc and the combined organic phases were dried (MgSO$_4$), filtered and concentrated in vacuo. The crude product was purified by flash chromatography using MeOH/CH$_2$Cl$_2$ 1:50 as the eluent. This afforded the title compound as oil. $^{13}$C NMR (CDCl$_3$) δ 196.7, 159.0 (dd), 155.4 (dd), 147.3, 146.0, 139.6, 135.0, 133.5, 132.0, 129.9, 126.7, 124.6 (dd), 124.0 (dd), 116.3, 115.9, 114.6, 112.8, 111.6 (dd), 104.9 (dd), 67.5, 42.1, 38.0, 24.0, 19.4

Example 182

[2-Chloro-4-(2,4-difluoro-phenylamino)-phenyl]-(3'-hydroxymethyl-4-methyl-biphenyl-3-yl)-methanone (Compound 282)

Compound 495 (0.039 g, 0.081 mmol) was dissolved in 1,2-dimethoxyethane (0.8 mL) in a screw cap vessel. 3-(Hydroxymethyl)phenylboronic acid (0.015 g, 0.097 mmol) and saturated aqueous NaHCO$_3$ (0.4 mL) were added. Argon was blown over the mixture and Pd(PPh$_3$)$_4$ (0.005 g, 0.004 mmol) was added. The reaction mixture was stirred at reflux temperature under an argon atmosphere for 2 h. H$_2$O and EtOAc were added and the water phase was extracted with EtOAc (×2). The combined organic phases were dried (MgSO$_4$), filtered and concentrated in vacuo. The crude product was purified by flash chromatography using EtOAc/petroleum ether (40-60) 1:1 as the eluent. This afforded the title compound as oil. $^{13}$C NMR (CDCl$_3$) δ 196.3, 159.1 (dd), 155.5 (dd), 147.8, 141.5, 140.6, 139.6, 138.3, 137.0, 135.3, 133.7, 131.8, 129.4, 129.1, 128.0, 126.3, 126.0, 125.6, 124.4 (dd), 124.3 (dd), 116.3, 112.8, 111.6 (dd), 104.9 (dd), 65.3, 20.1

Example 183

[2-Chloro-4-(2,4-difluoro-phenylamino)-phenyl]-(3'-hydroxy-4-methyl-biphenyl-3-yl)-methanone (Compound 283)

The compound was prepared as described in the preparation of compound 282. Starting materials were compound 495 (0.039 g, 0.081 mmol), 3-hydroxyphenylboronic acid (0.013 g, 0.097 mmol) in 1,2-dimethoxyethane (0.8 mL), saturated aqueous $NaHCO_3$ (0.4 mL) and $Pd(PPh_3)_4$ (0.005 g, 0.004 mmol). The crude product was purified by flash chromatography using EtOAc/petroleum ether (40-60) 1:2 as the eluent. This afforded the title compound as yellow oil. $^{13}C$ NMR ($CDCl_3$) δ 196.7, 159.2 (dd), 156.1, 155.5 (dd), 147.9, 141.8, 139.4, 138.1, 137.1, 135.3, 133.7, 131.8, 130.0, 129.5, 129.3, 128.1, 124.3 (m), 119.4, 116.3, 114.5, 114.0, 112.8, 111.6 (dd), 104.9 (dd), 20.1

Example 184

[2-Chloro-4-(2,4-difluoro-phenylamino)-phenyl]-(4'-methoxy-4-methyl-biphenyl-3-yl)-methanone (Compound 284)

The compound was prepared as described in the preparation of compound 282. Starting materials were compound 495 (0.042 g, 0.087 mmol), 4-methoxyphenylboronic acid (0.016 g, 0.11 mmol) in 1,2-dimethoxyethane (1 mL), saturated aqueous $NaHCO_3$ (0.5 mL) and $Pd(PPh_3)_4$ (0.005 g, 0.004 mmol). The crude product was purified by flash chromatography using EtOAc/petroleum ether (40-60) 1:5 as the eluent. This afforded the title compound as yellow oil. $^{13}C$ NMR ($CDCl_3$) δ 196.4, 159.3, 159.1 (dd), 155.5 (dd), 147.7, 139.4, 138.1, 136.3, 135.2, 133.6, 132.7, 131.8, 129.6, 129.0, 128.0, 127.8, 124.4 (dd), 124.2 (dd), 116.3, 114.3, 112.8, 111.6 (dd), 104.9 (dd), 55.4, 20.1

Example 185

N-{3'-[2-Chloro-4-(2,4-difluoro-phenylamino)-benzoyl]-4'-methyl-biphenyl-3-yl}-acetamide (Compound 285)

The compound was prepared as described in the preparation of compound 282. Starting materials were compound 495 (0.048 g, 0.1 mmol), 3-acetamidophenylboronic acid (0.021 g, 0.12 mmol) in 1,2-dimethoxyethane (1 mL), saturated aqueous $NaHCO_3$ (0.5 mL) and $Pd(PPh_3)_4$ (0.006 g, 0.005 mmol). The crude product was purified by flash chromatography using EtOAc/petroleum ether (40-60) 1:1 as the eluent. This afforded the title compound as a slightly coloured solid. $^{13}C$ NMR (DMSO-$d_6$) δ 195.0, 168.4, 158.8 (dd), 155.8 (dd), 149.4, 140.0, 139.9, 139.6, 137.5, 135.8, 133.9, 133.8, 131.9, 129.4, 128.7, 126.6, 126.5, 126.4 (dd), 124.3 (dd), 121.2, 118.2, 116.9, 115.0, 112.0 (dd), 111.9, 105.1 (dd), 24.0, 19.4

Example 186

[2-Chloro-4-(2,4-difluoro-phenylamino)-phenyl]-(4-methyl-3'-trifluoromethoxy-biphenyl-3-yl)-methanone (Compound 286)

The compound was prepared as described in the preparation of compound 282. Starting materials were compound 495 (0.048 g, 0.1 mmol), 3-(trifluoromethoxy)benzeneboronic acid (0.025 g, 0.12 mmol) in 1,2-dimethoxyethane (1.2 mL), saturated aqueous $NaHCO_3$ (0.6 mL) and $Pd(PPh_3)_4$ (0.006 g, 0.005 mmol). The crude product was purified by flash chromatography using a gradient of EtOAc/petroleum ether (40-60) 2:98→10:90 as the eluent. This afforded the title compound as yellow oil.

Example 188

[2-Chloro-4-(2,4-difluoro-phenylamino)-phenyl]-(3',4',5'-trifluoro-4-methyl-biphenyl-3-yl)-methanone (Compound 288)

The compound was prepared as described in the preparation of compound 282. Starting materials were compound 495 (0.055 g, 0.11 mmol), 3,4,5-trifluorobenzeneboronic acid (0.024 g, 0.14 mmol) in 1,2-dimethoxyethane (1.2 mL), saturated aqueous $NaHCO_3$ (0.6 mL) and $Pd(PPh_3)_4$ (0.007 g, 0.006 mmol). The crude product was purified by flash chromatography using a gradient of EtOAc/petroleum ether (40-60) 2:98→10:90 as the eluent. This afforded the title compound as yellow oil. $^{13}C$ NMR ($CDCl_3$) δ 195.8, 159.3 (dd), 155.6 (dd), 151.4 (m), 148.1, 140.1, 139.3 (dt), 138.0, 136.3 (m), 135.5, 135.3, 133.8, 132.1, 128.9, 127.5, 124.6 (dd), 124.2 (dd), 116.2, 112.7, 111.6 (dd), 110.9 (m), 105.0 (dd), 20.1

Example 189

[2-Chloro-4-(2,4-difluoro-phenylamino)-phenyl]-(3',4'-dimethoxy-4-methyl-biphenyl-3-yl)-methanone (289)

The compound was prepared as described in the preparation of compound 282. Starting materials were compound 495 (0.055 g, 0.11 mmol), 3,4-dimethoxybenzeneboronic acid (0.025 g, 0.15 mmol) in 1,2-dimethoxyethane (1.2 mL), saturated aqueous $NaHCO_3$ (0.6 mL) and $Pd(PPh_3)_4$ (0.007 g, 0.006 mmol). The crude product was purified by flash chromatography using a gradient of EtOAc/petroleum ether (40-60) 12:88→50:50 as the eluent. This afforded the title compound as yellow oil. $^{13}C$ NMR ($CDCl_3$) δ 196.4, 159.1 (dd), 155.5 (dd), 149.2, 148.7, 147.8, 139.5, 138.4, 136.3, 135.2, 133.7, 133.2, 131.7, 129.3, 129.1, 127.8, 124.3 (m), 119.3, 116.3, 112.7, 111.6 (dd), 111.5, 110.4, 105.0 (dd), 56.0, 20.0

Example 190

3'-[2-Chloro-4-(2,4-difluoro-phenylamino)-benzoyl]-4'-methyl-biphenyl-3-carbonitrile (Compound 290)

The compound was prepared as described in the preparation of compound 282. Starting materials were compound 495 (0.057 g, 0.12 mmol), 3-cyanobenzeneboronic acid (0.021 g, 0.14 mmol) in 1,2-dimethoxyethane (1.2 mL), saturated aqueous $NaHCO_3$ (0.6 mL) and $Pd(PPh_3)_4$ (0.007 g, 0.006 mmol). The crude product was purified by flash chromatography using a gradient of EtOAc/petroleum ether (40-60) 2:3→4:1 as the eluent. This afforded the title compound as yellow oil. $^{13}C$ NMR ($CDCl_3$) δ 195.9, 159.2 (dd), 155.6 (dd), 148.1, 141.4, 140.1, 138.1, 136.2, 135.3, 133.7, 132.2, 131.4, 130.8, 130.5, 129.7, 129.2, 128.9, 127.7, 124.5 (dd), 124.2 (dd), 118.8, 116.2, 113.0, 112.8, 111.6 (dd), 105.0 (dd), 20.1

Preparation 96

3-[2-Chloro-4-(2,4-difluoro-phenylamino)-benzoyl]-4-methyl-benzenesulfonyl chloride (Compound 496)

Compound 494 (1.03 g, 2.76 mmol) was dissolved in $CH_3CN$ (65 mL) by heating. The solution was cooled to room temperature and concentrated HCl (37%, 1.2 mL, ca. 14 mmol) and AcOH (99%, 2.3 mL) were added. The solution was cooled on an ice bath and the internal temperature was monitored. NaNO$_2$ (0.23 g, 3.31 mmol) dissolved in H$_2$O (0.6 mL) was added over 15 minutes under stirring. The internal temperature did not exceed 2° C. The mixture was stirred on an ice bath for 20 minutes after which SO$_2$ gas was bubbled through the mixture for 45 minutes under stirring on ice bath. CuCl (0.37 g, 3.8 mmol) was added followed by CuCl$_2$.2H$_2$O (0.59 g, 3.46 mmol) dissolved in H$_2$O (0.6 mL). The mixture was stirred at 0° C. for 10 minutes followed by stirring at room temperature for 1 h. The mixture was concentrated in vacuo and dissolved in EtOAc and H$_2$O. The phases were separated and the water phase was extracted with EtOAc. The combined organic phases were washed with brine, dried (MgSO$_4$), filtered and concentrated in vacuo. The crude product was purified by flash chromatography using EtOAc/petroleum ether (40-60) 1:4 as the eluent to afford the title compound as a pale brown crystalline compound.

Example 191

3-[2-Chloro-4-(2,4-difluoro-phenylamino)-benzoyl]-N-(2-hydroxy-ethyl)-4-methyl-benzenesulfonamide (Compound 291)

Compound 496 (0.07 g, 0.15 mmol) was dissolved in pyridine (0.4 mL) and ethanolamine (0.011 mL, 0.18 mmol) was added. The solution was kept at room temperature for 1 h after which it was concentrated in vacuo. The residue was dissolved in EtOAc and H$_2$O and the phases were separated. The water phase was extracted with EtOAc (×2) and the combined organic phases were washed with brine, dried (MgSO$_4$), filtered and concentrated in vacuo. The crude product was purified by flash chromatography using a gradient of EtOAc/petroleum ether (40-60) 3:7→1:0 as the eluent. This afforded the title compound as a solid. $^{13}$C NMR (CD$_3$OD) δ 196.5, 161.2 (dd), 158.0 (dd), 151.9, 143.3, 142.0, 139.5, 136.5, 135.2, 133.2, 129.9, 128.2, 127.8, 127.8 (dd), 125.7 (dd), 116.5, 113.1, 112.7 (dd), 105.8 (dd), 61.8, 46.3, 20.3

Example 192

3-[2-Chloro-4-(2,4-difluoro-phenylamino)-benzoyl]-4-methyl-N-(2-morpholin-4-yl-ethyl)-benzenesulfonamide (Compound 292)

The compound was prepared and worked up as described in the preparation of compound 291. Starting materials were compound 496 (0.081 g, 0.18 mmol) and 4-(2-aminoethyl)morpholine (0.028 mL, 0.21 mmol) in pyridine (0.5 mL). The crude product was purified by flash chromatography using a gradient of EtOAc/petroleum ether (40-60) 1:1→1:0 as the eluent. This afforded the title compound as an amorphous compound. $^{13}$C NMR (CDCl$_3$) δ 194.5, 159.5 (dd), 155.9 (dd), 148.8, 142.8, 140.5, 137.0, 135.4, 134.0, 132.1, 128.7, 127.9, 127.3, 125.0 (dd), 123.9 (dd), 116.0, 112.9, 111.7 (dd), 105.1 (dd), 66.8, 56.2, 53.0, 38.9, 20.4

Example 193

N-Allyl-3-[2-chloro-4-(2,4-difluoro-phenylamino)-benzoyl]-4-methyl-benzenesulfonamide (Compound 293)

The compound was prepared and worked up as described in the preparation of compound 291. Starting materials were compound 496 (0.071 g, 0.16 mmol) and allylamine (0.014 mL, 0.19 mmol) in pyridine (0.4 mL). The crude product was purified by flash chromatography using a gradient of EtOAc/petroleum ether (40-60) 1:4→2:3 as the eluent. This afforded the title compound as oil. $^{13}$C NMR (CDCl$_3$) δ 194.6, 159.4 (dd), 155.8 (dd), 148.7, 143.0, 140.4, 137.4, 135.5, 133.9, 132.8, 132.1, 128.8, 128.0, 127.5, 124.9 (dd), 124.0 (dd), 118.0, 116.1, 112.9, 111.7 (dd), 105.0 (dd), 45.8, 20.4

Example 194

N-(2-{3-[2-Chloro-4-(2,4-difluoro-phenylamino)-benzoyl]-4-methyl-benzenesulfonylamino}-ethyl)-acetamide (Compound 294)

The compound was prepared and worked up as described in the preparation of compound 291. Starting materials were compound 496 (0.075 g, 0.17 mmol) and N-acetylethylenediamine (0.019 mL, 0.2 mmol) in pyridine (0.4 mL). The crude product was purified by flash chromatography using a gradient of DCM/MeOH 95:5→80:20 as the eluent. This afforded the title compound as oil. $^{13}$C NMR (CDCl$_3$) δ 194.6, 171.5, 159.5 (dd), 155.9 (dd), 149.0, 142.7, 140.5, 137.1, 135.6, 134.2, 132.2, 128.6, 127.4, 127.2, 125.2 (dd), 123.9 (dd), 116.1, 112.7, 111.7 (dd), 105.0 (dd), 43.2, 39.3, 23.1, 20.3

Example 195

3-[2-Chloro-4-(2,4-difluoro-phenylamino)-benzoyl]-4-methyl-N-propyl-benzenesulfonamide (Compound 295)

The compound was prepared and worked up as described in the preparation of compound 291. Starting materials were compound 496 (0.074 g, 0.16 mmol) and n-propylamine (0.016 mL, 0.2 mmol) in pyridine (0.4 mL). The crude product was purified by flash chromatography using a gradient of EtOAc/petroleum ether (40-60) 1:4→3:2 as the eluent. This afforded the title compound as oil. $^{13}$C NMR (CDCl$_3$) δ 194.7, 159.4 (dd), 155.8 (dd), 148.6, 142.8, 140.3, 137.4, 135.5, 133.9, 132.1, 128.8, 128.1, 127.5, 124.9 (dd), 124.0 (dd), 116.1, 112.9, 111.7 (dd), 105.0 (dd), 45.0, 22.9, 20.4, 11.1

Example 196

3-[2-Chloro-4-(2,4-difluoro-phenylamino)-benzoyl]-N-(2,3-dihydroxy-propyl)-4-methyl-benzenesulfonamide (Compound 296)

The compound was prepared and worked up as described in the preparation of compound 291. Starting materials were compound 496 (0.073 g, 0.16 mmol) and 3-amino-1,2-propanediol (0.017 g, 0.19 mmol) in pyridine (0.4 mL). The crude product was purified by flash chromatography using a gradient of EtOAc/petroleum ether (40-60) 1:1→1:0 as the eluent. This afforded the title compound as oil. $^{13}$C NMR (CDCl$_3$) δ 194.8, 159.5 (dd), 155.8 (dd), 149.0, 142.7, 140.5, 136.9, 135.6, 134.2, 132.2, 128.7, 127.4, 127.2, 125.1 (bd), 123.9 (dd), 116.1, 112.7, 111.7 (dd), 105.0 (dd), 70.4, 64.0, 45.4, 20.3

Example 197

3-[2-Chloro-4-(2,4-difluoro-phenylamino)-benzoyl]-N-(2-methoxy-ethyl)-4-methyl-benzenesulfonamide (Compound 297)

The compound was prepared and worked up as described in the preparation of compound 291. Starting materials were compound 496 (0.03 g, 0.066 mmol) and 2-methoxy-ethylamine (0.007 mL, 0.08 mmol) in pyridine (0.15 mL). The crude product was purified by flash chromatography using EtOAc/petroleum ether (40-60) 3:2 as the eluent. This afforded the title compound as oil. $^{13}$C NMR (CDCl$_3$) δ 194.5, 159.4 (dd), 155.8 (dd), 148.6, 142.9, 140.3, 137.3, 135.5, 134.0, 132.1, 128.7, 128.1, 127.5, 124.9 (dd), 124.0 (dd), 116.1, 112.9, 111.7 (dd), 105.0 (dd), 70.4, 58.8, 42.9, 20.4

Preparation 97

2-Methyl-5-nitro-benzoic acid methyl ester (Compound 497)

Acetyl chloride (15 ml) was added to MeOH (500 ml) at room temperature. After 10 min, 2-methyl-5-nitro-benzoic acid (25.00 g, 138.00 mmol) was added. The reaction solution was heated for reflux for 18 h. The solution was then concentrated in vacuo. The residue was dissolved in diethyl ether and washed with H$_2$O and saturated aqueous solution of NaHCO$_3$ respectively. The organic phase was dried over MgSO$_4$ and concentrated in vacuo to provide the title compound as a white solid.

Preparation 98

5-Amino-2-methyl-benzoic acid methyl ester (Compound 498)

Compound 497 (26.5 g, 135.78 mmol) in ethanol (200 ml) was hydrogenated under 1 atmosphere at room temperature in the presence of Pd/C 5% (2.00 g) for 3 h. After reaction, the catalyst was filtered off. The filtrate was concentrated in vacuo, providing the title compound as a brownish oil.

Preparation 99

5-Hydroxy-2-methyl-benzoic acid methyl ester (Compound 499)

To 2 NH$_2$SO$_4$ (200 ml) was dropwise added NaNO$_2$ (11.50 g, 167.00 mmol) in H$_2$O (100 ml) at 0° C. After being stirred at the same temperature for 20 min, the reaction mixture was heated for reflux for 2 h. Then the solution was cooled to room temperature and stirred at the same temperature overnight. The mixture was extracted three times with CHCl$_3$. The combined organic phases were dried over MgSO$_4$ and concentrated in vacuo. The residue was purified by chromatography (CH$_2$Cl$_2$/ethyl acetate 50:1), furnishing the title compound as a red solid.

Preparation 100

5-(4-Methoxy-benzyloxy)-2-methyl-benzoic acid methyl ester (Compound 500)

A mixture of compound 499 (4.4 g, 26.48 mmol), 4-methoxybenzyl chloride (4.4 g, 28.09 mmol), K$_2$CO$_3$ (4.4 g, 31.83 mmol) and NaI (20 mg) was heated for reflux for 3 h. After reaction, the solid was filtered off. The filtrate was concentrated in vacuo. The residue was purified by chromatography (petroleum ether/CH$_2$Cl$_2$ 2:1, then CH$_2$Cl$_2$), giving the title compound as a yellow solid.

Preparation 101

[5-(4-Methoxy-benzyloxy)-2-methyl-phenyl]-methanol (Compound 501)

To a solution of compound 500 (6.0 g, 21.00 mmol) in CH$_2$Cl$_2$ (100 ml) at −78° C. was added DIBAL-H (1 M in n-hexane, 55 ml, 55 mmol). The solution was warmed to room temperature and stirred for 1 h. Then the reaction solution was quenched with saturated aqueous solution of NH$_4$Cl. The mixture was filtered and washed with acetone. The combined liquids were concentrated in vacuo to remove acetone and CH$_2$Cl$_2$. The aqueous mixture was extracted three times with CH$_2$Cl$_2$. The combined organic phases were dried over MgSO$_4$ and concentrated in vacuo, furnishing the title compound as greyish solid.

Preparation 102

5-(4-Methoxy-benzyloxy)-2-methyl-benzaldehyde (Compound 502)

To a solution of compound 501 (5.06 g, 19.59 mmol) in CH$_2$Cl$_2$ (100 ml) was added Dess-Martin periodinane (8.36 g, 19.71 mmol) at room temperature over a 20 min period. The mixture was then stirred for 1 h. After total conversion, the reaction mixture was concentrated in vacuo together with silica gel. The residue was purified by chromatography (CH$_2$Cl$_2$), furnishing the title compound as a yellow solid.

Preparation 103

(4-Bromo-2-nitro-phenyl)-[5-(4-methoxy-benzyloxy)-2-methyl-phenyl]-methanol (Compound 503)

To a solution of 1,4-dibromo-2-nitro-benzene (5.89 g, 21.00 mmol) in THF (300 ml) was added a solution of PhLi (1.8 M in cyclohexane/diethyl ether 7:3, 12.8 ml, 23.1 mmol) at −110° C. The mixture was stirred at the same temperature for 1 h. Compound 502 (4.45 g, 17.4 mmol) in THF (100 ml) was dropwise added to the mixture. The reaction mixture was then allowed to warm to −78° C. and stirred at the same temperature for 4 h. Afterwards, the reaction mixture was quenched with saturated aqueous solution of NH$_4$Cl. the aqueous phase was extracted once with diethyl ether. The combined organic phases were dried over MgSO$_4$ and concentrated in vacuo. The residue was purified by chromatography (petroleum ether/ethyl acetate 5:1), furnishing a reddish foam.

Preparation 104

(4-Bromo-2-nitro-phenyl)-[5-(4-methoxy-benzyloxy)-2-methyl-phenyl]-methanone (Compound 504)

To a solution of compound 503 (6.47 g, 14.12 mmol) was added Dess-Martin periodinane (8.00 g, 18.86 mmol) in one portion at room temperature. After stirring at room temperature for 3 h, the reaction mixture was purified by chromatography (petroleum ether/ethyl acetate 10:1) to provide the title compound as a brownish oil.

Example 198

(4-(4-Fluoro-2-methyl-phenylamino)-2-nitro-phenyl)-[5-(4-methoxy-benzyloxy)-2-methyl-phenyl]-methanone (Compound 298)

Compound 504 (0.6 g, 1.35 mmol) was dissolved in 1,4-dioxan (15 mL). 4-Fluoro-2-methylaniline (0.22 mL, 2.0 mmol), Cs$_2$CO$_3$ (0.61 g, 1.88 mmol), BINAP (0.06 g, 0.1 mmol) and Pd$_2$(dba)$_3$ (0.031 g, 0.03 mmol) were added and the reaction mixture was stirred under an argon atmosphere at 100° C. for 18 h. H$_2$O was added and the water phase was extracted with EtOAc (×2). The combined organic phases were washed with brine, dried (MgSO$_4$), filtered and concentrated in vacuo. The crude product was purified by flash chromatography using a gradient of EtOAc/petroleum ether (40-60) 0:100→30:70. This afforded the title compound. $^1$H NMR (CDCl$_3$) δ 7.32 (d, 1H), 7.30-7.14 (m, 4H), 7.11 (d, 1H), 7.06-6.91 (m, 3H), 6.88 (m, 2H), 6.84-6.77 (m, 2H), 5.87 (bs, 1H), 4.88 (s, 2H), 3.80 (s, 3H), 2.49 (s, 3H), 2.25 (s, 3H).

Preparation 105

[4-(4-Fluoro-2-methyl-phenylamino)-2-nitro-phenyl]-(5-hydroxy-2-methyl-phenyl)-methanone (Compound 505)

Compound 298 (0.57 g, 1.14 mmol) was dissolved in CH$_2$Cl$_2$ (10 mL) and CF$_3$COOH (10 mL) was added. The reaction mixture was stirred at room temperature for 2 h after which the solvent was concentrated. The solid was recrystallized from CH$_2$Cl$_2$. This gave the title compound as a solid.

Example 199

[4-(4-Fluoro-2-methyl-phenylamino)-2-nitro-phenyl]-[5-(3-hydroxy-propoxy)-2-methyl-phenyl]-methanone (Compound 299)

Compound 505 (0.05 g, 0.13 mmol) and 3-chloro-propanol (0.022 mL, 0.26 mmol) were dissolved in CH$_3$CN (3 mL). K$_2$CO$_3$ (0.1 g, 0.72 mmol) and NaI (0.005 g, 0.03 mmol) were added and the suspension was heated in a microwave oven at 100° C. for 20 minutes. The suspension was filtered and the filtrate was concentrated in vacuo. The crude product was purified by flash chromatography using EtOAc/CH$_2$Cl$_2$ 1:9 as the eluent. This afforded the title compound. $^1$H NMR (CDCl$_3$) δ 7.36 (d, 1H), 7.22 (dd, 1H), 7.17 (d, 1H), 7.10 (d, 1H), 7.06-6.89 (m, 3H), 6.83 (dd, 1H), 6.79 (d, 1H), 5.88 (bs, 1H), 4.04 (t, 2H), 3.82 (t, 2H), 2.47 (s, 3H), 2.25 (s, 3H), 1.99 (m, 2H)

Example 200

[2-Amino-4-(4-fluoro-2-methyl-phenylamino)-phenyl]-[5-(3-hydroxy-propoxy)-2-methyl-phenyl]-methanone (Compound 300)

Compound 299 (0.026 g, 0.059 mmol) was dissolved in MeOH (2 mL). A catalytic amount of palladium on charcoal was added and the mixture was stirred under a hydrogen atmosphere for 1 h. The suspension was filtered and the filtrate was concentrated in vacuo. The crude product was purified by flash chromatography using EtOAc/petroleum ether (40-60) 1:1→3:1 as the eluent. This afforded the title compound. $^1$H NMR (CDCl$_3$) δ 7.18 (dd, 1H), 7.11 (d, 1H), 7.03 (d, 1H), 7.00-6.80 (m, 3H), 6.76 (d, 1H), 6.45 (bs, 2H), 5.89 (dd, 1H), 5.75 (d, 1H), 5.59 (s, 1H), 4.08 (t, 2H), 3.83 (t, 2H), 2.22 (s, 3H), 2.18 (s, 3H), 2.01 (m, 2H)

Preparation 106

Toluene-4-sulfonic acid 2,2-dimethyl-[1,3]dioxolan-4-ylmethyl ester (Compound 506)

2,2-Dimethyl-4-hydroxymethyl-1,3-dioxolan (3.96 g, 30 mmol) and triethyl amine (5 mL) were dissolved in CH$_2$Cl$_2$ (50 mL). p-Toluenesulphonyl chloride (3.8 g, 20 mmol) was added. The solution was stirred for 3 h after which 4-dimethylaminopyridine (0.05 g, 0.04 mmol) was added. The solution was stirred for 0.5 h after which the solution was concentrated in vacuo. The residue was taken up in CH$_2$Cl$_2$ and the organic phase was washed with H$_2$O, dried (MgSO$_4$), filtered and concentrated in vacuo. The crude product was purified by flash chromatography to afford the title compound.

Example 201

[5-(2,2-Dimethyl-[1,3]dioxolan-4-ylmethoxy)-2-methyl-phenyl]-[4-(4-fluoro-2-methyl-phenylamino)-2-nitro-phenyl]-methanone (Compound 301)

Compound 505 (0.05 g, 0.13 mmol) and compound 506 (0.056 g, 0.2 mmol) were dissolved in CH$_3$CN (3 mL). K$_2$CO$_3$ (0.1 g, 0.72 mmol) and NaI (0.005 g, 0.03 mmol) were added and the suspension was heated in a microwave oven at 100° C. for 20 minutes and stirred at room temperature for 16 h. The suspension was filtered and the filtrate was concentrated in vacuo. The crude product was purified by flash chromatography using a gradient of EtOAc/petroleum ether (40-60) 0:1→1:4 as the eluent. This afforded the title compound. $^1$H NMR (CDCl$_3$) δ 7.34 (d, 1H), 7.22 (dd, 1H), 7.17 (d, 1H), 7.10 (d, 1H), 7.05-6.87 (m, 3H), 6.85-6.77 (m, 2H), 5.99 (bs, 1H), 4.42 (m, 1H), 4.17-4.06 (m, 1H), 3.96 (dd, 1H), 3.90-3.78 (m, 2H), 2.46 (s, 3H), 2.25 (s, 3H), 1.43 (s, 3H), 1.38 (s, 3H)

Example 202

[5-(2,3-Dihydroxy-propoxy)-2-methyl-phenyl]-[4-(4-fluoro-2-methyl-phenylamino)-2-nitro-phenyl]-methanone (Compound 302)

Compound 301 (0.025, 0.05 mmol) was dissolved in THF (2 mL) and 1 M HCl (0.2 mL) was added. The solution was kept at room temperature for 3 h after which the solution was concentrated in vacuo. This afforded the title compound. $^1$H NMR (CDCl$_3$) δ 7.36 (d, 1H), 7.22 (dd, 1H), 7.18 (d, 1H), 7.10 (d, 1H), 7.06-6.88 (m, 3H), 6.87-6.77 (m, 2H), 5.89 (bs, 1H), 4.05 (m, 1H), 3.95 (m, 2H), 3.85-3.65 (m, 2H), 2.46 (s, 3H), 2.25 (s, 3H)

Example 203

[2-Amino-4-(4-fluoro-2-methyl-phenylamino)-phenyl]-[5-(2,3-dihydroxy-propoxy)-2-methyl-phenyl]-methanone (303)

Compound 302 (0.025 g, 0.055 mmol) was dissolved in MeOH (2 mL). A catalytic amount of palladium on charcoal was added and the mixture was stirred under a hydrogen atmosphere for 1 h. The suspension was filtered and the filtrate was concentrated in vacuo. The crude product was purified by preparative HPLC. This afforded the title compound. $^1$H NMR (CDCl$_3$) δ 7.19 (dd, 1H), 7.13 (d, 1H), 7.05-6.82 (m, 4H), 6.76 (d, 1H), 6.46 (bs, 2H), 5.89 (dd, 1H), 5.75 (d, 1H), 5.56 (bs, 1H), 4.15-3.93 (m, 3H), 3.80 (dd, 1H), 3.71 (dd, 1H), 2.65 (bs, 1H), 2.23 (s, 3H), 2.19 (s, 3H), 2.10 (bs, 1H)

Example 204

[4-(4-Fluoro-2-methyl-phenylamino)-2-nitro-phenyl]-[2-methyl-5-(2-morpholin-4-yl-ethoxy)-phenyl]-methanone (304)

Compound 505 (0.083 g, 0.22 mmol) and N-(2-chloroethyl)morpholine hydrochloride (0.082 g, 0.44 mmol) were suspended in $CH_3CN$ (5 mL). $K_2CO_3$ (0.17 g, 1.2 mmol) and NaI (0.008 g, 0.05 mmol) were added and the suspension was heated in a microwave oven at 130° C. for 40 minutes. The suspension was filtered and the filtrate was concentrated in vacuo. The crude product was purified by flash chromatography using a gradient of EtOAc/petroleum ether (40-60) 2:3→1:0 as the eluent. This afforded the title compound. $^1H$ NMR ($CDCl_3$) δ 7.34 (d, 1H), 7.21 (dd, 1H), 7.17 (d, 1H), 7.10 (d, 1H), 7.05-6.88 (m, 3H), 6.85-6.78 (m, 2H), 6.16 (s, 1H), 4.02 (t, 2H), 3.72 (m, 4H), 2.75 (t, 2H), 2.54 (m, 4H), 2.45 (s, 3H), 2.25 (s, 3H)

Example 205

[2-Amino-4-(4-fluoro-2-methyl-phenylamino)-phenyl]-[2-methyl-5-(2-morpholin-4-yl-ethoxy)-phenyl]-methanone (Compound 305)

Compound 304 (0.041 g, 0.083 mmol) was dissolved in MeOH (2 mL). A catalytic amount of palladium on charcoal was added and the mixture was stirred under a hydrogen atmosphere for 1 h. The suspension was filtered and the filtrate was concentrated in vacuo. The crude product was purified by flash chromatography using EtOAc/petroleum ether (40-60) 3:1→6:1 as the eluent. This afforded the title compound. $^1H$ NMR ($CDCl_3$) δ 7.19 (dd, 1H), 7.1.1 (d, 1H), 7.03 (d, 1H), 7.00-6.80 (m, 3H), 6.76 (d, 1H), 6.46 (bs, 2H), 5.89 (dd, 1H), 5.75 (d, 1H), 5.60 (s, 1H), 4.07 (t, 2H), 3.71 (m, 4H), 2.77 (t, 2H), 2.55 (m, 4H), 2.23 (s, 3H), 2.18 (s, 3H)

Example 206

[4-(2,4-Difluoro-phenylamino)-2-nitro-phenyl]-[5-(4-methoxy-benzyloxy)-2-methyl-phenyl]-methanone (Compound 306)

2,4-Difluoro-phenylamine (26 µL, 0.25 mmol) was dissolved in dry 1,4-dioxane (3 mL) in a vial under an argon atmosphere. Compound 504 (114 mg, 0.25 mmol) was added and dissolved in the solvent. Rac-BINAP (7.0 mg, 0.012 mmol), $Pd_2(dba)_3$ (7.0 mg, 0.008 mmol) and $Cs_2CO_3$ (114 mg, 0.35 mmol) were added, and the reaction mixture was stirred under an argon atmosphere at 100° C. for 16 h. The reaction mixture was filtered through Celite and then purified by continuous gradient flash chromatography using EtOAc/petroleum ether (40-60) (v:v=1:9 to 1:3) as the eluent to afford the title compound as curry yellow solid. $^{13}C$ NMR ($CDCl_3$) δ 194.5, 159.6 (dd), 159.5, 156.1, 155.9 (dd), 149.6, 147.1, 137.2, 132.8, 131.8, 131.7, 129.2, 128.5, 126.8, 124.8 (dd), 123.8 (dd), 117.9, 117.1, 114.1, 111.8 (dd), 109.5, 105.2 (dd), 70.1, 55.3, 19.9

Preparation 107

[4-(2,4-Difluoro-phenylamino)-2-nitro-phenyl]-5-hydroxy-2-methyl-phenyl)-methanone (Compound 507)

Compound 306 (90 mg, 0.178 mmol) was dissolved in dry DCM (5 mL). TFA (5 mL) was added, and the reaction mixture was stirred at RT for 1 h and then concentrated in vacuo, affording the crude product as beige/off-white solid.

Example 207

[4-(2,4-Difluoro-phenylamino)-2-nitro-phenyl]-[5-(3-hydroxy-propoxy)-2-methyl-phenyl]-methanone (Compound 307)

Compound 507 (66 mg, 0.17 mmol) was dissolved in acetonitrile (3 mL) in a reaction vial. 3-chloro-propan-1-ol (22 µL, 0.26 mmol), $K_2CO_3$ (36 mg, 0.26 mmol) and NaI (cat. amount) were added. The reaction vial was flushed with argon, closed and then stirred at 170° C. for 15 min. In a microwave oven. The reaction mixture was allowed to cool to RT and then poured into a mixture of EtOAc/water. The layers were separated and the organic phase was dried ($MgSO_4$), filtered and concentrated in vacuo affording the crude product. Purified by continuously gradient flash chromatography using EtOAc/petroleum ether (40-60) (v:v=1:9 to 1:1) as the eluent, affording the title compound as a yellow oil. $^{13}C$ NMR ($CDCl_3$) δ 194.4, 159.7 (dd), 156.2, 155.9 (dd), 149.9, 147.4, 137.4, 132.8, 131.9, 131.6, 126.5, 125.0 (dd), 123.8 (dd), 117.8, 117.5, 116.4, 111.9 (dd), 109.4, 105.2 (dd), 65.8, 60.2, 31.9, 19.8

Example 208

[2-Amino-4-(2,4-difluoro-phenylamino)-phenyl]-[5-(3-hydroxy-propoxy)-2-methyl-phenyl]-methanone (Compound 308)

Compound 307 (46 mg, 0.1 mmol) was dissolved in EtOH (5 mL), flushed with argon and added Pd/C (cat. amount). The flask was purged with $H_2$ for 2 min. and stirred under an $H_2$-atmosphere at RT for 1 h. The reaction mixture was filtered through Celite and concentrated in vacuo. Purified by continuously gradient flash chromatography using DCM/MeOH (v:v=100:0 to 95:5) as the eluent, affording the title compound as a yellow oil. $^{13}C$ NMR (DMSO-$d_6$) δ 196.3, 158.9 (dd), 156.2, 155.6 (dd), 154.2, 150.8, 142.2, 135.6, 131.1, 127.0 (dd), 125.2, 124.8 (dd), 114.5, 112.2, 111.6 (dd), 109.7, 104.8 (dd), 104.0, 96.9, 64.6, 57.2, 32.1, 17.9

Example 209

[4-(2,4-Difluoro-phenylamino)-2-nitro-phenyl]-[2-methyl-5-(2-morpholin-4-yl-ethoxy)-phenyl]-methanone (Compound 309)

Compound 507 (50 mg, 0.13 mmol) was dissolved in acetonitrile (3 mL) in a reaction vial. 4-(2-Chloro-ethyl)-morpholine hydrochloride (48 mg, 0.26 mmol), $K_2CO_3$ (72 mg, 0.52 mmol) and NaI (cat. amount) were added. The reaction vial was flushed with argon, closed and then stirred at 170° C. for 10 min. in a microwave oven, followed by reflux in a oil bath for 40 h. The reaction mixture was added EtOAc (30 mL) and washed with $H_2O$ (2×20 mL), brine (2×20 mL). The organic phase was dried ($Na_2SO_4$), filtered, concentrated in vacuo and purified by continuously gradient flash chromatography using EtOAc/petroleum ether (40-60)(v:v=2:1 to 100:0) as the eluent, affording the title compound as a yellow oil. $^{13}C$ NMR ($CDCl_3$) δ 194.3, 159.7 (dd), 156.1, 155.9 (dd), 149.9, 147.3, 137.4, 132.8, 131.9, 131.8, 126.7, 124.9 (dd), 123.8 (dd), 117.9, 117.6, 116.6, 111.9 (dd), 109.4, 105.2 (dd), 66.8, 65.7, 57.5, 54.0, 19.8

Example 210

[2-Amino-(2,4-difluoro-phenylamino)-phenyl]-[2-methyl-5-(2-morpholin-4-yl-ethoxy)-phenyl]-methanone (Compound 310)

The reaction was carried out as described in the preparation of compound 308, using compound 309 (18 mg, 0.036 mmol) as the nitro-compound. Stirred under an $H_2$-atmosphere for 16 h. Purified by flash chromatography using EtOAc as the eluent, affording the title compound as oil. $^{13}$C NMR (CDCl$_3$) δ 198.4, 156.4, 153.5, 149.7, 141.9, 137.1, 131.4, 126.9, 124.8 (dd), 115.5, 112.8, 112.2, 111.3 (dd), 105.1, 104.8, 104.7 (dd), 98.9, 66.9, 66.1, 57.7, 54.1, 18.4

Example 211

[4-(2,4-Difluoro-phenylamino)-2-nitro-phenyl]-[5-(2,2-dimethyl-[1,3]dioxolan-4-ylmethoxy)-2-methyl-phenyl]-methanone (Compound 311)

Compound 507 (50 mg, 0.13 mmol) was dissolved in acetonitrile (3 mL) in a reaction vial. Compound 506 (75 mg, 0.26 mmol), $K_2CO_3$ (36 mg, 0.26 mmol) and NaI (cat. amount) was added. The reaction vial was flushed with argon, closed and then stirred at 170° C. for 10 min. in a microwave oven, followed by reflux in a oil bath for 40 h. The reaction mixture was added EtOAc (30 mL) and washed with $H_2O$ (2×20 mL), brine (2×20 mL). The organic phase was dried ($Na_2SO_4$), filtered, concentrated in vacuo and purified by continuously gradient flash chromatography using EtOAc/petroleum ether (40-60)(v:v=1:9 to 1:3) as the eluent, affording the title compound as a yellow oil. $^{13}$C NMR (CDCl$_3$) δ 194.3, 159.7 (dd), 156.0, 155.9 (dd), 149.9, 147.3, 137.5, 132.8, 132.0, 131.8, 126.6, 124.9 (dd), 123.8 (dd), 117.9, 117.3, 116.6, 111.9 (dd), 109.9, 109.5, 105.2 (dd), 73.9, 69.2, 66.7, 26.8, 25.3, 19.8

Example 212

[4-(2,4-Difluoro-phenylamino)-2-nitro-phenyl]-[5-(2,3-dihydroxy-propoxy)-2-methyl-phenyl]-methanone (Compound 312)

Compound 311 (48 mg, 0.01 mmol) was dissolved in TFA:$H_2O$ (3:1, 8 mL) and stirred at RT for 2 h. The reaction mixture was concentrated in vacuo and purified by flash chromatography using EtOAc/petroleum ether (40-60)(v:v=1:1) as the eluent, affording the title compound as a yellow oil. $^{13}$C NMR (DMSO-d$_6$) δ 193.5, 156.3, 150.1, 148.8, 137.5, 132.5, 132.3, 129.3, 126.6 (dd), 123.9 (dd), 122.9, 117.3, 116.1, 115.6, 112.1 (dd), 108.6, 105.1 (dd), 69.8, 62.5, 19.0

Example 213

[2-Amino-4-(2,4-difluoro-phenylamino)-phenyl]-[5-(2,3-dihydroxy-propoxy)-2-methyl-phenyl]-methanone (Compound 313)

The reaction was carried out as described in the preparation of compound 308, using compound 312 (48 mg, 0.096 mmol) as the nitro-compound. Stirred under an $H_2$-atmosphere for 16 h. Purified by flash chromatography using EtOAc/petroleum ether (40-60) (1:1) as the eluent, affording the title compound as colourless oil. $^1$H NMR (DMSO-d$_6$) δ 8.32 (s, 1H), 7.42-7.29 (m, 2H), 7.15 (d, 1H), 7.09 (m, 1H), 6.89 (dd, 1H), 6.82 (d, 1H), 6.66 (d, 1H), 6.02-5.92 (m, 2H), 3.97 (dd, 1H), 3.87-3.30 (m, 4H), 2.05 (s, 3H)

Preparation 108

2-Fluoro-5-hydroxy-benzaldehyde (Compound 508)

2-Fluoro-5-methoxy-benzaldehyde (4 g, 26 mmol) was dissolved in dry DCM (25 mL) under an argon atmosphere, cooled to 0° C. and slowly added boron tribromide (26 mL, 1.0 M in DCM, 26 mmol). On completion of the addition the reaction mixture was allowed to warm to RT and stirred for 16 h under an argon atmosphere. The reaction was carefully quenched with water (10 mL), added sat. NaHCO$_3$ (30 mL), then shaken and the layers were separated. The aqueous phase was extracted with two more portions of DCM. The organic phases were combined, extracted with 2N NaOH (2×100 mL). The combined NaOH-phases were acidified with HCl (konc.) and extracted with DCM (4×150 mL). The organic phases were combined, dried (MgSO$_4$), filtered, and concentrated in vacuo to afford the crude product. Purified by chromatography using EtOAc/petroleum ether (40-60)(v:v=1:5) as the eluent, affording the title compound as a white solid.

Preparation 109

5-(tert-Butyl-dimethyl-silanyloxy)-2-fluoro-benzaldehyde (Compound 509)

Compound 508 (1.5 g, 10.7 mmol) was dissolved in dry DMF (40 mL) under an argon atmosphere. tert-Butyl-chlorodimethyl-silane (2.43 g, 16.1 mmol) and imidazole (1.1 g, 16.1 mmol) was added. Stirred at RT for 2 h, added EtOAc (250 mL) and then washed with water (2×100 mL), 4% MgSO$_4$ (2×75 mL), dried (MgSO$_4$), filtered, and concentrated in vacuo to afford the crude product as yellow oil. Purified by chromatography using EtOAc/petroleum ether (40-60)(1:20) as the eluent, affording the title compound as an colourless, clear oil.

Preparation 110

(4-Bromo-2-chloro-phenyl)-[5-(tert-butyl-dimethyl-silanyloxy)-2-fluoro-phenyl]-methanol (Compound 510)

A dry flask was charged with 4-bromo-2-chloro-1-Iodo-benzene (10.9 g, 34.5 mmol) and the flask was evaporated and then filled with argon, this process repeated twice. Dry THF (100 mL) was added, and the solution cooled to −50° C.; then isopropylmagnesium chloride (17.3 mL, 2.0 M in diethyl ether, 34.5 mmol) was added slowly over 15 min. keeping the temperature below −40° C. On completion of the addition the reaction mixture was stirred at −40° C. for 45 min. The temperature was raised to −25° C. for 5 min. and then lowered to −40° C., followed by slowly addition of a solution of compound 509 in dry THF (15 mL). On completion of the addition the reaction mixture was stirred at −40° C. for 10 min. and was then allowed to warm to 5° C. over a period of 2.5 h. The reaction mixture was slowly poured into ice-cold 2N H$_2$SO$_4$ (200 mL) and extracted with EtOAc. The aqueous phase was extracted with four more portions of EtOAc. The organic phases were combined, dried (MgSO$_4$), filtered, and concentrated in vacuo to afford the crude product as brown oil. Used without further purification.

Preparation 111

(4-Bromo-2-chloro-phenyl)-(2-fluoro-5-hydroxy-phenyl)-methanone (Compound 511)

Compound 510 (15.9 g, 35.6 mmol) was dissolved in dry DCM (80 mL) and dry acetonitrile (10 mL) under an argon atmosphere. The mixture was cooled to 0° C. and added 4-methyl-morpholine 4-oxide (6.27 g, 53.5 mmol), grinded molecular sieve (4 Å, 17.8 g). Tetra-N-propylammonium perruthenate (VII) (250 mg, 0.71 mmol) was added in 5 portions (5×50 mg) and the reaction mixture was stirred for 10 min. at 0° C., evaporated to ⅓ volume and filtered through silica. The silica was washed with EtOAc (300 mL). The organic phase was concentrated in vacuo affording the crude product. Purified by continuously gradient flash chromatography using EtOAc/petroleum ether (40-60)(v:v=1:80 to 1:10) as the eluent, affording the title compound as a yellow solid.

Preparation 112

[2-Chloro-4-(2,4-difluoro-phenylamino)-phenyl]-(2-fluoro-5-hydroxy-phenyl)-methanone (Compound 512)

Compound 511 (200 mg, 0.6 mmol) was dissolved in dry 1,4-dioxane (5 mL) in a reaction vial under an argon atmosphere. 2,4-Difluoro-phenylamine (78 mg, 62 µL, 0.6 mmol) was added and dissolved in the solvent. Rac-BINAP (17 mg, 0.028 mmol), $Pd_2(dba)_3$ (17 mg, 0.018 mmol) and $Cs_2CO_3$ (277 mg, 0.85 mmol) were added. The reaction vial was flushed with argon, closed and then stirred at 130° C. for 40 min. In a microwave oven. The reaction mixture was allowed to cool to RT, filtered through Celite and then purified by continuous gradient flash chromatography using EtOAc/petroleum ether (40-60)(v:v=1:7 to 1:3) as the eluent to afford the title compound as a yellow solid.

Example 214

[2-Chloro-4-(2,4-difluoro-phenylamino)-phenyl]-[2-fluoro-5-(3-hydroxy-propoxy)-phenyl]-methanone (Compound 314)

Compound 512 (38 mg, 0.1 mmol) was dissolved in acetonitrile (2 mL) in a reaction vial. 3-Chloro-propan-1-ol (11 µL, 0.12 mmol), $K_2CO_3$ (17 mg, 0.12 mmol) and NaI (cat. amount) were added. The reaction vial was flushed with argon, closed and then stirred at 130° C. for 20 min. in a microwave oven. The reaction mixture was allowed to cool to RT and then poured into a mixture of EtOAc/water. The aqueous phase was acidified with HCl (4N) and the layers were separated. The aqueous phase was extracted with more EtOAc. The organic phases were combined, dried ($MgSO_4$), filtered and concentrated in vacuo affording the crude product. Purified by continuously gradient flash chromatography using EtOAc/petroleum ether (40-60)(v:v=1:3 to 1:1) as the eluent, affording the title compound as a yellow solid. $^{13}C$ NMR ($CDCl_3$) δ 190.8, 159.1 (dd), 155.6 (dd), 155.3 (d), 155.0 (d), 148.0, 134.7, 133.0, 129.4, 127.9 (d), 124.4 (m), 120.4 (d), 117.1 (d), 116.0, 115.1 (d), 112.8, 111.6 (dd), 104.9 (dd), 66.3, 60.0, 32.0

Example 215

[2-Chloro-4-(2,4-difluoro-phenylamino)-phenyl]-[5-(2,2-dimethyl-[1,3]-dioxolan-4-ylmethoxy)-2-fluoro-phenyl]-methanone (Compound 315)

Compound 512 (54 mg, 0.14 mmol) was dissolved in acetonitrile (4 mL) in a reaction vial. Compound 506 (61 mg, 0.21 mmol) and $K_2CO_3$ (30 mg, 0.21 mmol) were added. The reaction vial was flushed with argon, closed and then stirred at 110° C. for 50 min. in a microwave oven, followed by reflux in a oil bath for 24 h. The reaction mixture was concentrated in vacuo and purified by continuously gradient flash chromatography using EtOAc/petroleum ether (40-60)(v:v=1:7 to 1:3) as the eluent, affording the title compound as a yellow oil. $^{13}C$ NMR ($CDCl_3$) δ 190.6, 159.1 (dd), 154.7, 154.5 (d), 154.4 (dd), 147.8, 134.7, 132.9, 129.6, 127.9 (d), 124.4 (dd), 124.2 (dd), 120.6 (d), 117.1 (d), 116.0, 115.1 (d), 112.9, 111.6 (dd), 109.9, 104.9 (dd), 73.9, 69.6, 66.6, 26.8, 25.4

Example 216

[2-Chloro-4-(2,4-difluoro-phenylamino)-phenyl]-[5-(2,3-dihydroxy-propoxy)-2-fluoro-phenyl]-methanone (Compound 316)

Compound 315 was dissolved in TFA:water (3:1, 8 mL) and stirred at RT for 1 h. The reaction mixture was concentrated in vacuo and purified by continuously gradient flash chromatography using EtOAc/petroleum ether (40-60)(v:v=1:2 to 100:0) as the eluent, affording the title compound as a yellow foam. $^{13}C$ NMR (DMSO-$d_6$) δ 189.3, 158.8 (dd), 155.7 (dd), 154.9 (d), 153.8 (d), 149.5, 133.5, 133.4, 127.8 (d), 126.5 (dd), 126.3, 124.1 (dd), 119.7 (d), 117.1 (d), 114.9 (d), 114.7, 112.0 (dd), 111.7, 105.0 (dd), 70.4, 69.8, 62.5

Preparation 113

[2-Chloro-4-(4-chloro-2-methyl-phenylamino)-phenyl]-(2-fluoro-5-hydroxy-phenyl)-methanone (Compound 513)

4-Chloro-2-methyl-phenylamine (73 µL, 0.60 mmol) was dissolved in 5 mL dry 1,4-dioxane in a reaction vial under an argon atmosphere. Compound 511 (200 mg, 0.60 mmol) was added and dissolved in the solvent. Rac-BINAP (18 mg, 0.028 mmol), $Pd_2(dba)_3$ (17 mg, 0.018 mmol) and $Cs_2CO_3$ (277 mg, 0.84 mmol) were added. The reaction vial was flushed with argon, closed and then stirred at 130° C. for 10 min. in a microwave oven. The reaction mixture was filtered through Celite and then purified by continuous gradient flash chromatography using EtOAc/petroleum ether (40-60) (v:v=1:9 to 1:4) as the eluent to afford the title compound as yellow solid. $^{13}C$ NMR ($CDCl_3$)

Example 217

2-{3-[2-Chloro-4-(4-chloro-2-methyl-phenylamino)-benzoyl]-4-fluoro-phenoxy}-N-methyl-acetamide (Compound 317)

Compound 513 (36 mg, 0.09 mmol) was dissolved in acetonitrile (2 mL) in a reaction vial. 2-Chloro-N-methyl-acetamide (30 mg, 0.28 mmol), $K_2CO_3$ (38 mg, 0.28 mmol) were added. The reaction vial was flushed with argon, closed and then stirred at 130° C. for 45 min. in a microwave oven. The reaction mixture was poured into a mixture of EtOAc:$H_2O$ (1:1, 10 mL). The layers were separated and the aqueous phase was extracted with EtOAc (3×5 mL). The combined organic layers were dried ($MgSO_4$), filtered, concentrated in vacuo and purified by continuously gradient flash chromatography using EtOAc/petroleum ether (40-60)(v:v=1:3 to 100:0) as the eluent, affording the title compound as a yellow oil. $^{13}C$ NMR ($CDCl_3$) δ 190.1, 168.2, 155.7 (d), 153.2 (d), 149.2, 136.6, 135.0, 134.5, 133.4, 131.2, 130.5, 128.7 (d), 128.1, 127.1, 125.3, 119.6 (d), 117.4 (d), 116.1 (d), 115.6, 112.4, 68.0, 25.8, 17.9

Example 218

[2-Chloro-4-(4-chloro-2-methyl-phenylamino)-phenyl]-[2-fluoro-5-(3-hydroxy-propoxy)-phenyl]-methanone (Compound 318)

The reaction was carried out as described in the preparation of compound 317, using compound 513 (31 mg, 0.079 mmol) as the phenol and 3-chloro-propan-1-ol (20 μL, 0.24 mmol) as the alkyl-chloride. Stirred at 130° C. for 15 min. in a microwave oven. Purified by continuous gradient flash chromatography using EtOAc/petroleum ether (40-60) (v:v=15:85 to 60:40) as the eluent, affording the title compound as yellow oil. $^{13}$C NMR (CDCl$_3$) δ 190.7, 155.2 (d), 154.9 (d), 148.8, 136.7, 134.9, 134.3, 133.2, 131.1, 130.4, 128.7, 128.1 (d), 127.1, 125.1, 120.2 (d), 117.0 (d), 115.7, 115.0 (d), 112.5, 66.3, 60.2, 32.0, 17.9

Example 219

2-{3-[2-Chloro-4-(4-chloro-2-methyl-phenylamino)-benzoyl]-4-fluoro-phenoxy}-N,N-dimethyl-acetamide (Compound 319)

The reaction was carried out as described in the preparation of compound 317, using compound 513 (36 mg, 0.092 mmol) as the phenol and 2-chloro-N,N-dimethyl-acetamide as the alkyl-chloride (29 μL, 0.28 mmol). Stirred at 130° C. for 15 min in a microwave oven. Purified by continuous gradient flash chromatography using EtOAc/petroleum ether (40-60) (v:v=1:1 to 100:0) as the eluent, affording the title compound as oil. $^{13}$C NMR (CDCl$_3$) δ 190.3, 167.2, 155.6 (d), 154.2 (d), 148.9, 136.7, 134.9, 134.3, 133.3, 131.1, 130.4, 128.4, 128.1 (d), 127.1, 125.1, 120.4 (d), 117.2 (d), 115.7, 112.4, 67.7, 36.5, 35.7, 17.9

Example 220

[2-Chloro-4-(4-chloro-2-methyl-phenylamino)-phenyl]-[5-(2,2-dimethyl-[1,3]dioxolan-4-ylmethoxy)-2-fluoro-phenyl]-methanone (Compound 320)

The reaction was carried out as described in the preparation of compound 311, using compound 513 (34 mg, 0.087 mmol) as the phenol. Stirred at 130° C. for 45 min. In a microwave oven. Purified by continuous gradient flash chromatography using EtOAc/petroleum ether (40-60) (v:v=1:9 to 1:1) as the eluent, affording the title compound as yellow oil. $^{13}$C NMR (CDCl$_3$) δ 190.5, 155.4 (d), 154.7 (d), 148.8, 136.7, 134.9, 134.3, 133.2, 131.2, 130.4, 128.6, 128.1 (d), 127.1, 125.1, 120.4 (d), 117.1 (d), 115.7, 115.1 (d), 112.5, 109.9, 73.9, 69.6, 66.6, 26.8, 25.3, 17.9

Example 221

[2-Chloro-4-(4-chloro-2-methyl-phenylamino)-phenyl]-[5-(2,3-dihydroxy-propoxy)-2-fluoro-phenyl]-methanone (Compound 321)

Compound 320 (31 mg, 0.07 mmol) was dissolved in TFA:H$_2$O (3:1, 10 mL) and stirred at RT for 1 h. The reaction mixture was concentrated in vacuo and purified by flash chromatography using DCM/MeOH (v:v=99.5:0.5 to 98.5:1.5) as the eluent, affording the title compound as oil. $^{13}$C NMR (CDCl$_3$) δ 190.5, 155.4 (d), 154.6 (d), 148.9, 136.7, 134.9, 134.3, 133.3, 131.2, 130.4, 128.5, 128.2 (d), 127.1, 125.1, 120.2 (d), 117.1 (d), 115.7, 115.2 (d), 112.5, 70.3, 69.9, 63.5, 17.9

Preparation 114

[2-Chloro-4-(4-fluoro-2-methyl-phenylamino)-phenyl]-(2-fluoro-5-hydroxy-phenyl)-methanone (Compound 514)

The reaction was carried out as described in the preparation of compound 513 using compound 511 (49 mg, 0.15 mmol) as the bromo compound and 4-fluoro-2-methyl-phenylamine (17 μL, 0.15 mmol) as the amine. Stirred at 110° C. for 40 min. in a microwave oven. Purified by continuous gradient flash chromatography using EtOAc/petroleum ether (40-60) (v:v=1:5 to 1:2) as the eluent, affording the title compound as yellow solid.

Example 222

[2-Chloro-4-(4-fluoro-2-methyl-phenylamino)-phenyl]-[2-fluoro-5-(3-hydroxy-propoxy)-phenyl]-methanone (Compound 322)

The reaction was carried out as described in the preparation of compound 317, using compound 514 (31 mg, 0.083 mmol) as the phenol and 3-chloro-propan-1-ol (21 μL, 0.25 mmol) as the alkyl chloride. Stirred at 130° C. for 75 min. in a microwave oven. Purified by continuous gradient flash chromatography using EtOAc/petroleum ether (40-60) (v:v=1:4 to 4:1) as the eluent, affording the title compound. $^{13}$C NMR (CDCl$_3$) δ 190.6, 160.6 (d), 155.1 (d), 154.9 (d), 149.9, 136.4 (d), 135.1, 133.8 (d), 133.4, 128.2 (d), 127.9, 127.2 (d), 120.1 (d), 117.8 (d), 117.0 (d), 115.1 (d), 114.9, 113.8 (d), 111.7, 66.3, 60.2, 32.0, 18.1

Preparation 115

[2-Chloro-4-(4-fluoro-phenylamino)-phenyl]-(2-fluoro-5-hydroxy-phenyl)-methanone (Compound 515)

The reaction was carried out as described in the preparation of compound 513, using compound 511 (99 mg, 0.3 mmol) as the bromo compound and 4-fluoro-phenylamine (29 μL, 0.3 mmol) as the amine. Stirred at 130° C. for 30 min. in a microwave oven. Purified by continuous gradient flash chromatography using EtOAc/petroleum ether (40-60) (v:v=1:5 to 1:2) as the eluent, affording the title compound as yellow solid.

Example 223

[2-Chloro-4-(4-fluoro-phenylamino)-phenyl]-[2-fluoro-5-(3-hydroxy-propoxy)-phenyl]-methanone (Compound 323)

The reaction was carried out as described in the preparation of compound 317 using compound 515 as the phenol and 3-chloro-propan-1-ol (24 μL, 0.29 mmol) as the alkyl-chloride. Stirred at 130° C. for 60 min. in a microwave oven. Purified by continuous gradient flash chromatography using EtOAc/petroleum ether (40-60) (v:v=1:4 to 4:1) as the eluent, affording the title compound. $^{13}$C NMR (CDCl$_3$) δ 190.7, 159.6 (d), 155.2 (d), 155.0 (d), 148.9, 136.0 (d), 134.9, 133.3, 128.5, 128.1 (d), 124.1 (d), 120.2 (d), 117.0 (d), 116.4 (d), 115.5, 115.1 (d), 112.3, 66.3, 60.0, 32.0

Example 224

[2-Chloro-4-(4-fluoro-phenylamino)-phenyl]-[5-(2,2-dimethyl-[1,3]-dioxolan-4-ylmethoxy)-2-fluoro-phenyl]-methanone (Compound 324)

The reaction was carried out as described in the preparation of compound 311, using compound 515 (35 mg, 0.097 mmol) as the phenol. Stirred at 130° C. for 75 min. in a microwave oven. Purified by continuous gradient flash chromatography using EtOAc/petroleum ether (40-60) (v:v=1:9 to 2:3) as the eluent, affording the title compound. $^{13}$C NMR (CDCl$_3$) δ 190.5, 159.7 (d), 155.4 (d), 154.7 (d), 148.8, 135.9 (d), 134.9, 133.2, 128.8, 128.1 (d), 124.2 (d), 120.4 (d), 117.1 (d), 116.5 (d), 115.5, 115.1 (d), 112.4, 109.9, 74.0, 69.6, 66.7, 26.8, 25.4

Preparation 116

[2-Chloro-4-(2-chloro-4-fluoro-phenylamino)-phenyl]-(2-fluoro-5-hydroxy-phenyl)-methanone (Compound 516)

The reaction was carried out as described in the preparation of compound 513, using compound 511 (95 mg, 0.29 mmol) as the bromo compound and 2-chloro-4-fluoro-phenylamine (35 μL, 0.29 mmol) as the amine. Stirred at 130° C. for 10 min. in a microwave oven. Purified by continuous gradient flash chromatography using EtOAc/petroleum ether (40-60) (v:v=1:5 to 1:2) as the eluent, affording the title compound as yellow solid.

Example 225

[2-Chloro-4-(2-chloro-4-fluoro-phenylamino)-phenyl]-[2-fluoro-5-(3-hydroxy-propoxy)-phenyl]-methanone (Compound 3251

The reaction was carried out as described in the preparation of compound 317 using compound 516 (27 mg, 0.068 mmol) as the phenol and 3-chloro-propan-1-ol (17 μL, 0.2 mmol) as the alkyl-chloride. Stirred at 130° C. for 60 min. In a microwave oven. Purified by continuous gradient flash chromatography using EtOAc/petroleum ether (40-60) (v:v=1:4 to 4:1) as the eluent, affording the title compound as yellow oil. $^{13}$C NMR (CDCl$_3$) δ 190.7, 158.5 (d), 155.2 (d), 155.0 (d), 147.1, 134.6, 133.7 (d), 132.8, 130.3, 127.7 (d), 126.7 (d), 122.5 (d), 120.6 (d), 117.5 (d), 117.1 (d), 116.9, 115.0, 114.9 (d), 113.7, 66.4, 60.2, 32.0

Preparation 117

[2-Chloro-4-(2-nitro-phenylamino)-phenyl]-(2-fluoro-5-hydroxy-phenyl)-methanone (Compound 517)

The reaction was carried out as described in the preparation of compound 513, using compound 511 (200 mg, 0.6 mmol) as the bromo compound and 2-nitro-phenylamine (84 mg, 0.6 mmol) as the amine. Stirred at 130° C. for 10 min. in a microwave oven. Purified by continuous gradient flash chromatography using EtOAc/petroleum ether (40-60) (v:v=1:9 to 1:4) as the eluent, affording the title compound as orange solid.

Preparation 118/Example 290

[2-Chloro-4-(2-nitro-phenylamino)-phenyl]-[2-fluoro-5-(2-morpholin-4-yl-ethoxy)-phenyl]-methanone (Compound 518)

Compound 517 (30 mg, 0.08 mmol) was dissolved in acetonitrile (2 mL) in a reaction vial. 4-(2-Chloro-ethyl)-morpholine hydrochloride (44 mg, 0.24 mmol) and K$_2$CO$_3$ (33 mg, 0.24 mmol) were added. The reaction vial was flushed with argon, closed and then stirred at 130° C. for a total of 105 min. in a microwave oven. The reaction mixture was poured into a mixture of EtOAc:H$_2$O (1:1, 10 mL). The layers were separated and the aqueous phase was extracted with EtOAc (2×10 mL). The combined organic layers were dried (MgSO$_4$), filtered, concentrated in vacuo and purified by continuously gradient flash chromatography using EtOAc/ petroleum ether (40-60)(v:v=1:9 to 3:2) as the eluent, affording the title compound as a light yellow oil.

Preparation 119/Example 291

[2-Chloro-4-(2-nitro-phenylamino)-phenyl]-[5-(2,2-dimethyl-[1,3]dioxolan-4-ylmethoxy)-2-fluoro-phenyl]-methanone (Compound 519)

The reaction was carried out as described in the preparation of compound 311, using compound 517 (36 mg, 0.093 mmol) as the phenol. Stirred at 130° C. for 15 min. In a microwave oven. Purified by continuous gradient flash chromatography using EtOAc/petroleum ether (40-60) (v:v=1:9 to 2:3) as the eluent, affording the title compound as light yellow oil.

Preparation 120/Example 292

[2-Chloro-4-(2-nitro-phenylamino)-phenyl]-[5-(2,3-dihydroxy-propoxy)-2-fluoro-phenyl]-methanone (Compound 520)

Compound 519 (46 mg, 0.092 mmol) was dissolved in TFA:H$_2$O (3:1, 10 mL) and stirred at RT for 1 h. The reaction mixture was concentrated in vacuo and purified by flash chromatography using DCM/MeOH (v:v=4:1 to 1:4) as the eluent, affording the title compound.

Example 226

[4-(2-Amino-phenylamino)-2-chloro-phenyl]-[5-(2,3-dihydroxy-propoxy)-2-fluoro-phenyl]-methanone (Compound 326)

Compound 520 (37 mg, 0.08 mmol) was dissolved in MeOH (2 mL), NH$_4$Cl (29 mg, 0.55 mmol) and Zn-dust (72 mg, 1.10 mmol) were added. Reflux for 0.5 h, allowed to cool to RT and filtered. Purified by flash chromatography using DCM:MeOH (v:v=95:5) as the eluent, affording the title compound. $^{13}$C NMR (CD$_3$OD) δ 192.4, 156.5 (d), 156.2 (d), 153.1, 144.8, 136.3, 135.1, 129.9 (d), 128.4, 128.1, 127.1, 126.8, 120.8 (d), 119.6, 118.0 (d), 117.7, 116.5 (d), 115.8, 112.5, 71.7, 71.2, 64.0

Example 227

[4-(2-Amino-phenylamino)-2-chloro-phenyl]-[2-fluoro-5-(2-morpholin-4-yl-ethoxy)-phenyl]-methanone (Compound 327)

The reaction was carried out as described in the preparation of compound 326, using compound 518 (37 mg, 0.074 mmol)

as the nitro compound. Purified by flash chromatography using DCM:MeOH (v:v=95:5) as the eluent, affording the title compound. $^{13}$C NMR (CDCl$_3$) δ 190.6, 155.2 (d), 154.6, 149.8, 142.9, 135.0, 133.4, 128.3 (d), 128.0, 127.7, 127.0, 125.2, 120.2 (d), 119.2, 117.0 (d), 116.4, 115.2 (d), 115.1, 111.9, 66.5, 66.1, 57.4, 53.9

Preparation 121

(4-Bromo-2-chloro-phenyl)-(2-chloro-5-methoxy-phenyl)-methanol (Compound 521)

To a solution of 4-bromo-2-chloro-1-iodo-benzene (10.0 g, 31.5 mmol) in THF (120 ml) was added 2 M solution of isopropylmagnesium chloride in THF (17.3 ml, 34.60 mmol) at −65° C. The reaction mixture was stirred at −40° C. for 20 min. After 2-chloro-5-methoxy-benzaldehyde (5.5 g, 32.20 mmol) was added, the reaction mixture was warmed to room temperature and stirred overnight. Then the solution was quenched with saturated aqueous solution of NH$_4$Cl. The aqueous phase was extracted twice with diethyl ether. The combined organic phases were dried over MgSO$_4$ and concentrated in vacuo. The crude material was purified by chromatography (petroleum ether/CH$_2$Cl$_2$ 1:1) to provide title compound as a yellowish oil.

Preparation 122

(4-Bromo-2-chloro-phenyl)-(2-chloro-5-methoxy-phenyl)-methanone (Compound 522)

To a solution of compound 521 (5.18 g, 14.3 mmol) in CH$_2$Cl$_2$ (100 ml) was portionwise added Dess-Martin periodinane (6.11 g, 14.40 mmol) at room temperature. After being stirred at room temperature for 1 h, the reaction mixture was concentrated together with silica gel in vacuo. The residue was purified by chromatography (petroleum ether/CH$_2$Cl$_2$ 1:1) to give the title compound as colourless oil.

Preparation 123

(4-Bromo-2-chloro-phenyl)-(2-chloro-5-hydroxy-phenyl)-methanone (Compound 523)

To a solution of compound 522 (4.63 g, 12.86 mmol) in CH$_2$Cl$_2$ (50 ml) was dropwise added a 1 M solution of BBr$_3$ in CH$_2$Cl$_2$ at −40° C. The reaction solution was warmed to room temperature and stirred overnight. After reaction, the solution was poured into brine. The aqueous phase was extracted twice with CH$_2$Cl$_2$. The combined organic phases were dried over MgSO$_4$ and concentrated in vacuo to give a solid, which was washed with petroleum ether/CH$_2$Cl$_2$ 1:1, giving the title compound as a greyish solid.

Preparation 124

[2-Chloro-4-(2,6-difluoro-phenylamino)-phenyl]-(2-chloro-5-hydroxy-phenyl)-methanone (Compound 524)

A mixture of compound 523 (1.00 g, 3.00 mmol), 2,6-difluoroaniline (0.47 g, 3.60 mmol), rac-BINAP (74 mg, 0.12 mmol), Pd$_2$(dba)$_3$ and Cs$_2$CO$_3$ (1.95 g, 6.00 mmol) in 1,4-dioxane (30 ml) was stirred at 120° C. for 2 days. The mixture was filtered and washed with 1,4-dioxane. The filtrate was concentrated together with silica gel in vacuo and purified by chromatography (petroleum ether/ethyl acetate 3:1) to provide the title compound as a solid.

Example 228

[2-Chloro-4-(2,6-difluoro-phenylamino)-phenyl]-[2-chloro-5-(2-morpholin-4-yl-ethoxy)-phenyl]-methanone (Compound 328)

A mixture of compound 524 (42 mg, 0.11 mmol), 4-(2-chloro-ethyl)-morpholine (50 mg, 0.27 mmol) and K$_2$CO$_3$ (100 mg, 0.72 mmol) in CH$_3$CN (2 ml) in a sealed glass was stirred at 90° C. for 18 h. The mixture was then filtered. The filtrate was concentrated in vacuo. The residue was purified by chromatography (ethyl acetate), furnishing the title compound as a brownish oil. $^{13}$C NMR (CDCl$_3$) δ 192.5, 157.5 (dd), 157.2, 148.2, 140.2, 135.6, 134.0, 131.0, 127.8, 126.1 (t), 123.5, 118.2, 116.7 (t), 116.4, 115.4, 112.7, 112.2 (m), 66.6, 66.1, 57.4, 54.0

Example 229

(±)-[2-Chloro-4-(2,6-difluoro-phenylamino)-phenyl]-[2-chloro-5-(2,3-dihydroxy-propoxy)-phenyl]-methanone (Compound 329)

A mixture of compound 524 (42 mg, 0.11 mmol), (±)-toluene-4-sulfonic acid 2,2-dimethyl-[1,3]dioxolan-4-ylmethyl ester (50 mg, 0.17 mmol) and K$_2$CO$_3$ (100 mg, 0.72 mmol) was treated as described for compound 328. Chromatography (petroleum ether/ethyl acetate 3:1) furnished an acetonide.

The acetonide was taken up in TFA/H$_2$O 3:1 (1 ml) at room temperature and the obtained solution was stirred at the same temperature for 0.5 h. The mixture was then concentrated in vacuo. The residue was purified by chromatography (ethyl acetate), giving the title compound as colourless foam. $^{13}$C NMR (CDCl$_3$) δ 192.6, 157.5 (dd), 157.1, 148.4, 140.3, 135.6, 134.1, 131.1, 127.5, 126.1 (t), 123.7, 118.0, 116.7 (t), 116.4, 115.4, 112.7, 112.2 (m), 70.2, 69.6, 63.4

Example 230

[5-(3-Bromo-propoxy)-2-chloro-phenyl]-[2-chloro-4-(2,5-difluoro-phenylamino)-phenyl]-methanone (Compound 330)

A mixture of compound 524 (0.20 g, 0.51 mmol), 1,3-dibromopropane (0.62 g, 3.06 mmol) and K$_2$CO$_3$ (0.21 g, 1.53 mmol) was treated as described for compound 328. Chromatography (petroleum ether/ethyl acetate 4:1) furnished the title compound. $^{13}$C NMR (CDCl$_3$) δ 192.6, 157.5 (dd), 157.3, 148.2, 140.2, 135.6, 134.1, 131.0, 127.8, 126.0 (t), 123.4, 118.0, 116.7 (t), 116.4, 115.3, 112.7, 112.2 (m), 65.8, 32.2, 29.7

Preparation 125

3-(4-Bromo-2-chloro-benzoyl)-4-methyl-benzoic acid methyl ester (Compound 525)

To a solution of 3-iodo-4-methyl-benzoic acid methyl ester (13.50 g, 48.92 mmol) in THF (260 mL) was added 2 M solution of isopropylmagnesium chloride in THF (24.5 mL, 49.00 mmol) at −50° C. After the reaction mixture was stirred at the same temperature for 30 min, compound 440 (13.39 g, 40.70 mmol) was added. The solution was warmed up to room temperature and stirred at the same temperature for 2 h. The reaction was then quenched with saturated aqueous solution of NH$_4$Cl. The aqueous phase was extracted twice with diethyl ether. The combined organic phases were dried over MgSO$_4$ and concentrated in vacuo. The crude material was taken up in ethanol and heated for reflux. The obtained solution was cooled down to room temperature. The crystals were filtered off and dried.

Preparation 126

(4-Bromo-2-chloro-phenyl)-(5-hydroxymethyl-2-methyl-phenyl)-methanol (Compound 526)

A mixture of compound 525 (4.01 g, 10.90 mmol) and LiAlH$_4$ (0.83 g, 21.82 mmol) in THF (100 mL) was heated for reflux for 1.5 h. After being cooled down to room temperature, the reaction mixture was poured into H$_2$O and aqueous solution of H$_2$SO$_4$ (2M, 50 mL) was added. This mixture was then extracted twice with diethyl ether. The combined organic phases were dried over Na$_2$SO$_4$ and concentrated in vacuo, giving the title compound.

Preparation 127

(4-Bromo-2-chloro-phenyl)-(2-methyl-5-triisopropylsilanyloxymethyl-phenyl)-methanol (Compound 527)

To a solution of compound 526 (3.68 g, 10.80 mmol) and imidazol (1.47 g, 21.60 mmol) in DMF (40 mL) was added TIPSCI (2.30 mL, 10.80 mmol) at room temperature. The reaction solution was stirred at the same temperature for 3 h and then poured into H$_2$O. The aqueous mixture was extracted three times with diethyl ether. The combined organic phases were washed with brine, dried over Na$_2$SO$_4$, and concentrated in vacuo. The residue was purified by chromatography (ethyl acetate/petroleum ether 1:10), furnishing the title compound.

Preparation 128

(4-Bromo-2-chloro-phenyl)-(2-methyl-5-triisopropylsilanyloxymethyl-phenyl)-methanone (Compound 528)

Compound 527 (4.12 g, 8.27 mmol) was treated as described for compound 522. Flash chromatography (petroleum ether/ethyl acetate 3:97) to provide the title compound.

Preparation 129

[2-Chloro-4-(2,4-difluoro-phenylamino)-phenyl]-(2-methyl-5-triisopropylsilanyloxymethyl-phenyl)-methanone (Compound 529)

A mixture of compound 528 (505 mg, 1.02 mmol), 2,4-difluoroaniline (0.14 mL, 1.32 mmol), Cs$_2$CO$_3$ (995 mg, 3.65 mmol), BINAP (26 mg, 0.041 mg), and Pd(OAc)$_2$ (9 mg, 0.041 mmol) in 1,4-dioxane (15 mL) was stirred in a sealed bottle at 100° C. for 18 h. The mixture was filtered. The filtrate was concentrated in vacuo together with silica gel. The residue was purified by flash chromatography (ethyl acetate/petroleum ether: graduated from 0/100 to 40/60), furnishing the title compound.

Example 231

[2-Chloro-4-(2,4-difluoro-phenylamino)-phenyl]-(5-hydroxymethyl-2-methyl-phenyl)-methanone (Compound 331)

To a solution of compound 529 (1.85 g, 3.40 mmol) in THF (40 mL) was added 1 M solution of TBAF in THF (4.1 mL, 4.10 mmol) at room temperature. The reaction solution was stirred at room temperature for 30 min and then poured into H$_2$O and extracted with diethyl ether. The combined organic phases were dried over Na$_2$SO$_4$ and concentrated in vacuo. The residue was purified by flash chromatography (ethyl acetate/petroleum ether: graduated from 20/80 to 50/50), giving the title compound. $^{13}$C NMR (DMSO-d$_6$) δ 195.4, 158.7 (dd), 155.7 (dd), 149.0, 139.9, 138.8, 134.8, 133.3, 130.8, 128.7, 127.1, 126.7, 126.3 (dd), 124.3 (dd), 114.8, 111.9 (dd), 111.7, 105.0 (dd), 62.1, 19.4

Example 232

[2-Chloro-4-(2,4-difluoro-phenylamino)-phenyl](5-chloromethyl-2-methyl-phenyl)-methanone (Compound 332)

To a solution of compound 331 (0.79 g, 2.09 mmol), Et$_3$N (0.58 mL, 4.18 mmol), and DMAP (10 mg) in CH$_2$Cl$_2$ (50 mL) was added p-toluenesulfonyl chloride (0.60 g, 3.14 mmol) at room temperature. The reaction mixture was stirred at the same temperature for 18 h and then poured into H$_2$O. The aqueous phase was extracted three times with CH$_2$Cl$_2$. The combined organic phases were dried over Na$_2$SO$_4$ and concentrated in vacuo. The residue was purified by chromatography (petroleum ether/ethyl acetate: graduated from 90/10 to 75/25), giving the title compound. $^{13}$C NMR (CDCl$_3$) δ 195.7, 159.2 (dd), 155.5 (dd), 147.8, 139.4, 138.3, 135.2, 134.8, 133.5, 131.8, 131.0, 129.6, 129.4, 124.4 (dd), 124.3 (dd), 116.2, 112.8, 111.6 (dd), 105.0 (dd), 45.6, 20.2

Example 233

(5-Azidomethyl-2-methyl-phenyl)-[2-chloro-4-(2,4-difluoro-phenylamino)-phenyl]-methanone (Compound 333)

A mixture of compound 332 (56 mg, 0.14 mmol) and NaN$_3$ (18 mg, 0.28 mmol) in DMF (4 mL) was stirred at 80° C. for 3 h. The reaction mixture was poured into H$_2$O and extracted three times with CH$_2$Cl$_2$. The combined organic phases were washed with brine, dried over Na$_2$SO$_4$, and concentrated in vacuo, furnishing the title compound. $^{13}$C NMR (CDCl$_3$) δ 195.9, 159.2 (dd), 155.6 (dd), 147.9, 139.6, 138.1, 135.2, 133.6, 132.6, 131.9, 130.6, 129.3, 124.4 (dd), 116.2, 112.8, 111.6 (dd), 105.0 (dd), 54.1, 20.2

Example 234

(5-Aminomethyl-2-methyl-phenyl)-[2-chloro-4-(2,4-difluoro-phenylamino)-phenyl]-methanone (Compound 334)

To a solution of compound 333 (46 mg, 0.11 mmol) was added triphenylphosphine (67 mg, 0.26 mmol) at room temperature. The solution was stirred at the same temperature for 18 h. H$_2$O (0.5 mL) was added. The mixture was then heated for reflux for 4 h and concentrated together with silica gel in vacuo. The residue was purified by chromatography (MeOH/ ethyl acetate: graduated from 13/87 to 30/70), providing the title compound. $^{13}$C NMR (CDCl$_3$) δ 196.4, 159.1 (dd), 155.5 (dd), 147.8, 139.6, 139.3, 136.5, 135.1, 133.5, 131.6, 129.8, 129.5, 128.3, 124.5 (dd), 124.3 (dd), 116.2, 112.8, 111.6 (dd), 104.9 (dd), 45.6, 20.1

Preparation 130

(4-Bromo-2-chloro-phenyl)-(5-hydroxymethyl-2-methoxy-phenyl)-methanol (Compound 530)

Compound 441 (1.05 g, 2.70 mmol) was treated as described for compound 526. Flash chromatography (ethyl acetate/petroleum ether: graduated from 25/75 to 45/55) provided the title compound.

Preparation 131

(4-Bromo-2-chloro-phenyl)-(2-methoxy-5-triisopropylsilanyloxymethyl-phenyl)-methanol (Compound 531)

Compound 530 (766 mg, 2.14 mmol) was treated as described for compound 527. Flash chromatography (ethyl acetate/petroleum ether: graduated from 4/96 to 30/70) furnished the title compound.

Preparation 132

(4-Bromo-2-chloro-phenyl)-(2-methoxy-5-triisopropylsilanyloxymethyl-phenyl)-methanone (Compound 532)

Compound 531 (710 mg, 1.38 mmol) was treated as described for compound 504. Flash chromatography (petroleum ether/ethyl acetate 3:97) to provide the title compound.

Preparation 133

[2-Chloro-4-(2,4-difluoro-phenylamino)-phenyl]-(2-methoxy-5-triisopropyl-silanyloxymethyl-phenyl)-methanone (533)

Compound 532 (449 mg, 0.87 mmol) and 2,4-difluoroaniline (0.12 mL, 1.14 mmol) were treated as described for compound 529. Flash chromatography (ethyl acetate/petroleum ether: graduated from 10/90 to 25/75) furnished the title compound.

Example 235

[2-Chloro-4-(2,4-difluoro-phenylamino)-phenyl]-(5-hydroxymethyl-2-methoxy-phenyl)-methanone (Compound 335)

Compound 533 (163 mg, 0.29 mmol) was treated as described for compound 331. Flash chromatography (ethyl acetate/petroleum ether: graduated from 50/50 to 75/25) gave the title compound. $^{13}$C NMR (CD$_3$OD) δ 196.0, 161.0 (dd), 158.9, 157.8 (dd), 150.8, 135.8, 135.1, 134.7, 133.0, 130.7, 130.1, 129.7, 127.3 (dd), 126.2 (dd), 116.4, 112.9, 112.9, 112.6 (dd), 105.7 (dd), 64.5, 56.4

Example 236

Acetic acid 3-[2-chloro-4-(2,4-difluoro-phenylamino)-benzoyl]-4-methoxy-benzyl ester (Compound 336)

To a solution of compound 335 (45 mg, 0.11 mmol), Et$_3$N (46 µL, 0.34 mmol), and DMAP (3 mg) in CH$_2$Cl$_2$ (5 mL) was added Ac$_2$O (13 µL, 0.13 mmol) at room temperature. The solution was stirred at room temperature for 0.5 h. The reaction solution was then washed with H$_2$O and saturated aqueous solution of NaHCO$_3$, dried over MgSO$_4$, and concentrated in vacuo. The residue was purified by chromatography (ethyl acetate/petroleum ether 1:4), giving the title compound. $^{13}$C NMR (CDCl$_3$) δ 193.1, 170.9, 158.9 (dd), 158.2, 155.3 (dd), 147.2, 134.7, 133.2, 133.2, 130.8, 130.4, 129.5, 128.3, 124.7 (dd), 123.8 (dd), 116.1, 112.9, 111.7, 111.5 (dd), 104.9 (dd), 65.6, 56.0, 21.0

Example 237

N-tert-Butoxy-3-[2-chloro-4-(2,4-difluoro-phenylamino)-benzoyl]-4-methoxy-benzamide (Compound 337)

To a mixture of compound 437 (51 mg, 0.12 mmol), O-tert-butylhydroxylamine (31 mg, 0.24 mmol), N-methylmorpholine (26 mg, 0.24 mmol) and 1-hydroxybenzotriazole (16 mg, 0.12 mmol) in CH$_2$Cl$_2$ (5 mL) was added EDCl (30 mg, 0.16 mmol) at room temperature. The reaction mixture was stirred at the same temperature for 6 h and then quenched with H$_2$O. The aqueous phase was extracted five times with CH$_2$Cl$_2$. The combined organic phases were dried over MgSO$_4$ and concentrated in vacuo. The residue was purified by flash chromatography (ethyl acetate/petroleum ether 2:1), furnishing the title compound. $^{13}$C NMR (DMSO-d$_6$) δ 191.6, 164.8, 159.4, 158.7 (dd), 155.7 (dd), 149.2, 133.8, 133.6, 131.7, 129.1, 128.4, 126.5, 126.4 (dd), 124.7, 124.2 (dd), 114.8, 111.9 (dd), 111.8, 111.7, 105.0 (dd), 80.8, 56.0, 26.4

Example 238

3-[2-Chloro-4-(2,4-difluoro-phenylamino)-benzoyl]-N-methoxy-4-methyl-benzamide (Compound 338)

Compound 424 (50 mg, 0.12 mmol) and N-methylhydroxylamine hydrochloride (21 mg, 0.25 mmol) were treated as described for compound 337. Flash chromatography (ethyl acetate/petroleum ether: graduated from 67/33 to 100/0) provided the title compound. $^{13}$C NMR (DMSO-d$_6$) δ 194.5, 158.8 (dd), 155.8 (dd), 149.5, 140.1, 139.5, 133.8, 133.7, 131.2, 129.4, 128.8, 126.9, 126.5 (dd), 126.2, 124.1 (dd), 114.8, 111.9 (dd), 111.8, 105.0 (dd), 63.2, 19.6

Example 239

N-Butoxy-3-[2-chloro-4-(2,4-difluoro-phenylamino)-benzoyl]-4-methyl-benzamide (Compound 339)

Compound 424 (100 mg, 0.25 mmol) and O-butyl-hydroxylamine (63 mg, 0.50 mmol) were treated as described for compound 337. Flash chromatography (ethyl acetate/petroleum ether: graduated from 20/80 to 60/40) provided the title compound. $^{13}$C NMR (CDCl$_3$) δ 195.4, 165.9, 159.3 (dd), 155.7 (dd), 148.3, 142.0, 139.8, 135.4, 133.8, 131.7, 129.5, 129.1, 128.6, 127.7, 124.6 (dd), 124.1 (dd), 116.2, 112.8, 111.7 (dd), 105.0 (dd), 76.9, 30.1, 20.4, 19.1, 13.8

Example 240

3-[2-Chloro-4-(2,4-difluoro-phenylamino)-benzoyl]-N-cyclohexylmethoxy-4-methyl-benzamide (Compound 340)

Compound 424 (50 mg, 0.12 mmol) and O-cyclohexyl-hydroxylamine (42 mg, 0.25 mmol) were treated as described for compound 337. Flash-chromatography (ethyl acetate/petroleum ether: graduated from 67/33 to 100/0) provided the title compound. $^1$H NMR (CDCl$_3$) δ 8.68 (bs, 1H), 7.72 (bd, 1H), 7.66 (bs, 1H), 7.43-7.28 (m, 3H), 7.00-6.82 (m, 3H), 6.75 (dd, 1H), 5.94 (bs, 1H), 3.80 (d, 2H), 2.44 (s, 3H), 1.89-1.56 (m, 6H), 1.35-1.09 (m, 3H), 1.07-0.84 (m, 2H)

Example 241

3-[2-Chloro-4-(2,4-difluoro-phenylamino)-benzoyl]-4-methyl-N-(2-methyl-thiazol-4-ylmethoxy)-benzamide (Compound 341)

Compound 424 (50 mg, 0.12 mmol) and O-(2-Methyl-thiazol-4-ylmethyl)-hydroxylamine (36 mg, 0.25 mmol) were treated as described for compound 337. Flash chromatography (ethyl acetate/petroleum ether: graduated from 67/33 to 100/0) provided the title compound. $^1$H NMR (CDCl$_3$) δ 10.0-9.0 (bs, 1H), 7.76 (dd, 1H), 7.67 (d, 1H), 7.42-7.30 (m, 3H), 7.15 (s, 1H), 7.00-6.84 (m, 3H), 6.75 (dd, 1H), 5.98 (bs, 1H), 5.04 (s, 2H), 2.64 (s, 3H), 2.45 (s, 3H)

Example 242

N-benzyloxy-3-[2-chloro-4-(2,4-difluoro-phenylamino)-benzoyl]-4-methyl-benzamide (Compound 342)

Compound 424 (100 mg, 0.25 mmol) and O-benzyl-hydroxylamine (80 mg, 0.50 mmol) were treated as described for compound 337. Flash chromatography (ethyl acetate/petroleum ether: graduated from 80/20 to 60/40) provided the title compound. $^{13}$C NMR (CDCl$_3$) δ 195.3, 165.8, 159.3 (dd), 155.7 (dd), 148.2, 142.2, 139.8, 135.4, 135.1, 133.8, 131.7, 129.4, 129.1, 128.9, 128.7, 127.8, 124.6 (dd), 124.1 (dd), 116.2, 112.8, 111.7 (dd), 105.0 (dd), 78.5, 20.4

Example 243

3-[2-Chloro-4-(2,4-difluoro-phenylamino)-benzoyl]-N-(4-methoxy-benzyloxy)-4-methyl-benzamide (Compound 343)

Compound 424 (100 mg, 0.25 mmol) and O-(4-methoxy-benzyl)-hydroxylamine (65 mg, 0.34 mmol) were treated as described for compound 337. Flash chromatography (ethyl acetate/petroleum ether: graduated from 80/20 to 60/40) provided the title compound. $^{13}$C NMR (CDCl$_3$) δ 195.3, 165.6, 160.1, 159.3 (dd), 155.7 (dd), 148.2, 142.1, 139.7, 135.3, 133.8, 131.7, 131.1, 129.4, 129.1, 128.6, 127.8, 127.2, 124.6 (dd), 124.2 (dd), 116.2, 114.1, 112.8, 111.6 (dd), 105.0 (dd), 78.0, 55.3, 20.4

Example 244

3-[2-Chloro-4-(2,4-difluoro-phenylamino)-benzoyl]-4-methyl-benzoic acid N',N'-dimethyl-hydrazide (Compound 344)

Compound 424 (50 mg, 0.12 mmol) and N,N-dimethyl-hydrazine (19 μL, 0.25 mmol) were treated as described for compound 337. Flash chromatography (ethyl acetate/petroleum ether: graduated from 67/33 to 80/20) provided the title compound. $^{13}$C NMR (DMSO-d$_6$) δ 194.7, 163.2, 158.9 (dd), 155.9 (dd), 149.6, 139.6, 139.5, 133.9, 133.8, 131.3, 131.0, 129.1, 127.2, 126.7 (dd), 126.3, 124.2 (dd), 114.9, 112.0 (dd), 111.9, 105.1 (dd), 46.1, 19.6

Example 245

3-[2-Chloro-4-(2,4-difluoro-phenylamino)-benzoyl]-4-methyl-N-morpholin-4-yl-benzamide (Compound 345)

Compound 424 (50 mg, 0.12 mmol) and N-amino-morpholine hydrochloride (35 mg, 0.25 mmol) were treated as described for compound 337. Flash chromatography (ethyl acetate/petroleum ether: graduated from 67/33 to 100/0) provided the title compound. $^{13}$C NMR (DMSO-d$_6$) δ 194.5, 168.2, 158.9 (dd), 155.8 (dd), 149.5, 139.1, 138.2, 133.7, 133.7, 132.9, 131.3, 129.3, 127.5, 126.5 (dd), 126.5, 124.3 (dd), 114.8, 112.0 (dd), 111.9, 105.1 (dd), 66.0, 19.7

Example 246

3-[2-Chloro-4-(2,4-difluoro-phenylamino)-benzoyl]-N-hydroxy-4-methyl-benzamide (Compound 346)

Compound 424 (202 mg, 0.50 mmol) and O-[(dimethyl-t-butyl)silyl]-hydroxylamine (148 mg, 1.01 mmol) were treated as described for compound 337. Flash chromatography (ethyl acetate/petroleum ether: graduated from 67/33 to 100/0) provided the title compound. $^{13}$C NMR (DMSO-d$_6$) δ 194.6, 162.9, 158.8 (dd), 155.8 (dd), 149.4, 139.5, 139.1, 133.6, 131.1, 130.3, 128.7, 127.0, 126.5 (m), 126.4, 124.1 (dd), 114.8, 111.9 (dd), 111.8, 105.0 (dd), 19.6

Preparation 134

4-(4-Bromo-2-chloro-benzoyl)-3-methyl-benzoic acid methyl ester (Compound 534)

4-Iodo-3-methyl-benzoic acid methyl ester (0.83 g, 3.00 mmol) and compound 440 (0.75 g, 3.00 mmol) were treated as described for compound 525. Flash chromatography (ethyl acetate/petroleum ether 1:15) provided the title compound as a white solid.

Preparation 135

4-[2-Chloro-4-(2,4-difluoro-phenylamino)-benzoyl]-3-methyl-benzoic acid methyl ester (Compound 535)

Compound 534 (184 mg, 0.50 mmol) and 2,4-difluoroaniline (0.066 mL, 0.65 mmol) were treated as described for compound 529. Flash chromatography (ethyl acetate/petroleum ether: graduated from 0/100 to 20/80) gave the title compound.

Example 247

4-[2-Chloro-4-(2,4-difluoro-phenylamino)-benzoyl]-N-(2-hydroxy-ethyl)-3-methyl-benzamide (Compound 347)

A mixture of compound 535 (127 mg, 0.30 mmol) and $K_2CO_3$ (63 mg, 0.45 mmol) in ethanolamine/$CH_3CN$ 1:1 (4 mL) was stirred at room temperature for 18 h. The reaction mixture was then poured into $H_2O$ and extracted three times with ethyl acetate. The combined organic phases were washed with brine, dried over $MgSO_4$, and concentrated in vacuo. The residue was purified by chromatography (ethyl acetate/petroleum ether 5:1), furnishing the title compound as a yellow solid. $^{13}C$ NMR ($CD_3OD$) δ 197.7, 169.8, 161.2 (dd), 158.0 (dd), 151.7, 144.0, 138.5, 137.5, 136.4, 135.1, 131.0, 130.0, 128.2, 127.7 (dd), 125.8 (dd), 125.7, 116.5, 113.0, 112.7 (dd), 105.8 (dd), 61.6, 43.7, 20.3

Example 248

[2-Chloro-4-(2,4-difluoro-phenylamino)-phenyl]-[5-(3-hydroxy-propenyl)-2-methyl-phenyl]-methanone (Compound 348)

Compound 495 (0.132 g, 0.27 mmol) was dissolved in dry 1,4-dioxan (1.5 mL) in a screw cap vessel under an argon atmosphere. Tri(2-furyl)phosphine (0.013 g, 0.05 mmol) and tris(dibenzylldeneacetone)dipalladium(0) (0.007 g, 0.008 mmol) were added and shaken. (E)-3-(tri-n-butyltin)prop-2-en-1-ol (0.104 g, 0.3 mmol) was added and the reaction mixture was heated under an argon atmosphere at 100° C. for 16 h on a shaking table. $CH_3CN$ was added to the reaction mixture and the solution was washed three times with petroleum ether. The acetonitrile phase was concentrated in vacuo and purified by flash chromatography using a gradient of EtOAc/petroleum ether (40-60) 1:3→3:1 as the eluent. This afforded the title compound as yellow oil.

Example 249

4-{3-[2-Chloro-4-(2,4-difluoro-phenylamino)-benzoyl]-4-methyl-benzoylamino}-thiophene-3-carboxylic acid methyl ester (Compound 349)

The reaction was carried out similarly as described in the preparation of compound 120, using 4-amino-thiophene-3-carboxylic acid methyl ester (0.5 mmol) and compound 439 (0.5 mmol). Purification was done by flash chromatography to afford the title compound as foam. $^{13}C$ NMR ($CDCl_3$) δ 195.6, 164.8, 163.9, 159.1 (dd), 155.5 (dd), 147.9, 142.4, 139.7, 136.5, 135.2, 133.6, 132.6, 131.9, 131.3, 129.1, 128.9, 128.6, 124.4 (dd), 124.2 (dd), 121.6, 116.3, 113.0, 111.6 (dd), 110.8, 104.9 (dd), 52.1, 20.5

Example 250

3-[2-Chloro-4-(2,4-difluoro-phenylamino)-benzoyl]-N-furan-2-ylmethyl-4-methyl-benzamide (Compound 350)

The reaction was carried out similarly as described in the preparation of compound 120, using furan-2-yl-methylamine (0.5 mmol) and compound 439 (0.5 mmol). Purification was done by flash chromatography to afford the title compound as foam. $^{13}C$ NMR ($CDCl_3$) δ 195.6, 166.4, 159.2 (dd), 155.6 (dd), 151.0, 148.2, 142.4, 141.6, 139.8, 135.3, 133.7, 131.6, 128.9, 128.8, 127.8, 124.5 (dd), 124.2 (dd), 116.2, 112.8, 111.6 (dd), 110.5, 107.8, 105.0 (dd), 37.0, 20.4

Example 251

3-[2-Chloro-4-(2,4-difluoro-phenylamino)-benzoyl]-N-(3-methoxy-phenyl)-4-methyl-benzamide (Compound 351)

The reaction was carried out similarly as described in the preparation of compound 120, using 3-methoxy-phenylamine (0.5 mmol) and compound 439 (0.5 mmol). Purification was done by flash chromatography to afford the title compound as foam. $^{13}C$ NMR ($CDCl_3$) δ 195.5, 165.0, 160.2, 159.3 (dd), 155.7 (dd), 148.3, 141.8, 139.9, 139.1, 135.4, 133.8, 132.3, 131.8, 129.7, 129.0, 128.5, 127.7, 124.6 (dd), 124.1 (dd), 116.2, 112.8, 112.3, 111.6 (dd), 110.6, 105.9, 105.0 (dd), 55.3, 20.4

Example 252

2-{3-[2-Chloro-4-(2,4-difluoro-phenylamino)-benzoyl]-4-methyl-benzoylamino}-benzoic acid methyl ester (Compound 352)

The reaction was carried out similarly as described in the preparation of compound 120, using 2-amino-benzoic acid methyl ester (0.5 mmol) and compound 439 (0.5 mmol). Purification was done by flash chromatography to afford the title compound as foam. $^{13}C$ NMR ($CDCl_3$) δ 195.6, 169.0, 164.9, 159.1 (dd), 155.5 (dd), 147.8, 142.4, 141.7, 139.6, 135.2, 134.8, 133.6, 132.3, 131.9, 130.9, 129.3, 129.1, 129.0, 124.4 (dd), 124.2 (dd), 122.7, 120.4, 116.3, 115.2, 113.0, 111.6 (dd), 104.9 (dd), 52.4, 20.6

Example 253

3-{3-[2-Chloro-4-(2,4-difluoro-phenylamino)-benzoyl]-4-methyl-benzoylamino}-thiophene-2-carboxylic acid methyl ester (Compound 353)

The reaction was carried out similarly as described in the preparation of compound 120, using 3-amino-thiophene-2-carboxylic acid methyl ester (1.0 mmol) and compound 439 (0.5 mmol). Purification was done by flash chromatography to afford the title compound as foam. $^{13}C$ NMR (DMSO-$d_6$) δ 194.2, 163.9, 162.4, 158.8 (dd), 155.7 (dd), 149.6, 143.7, 141.4, 139.8, 133.8, 133.7, 133.3, 131.9, 130.6, 128.7, 127.5, 126.5 (dd), 126.0, 124.1 (dd), 121.9, 114.8, 112.0 (dd), 111.9, 105.0 (dd), 52.1, 19.7

Example 254

4-{3-[2-Chloro-4-(2,4-difluoro-phenylamino)-benzoyl]-4-methyl-benzoylamino}-thiophene-3-carboxylic acid (Compound 354)

To a suspension of compound 349 (75 mg, 0.14 mmol) in methanol (5 mL) was added water (0.5 mL) followed by lithium hydroxide (17 mg, 0.7 mmol). The mixture was then stirred at reflux for 30 min. The reaction mixture was made acidic (pH=5) by slowly addition of HCl (1N), and then poured into a mixture of EtOAc/water. The aqueous phase was extracted with more EtOAc. The organic phases were combined, dried ($MgSO_4$), filtered, and concentrated in vacuo to afford the title compound as solid. $^{13}C$ NMR (DMSO-$d_6$) δ 194.3, 165.6, 162.6, 158.8 (dd), 155.8 (dd), 149.6, 140.7, 139.9, 135.8, 133.9, 133.8, 131.8, 131.0, 128.2, 127.0, 126.5 (dd), 126.0, 124.0 (dd), 122.6, 114.8, 112.1, 112.0 (dd), 111.9, 110.8, 105.0 (dd), 19.6

Example 255

2-{3-[2-Chloro-4-(2,4-difluoro-phenylamino)-benzoyl]-4-methyl-benzoylamino}-benzoic acid (Compound 355)

The reaction was carried out similarly as described in the preparation of compound 354, using compound 352 (0.5 mmol). The title compound was obtained as solid. $^{13}$C NMR (DMSO-d$_6$) δ 194.3, 169.9, 163.7, 158.8 (dd), 155.8 (dd), 149.6, 140.8, 140.6, 140.0, 134.0, 133.9, 133.8, 131.9, 131.7, 131.1, 128.5, 127.2, 126.6 (dd), 125.9, 124.0 (dd), 122.9, 119.9, 117.0, 114.9, 112.0 (dd), 111.9, 105.0 (dd), 19.6

Preparation 136

2-{3-[2-Chloro-4-(2,4-difluoro-phenylamino)-benzoyl]-4-methyl-benzoylamino}-benzoyl chloride (Compound 536)

A suspension of compound 355 (68 mg, 0.13 mmol) in toluene (2 mL) was added thionyl chloride (19 μL, 0.26 mmol) and then refluxed for 2 h. The reaction mixture was concentrated in vacuo to afford the title compound without any further purification.

Example 256

3-[2-Chloro-4-(2,4-difluoro-phenylamino)-benzoyl]-N-[2-(2-hydroxy-ethylcarbamoyl)-phenyl]-4-methyl-benzamide (Compound 356)

The reaction was carried out similarly as described in the preparation of compound 120, using 2-amino-ethanol (0.26 mmol) and compound 536 (0.13 mmol). Purification was done by flash chromatography to afford the title compound as foam. $^{13}$C NMR (CDCl$_3$) δ 195.8, 169.9, 164.8, 159.0 (dd), 155.4 (dd), 147.9, 142.2, 139.8, 139.5, 135.2, 133.6, 132.8, 132.2, 131.9, 129.1, 128.9, 126.7, 124.5 (m), 124.1 (m), 123.0, 121.5, 120.2, 116.4, 113.0, 111.6 (dd), 104.9 (dd), 61.8, 42.5, 20.5

Example 257

3-{3-[2-Chloro-4-(2,4-difluoro-phenylamino)-benzoyl]-4-methyl-benzoylamino}-thiophene-2-carboxylic acid (2-hydroxy-ethyl)-amide (Compound 357)

A solution of compound 353 (124 mg, 0.23 mmol) in acetonitrile (2.0 mL) and 2-amino-ethanol (0.50 mL) was added K$_2$CO$_3$ (50 mg, 0.36 mmol) and stirred for 18 h at RT. The reaction mixture was poured into a mixture of EtOAc/water. The aqueous phase was extracted with more EtOAc. The organic phases were combined and concentrated on silica gel in vacuo. Purification was done by flash chromatography eluting with mixtures of MeOH/DCM to afford the title compound. $^{13}$C NMR (DMSO-d$_6$) δ 193.8, 163.5, 161.5, 158.2 (dd), 155.2 (dd), 149.0, 141.8, 140.5, 139.3, 133.2, 133.2, 131.3, 130.5, 128.5, 127.8, 127.1, 125.9 (dd), 125.6, 123.6 (dd), 121.1, 114.3, 113.3, 111.4 (dd), 111.4, 104.5 (dd), 58.8, 41.3, 19.2

Preparation 137

3-(2-Chloro-4-nitro-benzoyl)-4-methyl-benzonitrile (Compound 537)

A dry flask was charged with 3-iodo-4-methyl-benzonitrile (5.15 g, 21.2 mmol) and the flask was evaporated and then filled with argon and this process repeated twice. Dry THF (15 mL) was added, and the solution cooled to −35° C.; then isopropylmagnesium chloride (10.6 mL, 2.0 M in diethyl ether, 21 mmol) was added slowly over 20 min keeping the temperature below −35° C. On completion of the addition the reaction mixture was stirred at −35° C. for 30 min. A THF solution of ZnCl$_2$ (3.61 g, 26.5 mmol, 1.0 M) was added dropwise over 20 min. The reaction mixture was stirred at 0° C. for 20 min; then 2-chloro-4-nitro-benzoyl chloride (4.9 g, 22.3 mmol) and Cu(OAc)$_2$ (85 mg, 0.42 mmol) were added and the reaction mixture was allowed to warm to room temperature. After 16 h the reaction mixture was poured into a mixture of EtOAc/water, then shaken and separated. The aqueous phase was extracted with more EtOAc. The organic phases were combined, dried (MgSO$_4$), filtered, and concentrated in vacuo to afford the crude product. The crude product was purified by flash chromatography using EtOAc/petroleum ether (40-60) 1:6 followed by 1:4 as the eluent to give the title compound as yellow solid.

Preparation 138

3-(4-Amino-2-chloro-benzoyl)-4-methyl-benzonitrile (Compound 538)

A mixture of compound 537 (1.05 g, 3.49 mmol) and stannous chloride dihydrate (3.31 g, 17.46 mmol) in absolute ethanol (20 mL) was heated to reflux. After 90 min the solution was cooled to RT and then poured into a mixture of ice/aqueous NaOH (7N)/EtOAc. The aqueous phase was extracted with more EtOAc followed by DCM. The organic phases were combined, washed with brine, dried (MgSO$_4$), filtered and concentrated in vacuo. The crude product was purified by flash chromatography using EtOAc/petroleum ether 1:2 as the eluent to give the title compound as yellow solid.

Preparation 139

3-[2-Chloro-4-(4-fluoro-2-methyl-phenylamino)-benzoyl]-4-methyl-benzonitrile compound 539)

A screw-capped vial (8 mL) was charged with compound 538 (100 mg, 0.37 mmol) in 1,4-dioxane (2 mL), 2-bromo-5-fluoro-toluene (55 μL, 0.44 mmol), Cs$_2$CO$_3$ (169 mg, 0.52 mmol), Pd$_2$(dba)$_3$ (9 mg, 0.009 mmol), and rac-BINAP (9 mg, 0.014 mmol). The tube was capped with a rubber septum, flushed with argon for 5 min, and then stirred at 100° C. for 18 h. The reaction mixture was allowed to cool to room temperature, and then poured into a mixture of water and EtOAc. The aqueous phase was extracted twice with more EtOAc. The combined organic phases were washed with brine, dried (MgSO$_4$), filtered and concentrated in vacuo. The crude product was purified by chromatography eluting with EtOAc/petroleum ether 1:3 to afford the title compound as light brown oil.

Example 258

[2-Chloro-4-(4-fluoro-2-methyl-phenylamino)-phenyl]-[2-methyl-5-(1H-tetrazol-5-yl)-phenyl]-methanone (Compound 358)

To a screw-capped vial with a magnetic stirrer were added compound 539 (100 mg, 0.26 mmol), TBAF.H$_2$O (41 mg, 0.13 mmol) and TMSN$_3$ (105 µL, 0.80 mmol) and THF (0.3 mL), and the resulting mixture were heated under vigorous stirring at 85° C. for 18 h. The reaction mixture was allowed to cool to room temperature, and then poured into a mixture of HCl (1N) and EtOAc. The aqueous phase was extracted with more EtOAc. The combined organic phases were washed with brine, dried (MgSO$_4$), filtered and concentrated in vacuo. The crude product was purified by chromatography eluting with DCM/MeOH/CH$_3$COOH 100:2.5:0.25 to afford the title compound as yellow foam. $^{13}$C NMR (DMSO-d$_6$) δ 193.9, 159.5 (d), 154.8, 151.1, 140.7, 139.4, 136.2 (d), 134.4, 134.3, 132.1, 128.5, 127.1 (d), 126.4, 124.7, 121.8, 117.4 (d), 114.1, 113.5 (d), 111.1, 19.5, 17.6

Preparation 140

(5-Bromo-2-methyl-phenyl)-(2-chloro-4-nitro-phenyl)-methanone (Compound 540)

A dry flask was charged with 4-bromo-2-iodo-1-methyl-benzene (6.85 g, 23.1 mmol) and the flask was evaporated and then filled with argon and this process repeated twice. Dry THF (20 mL) was added, and the solution cooled to −35° C.; then isopropylmagnesium chloride (11.5 mL, 2.0 M in diethyl ether, 23 mmol) was added slowly over 40 min keeping the temperature below −35° C. On completion of the addition the reaction mixture was stirred at −35° C. for 30 min. A THF solution of ZnCl$_2$ (3.93 g, 28.9 mmol, 0.7 M) was added dropwise over 20 min. The reaction mixture was stirred at 0° C. for 20 min; then 2-chloro-4-nitro-benzoyl chloride (5.33 g, 24.2 mmol) and Cu(OAc)$_2$ (92 mg, 0.46 mmol) were added and the reaction mixture was allowed to warm to room temperature. After 16 h the reaction mixture was poured into a mixture of EtOAc/water, then shaken and separated. The aqueous phase was extracted with more EtOAc. The organic phases were combined, dried (MgSO$_4$), filtered, and concentrated in vacuo to afford the crude product. The crude product was purified by flash chromatography using EtOAc/petroleum ether 1:14 as the eluent to give the title compound as almost white solid.

Preparation 141

(4-Amino-2-chloro-phenyl)-(5-bromo-2-methyl-phenyl)-methanone (Compound 541)

The reaction was carried out similarly as described in the preparation of compound 538, using compound 540 (5.64 mmol) as the nitro compound. Purification was done by flash chromatography to afford the title compound as yellow solid.

Preparation 142

(5-Bromo-2-methyl-phenyl)-[2-chloro-4-(2-nitro-phenylamino)-phenyl]-methanone (Compound 542)

A solution of compound 541 (1.42 g, 4.37 mmol) and 1-fluoro-2-nitrobenzene (0.42 mL, 4.0 mmol) in DMSO (10 mL) was slowly added potassium tert-butoxide (992 mg, 8.84 mmol) under stirring. After 20 h at RT the reaction mixture was poured into a mixture of EtOAc/water. The aqueous phase was extracted with more EtOAc. The organic phases were combined, dried (MgSO$_4$), filtered, and concentrated in vacuo to afford the crude product. The crude product was purified by chromatography eluting with EtOAc/petroleum ether 1:8 to afford the title compound as orange solid.

Preparation 143

[4-(2-Amino-phenylamino)-2-chloro-phenyl]-(5-bromo-2-methyl-phenyl)-methanone (Compound 543

The reaction was carried out similarly as described in the preparation of compound 538, using compound 542 (2.36 mmol) as the nitro compound. Purification was done by flash chromatography to afford the title compound as yellow solid.

Preparation 144

[4-(2-Amino-phenylamino)-2-chloro-phenyl]-(2-methyl-5-trimethylsilanylethynyl-phenyl)-methanone (Compound 544)

In a screw-capped vial (8 mL) was placed dry degassed triethylamine (3.0 mL) and a magnetic stirrer under argon. Compound 543 (200 mg, 0.48 mmol), Pd$_2$(dba)$_3$ (9.0 mg, 0.01 mmol), triphenyl phosphine (13 mg, 0.048 mmol), CuI (2 mg) and ethynyl-trimethyl-silane (66 µL, 0.48 mmol) were added to the vial and the reaction mixture was heated under vigorously stirring at 90° C. for 20 h. The cooled reaction mixture was filtered through Decalite and concentrated in vacuo. The crude product was purified by continuous gradient flash chromatography using EtOAc/petroleum ether (40-60) (v:v=5:95 to 30:70) as the eluent to afford the title compound as yellow foam.

Example 259

[4-(2-Amino-phenylamino)-2-chloro-phenyl]-(5-ethynyl-2-methyl-phenyl)-methanone (Compound 359)

A mixture of compound 544 (59 mg, 0.14 mmol) and K$_2$CO$_3$ (28 mg, 0.20 mmol) in methanol (1.0 mL) was stirred at RT for 3 h. The reaction mixture was poured into a mixture of EtOAc/water. The aqueous phase was extracted with more EtOAc. The organic phases were combined, dried (MgSO$_4$), filtered, and concentrated in vacuo to afford the title compound without any further purification. $^{13}$C NMR (CDCl$_3$) δ 195.5, 149.9, 142.9, 139.8, 138.5, 135.5, 133.9, 132.6, 131.3, 127.8, 127.4, 127.0, 125.1, 119.3, 119.2, 116.4, 115.4, 111.8, 83.0, 20.3

Example 260

[4-(2-Amino-phenylamino)-2-chloro-phenyl]-(2-methyl-5-({1-[2-(tetrahydro-pyran-2-yloxy)-ethyl]-1H-[1,2,3]triazol-4-yl}-phenyl)-methanone (Compound 360)

To a screw-capped vial with a magnetic stirrer were added compound 359 (25 mg, 0.07 mmol), 2-(2-azido-ethoxy)-tetrahydro-pyran (25 mg, 0.14 mmol) and EtOH (0.5 mL), followed by CuSO$_4$.H$_2$O (0.3 mg) and an aqueous solution of sodium-L-ascorbate (200 µL, 0.2 mmol, 1M). The reaction mixture was stirred at RT for 3 h and then at 40° C. for 30 min. The reaction mixture was concentrated on silica gel and purified by continuous gradient flash chromatography using EtOAc/petroleum ether (40-60) (v:v=50:50 to 100:0) as the eluent to afford the title compound as yellow foam. $^{13}$C NMR (CDCl$_3$) δ 196.1, 149.9, 147.0, 142.9, 140.2, 137.4, 135.5, 134.1, 131.7, 128.1, 127.7, 127.6, 127.0, 126.3, 125.2, 120.8, 119.1, 116.4, 115.4, 111.8, 99.1, 65.7, 62.4, 50.5, 30.4, 25.2, 20.1, 19.4

Example 261

[4-(2-Amino-phenylamino)-2-chloro-phenyl]-{5-[1-(2-hydroxy-ethyl)-1H-[1,2,3]triazol-4-yl]-2-methyl-phenyl}-methanone (Compound 361)

A solution of compound 360 (20 mg, 0.038 mmol) and toluene-4-sulfonic add (11 mg, 0.057 mmol) in MeOH (0.3 mL) was stirred at RT for 2 h. The reaction mixture was poured into a mixture of aqueous NaOH (2N) and EtOAc. The aqueous phase was washed with more EtOAc. The organic phases were combined and washed with brine, dried (MgSO$_4$), filtered and then purified by continuous gradient flash chromatography using EtOAc/petroleum ether (40-60) (v:v=40:60 to 20:80) as the eluent to afford the title compound as solid. $^{13}$C NMR (DMSO-d$_6$) δ 194.7, 151.0, 145.3, 143.3, 140.4, 135.4, 134.0, 131.4, 128.3, 126.7, 126.5, 126.1, 124.7, 124.6, 124.4, 121.8, 116.8, 115.8, 114.3, 111.3, 59.7, 52.3, 19.3

Preparation 145

[2-Chloro-4-(2,4-difluoro-phenylamino)-phenyl]-(2-methyl-5-trimethylsilanylethynyl-phenyl)-methanone (Compound 545)

In a screw-capped vial (8 mL) was placed dry degassed triethylamine (4.0 mL) and a magnetic stirrer under argon. Compound 495 (100 mg, 0.21 mmol), Pd$_2$(dba)$_3$ (3.8 mg), triphenyl phosphine (5.4 mg, 0.02 mmol), CuI (1 mg) and ethynyl-trimethyl-silane (29 µL, 0.21 mmol) were added to the vial and the reaction mixture was heated under vigorously stirring at 90° C. for 20 h. The cooled reaction mixture was filtered through Decalite and concentrated in vacuo. The crude product was purified by continuous gradient flash chromatography using EtOAc/petroleum ether (40-60) (v:v=0:100 to 10:90) as the eluent to afford the title compound as foam.

Example 262

[2-Chloro-4-(2,4-difluoro-phenylamino)-phenyl]-(5-ethynyl-2-methyl-phenyl)-methanone (Compound 362)

A mixture of compound 545 (36 mg, 0.08 mmol) and K$_2$CO$_3$ (17 mg, 0.13 mmol) in methanol (3.0 mL) was stirred at RT for 3 h. The reaction mixture was poured into a mixture of EtOAc/water. The aqueous phase was extracted with more EtOAc. The organic phases were combined, dried (MgSO$_4$), filtered, and concentrated in vacuo. The crude product was purified by continuous gradient flash chromatography using EtOAc/petroleum ether (40-60) (v:v=0:100 to 20:80) as the eluent to afford the title compound as foam. $^{13}$C NMR (CDCl$_3$) δ 195.4, 159.2 (dd), 155.5 (dd), 147.8, 139.3, 138.8, 135.2, 134.2, 133.5, 132.9, 131.5, 129.2, 124.3 (dd), 119.4, 116.2, 112.8, 111.6 (dd), 105.0 (dd), 82.9, 20.4

Example 263

3-[2-Chloro-4-(4-fluoro-phenylamino)-benzoyl]-4-methyl-benzoic acid hydrazide (Compound 363)

A mixture of compound 451 (100 mg, 0.25 mmol) and hydrazine hydrate (0.12 mL, 2.5 mmol) in methanol (5 mL) was stirred at reflux for 24 h. The reaction mixture was concentrated on silica gel in vacuo. The crude product was purified by flash chromatography using MeOH/DCM 2:98 as the eluent to afford the title compound as yellow foam. $^{13}$C NMR (CDCl$_3$) δ 195.5, 167.8, 159.7 (d), 149.2, 141.9, 139.9, 135.7 (d), 135.4, 133.9, 131.7, 129.9, 128.9, 127.7, 127.5, 124.3 (d), 116.5 (d), 115.6, 112.3, 20.4

Example 264

3-[2-Chloro-4-(2,4-difluoro-phenylamino)-benzoyl]-4-methyl-benzoic acid hydrazide (Compound 364)

A mixture of compound 423 (1.00 g, 2.4 mmol) and hydrazine hydrate (1.17 mL, 24 mmol) in methanol (40 mL) was stirred at reflux for 48 h. The reaction mixture was poured into a mixture of EtOAc/water. The aqueous phase was extracted with more EtOAc. The organic phases were combined and concentrated in vacuo. The crude product was purified by continuous gradient flash chromatography using MeOH/DCM (v:v=5:95 to 10:90) as the eluent to afford the title compound as yellow foam. $^{13}$C NMR (CDCl$_3$) δ 195.5, 167.8, 159.3 (dd), 155.7 (dd), 148.3, 142.0, 139.7, 135.3, 133.7, 131.8, 129.9, 129.0, 128.6, 127.7, 124.6 (dd), 124.2 (dd), 116.1, 112.8, 111.6 (dd), 105.0 (dd), 20.4

Example 265

1-{3-[2-Chloro-4-(2,4-difluoro-phenylamino)-benzoyl]-4-methyl-benzoyl}-4-ethyl-3-thio semicarbazide (Compound 365)

In a screw-capped vial (8 mL) was placed isothiocyanato-ethane (69 µL, 0.79 mmol), compound 364 (300 mg, 0.72 mmol), methanol (6 mL) and a magnetic stirrer. The reaction mixture was heated under stirring at 95° C. for 3 h. The cooled reaction mixture was filtered through Decalite and concentrated in vacuo. The crude product was purified by flash chromatography using THF/petroleum ether 2:3 as the eluent to afford the title compound as yellow foam. $^{13}$C NMR (DMSO-d$_6$) δ 194.6, 181.3, 165.0, 158.8 (dd), 155.8 (dd), 149.5, 140.3, 139.4, 133.8, 133.8, 130.9, 129.9, 129.7, 127.7, 126.6 (dd), 126.2, 124.1 (dd), 114.8, 112.0 (dd), 111.7, 105.0 (dd), 38.4, 19.6, 14.4

Example 266

[2-Chloro-4-(2,4-difluoro-phenylamino)-phenyl]-[5-(5-ethylamino-[1,3,4]thiadiazol-2-yl)-2-methyl-phenyl]-methanone (Compound 366)

A mixture of compound 365 (122 mg, 0.24 mmol) and POCl$_3$ (29 µL, 0.32 mmol) in 1,4-dioxane (1.0 mL) was stirred at 95° C. for 20 h. The reaction mixture was poured into a mixture of EtOAc/sat. aq. NaHCO$_3$. The aqueous phase was extracted with more EtOAc. The organic phases were combined, dried (MgSO$_4$), filtered, and concentrated in vacuo. The crude product was purified by continuous gradient flash chromatography using EtOAc/petroleum ether (40-60) (v:v=20:80 to 50:50) as the eluent to afford the title compound as yellow solid $^{13}$C NMR (DMSO-d$_6$) δ 194.4, 168.3, 158.8 (dd), 155.8 (dd), 154.7, 149.5, 139.9, 137.9, 133.8, 133.7, 131.9, 128.4, 126.5 (dd), 126.2, 125.7, 124.1 (dd), 114.8, 112.0 (dd), 111.8, 105.0 (dd), 39.6, 19.5, 14.1

Preparation 146

3-[2-Chloro-4-(2,4-difluoro-phenylamino)-benzoyl]-4-methyl-benzonitrile (Compound 546)

A flask was charged with compound 538 (500 mg, 1.85 mmol) in toluene (10 mL), 1-bromo-2,4-difluorobenzene (0.25 mL, 2.22 mmol), $Cs_2CO_3$ (841 mg, 2.59 mmol), $Pd(OAc)_2$ (8 mg, 0.04 mmol), and 4,5-bis-diphenylphosphanyl-9,9-dimethyl-9H-xanthene (32 mg, 0.056 mmol). The flask was flushed with argon for 5 min, closed and then warmed slowly to 120° C. The reaction vial was stirred at 120° C. for 24 h. The reaction mixture was allowed to cool to room temperature, and then filtered through Decalite. Concentration in vacuo gave the crude product. The crude product was purified by continuous gradient flash chromatography using EtOAc/petroleum ether (40-60) (v:v=15:85 to 33:67) as the eluent to afford the title compound as brown foam.

Example 267

[2-Chloro-4-(2,4-difluoro-phenylamino)-phenyl]-[2-methyl-5-(1H-tetrazol-5-yl)-phenyl]-methanone (Compound 367)

The reaction was carried out similarly as described in the preparation of compound 358, using compound 546 (0.84 mmol) as the nitrile. Purification was done by flash chromatography to afford the title compound as yellow solid. $^{13}C$ NMR (DMSO-$d_6$) δ 194.2, 171.9, 158.9 (dd), 155.8 (dd), 149.7, 140.3, 139.7, 134.0, 133.9, 132.2, 128.7, 126.6, 126.0, 124.0 (dd), 121.7, 114.8, 112.0 (dd), 111.8, 105.0 (dd), 19.6

Example 268

3-{3-[2-Chloro-4-(2,4-difluoro-phenylamino)-benzoyl]-4-methyl-phenyl}-3-oxo-propionic acid ethyl ester (Compound 368)

A solution of potassium ethoxycarbonyl-acetate (136 mg, 0.80 mmol) in EtOAc (1.25 mL) was cooled to 0° C. in an ice-bath. Triethyl amine (279 µL, 2.0 mmol) and anhydrous magnesium chloride (91 mg, 0.96 mmol) was added to the solution and the mixture was stirred at 35° C. for 7 h. The reaction mixture was cooled to 0° C. and a solution of compound 439 (230 mg, 0.57 mmol) in EtOAc (1 mL) was added. The temperature was raised to RT and stirring was continued for 18 h. The reaction mixture was cooled to 0° C. and aqueous HCl (1.5 mL, 12%) was added slowly. The aqueous phase was separated and washed with EtOAc (10 mL). The organic phases were combined, washed with aqueous HCl (5 mL, 12%), aqueous $NaHCO_3$ (5 mL, 50%), water (5 mL) and brine (5 mL) and then dried ($MgSO_4$), filtered, and concentrated in vacuo. The crude product was purified by flash chromatography using DCM/petroleum ether 2:3 followed by diethyl ether/petroleum ether 1:2 as the eluent to afford the title compound as yellow solid $^{13}C$ NMR (CDCl$_3$) δ 195.2, 191.6, 167.3, 159.3 (dd), 155.6 (dd), 148.2, 144.2, 139.9, 135.4, 133.7, 133.6, 131.9, 130.5, 129.2, 128.7, 124.6 (d), 124.2 (dd), 116.2, 112.9, 111.7 (dd), 105.0 (t), 61.5, 46.0, 20.7, 14.1

Example 269

[2-Chloro-4-(2,4-difluoro-phenylamino)-phenyl]-[5-(4,5-dihydro-oxazol-2-yl)-2-methyl-phenyl]-methanone (Compound 369)

To a suspension of compound 115 (400 mg, 0.90 mmol) in DCM (4.0 mL) was added thionyl chloride (229 µL, 3.15 mmol) at the resulting mixture was stirred at RT for 1 h. Ice-water was added to the reaction mixture followed by EtOAc. The organic phase was separated, washed with brine, dried ($MgSO_4$), filtered, and concentrated in vacuo. The crude product was purified by continuous gradient flash chromatography using EtOAc/petroleum ether (40-60) (v:v=5:95 to 40:60) as the eluent to afford the title compound as foam. $^{13}C$ NMR (CDCl$_3$) δ 195.6, 164.0, 159.2 (dd), 155.5 (dd), 147.9, 141.4, 139.5, 135.3, 133.7, 131.5, 130.2, 129.1, 128.9, 125.2, 124.3 (m), 116.2, 112.8, 111.6 (dd), 105.0 (dd), 67.7, 54.9, 20.5

Example 270

3-{2-Chloro-4-[2-(3-ethyl-ureido)-phenylamino]-benzoyl}-N-(2-hydroxy-ethyl)-4-methyl-benzamide (Compound 370)

To a solution of compound 112 (100 mg, 0.24 mmol) in dry pyridine (1 mL) was added ethyl isocyanate (28 µL, 0.35 mmol) under stirring. After 1 h the reaction mixture was poured into a mixture of EtOAc/water. The aqueous phase was extracted with more EtOAc. The organic phases were combined, dried ($MgSO_4$), filtered, and concentrated in vacuo to afford the crude product. The crude product was purified by continuous gradient flash chromatography eluting with EtOAc/MeOH (v:v=100:0 to 98:2) to afford the title compound as yellow syrup. $^{13}C$ NMR (DMSO-$d_6$): δ 194.6, 165.3, 155.0, 151.1, 139.6, 139.3, 136.3, 133.9, 133.8, 131.7, 130.8, 128.8, 128.1, 127.1, 126.2, 126.1, 125.3, 121.8, 120.2, 114.7, 111.4, 59.6, 42.1, 33.8, 19.5, 15.2

The invention claimed is:
1. A compound of general formula I

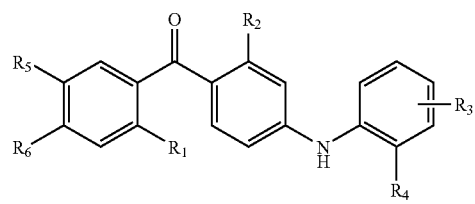

wherein
$R_1$ methyl;
$R_2$ is chloro;
$R_3$ represents fluoro;
$R_4$ is fluoro;
wherein $R_3$ is in the meta position with respect to $R_4$ and para with respect to —NH;
$R_a$, $R_b$ and $R_c$ are the same or different, each representing hydrogen, $C_{1-4}$alkyl, $C_{2-4}$alkenyl, $C_{2-4}$ alkynyl, $C_{3-8}$carbocyclyl, $C_{1-12}$heterocyclyl or aryl, each of $C_{1-4}$alkyl, $C_{2-4}$alkenyl, $C_{2-4}$ alkynyl, $C_{3-8}$carbocyclyl, $C_{1-12}$heterocyclyl or aryl being optionally substituted by one or more, same or different substituents represented by $R_7$;
$R_7$ is halogen, hydroxy, mercapto, trifluoromethyl, amino, $C_{1-4}$alkyl, $C_{1-6}$hydroxyalkyl, $C_{1-4}$alkoxy, $C_{1-4}$alkylthio, $C_{1-6}$ alkylamino, $C_{1-4}$alkoxycarbonyl, $C_{1-9}$ trialkylammonium in association with an anion, cyano, azido, nitro, —S(O)$_2$NH$_2$, —S(O)$_2$NR$_a$R$_b$, —S(O)$_2$R, —COOH, —CONH$_2$, —NR$_a$C(O)R', —CONHR' or —CONRR', wherein R and R' are same or different, each representing hydrogen or $C_{1-3}$alkyl;

one of $R_5$ and $R_6$ is —COOH, —C(O)NHOH, —C(O)NHNH$_2$, $Y_2R_9$, $Y_2R_9Y_3R_{10}$, $C_{1-6}$alkyl-$Y_2R_9$, $C_{1-6}$alkyl-$Y_2R_9Y_3R_{10}$, $C_{2-6}$alkenyl-$Y_2R_9$, $C_{2-6}$alkenyl-$Y_2R_9Y_3R_{10}$, $Y_2R_9$—$C_{1-6}$-alkyl-$Y_3R_{10}$, $Y_2R_9$—$C_{2-6}$-alkenyl-$Y_3R_{10}$, $C_{3-12}$carbocyclyl-$Y_2R_9$, $C_{3-12}$carbocyclyl-$Y_2R_9Y_3R_{10}$, $C_{1-12}$heterocyclyl-$Y_2R_9$, $C_{1-12}$heterocyclyl-$Y_2R_9Y_3R_{10}$, $C_{3-12}$carbocyclyl-$C_{1-6}$-alkyl-$Y_2R_9$, $C_{3-12}$carbocyclyl-$C_{1-6}$-alkyl-$Y_2R_9Y_3R_{10}$, $C_{1-12}$heterocyclyl-$C_{1-6}$-alkyl-$Y_2R_9$, $C_{1-12}$heterocyclyl-$C_{1-6}$-alkyl-$Y_2R_9Y_3R_{10}$, $C_{3-12}$carbocyclyl-$C_{1-6}$-alkyl-$Y_3R_{10}$, $C_{1-12}$heterocyclyl-$C_{1-6}$-alkyl-$Y_3R_{10}$, $C_{1-12}$heterocyclyl-$C_{1-10}$alkyl, $C_{3-12}$carbocyclyl-$C_{1-10}$alkyl, $C_{1-10}$alkyl-$C_{1-12}$heterocyclyl, $C_{1-10}$alkyl-$C_{3-12}$carbocyclyl, $C_{1-10}$alkyl, $C_{2-10}$alkenyl, $C_{2-10}$ alkynyl, $C_{3-12}$carbocyclyl or $C_{1-12}$heterocyclyl, each of which being optionally substituted by one or more, same or different substituents represented by $R_7$, and the other is hydrogen, halogen, hydroxy, mercapto, trifluoromethyl, amino, $C_{1-4}$alkyl, $C_{2-4}$alkenyl, $C_{2-4}$alkynyl, $C_{1-4}$alkoxy, $C_{1-4}$ alkylthio, $C_{1-6}$alkylamino, $C_{1-4}$alkoxycarbonyl, cyano, —CONH$_2$ or nitro, with the proviso that when $R_5$ or $R_6$ is phenyl, $C_{1-5}$alkyl or $C_{2-3}$alkenyl, said $R_5$ or $R_6$ is substituted by one or more, same or different substituents represented by $R_7$ (except three fluorine when $R_5$ or $R_6$ is methyl), $Y_2$ is —O—, —S—, —S(O)—, —S(O)$_2$—, —NR$_a$—, —NR$_a$C(O)NR$_b$—, —NR$_a$C(O)—, —C(O)NR$_a$—, —C(O)NR$_a$O—, —C(O)—, —NR$_a$C(O)O—, —NR$_a$S(O)$_2$—, —OC(O)—, —C(O)O—, —C(O)NR$_a$NR$_b$C(S)NR$_c$—, —C(O)NR$_a$NR$_b$—, or —S(O)$_2$NR$_a$—;

$R_9$ is $C_{1-10}$alkyl-$C_{1-12}$heterocyclyl, $C_{1-10}$alkyl-$C_{3-12}$carbocyclyl, $C_{1-10}$alkyl, $C_{2-10}$alkenyl, $C_{2-10}$ alkynyl, $C_{3-12}$carbocyclyl, $C_{1-12}$heterocyclyl, $C_{3-12}$carbocyclyl-$C_{1-10}$alkyl, or $C_{1-12}$heterocyclyl-$C_{1-10}$alkyl, $C_{3-6}$carbocyclyl-$C_{1-6}$alkenyl, $C_{3-6}$carbocyclyl-$C_{2-6}$alkynyl, each being optionally substituted by one or more, same or different substituents represented by $R_7$, with the proviso that when $Y_2$ is —O—, —NR$_a$—, —S— or —C(O)O—, and $R_9$ is $C_{1-6}$alkyl, said $C_{1-6}$alkyl is substituted by one or more, same or different substituents represented by $R_7$;

$Y_3$ is —O—, —S—, —S(O)—, —S(O)$_2$—, —NR$_a$—, —NR$_a$C(O)NR$_b$—, —NR$_a$C(O)—, —C(O)NR$_a$—, —C(O)NR$_a$O—, —C(O)—, —NR$_a$C(O)O—, —NR$_a$S(O)$_2$—, —OC(O)— or —C(O)O—;

$R_{10}$ is $C_{1-10}$alkyl-$C_{1-12}$heterocyclyl, $C_{1-10}$alkyl-$C_{3-12}$carbocyclyl, $C_{1-10}$alkyl, $C_{2-10}$alkenyl, $C_{2-10}$ alkynyl, $C_{3-12}$carbocyclyl or $C_{1-12}$heterocyclyl, each being optionally substituted by one or more, same or different substituents represented by $R_7$;

or, when one of $R_5$ or $R_6$ is the group —C(O)NR$_a$R$_9$, R$_a$ and $R_9$ together with the nitrogen atom to which they are attached form a $C_{1-12}$heterocyclic ring optionally comprising one or more additional heteroatoms selected from the group consisting of O, S and N, optionally substituted with one or more substituents represented by $R_7$;

or a pharmaceutically acceptable salt, solvate, or ester thereof.

2. A compound according to claim 1, wherein $R_7$ is halogen, hydroxy, amino, —S(O)$_2$CH$_3$, trifluoromethyl, cyano, $C_{1-4}$hydroxyalkyl, $C_{1-4}$alkoxy, $C_{1-4}$alkyl, $C_{1-4}$alkylthio, $C_{1-4}$alkylamino, $C_{1-4}$alkoxycarbonyl, —COOH, —CONH$_2$, —S(O)$_2$NH$_2$, azido, —CONHR' or —CONRR', wherein R and R' are as indicated in claim 1.

3. A compound according to claim 1, wherein $R_7$ is methyl, ethyl, methoxy, ethoxy, hydroxy, methoxycarbonyl, ethoxycarbonyl, dimethylamino, ethylamino, amino, —COOH, fluoro, chloro, bromo, —CONH$_2$, —S(O)$_2$NH$_2$, azido, methylthio, —S(O)$_2$CH$_3$, trifluoromethyl, cyano or hydroxymethyl.

4. A compound according to claim 1, wherein one of $R_5$ and $R_6$ is $Y_2R_9$, $C_{1-4}$alkyl-$Y_2R_9$, $Y_2R_9Y_3R_{10}$, $C_{1-4}$alkyl-$Y_2R_9Y_3R_{10}$, $C_{2-4}$alkenyl-$Y_2R_9$, $C_{2-4}$alkenyl-$Y_2R_9Y_3R_{10}$, $Y_2R_9$—$C_{1-4}$-alkyl-$Y_3R_{10}$, $Y_2R_9$—$C_{2-4}$-alkenyl-$Y_3R_{10}$, $C_{1-6}$heterocyclyl-$C_{1-4}$-alkyl-$Y_2R_9$, $C_{1-4}$alkyl-$C_{1-6}$heterocyclyl, $C_{1-4}$alkyl-$C_{3-6}$carbocyclyl, $C_{3-6}$carbocyclyl-$C_{1-4}$alkyl, $C_{1-4}$alkyl substituted by $R_7$, $C_{2-4}$alkenyl, $C_{2-4}$ alkynyl, $C_{3-6}$carbocyclyl, $C_{1-6}$heterocyclyl, —COOH, —C(O)NHOH, or C(O)NHNH$_2$, and the other is hydrogen, halogen, $C_{1-4}$alkyl or $C_{1-4}$alkoxy; wherein $R_9$ is $C_{1-4}$alkyl-$C_{1-6}$ heterocyclyl, $C_{1-4}$alkyl-$C_{3-6}$carbocyclyl, $C_{1-6}$alkyl, $C_{2-4}$alkenyl, $C_{2-4}$ alkynyl, $C_{3-10}$carbocyclyl, $C_{1-6}$heterocyclyl, $C_{3-6}$carbocyclyl-$C_{1-6}$alkyl, $C_{1-6}$heterocyclyl-$C_{1-6}$alkyl, $C_{3-6}$carbocyclyl-$C_{2-4}$alkenyl or $C_{3-6}$carbocyclyl-$C_{2-4}$alkynyl; and wherein $R_{10}$ is $C_{1-4}$alkyl, $C_{2-4}$alkenyl, $C_{3-6}$carbocyclyl or $C_{1-6}$heterocyclyl.

5. A compound according to claim 1, wherein $R_5$ is $Y_2R_9$, $C_{1-4}$alkyl-$Y_2R_9$, $Y_2R_9Y_3R_{10}$, $C_{1-4}$alkyl-$Y_2R_9Y_3R_{10}$, $C_{2-4}$alkenyl-$Y_2R_9$, $C_{2-4}$alkenyl-$Y_2R_9Y_3R_{10}$, $Y_2R_9$—$C_{1-4}$-alkyl-$Y_3R_{10}$, $Y_2R_9$—$C_{2-4}$-alkenyl-$Y_3R_{10}$, $C_{1-6}$heterocyclyl-$C_{1-4}$-alkyl-$Y_2R_9$, $C_{1-4}$alkyl-$C_{1-6}$heterocyclyl, $C_{1-4}$alkyl-$C_{3-6}$carbocyclyl, $C_{3-6}$carbocyclyl-$C_{1-4}$alkyl, $C_{1-4}$alkyl substituted by $R_7$, $C_{2-4}$alkenyl, $C_{2-4}$ alkynyl, $C_{3-6}$carbocyclyl, $C_{1-6}$heterocyclyl, —COOH, —C(O)NHOH, or C(O)NHNH$_2$, and $R_6$ is hydrogen, halogen, $C_{1-4}$alkyl or $C_{1-4}$alkoxy; wherein $R_9$ is $C_{1-4}$heterocyclyl, $C_{1-6}$alkyl, $C_{1-3}$alkyl-$C_{1-5}$heterocyclyl, $C_{6-10}$carbocyclyl, $C_{1-3}$alkyl-$C_6$carbocyclyl, $C_3$alkenyl, $C_6$carbocyclyl-$C_1$alkyl, $C_6$carbocyclyl-$C_3$alkenyl or $C_6$carbocyclyl-$C_2$alkynyl; and wherein $R_{10}$ is methyl, ethyl, methacryl, tert-butyl, tetrahydropyranyl or ethenyl.

6. A compound according to claim 1, wherein one of $R_5$ and $R_6$ is $Y_2R_9$, $Y_2R_9Y_3R_{10}$, phenyl, methylphenyl, methyl, propenyl, methyl-$Y_2R_9$, tetrazole, ethynyl, triazole, thiadiazole, dihydrooxazole, —COOH, —C(O)NHOH, or C(O)NHNH$_2$, and the other is hydrogen, fluoro, chloro, methyl or methoxy; wherein $R_9$ is morpholinyl, propylmorpholinyl, piperazinyl, methyl, ethyl, n-propyl, n-butyl, tert-butyl, isobutyl, hexyl, isopropyl, dimethylpropyl, methyltetrahydrofuranyl, methylpyridinyl, ethylpiperazinyl, cyclohexyl, propyloxypyrrolidinyl, benzyl, methylcyclohexyl, propylphenyl, ethylmorpholinyl, allyl, ethylfuranyl, phenyl, methyldioxoimidazolidinyl, dioxohexahydropyrimidinyl, thiazolyl, methylphenyl, ethylphenyl, methyldioxolanyl, methylthiazolyl, propenylphenyl, methylfuranyl, thiophenyl, tetrahydropyranyl or ethynylphenyl; and wherein $R_{10}$ is methyl, ethyl, methacryl, tert-butyl, tetrahydropyranyl or ethenyl.

7. A compound according to claim 1, wherein $R_6$ is hydrogen.

8. A compound according to claim 1, wherein $R_5$ is hydrogen.

9. A compound according to claim 1, wherein $Y_2$ is —O—, —NR$_a$—, —NR$_a$C(O)NR$_b$—, —NR$_a$C(O)—, —C(O)NR$_a$—, —C(O)NR$_a$O—, —C(O)—, —NR$_a$C(O)O—, —NR$_a$S(O)$_2$—, —C(O)NR$_a$NR$_b$— or —S(O)$_2$NR$_a$—.

10. A compound according to claim 1, wherein $Y_3$ is —O—, —NR$_a$—C(O)—, —C(O)NR$_a$—, —C(O)—, —C(O)O— or —NR$_a$C(O)O—.

11. A compound according to claim 1, wherein said heterocycle or heterocyclyl contains one or two oxygen atoms or one sulphur atom, and/or up to two nitrogen atoms, or three or four nitrogen atoms, wherein optionally one or two CH$_2$ ring fragments is/are replaced by one or two —C(O)— fragments respectively.

12. A compound according to claim 1, wherein Ra, Rb, or Rc independently represent hydrogen, methyl, ethyl, 2-hydroxyethyl or 2-methoxyethyl.

13. A compound according to claim 1 selected from the group consisting of
3-[2-Chloro-4-(2,4-difluorophenylamino)benzoyl]-N-(2-hydroxyethyl)-4-methylbenzamide (Compound 115),
N-Carbamoylmethyl-3-[2-chloro-4-(2,4-difluoro-phenylamino)-benzoyl]-4-methyl-benzamide (Compound 145),
N-Benzyl-3-[2-chloro-4-(2,4-difluoro-phenylamino)-benzoyl]-4-methyl-benzamide (compound 146),
3-[2-Chloro-4-(2,4-difluoro-phenylamino)-benzoyl]-N-(2-fluoro-ethyl)-4-methyl-benzamide (compound 147),
3-[2-Chloro-4-(2,4-difluoro-phenylamino)-benzoyl]-4-methyl-N-(2,2,2-trifluoro-ethyl)-benzamide (compound 148),
3-[2-Chloro-4-(2,4-difluoro-phenylamino)-benzoyl]-N-ethyl-4-methyl-benzamide (compound 149),
3-[2-Chloro-4-(2,4-difluoro-phenylamino)-benzoyl]-N-cyclohexylmethyl-4-methyl-benzamide (compound 150),
3-[2-Chloro-4-(2,4-difluoro-phenylamino)-benzoyl]-N-(2-hydroxy-propyl)-4-methyl-benzamide (compound 151),
3-[2-Chloro-4-(2,4-difluoro-phenylamino)-benzoyl]-(2,3-dihydroxy-propyl)-4-methyl-benzamide (compound 152),
3-[2-Chloro-4-(2,4-difluoro-phenylamino)-benzoyl]-N-(1-hydroxymethyl-propyl)-4-methyl-benzamide (compound 153),
3-[2-Chloro-4-(2,4-difluoro-phenylamino)-benzoyl]-4-methyl-N-(2,2,3,3,3-pentafluoro-propyl)-benzamide (compound 154),
3-[2-Chloro-4-(2,4-difluoro-phenylamino)-benzoyl]-N-(3-hydroxy-propyl)-4-methyl-benzamide (compound 155),
3-[2-Chloro-4-(2,4-difluoro-phenylamino)-benzoyl]-N-(2-hydroxy-1,1-dimethyl-ethyl)-4-methyl-benzamide (compound 156),
3-[2-Chloro-4-(2,4-difluoro-phenylamino)-benzoyl]-N-(2-hydroxy-1-hydroxymethyl-1-methyl-ethyl)-4-methyl-benzamide (compound 157),
{3-[2-Chloro-4-(2,4-difluoro-phenylamino)-benzoyl]-4-methyl-benzoylamino}-acetic acid ethyl ester (compound 158),
3-[2-Chloro-4-(2,4-difluoro-phenylamino)-benzoyl]-(4-hydroxy-butyl)-4-methyl-benzamide (compound 159),
3-[2-Chloro-4-(2,4-difluoro-phenylamino)-benzoyl]-N-(3-hydroxy-1,1-dimethyl-butyl)-4-methyl-benzamide (compound 160),
3-[2-Chloro-4-(2,4-difluoro-phenylamino)-benzoyl]-4-methyl-N-(3-phenyl-propyl)-benzamide (compound 161),
(R)-3-[2-Chloro-4-(2,4-difluoro-phenylamino)-benzoyl]-(1-hydroxymethyl-3-methyl-butyl)-4-methyl-benzamide (compound 162),
3-[2-Chloro-4-(2,4-difluoro-phenylamino)-benzoyl]-N-isopropyl-4-methyl-benzamide (compound 164),
3-[2-Chloro-4-(2,4-difluoro-phenylamino)-benzoyl]-N-cyclohexyl-4-methyl-benzamide (compound 165),
3-[2-Chloro-4-(2,4-difluoro-phenylamino)-benzoyl]-N-(2,2-difluoro-ethyl)-4-methyl-benzamide (compound 166),
5-{3-[2-Chloro-4-(2,4-difluoro-phenylamino)-benzoyl]-4-methyl-benzoylamino}-4-oxo-pentanoic acid methyl ester (compound 167),
N-[(2-Carbamoyl-ethylcarbamoyl)-methyl]-3-[2-chloro-4-(2,4-difluoro-phenylamino)-benzoyl]-4-methyl-benzamide (compound 168),
(2-{3-[2-Chloro-4-(2,4-difluoro-phenylamino)-benzoyl]-4-methyl-benzoylamino}-acetylamino)-acetic acid ethyl ester (compound 169),
N-Allyl-3-[2-chloro-4-(2,4-difluoro-phenylamino)-benzoyl]-4-methyl-benzamide (compound 170),
3-[2-Chloro-4-(2,4-difluoro-phenylamino)-benzoyl]-4-methyl-N-(2-sulfamoyl-ethyl)-benzamide (compound 171),
N-(2-Acetylamino-ethyl)-3-[2-chloro-4-(2,4-difluoro-phenylamino)-benzoyl]-4-methyl-benzamide (compound 172),
N-{3-[2-Chloro-4-(2,4-difluoro-phenylamino)-benzoyl]-4-methyl-phenyl}-3-methoxy-propionamide (compound 241),
N-{3-[2-Chloro-4-(2,4-difluoro-phenylamino)-benzoyl]-4-methyl-phenyl}-propionamide (compound 242),
N-{3-[2-Chloro-4-(2,4-difluoro-phenylamino)-benzoyl]-4-methyl-phenyl}-2-(2-methoxy-ethoxy)-acetamide (compound 243),
N-{3-[2-Chloro-4-(2,4-difluoro-phenylamino)-benzoyl]-4-methyl-phenyl}-3-morpholin-4-yl-propionamide (compound 244),
N-{3-[2-Chloro-4-(2,4-difluoro-phenylamino)-benzoyl]-4-methyl-phenyl}-3-hydroxy-propionamide (compound 245),
N-{3-[2-Chloro-4-(2,4-difluoro-phenylamino)-benzoyl]-4-methyl-phenyl}-3-furan-2-yl-propionamide (compound 246),
N-{3-[2-Chloro-4-(2,4-difluoro-phenylamino)-benzoyl]-4-methyl-phenyl}-2-hydroxy-benzamide (compound 247),
N-{3-[2-Chloro-4-(2,4-difluoro-phenylamino)-benzoyl]-4-methyl-phenyl}-2-(2,5-dioxo-imidazolidin-4-yl)-acetamide (compound 248),
2,6-Dioxo-hexahydro-pyrimidine-4-carboxylic acid {3-[2-chloro-4-(2,4-difluoro-phenylamino)-benzoyl]-4-methyl-phenyl}-amide (compound 249),
Acrylic acid 2-{3-[2-chloro-4-(2,4-difluoro-phenylamino)-benzoyl]-4-methyl-phenylcarbamoyl}-ethyl ester (compound 250),
N-{3-[2-Chloro-4-(2,4-difluoro-phenylamino)-benzoyl]-4-methyl-phenyl}-3-methyl sulfanyl-propionamide (compound 251),
N-{3-[2-Chloro-4-(2,4-difluoro-phenylamino)-benzoyl]-4-methyl-phenyl}-3-methanesulfonyl-propionamide (compound 252),
Ethanesulfonic acid {3-[2-chloro-4-(2,4-difluoro-phenylamino)-benzoyl]-4-methyl-phenyl}-amide (compound 253),
N-{3-[2-Chloro-4-(2,4-difluoro-phenylamino)-benzoyl]-4-methyl-phenyl}-4-methoxy-benzenesulfonamide (compound 254),
N-(5-{3-[2-Chloro-4-(2,4-difluoro-phenylamino)-benzoyl]-4-methyl-phenylsulfamoyl}-4-methyl-thiazol-2-yl)-acetamide (compound 255),
5-Acetyl-2-chloro-N-{3-[2-chloro-4-(2,4-difluoro-phenylamino)-benzoyl]-4-methyl-phenyl}-benzenesulfonamide (compound 256),
Naphthalene-2-sulfonic acid {3-[2-chloro-4-(2,4-difluoro-phenylamino)-benzoyl]-4-methyl-phenyl}-amide (compound 257), N-{3-[2-Chloro-4-(2,4-difluoro-phenylamino)-benzoyl]-4-methyl-phenyl}-C-phenyl-methanesulfonamide (compound 258),
2-Methyl-acrylic acid 2-(3-{3-[2-chloro-4-(2,4-difluoro-phenylamino)-benzoyl]-4-methyl-phenyl}-ureido)-ethyl ester (compound 259),
1-{3-[2-Chloro-4-(2,4-difluoro-phenylamino)-benzoyl]-4-methyl-phenyl}-3-(2-hydroxy-ethyl)-urea (compound 260),
(3-{3-[2-Chloro-4-(2,4-difluoro-phenylamino)-benzoyl]-4-methyl-phenyl}-ureido)-acetic acid ethyl ester (compound 261),
1-{3-[2-Chloro-4-(2,4-difluoro-phenylamino)-benzoyl]-4-methyl-phenyl}-3-(3-methoxy-phenyl)-urea (compound 262),
1-{3-[2-Chloro-4-(2,4-difluoro-phenylamino)-benzoyl]-4-methyl-phenyl}-3-(3-trifluoromethyl-phenyl)-urea (compound 263),
1-{3-[2-Chloro-4-(2,4-difluoro-phenylamino)-benzoyl]-4-methyl-phenyl}-3-propyl-urea (compound 264),
3-(3-{3-[2-Chloro-4-(2,4-difluoro-phenylamino)-benzoyl]-4-methyl-phenyl}-ureido)-propionic acid ethyl ester (compound 265),
1-{3-[2-Chloro-4-(2,4-difluoro-phenylamino)-benzoyl]-4-methyl-phenyl}-3-cyclohexyl-urea (compound 266),
1-Allyl-3-{3-[2-chloro-4-(2,4-difluoro-phenylamino)-benzoyl]-4-methyl-phenyl}-urea (compound 267),
1-Benzyl-3-{3-[2-chloro-4-(2,4-difluoro-phenylamino)-benzoyl]-4-methyl-phenyl}-urea (compound 268),
1-{3-[2-Chloro-4-(2,4-difluoro-phenylamino)-benzoyl]-4-methyl-phenyl}-3-ethyl-urea (compound 269),
1-{3-[2-Chloro-4-(2,4-difluoro-phenylamino)-benzoyl]-4-methyl-phenyl}-3-phenyl-urea (compound 270),
1-Butyl-3-{3-[2-chloro-4-(2,4-difluoro-phenylamino)-benzoyl]-4-methyl-phenyl}-urea (compound 271),
1-{3-[2-Chloro-4-(2,4-difluoro-phenylamino)-benzoyl]-4-methyl-phenyl}-3-phenethyl-urea (compound 272),
2-(3-{3-[2-Chloro-4-(2,4-difluoro-phenylamino)-benzoyl]-4-methyl-phenyl}-ureido)-benzoic acid methyl ester (compound 273),
1-{3-[2-Chloro-4-(2,4-difluoro-phenylamino)-benzoyl]-4-methyl-phenyl}-3-(3-cyano-phenyl)-urea (compound 274),
1-{3-[2-Chloro-4-(2,4-difluoro-phenylamino)-benzoyl]-4-methyl-phenyl}-3-isopropyl-urea (compound 275),
1-{3-[2-Chloro-4-(2,4-difluoro-phenylamino)-benzoyl]-4-methyl-phenyl}-3-(4-methoxy-phenyl)-urea (compound 276),
{3-[2-Chloro-4-(2,4-difluoro-phenylamino)-benzoyl]-4-methyl-phenyl}-carbamic acid benzyl ester (compound 277),
{3-[2-Chloro-4-(2,4-difluoro-phenylamino)-benzoyl]-4-methyl-phenyl}-carbamic acid allyl ester (compound 278),
{3-[2-Chloro-4-(2,4-difluoro-phenylamino)-benzoyl]-4-methyl-phenyl}-carbamic acid ethyl ester (compound 279),
[2-Chloro-4-(2,4-difluoro-phenylamino)-phenyl]-[5-(3-hydroxy-butylamino)-2-methyl-phenyl]-methanone (compound 281),
[2-Chloro-4-(2,4-difluoro-phenylamino)-phenyl]-(3'-hydroxymethyl-4-methyl-biphenyl-3-yl)-methanone (compound 282),
[2-Chloro-4-(2,4-difluoro-phenylamino)-phenyl]-(3'-hydroxy-4-methyl-biphenyl-3-yl)-methanone (compound 283),
[2-Chloro-4-(2,4-difluoro-phenylamino)-phenyl]-(4'-methoxy-4-methyl-biphenyl-3-yl)-methanone (compound 284),
N-{3'-[2-Chloro-4-(2,4-difluoro-phenylamino)-benzoyl]-4'-methyl-biphenyl-3-yl}-acetamide (compound 285),
[2-Chloro-4-(2,4-difluoro-phenylamino)-phenyl]-(4-methyl-3'-trifluoromethoxy-biphenyl-3-yl)-methanone (compound 286),
[2-Chloro-4-(2,4-difluoro-phenylamino)-phenyl]-(3',4',5'-trifluoro-4-methyl-biphenyl-3-yl)-methanone (compound 288),
[2-Chloro-4-(2,4-difluoro-phenylamino)-phenyl]-(3',4'-dimethoxy-4-methyl-biphenyl-3-yl)-methanone (289),
3'-[2-Chloro-4-(2,4-difluoro-phenylamino)-benzoyl]-4'-methyl-biphenyl-3-carbonitrile (compound 290),
3-[2-Chloro-4-(2,4-difluoro-phenylamino)-benzoyl]-N-(2-hydroxy-ethyl)-4-methyl-benzenesulfonamide (compound 291),
3-[2-Chloro-4-(2,4-difluoro-phenylamino)-benzoyl]-4-methyl-N-(2-morpholin-4-yl-ethyl)-benzenesulfonamide (compound 292),
N-Allyl-3-[2-chloro-4-(2,4-difluoro-phenylamino)-benzoyl]-4-methyl-benzenesulfonamide (compound 293),
N-(2-{3-[2-Chloro-4-(2,4-difluoro-phenylamino)-benzoyl]-4-methyl-benzenesulfonylamino}-ethyl)-acetamide (compound 294),
3-[2-Chloro-4-(2,4-difluoro-phenylamino)-benzoyl]-4-methyl-N-propyl-benzenesulfonamide (compound 295),
3-[2-Chloro-4-(2,4-difluoro-phenylamino)-benzoyl]-N-(2,3-dihydroxy-propyl)-4-methyl-benzenesulfonamide (compound 296),
3-[2-Chloro-4-(2,4-difluoro-phenylamino)-benzoyl]-N-(2-methoxy-ethyl)-4-methyl-benzenesulfonamide (compound 297),
[2-Chloro-4-(2,4-difluoro-phenylamino)-phenyl]-(5-hydroxymethyl-2-methyl-phenyl)-methanone (compound 331),
[2-Chloro-4-(2,4-difluoro-phenylamino)-phenyl]-(5-chloromethyl-2-methyl-phenyl)-methanone (compound 332),
(5-Azidomethyl-2-methyl-phenyl)-[2-chloro-4-(2,4-difluoro-phenylamino)-phenyl]-methanone (compound 333),
(5-Aminomethyl-2-methyl-phenyl)-[2-chloro-4-(2,4-difluoro-phenylamino)-phenyl]-methanone (compound 334),
3-[2-Chloro-4-(2,4-difluoro-phenylamino)-benzoyl]-N-methoxy-4-methyl-benzamide (compound 338),
N-Butoxy-3-[2-chloro-4-(2,4-difluoro-phenylamino)-benzoyl]-4-methyl-benzamide (compound 339),
3-[2-Chloro-4-(2,4-difluoro-phenylamino)-benzoyl]-N-cyclohexylmethoxy-4-methyl-benzamide (compound 340),
3-[2-Chloro-4-(2,4-difluoro-phenylamino)-benzoyl]-4-methyl-N-(2-methyl-thiazol-4-ylmethoxy)-benzamide (compound 341),
N-benzyloxy-3-[2-chloro-4-(2,4-difluoro-phenylamino)-benzoyl]-4-methyl-benzamide (compound 342),
3-[2-Chloro-4-(2,4-difluoro-phenylamino)-benzoyl]-N-(4-methoxy-benzyloxy)-4-methyl-benzamide (compound 343),
3-[2-Chloro-4-(2,4-difluoro-phenylamino)-benzoyl]-4-methyl-benzoic acid N',N'-dimethyl-hydrazide (compound 344),
3-[2-Chloro-4-(2,4-difluoro-phenylamino)-benzoyl]-4-methyl-N-morpholin-4-yl-benzamide (compound 345), 3-[2-Chloro-4-(2,4-difluoro-phenylamino)-benzoyl]-N-hydroxy-4-methyl-benzamide (compound 346),
4-[2-Chloro-4-(2,4-difluoro-phenylamino)-benzoyl]-N-(2-hydroxy-ethyl)-3-methyl-benzamide (compound 347),
[2-Chloro-4-(2,4-difluoro-phenylamino)-phenyl]-[5-(3-hydroxy-propenyl)-2-methyl-phenyl]-methanone (compound 348),
4-{3-[2-Chloro-4-(2,4-difluoro-phenylamino)-benzoyl]-4-methyl-benzoylamino}-thiophene-3-carboxylic acid methyl ester (compound 349),
3-[2-Chloro-4-(2,4-difluoro-phenylamino)-benzoyl]-N-furan-2-ylmethyl-4-methyl-benzamide (compound 350),
3-[2-Chloro-4-(2,4-difluoro-phenylamino)-benzoyl]-N-(3-methoxy-phenyl)-4-methyl-benzamide (compound 351),
2-{3-[2-Chloro-4-(2,4-difluoro-phenylamino)-benzoyl]-4-methyl-benzoylamino}-benzoic acid methyl ester (compound 352),
3-{3-[2-Chloro-4-(2,4-difluoro-phenylamino)-benzoyl]-4-methyl-benzoylamino}-thiophene-2-carboxylic acid methyl ester (compound 353),
4-{3-[2-Chloro-4-(2,4-difluoro-phenylamino)-benzoyl]-4-methyl-benzoylamino}-thiophene-3-carboxylic acid (compound 354),
2-{3-[2-Chloro-4-(2,4-difluoro-phenylamino)-benzoyl]-4-methyl-benzoylamino}-benzoic acid (compound 355),
3-[2-Chloro-4-(2,4-difluoro-phenylamino)-benzoyl]-N-[2-(2-hydroxy-ethylcarbamoyl)-phenyl]-4-methyl-benzamide (compound 356),
3-{3-[2-Chloro-4-(2,4-difluoro-phenylamino)-benzoyl]-4-methyl-benzoylamino}-thiophene-2-carboxylic acid (2-hydroxy-ethyl)-amide (compound 357),
[2-Chloro-4-(2,4-difluoro-phenylamino)-phenyl]-(5-ethynyl-2-methyl-phenyl)-methanone (compound 362),
3-[2-Chloro-4-(2,4-difluoro-phenylamino)-benzoyl]-4-methyl-benzoic acid hydrazide (compound 364),
1-{3-[2-Chloro-4-(2,4-difluoro-phenylamino)-benzoyl]-4-methyl-benzoyl}-4-ethyl-3-thio semicarbazide (compound 365),
[2-Chloro-4-(2,4-difluoro-phenylamino)-phenyl]-[5-(5-ethylamino-[1,3,4]thiadiazol-2-yl)-2-methyl-phenyl]-methanone (compound 366),
[2-Chloro-4-(2,4-difluoro-phenylamino)-phenyl]-[2-methyl-5-(1H-tetrazol-5-yl)-phenyl]-methanone (compound 367),
3-{3-[2-Chloro-4-(2,4-difluoro-phenylamino)-benzoyl]-4-methyl-phenyl}-3-oxo-propionic acid ethyl ester (compound 368),
[2-Chloro-4-(2,4-difluoro-phenylamino)-phenyl]-[5-(4,5-dihydro-oxazol-2-yl)-2-methyl-phenyl]-methanone (compound 369),
3-[2-Chloro-4-(2,4-difluorophenylamino)benzoyl]-4-methylbenzoic acid (Compound 424),
2-Methylacrylic acid 2-{3-[2-chloro-4-(2,4-difluorophenylamino)benzoyl]-4-methylbenzoylamino}ethyl ester (Compound 425).

14. A pharmaceutical composition comprising a compound according to claim 1 or a pharmaceutically acceptable salt or ester thereof together with a pharmaceutically acceptable vehicle or excipient.

15. A method for producing a compound of general structure I,

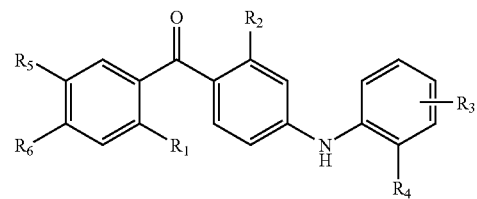

wherein $R_1$, $R_2$, $R_3$, $R_4$, $R_5$, and $R_6$ are defined as in claim 1, comprising the steps of a) transforming a compound general structure VI,

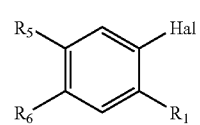

wherein Hal is a halogen, and $R_1$, $R_5$ and $R_6$ are defined as in claim 1, each of which are independently protected or unprotected, into an organometallic intermediate;

b) transmetalating said organometallic intermediate to an organozinc intermediate;

c) coupling said organozinc intermediate with an acid halide of general structure V,

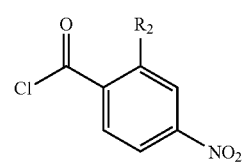

wherein $R_2$ is defined as in claim 1, protected or unprotected, in the presence of a catalyst to give a compound of general structure IV,

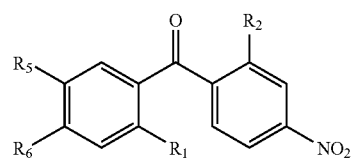

wherein $R_1$, $R_2$, $R_5$, and $R_6$ are defined as above, each of which are independently protected or unprotected;

d) optionally transforming, protecting or deprotecting one or more substituents or functional groups of $R_1$, $R_2$, $R_5$, and $R_6$ of the compound of general structure IV to give another compound of general structure IV;

e) reducing the compound of general structure IV from step c) or d) to an amine of general structure III,

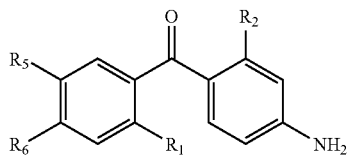

wherein $R_1$, $R_2$, $R_5$, and $R_6$ are defined as above, each of which are independently protected or unprotected;
f) optionally transforming, protecting or deprotecting one or more substituents or functional groups of $R_1$, $R_2$, $R_5$, and $R_6$ of the compound of general structure III to give another compound of general structure III;
g) coupling of the amine of general structure III from step e) or f) with a compound of general structure II,

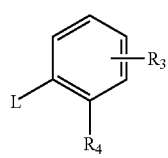

wherein L is triflate or halogen, $R_3$ and $R_4$ are defined in claim 1, each of which are independently protected or unprotected, to give a compound of general structure I, wherein $R_1$, $R_2$, $R_3$, $R_4$, $R_5$, and $R_6$ are defined as above, each of which are independently protected or unprotected;
h) optionally transforming, protecting or deprotecting one or more substituents or functional groups of $R_1$, $R_2$, $R_3$, $R_4$, $R_5$, or $R_6$ of the compound of general structure I from step g) to give a another compound of general structure I.

16. A method for producing a compound of general structure I,

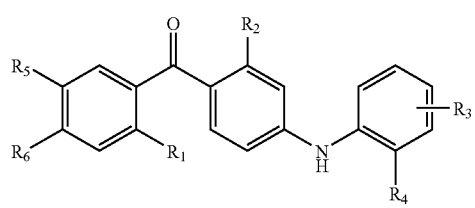

wherein $R_1$, $R_2$, $R_3$, $R_4$, $R_5$, and $R_6$ are defined as in claim 1, comprising the steps of
a) transforming a compound general structure VIIa,

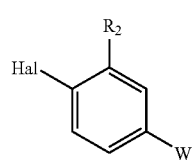

wherein Hal is halogen, W is halogen or triflate, and $R_2$ is as defined in claim 1, protected or unprotected, into an organometallic intermediate;

b) transmetalating said organometallic intermediate to an organozinc intermediate;
c) coupling said organozinc intermediate with an acid halide of general structure VIII,

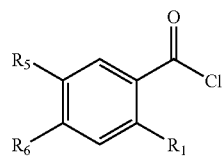

wherein $R_1$, $R_5$, and $R_6$ are as defined in claim 1, each of which are independently protected or unprotected, in the presence of a catalyst to give a compound of general structure IIIa,

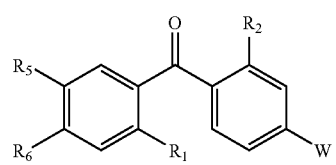

wherein W, $R_1$, $R_2$, $R_5$, and $R_6$ are defined as above, each of which are independently protected or unprotected;
d) optionally transforming, protecting or deprotecting one or more substituents or functional groups of W, $R_1$, $R_2$, $R_5$, and $R_6$ of the compound of general structure IIIa to give another compound of general structure IIIa;
e) coupling of the compound of general structure IIIa from step c) or d) with an amine of general structure IIa,

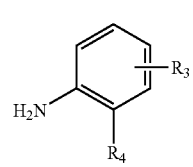

wherein $R_3$ and $R_4$ are defined as in claim 1, each of which are independently protected or unprotected, to give a compound of general structure I,
wherein $R_1$, $R_2$, $R_3$, $R_4$, $R_5$, and $R_6$ are defined as above, each of which are independently protected or unprotected;
f) optionally transforming, protecting or deprotecting one or more substituents or functional groups of $R_1$, $R_2$, $R_3$, $R_4$, $R_5$, or $R_6$ of the compound of general structure I from step e) to give another compound of general structure I.

17. A composition according to claim 14 further comprising another active component selected from the group consisting of glucocorticoids, vitamin D analogues, anti-histamines, platelet activating factor (PAF) antagonists, anticholinergenic agents, methyl xanthines, β-adregenic agents, COX-2 inhibitors, salicylates, indomethacin, flufenamate, naproxen, timegadine, gold salts, penicilamine, serum cholesterol reducing agents, retinoids, zinc salts and salicylazosulfapyridin.

* * * * *